(12) United States Patent
Gottschling et al.

(10) Patent No.: US 6,387,619 B1
(45) Date of Patent: May 14, 2002

(54) TELOMERASE COMPOSITIONS AND METHODS

(75) Inventors: Daniel E. Gottschling; Miriam S. Singer, both of Chicago, IL (US)

(73) Assignee: Arch Development, Chicago, IL (US)

( * ) Notice: Subject to any disclaimer, the term of this patent is extended or adjusted under 35 U.S.C. 154(b) by 0 days.

(21) Appl. No.: 09/345,294

(22) Filed: Jun. 30, 1999

Related U.S. Application Data

(60) Division of application No. 08/938,534, filed on Sep. 26, 1997, now Pat. No. 5,916,752, and a division of application No. 08/431,080, filed on Apr. 28, 1995, now Pat. No. 5,698,686, application No. 09/345,294, which is a continuation-in-part of application No. 08/326,781, filed on Oct. 20, 1994, now abandoned.

(51) Int. Cl.$^7$ .......................... C12Q 1/68; C12P 19/34; C07H 21/02; C07H 21/04

(52) U.S. Cl. ..................... 435/6; 435/41.2; 536/23.1; 536/24.3

(58) Field of Search ................. 435/6, 91.2; 536/23.1, 536/24.3

(56) References Cited

U.S. PATENT DOCUMENTS

| | | |
|---|---|---|
| 3,791,932 A | 2/1974 | Schuurs et al. ........ 195/103.5 R |
| 3,949,064 A | 4/1976 | Bornstein et al. .............. 424/1 |
| 4,889,806 A | 12/1989 | Olson et al. ............. 435/172.3 |
| 5,025,164 A | 6/1991 | Sidwell et al. ............ 250/483.1 |
| 5,270,201 A | 12/1993 | Richards et al. .......... 435/240.4 |
| 5,366,889 A | 11/1994 | MacDonald et al. ...... 435/252.3 |
| 5,489,508 A | 2/1996 | West et al. ..................... 435/6 |
| 5,583,016 A | 12/1996 | Villeponteau et al. ...... 435/91.3 |
| 5,629,154 A | 5/1997 | Kim et al. ..................... 435/6 |
| 5,639,613 A | 6/1997 | Shay et al. .................... 435/6 |
| 5,645,986 A | 7/1997 | West et al. .................... 435/6 |
| 5,648,215 A | 7/1997 | West et al. .................... 435/6 |
| 5,686,245 A | 11/1997 | West et al. .................... 435/6 |
| 5,686,306 A | 11/1997 | West et al. .................. 435/346 |
| 5,693,474 A | 12/1997 | Shay et al. .................... 435/6 |
| 5,695,932 A | 12/1997 | West et al. .................... 435/6 |
| 5,698,686 A | 12/1997 | Gottschling et al. ....... 536/23.1 |
| 5,707,795 A | 1/1998 | West et al. .................... 435/5 |
| 5,733,730 A | 3/1998 | De Lange ..................... 435/6 |
| 5,747,317 A | 5/1998 | Cao ........................... 435/194 |
| 5,916,752 A | 6/1999 | Gottschling et al. ........... 435/6 |

FOREIGN PATENT DOCUMENTS

| | | |
|---|---|---|
| CA | 2021489 | 1/1991 |
| CA | 1295560 | 2/1992 |
| CA | 1301671 | 5/1992 |
| CA | 2078377 | 3/1994 |
| DE | 3919169 | 12/1989 |
| EP | 0318301 | 5/1989 |
| EP | 066313 | 8/1995 |
| FR | 2665908 | 2/1992 |
| WO | WO 89/09219 | 10/1989 |
| WO | WO 91/05044 | 4/1991 |
| WO | WO 91/09140 | 6/1991 |
| WO | WO 92/07080 | 4/1992 |
| WO | WO 92/13101 | 8/1992 |
| WO | WO 93/13649 | 7/1993 |
| WO | WO 93/23572 | 11/1993 |
| WO | WO 94/08053 | 4/1994 |
| WO | WO 95/13381 | 5/1995 |
| WO | WO 95/13382 | 5/1995 |
| WO | WO 95/13383 | 5/1995 |

OTHER PUBLICATIONS

Holt et al, "Functional requirement of p23 and Hsp90 in telomerase complexes", Genes and Development 13:817–826, 1999.*

Johnson et al, "Characterization of a novel 23 kilodalton protein of unactive progesterone complexes", Mol. Cell. Biol. 14(3):1956–1963, Mar. 1994.*

Allsopp et al., "Telomere Length Predicts Replicative Capacity of Human Fibroblasts," *Proc. Natl. Acad. Sci. U.S.A.*, 89(21):10114–10118, 1992.

Aparicio & Gottschling, "Overcoming telomeric silencing: a trans–activator competes to establish gene expression in a cell cycle–dependent way," *Genes Dev.*, 8:1133–1146, 1994.

Aparicio et al., "Modifiers of Position Effect Are Shared Between Telomeric and Silent Mating–Type Loci in *S cerevisiae*", *Cell*, 66:1279–1287, 1991.

Autexier & Greider, "Functional reconstitution of wild–type and mutant Tetrahymena telomerase," *Genes Dev.*, 8(5):563–575, 1994.

Blackburn, "Telomeres: No End in Sight," *Cell*, 77:621–623, 1994.

Blackburn, "Telomerase," In: *The RNA World*, Gesteland & Atkins, Eds., Cold Spring Harbor Laboratory Press, pp. 557–576, 1993.

Cech, "Chromosome End Games," *Science*, 266:387–388, 1994.

Counter et al., "Stabilization of short telomeres and telomerase activity accompany immortalization of Epstein–Barr virus–transformed human B lymphocytes," *J. Virol.*, 68(5):3410–3414, 1994.

Counter et al., "Telomerase activity in human ovarian carcinoma," *Proc. Natl. Acad. Sci. U.S.A.*, 91(8):2900–2904, 1994.

de Lange, "Activation of telomerase in a human tumor," *Proc. Natl. Acad. Sci. U.S.A.*, 91(8):2882–2885, 1994.

Gottschling & Zakian, "Telomere proteins: specific recognition and protection of the natural termini of Oxytricha macronuclear DNA", *Cell*, 47:195–205, 1986.

Gottschling et al., "Position effect at *S. cerevisiae* telomeres: reversible repression of Pol II transcription", *Cell*, 63:751–762, 1990.

(List continued on next page.)

*Primary Examiner*—Jeffrey Fredman
(74) *Attorney, Agent, or Firm*—Fulbright & Jaworski, LLP

(57) ABSTRACT

Disclosed are various methods, compositions and screening assays connected with telomerase, including genes encoding the template RNA of *S. cerevisiae* telomerase and various telomerase-associated polypeptides.

10 Claims, 11 Drawing Sheets

OTHER PUBLICATIONS

Gottschling, "Telomere–proximal DNA in *Saccharomyces cerevisiae* is refractory to methyltransferase activity in vivo", *Proc. Natl. Acad. Sci. USA,* 89:4062–4065, 1992.

Greider, "Mammalian telomere dynamics: healing, fragmentation shortening and stabilization," *Curr. Opinion in Gen. and Dev.,* 4(2):203–211, 1994.

Harley et al., "The telomere hypothesis of cellular aging," *Exp. Gerontol.,* 27(4):375–382, 1992.

Klingelhutz et al., "Restoration of Telomeres in Human Papillomarivus–Immortalized Human Anogenital Epithelial Cells," *Mol. Cell. Biol.,* 14:961–969, 1994.

Kramer & Haber, "New telomeres in yeast are initiated with a highly selected subset of TG1–3 repeats," *Genes Dev.,* 7(12A):2345–2356, 1993.

Lingner et al., "Telomerase RNAs of different ciliates have a common secondary structure and a permuted template," *Genes Dev.,* 8:1984, 1994.

Lundblad & Szostak, "A mutant with a defect in telomere elongation leads to senescence in yeast", *Cell,* 57:633–43, 1989.

Mantell & Greider, "Telomerase activity in germline and embryonic cells of Xenopus," *EMBO J.,* 13(13):3211–3217, 1994.

Prowse et al., "Identification of a nonprocessive telomerase activity from mouse cells," *Proc. Natl. Acad. Sci. U.S.A.,* 90:1493–1497, 1993.

Renauld et al., "Silent domains are assembled continuously from the telomere and are defined by promoter distance and strength, and by SIR3 dosage", *Genes and Development,* 7:1133–1145, 1993.

Romero & Blackburn, "A Conserved Secondary Structure for Telomerase RNA," *Cell,* 67(2):343–353, 1991.

Sandell & Zakian, "Loss of a yeast telomere: arrest, recovery, and chromosome loss," *Cell,* 75:729–739, 1993.

Singer & Gottschling, "TLC1: Template RNA Component of *Saccharomyces cerevisiae* Telomerase," *Science,* 266:404–409, 1994.

ten Dam et al., "A conserved psdeudoknot in telomerase RNA," *Nucleic Acids Res.,* 19:6951, 1991.

Zakian, "Structure and function of telomeres", *Annul. Rev. Genet.,* 23:579–604, 1989.

Kim et al., "Specific Association of Human Telomerase Activity with Immortal Cells and Cancer," *Science,* 266:2011–2015, 1994.

Brodeur, "Do the ends justify the means?," *Nature Medicine,* 1(3):203–205, 1995.

Counter et al., "Telomere shortening associated with chromosome instability is arrested in immortal cells which express telomerase activity," *EMBO J.,* 11(5):1921–1929, 1992.

Maine et al., "In vitro investigations of processive and nonpprocessive telomerase activities," *Molecular Bio./Biochem.,* 36:554, 1995.

McEachern et al., "The yeast *kluyveromyces lactis* as a model system to study telomere length regulation and the ability of cells to grow in the absence of telomerase," *Proc. of American Assoc. Cancer Res.,* 36:670–674, 1995.

Morin, "Is telomerase a universal cancer target?", *J. Natl. Cancer Inst.,* 87(12):869–861, 1995.

Morin, "The human telomere terminal transferase enzyme is a ribonucleoprotein that synthesizes TTAGGG repeats," *Cell,* 59:521–529,. 1989.

Moyzis et al., "A highly conserved repetitive DNA sequence, (TTAGGG), present at the telomeres of human chromosomes," *Proc. Natl. Acad. Sci. USA,* 85:6622–6626, 1988.

Ohara et al., "One–sided polymerase chain reaction: The amplification of cDNA," *Proc. Natl. Acad. Sci. USA,* 86:5673–5677, 1989.

Ohyashiki et al., "Telomere shortening associated with disease evolution patterns in myelodysplastic syndromes," *Cancer Res.,* 54:3557–3560, 1994.

Rhyu, "Telomeres, telomerase and immortality," *J. Natl. Cancer Inst.,* 87(12):884–889, 1995.

Barrell, B. and M. Rajandream, "*S. cerevisiae* chromosome IX lambda clone," EMBL Database Entry SC4554; Accession No. Z38113 (Version 1), Oct. 15, 1994.

Dietrich, F., EMBL Database Entry YER8 Yeast; Accession No. P40059, Feb. 1, 1995.

Kyrion et al, "RAP1 and telomere structure regulate telomere position effects in *Saccharomyces cerevisiae,*" *Genes & Development,* 7:1146–1159, Jul. 1993.

Liu et al, "A yeast protein that binds to vertebrate telomeres and conserved yeast telomeric junctions," *Genes & Development,* 5:49–59, 1991.

Smits et al., EMBL Database Entry SCGAL1; Accession No. X76078 (Version 6), Jun. 16, 1994.

Waterson, R., EMBL Database Entry Sch9986; Accession No. U00027 (Version 2), Nov. 21, 1994.

International Search Report for PCT/US95/13801 mailed Jun. 17, 1996.

\* cited by examiner

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 1301 base pairs
      (B) TYPE: nucleic acid
      (C) STRANDEDNESS: single
      (D) TOPOLOGY: linear (xi) SEQUENCE DESCRIPTION: SEQ ID NO: 1:

```
AATAAAACTA GAGAGGAAGA TAGGTACCCT ATGAAAATGT CAATGGCTGT T GCGTTTGCT      60

TAATCGTATT TTTTTTTTTT TCAGTCCGTG TTTTTTGTAC ATTCTACGTT T GAGTTTTCC     120

ATCATGCAGG CCTCAGAAAT TTGGTAGGCA CTCGATGGTG AAGAGATAGT G TCGGATTTC     180

GGATTGATCT TTCAGTTGAT AGCCTGCTGC TCTTTTCTTT TCCAAAGAAT T TCGAGTATG     240

CTGGTGTCAG TGTAGATGCT TGTGTGTGCG CAATTTGTGG TTTTTTATTG T GTTTCTACT    300

TATAGATGGC TAAAATCTGA GTTTAGAAAA TGCAAACCGT AAATTCTTAA A CACTGCTAT     360

TGCATTTAGT TGCTAAAGCA GTGTTTTTGA ACTTATTCCT GTTATTCCTT C TTCGTACCG     420

ATCCTCTTCT CGACCTAACC TTTTAATTAC CATGGGAAGC CTACCATCAC C ACACCCACA     480

CACAAATGTT ACAGCTAATT GTTTATTAGC AAAGTTTGCA CGAGTTCGCT G TTTATTTTT     540

TTCTCGTTTT CTTATACCTA GTATTTTTTC TGACACTGTT TAAGGTGACA G AAAAAAAGG     600

AGTTTAAGTT AGATTTGCAA ACAGACGGTG CTAAGCGCTG TCACTTTATG T CTATCTTAT     660

CGTTAACTCT GGAAAAAGAA AAAGGAAAAA GAACGTCAGG GAACATGAGT A TATATAGAA     720

ATGGTTTATT CTAGTTTTTT CCGTTTTTTC AGTAGATTTT TGCCTTTAAA A GAATAAATC     780

CCACTACAAA AAGGTAAAAT AAAAAATCTA TTCACTGAAC TTACTGATGA A ATTTCCAAA     840

TGTGCCCCGT ACATCGAACG ATGTGACAGA GAAAAATACG AGTAGGTAAA T AAGCCAAAA     900

GGCAAGGGTG TCCTTTCTTA AGCATCGGTT AGGTTTGCGG GCGATCAGTA A CTGAACAAT     960

GACACAAGAT CAAGAACGTA ATTTGAGATT TTTCAAGATG GTTTTTTTAG G TATCTATTA   1020
```

-continued

```
AAACTACTTT GATGATCAAT ACGGTATTTT TGTCGCATTA TTTTCCAAGC G GAAGGAACC    1080

GTGTGTTCAT TTTATGAATC TTGGTGTTGT ATTCACAGCT ACTTCTCCTA A TGCCTTCGA    1140

TGCATTTAGA TAATTTTTGG AAACATTTTT TTTCTTGATG TATATTTTTT G TATTGTAGA    1200

AATCGCGCGT ACTGTACTTG TATATCGCTT TATAAGCGCT TTTAATTGAT T GTTCATGAC    1260

GAGGATAGGC GGATAGGCGG AAGTATGCCT CTTAATATTT A                          1301
```

(2) INFORMATION FOR SEQ ID NO: 2:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO: 2:

```
GTGTGTGGGT GTG                                                          13
```

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 3:

```
CACCACACCC ACACAC                                                       16
```

(2) INFORMATION FOR SEQ ID NO: 4:

(i) SEQUENCE CHARACTERISTICS:
        (A) LENGTH: 1301 base pairs
        (B) TYPE: nucleic acid
        (C) STRANDEDNESS: single
        (D) TOPOLOGY: linear (xi) SEQUENCE DESCRIPTION: SEQ ID NO: 4:

```
TAAATATTAA GAGGCATACC TCCGCCTATC CGCCTATCCT CGTCATGAAC A ATCAATTAA      60

AAGCGCTTAT AAAGCGATAT ACAAGTACAG TACGCGCGAT TTCTACAATA C AAAAAATAT    120

ACATCAAGAA AAAAAATGTT TCCAAAAATT ATCTAAATGC ATCGAAGGCA T TAGGAGAAG    180

TAGCTGTGAA TACAACACCA AGATTCATAA AATGAACACA CGGTTCCTTC C GCTTGGAAA    240

ATAATGCGAC AAAAATACCG TATTGATCAT CAAAGTAGTT TTAATAGATA C CTAAAAAAA    300

CCATCTTGAA AAATCTCAAA TTACGTTCTT GATCTTGTGT CATTGTTCAG T TACTGATCG    360

CCCGCAAACC TAACCGATGC TTAAGAAAGG ACACCCTTGC CTTTTGGCTT A TTTACCTAC    420

TCGTATTTTT CTCTGTCACA TCGTTCGATG TACGGGCAC ATTTGGAAAT T TCATCAGTA     480

AGTTCAGTGA ATAGATTTTT TATTTTACCT TTTTGTAGTG GGATTATTC T TTTAAAGGC     540

AAAAATCTAC TGAAAAAACG GAAAAAACTA GAATAAACCA TTTCTATATA T ACTCATGTT    600

CCCTGACGTT CTTTTTCCTT TTTCTTTTTC CAGAGTTAAC GATAAGATAG A CATAAAGTG    660

ACAGCGCTTA GCACCGTCTG TTTGCAAATC TAACTTAAAC TCCTTTTTTT C TGTCACCTT    720

AAACAGTGTC AGAAAAAATA CTAGGTATAA GAAAACGAGA AAAAAATAAA C AGCGAACTC    780

GTGCAAACTT TGCTAATAAA CAATTAGCTG TAACATTTGT GTGTGGGTGT G GTGATGGTA    840

GGCTTCCCAT GGTAATTAAA AGGTTAGGTC GAGAAGAGGA TCGGTACGAA G AAGGAATAA    900

CAGGAATAAG TTCAAAAACA CTGCTTTAGC AACTAAATGC AATAGCAGTG T TTAAGAATT    960
```

| | | |
|---|---|---|
| TACGGTTTGC ATTTTCTAAA CTCAGATTTT AGCCATCTAT AAGTAGAAAC A CAATAAAAA | | 1020 |
| ACCACAAATT GCGCACACAC AAGCATCTAC ACTGACACCA GCATACTCGA A ATTCTTTGG | | 1080 |
| AAAAGAAAAG AGCAGCAGGC TATCAACTGA AAGATCAATC CGAAATCCGA C ACTATCTCT | | 1140 |
| TCACCATCGA GTGCCTACCA AATTTCTGAG GCCTGCATGA TGGAAAACTC A AACGTAGAA | | 1200 |
| TGTACAAAAA ACACGGACTG AAAAAAAAAA AAATACGATT AAGCAAACGC A ACAGCCATT | | 1260 |
| GACATTTTCA TAGGGTACCT ATCTTCCTCT CTAGTTTTAT T | | 1301 |

(2) INFORMATION FOR SEQ ID NO: 5:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO: 5:

| | |
|---|---|
| TAATTACCAT GGGAAGCCTA CCATCACCAG GCCCACACAC AAATG | 45 |

(2) INFORMATION FOR SEQ ID NO: 6:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO: 6:

| | |
|---|---|
| CCGGAATTCA TACGAAGATG ATGATTAAAT C | 31 |

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 7:

| | |
|---|---|
| GGCTTGCCAT AGACTTGCTC G | 21 |

(2) INFORMATION FOR SEQ ID NO: 8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 8:

| | |
|---|---|
| TTCGGTAATC TCCGAA | 16 |

(2) INFORMATION FOR SEQ ID NO: 9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO: 9:

| | |
|---|---|
| CGGACGACTG TCGTCCGTCA AAAAAATTTC AAGGAAACCG | 40 |

(2) INFORMATION FOR SEQ ID NO: 10:

(i) SEQUENCE CHARACTERISTICS:
       (A) LENGTH: 37 base pairs
       (B) TYPE: nucleic acid
       (C) STRANDEDNESS: single
       (D) TOPOLOGY: linear (xi) SEQUENCE DESCRIPTION: SEQ ID NO: 10:

CGGACGACAG TCGTCCGCAG AAGGAAGAAC GAAGGAA                                37

(2) INFORMATION FOR SEQ ID NO: 11:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO: 11:

CGAACGGATC CCCTTCAGCC ACTACAGCCT ACTT                                   34

(2) INFORMATION FOR SEQ ID NO: 12:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (xi) SEQUENCE DESCRIPTION: SEQ ID NO: 12:

CGAAGGGATC CGCCAATTGC GAATGCACTC ACCG                                   34

(2) INFORMATION FOR SEQ ID NO: 13:

(i) SEQUENCE CHARACTERISTICS:
       (A) LENGTH: 33 base pairs
       (B) TYPE: nucleic acid
       (C) STRANDEDNESS: single
       (D) TOPOLOGY: linear (xi) SEQUENCE DESCRIPTION: SEQ ID NO: 13:

CCGGATCCTG CCTCGGTAAT GATTTCATTT TTT                                    33

(2) INFORMATION FOR SEQ ID NO: 14:

(i) SEQUENCE CHARACTERISTICS:
       (A) LENGTH: 36 base pairs
       (B) TYPE: nucleic acid
       (C) STRANDEDNESS: single
       (D) TOPOLOGY: linear (xi) SEQUENCE DESCRIPTION: SEQ ID NO: 14:

CCGGATCCTC TCGAGTTCAA GAGAAAAAAA AAGAAA                                 36

(2) INFORMATION FOR SEQ ID NO: 15:

(i) SEQUENCE CHARACTERISTICS:
       (A) LENGTH: 1882 base pairs
       (B) TYPE: nucleic acid
       (C) STRANDEDNESS: single
       (D) TOPOLOGY: linear (xi) SEQUENCE DESCRIPTION: SEQ ID NO: 15:

GATTTTTATA AGTTACACTT GTGTACATGT TATTTCTACT TAGTTATTCA T ACTCATCGT      60

TAAAAGCCGT TCAAAGTGCC TCATCTGGTA TACTTCACCG GCGTACCTCT G TTCCTCCTA     120

CCTCTTGCAG CAGGGCTGAA TAAACTTTCG TCCACATCCT CCATCACTGT T GATATATAA    180

-continued

```
TACTCTCCGC CACTATGCGT CCATGAAACA CTATCCTCCT AAGATCATA C CTTTGCACC        240

TTTAATCTAT TGAAGATGTT CTCAACATTG TAGAAGTTGA TCTGATAAGT G AGGCTTCTT       300

AAACTTTTCA AACTTATGAT CTTACATCCA ACTTTTGCCG TTTGTAGTAT C TTTTCGACT       360

TTTTTATTCA AATCTTCATC AAATAAAAAA TTATTTACGA GGATAACATC G CACTGAGGA       420

ATTAGTTCAG CGACCCTGTT ATTGTCCACA AAGCTTTTCT TCAATGAAAA C TCCACGTTG       480

TTCAAACGCA TCCCATATAA CTTACACCTC TTCTTTAGTT CCTCGTACTG C AGTATAGTT       540

AAATCGCTAG CATCATCCAT GATTTCACAT CCGAAGCTTA ATGCACATCC A CATTCCAAC       600

GCAGCTTGTA CTACGCAATT ACCTACTCCC GAACCGAGAT CCATGAAAGT G TCACCCTTC       660

TTCAACTGGC ATTGTTGATA TACATCAGAT AGGAAATTGG GCAAAAGTTC T CCATAAACA       720

TAATTGCTGA ATGCTTTGTA ATGTTTCAAT TTATTCGCCT GCGGATGGAT A CTCCTGGTA       780

TAGACGATAT GCAAGAAGTC ATGAATGAAT GAACGAGGAA TTTTATCAAT T GTTCTAAA       840

TGGTCAATTA TTCTTTGCCT AGGAATTTCA CGAATCATTT TGTTGTATAA A TTTATAGCA       900

TTCACGAAAC CTTTCGTGTC AGAGTTATCA AATGATGCAT TTAGGTCCGG T AGTATAGTT       960

TCCTTCAATT GTTCAGCATA AGGTGAAGGT AAAAAGACCA GGCAGCTGTA T TCAATTAAT      1020

TTACCAATTT CACTCATTGG ATTATAAATG GCTGTTGACC TTTTGAAGTC G ACTTTGTAC      1080

TCTTCCATAT AATTTGAAAA TAAAATACTC TGCAACTTTG CTGTCGTTAC T GAGGAAGTG      1140

TCGTTATCTG ATGTCAAGCT CGTTGGCTGT GGAGAATTTG TTCTTAAACT A ATGGATTGT      1200

ATAGGAGTTC CAGAATATAT TTCATGTGAT CTTAAGTACT CTATGTCAAA T AATGGATAT      1260

TGTAACCGTA GACACGGGCC ATTCCAATCA ACAAATGTTG ATGAAGGACT A TCGCGATCA      1320

TTCTTCTTGT TTGCCCGACC TTTTTTCAAT GGCTTTTTTT CTCGTGCAGT A TCTATTTCT      1380

TGCTTTGAAA TTGGGGTATG TTTATGGTTA GTCCTGCCAT TTTTTCCTTT T ACTTTTGCA      1440

GCTTTTGGCT TCTTTACATC CTTCTTCGTG GTGGTAGATG ACTTCTTCCT T GTGTTTCTA      1500

TTATTGGTTT TCTTGTGAAT GGGAGGTATA ACCTTCTCCA CCAGCGGAAC C AACCCATTA      1560

TCCTTACCCT TGGTGTTTCT ATCTCTTAAA AATCCTCGAG GTAAAGATGA C CCATATATT      1620

GGATCGTATT TATTAGCTTC TTCTAATAAA TTTTGTACTT GCTTAGAGAG A AGCGTACCT      1680

TTAGAATAGC TTGAAAGCGA CTTGGTTTGC ATATCGGTGC CTTTCTTCTC A TCAATAGGT      1740

GATATTGAAG ATTCCTGAGA GTCTAAGTTG GGGACGACA TAATGAATGA G TCTGAGTTA      1800

TTATTTGATA TACTTTCTTG ATCGCCCATT ACTGTACAAC AAAATGTAAC C AAAGCGCAC      1860

AATTACTGGT GACCTCCTTG AT                                                1882
```

(2) INFORMATION FOR SEQ ID NO: 16:

(i) SEQUENCE CHARACTERISTICS:
        (A) LENGTH: 582 amino acids
        (B) TYPE: amino acid
        (C) STRANDEDNESS: single
        (D) TOPOLOGY: linear (xi) SEQUENCE DESCRIPTION: SEQ ID NO: 16:

```
Met Gly Asp Gln Glu Ser Ile Ser Asn Asn A sn Ser Asp Ser Phe Ile
1               5                   10                  15

Met Ser Ser Pro Asn Leu Asp Ser Gln Glu S er Ser Ile Ser Pro Ile
            20                  25                  30

Asp Glu Lys Lys Gly Thr Asp Met Gln Thr L ys Ser Leu Ser Ser Tyr
        35                  40                  45
```

```
Ser Lys Gly Thr Leu Leu Ser Lys Gln Val Gln Asn Leu Leu Glu Glu
 50                      55                  60

Ala Asn Lys Tyr Asp Pro Ile Tyr Gly Ser Ser Leu Pro Arg Gly Phe
 65                      70                  75                  80

Leu Arg Asp Arg Asn Thr Lys Gly Lys Asp Asn Gly Leu Val Pro Leu
                 85                  90                  95

Val Glu Lys Val Ile Pro Pro Ile His Lys Lys Thr Asn Asn Arg Asn
            100                 105                 110

Thr Arg Lys Lys Ser Ser Thr Thr Thr Lys Lys Asp Val Lys Lys Pro
            115                 120                 125

Lys Ala Ala Lys Val Lys Gly Lys Asn Gly Arg Thr Asn His Lys His
130                 135                 140

Thr Pro Ile Ser Lys Gln Glu Ile Asp Thr Ala Arg Glu Lys Lys Pro
145                 150                 155                 160

Leu Lys Lys Gly Arg Ala Asn Lys Lys Asn Asp Arg Asp Ser Pro Ser
                165                 170                 175

Ser Thr Phe Val Asp Trp Asn Gly Pro Cys Leu Arg Leu Gln Tyr Pro
            180                 185                 190

Leu Phe Asp Ile Glu Tyr Leu Arg Ser His Glu Ile Tyr Ser Gly Thr
            195                 200                 205

Pro Ile Gln Ser Ile Ser Leu Arg Thr Asn Ser Pro Gln Pro Thr Ser
            210                 215                 220

Leu Thr Ser Asp Asn Asp Thr Ser Ser Val Thr Thr Ala Lys Leu Gln
225                 230                 235                 240

Ser Ile Leu Phe Ser Asn Tyr Met Glu Glu Tyr Lys Val Asp Phe Lys
                245                 250                 255

Arg Ser Thr Ala Ile Tyr Asn Pro Met Ser Glu Ile Gly Lys Leu Ile
            260                 265                 270

Glu Tyr Ser Cys Leu Val Phe Leu Pro Ser Pro Tyr Ala Glu Gln Leu
            275                 280                 285

Lys Glu Thr Ile Leu Pro Asp Leu Asn Ala Ser Phe Asp Asn Ser Asp
290                 295                 300

Thr Lys Gly Phe Val Asn Ala Ile Asn Leu Tyr Asn Lys Met Ile Arg
305                 310                 315                 320

Glu Ile Pro Arg Gln Arg Ile Ile Asp His Leu Glu Thr Ile Asp Lys
                325                 330                 335

Ile Pro Arg Ser Phe Ile His Asp Phe Leu His Ile Val Tyr Thr Arg
            340                 345                 350

Ser Ile His Pro Gln Ala Asn Lys Leu Lys His Tyr Lys Ala Phe Ser
            355                 360                 365

Asn Tyr Val Tyr Gly Glu Leu Leu Pro Asn Phe Leu Ser Asp Val Tyr
370                 375                 380

Gln Gln Cys Gln Leu Lys Lys Gly Asp Thr Phe Met Asp Leu Gly Ser
385                 390                 395                 400

Gly Val Gly Asn Cys Val Val Gln Ala Ala Leu Glu Cys Gly Cys Ala
                405                 410                 415

Leu Ser Phe Gly Cys Glu Ile Met Asp Asp Ala Ser Asp Leu Thr Ile
            420                 425                 430

Leu Gln Tyr Glu Glu Leu Lys Lys Arg Cys Lys Leu Tyr Gly Met Arg
            435                 440                 445

Leu Asn Asn Val Glu Phe Ser Leu Lys Lys Ser Phe Val Asp Asn Asn
450                 455                 460

Arg Val Ala Glu Leu Ile Pro Gln Cys Asp Val Ile Leu Val Asn Asn
```

```
465              470              475              480
Phe Leu Phe Asp Glu Asp Leu Asn Lys Lys Val Glu Lys Ile Leu Gln
                    485              490              495
Thr Ala Lys Val Gly Cys Lys Ile Ile Ser Leu Lys Ser Leu Arg Ser
                500              505              510
Leu Thr Tyr Gln Ile Asn Phe Tyr Asn Val Glu Asn Ile Phe Asn Arg
            515              520              525
Leu Lys Val Gln Arg Tyr Asp Leu Lys Glu Asp Ser Val Ser Trp Thr
        530              535              540
His Ser Gly Gly Glu Tyr Tyr Ile Ser Thr Val Met Glu Asp Val Asp
545              550              555              560
Glu Ser Leu Phe Ser Pro Ala Ala Arg Gly Arg Arg Asn Arg Gly Thr
                    565              570              575
Pro Val Lys Tyr Thr Arg
                580
```

(2) INFORMATION FOR SEQ ID NO: 17:

(i) SEQUENCE CHARACTERISTICS:
        (A) LENGTH: 1094 base pairs
        (B) TYPE: nucleic acid
        (C) STRANDEDNESS: single
        (D) TOPOLOGY: linear (xi) SEQUENCE DESCRIPTION: SEQ ID NO: 17:

```
GTCTTCTTCA TTCTCATAAA ATGCATTGCC TGTTTTGGCT TGATTGTCTA C ATTTTCATG    60
ATCTTCAATT TCTCCTCTCG ATTTTGTGTT ATCATTCTTC CCACAACTTT C CTGGGCTCC   120
ACTTTTTTGA TTGGTGTTGC CTTGAATTGT TATCTGACTC TCACTCTTGC G TTTCTCAAC   180
ATACTTTTGA GTTAAAATAT CTATCAAAGA GTCATCGCCA TCGTTGCTAT C TCCTGTTGA   240
ATCCATTTTA TCTACTTCTT CTGCATTCAC CTCTGCTTTT TTTTCAACGT T GGGTGCCTT   300
GATGGGTGAA GATGGCAAAT CGCTGAATTT CGTTATCGTC GGTTTTATAG T TAAATCGCC   360
CTCTATATCA TCGAGAATAT CATCTATATT ACGGAGAGAC TCCCTGGTAG A TATTTCTGC   420
TGGTTTAGGA CGCACTTGCT CATTTCCATT TCTTGAATG AGTTGATTTA C GTCAGCGTT    480
GGGTACTTGG ATATTTGTGA AACTAAGAAC AGTTTTCAGT CGATTAGGGA C TATAGGTGT   540
AGAAGAGGGA TTTTGGACAT CTTCGTAGTC ATCAGAGTAT TCGGCAGCGC T TGTTGTTTT   600
GTCGGACATA TCTCGTTGTA AAGGTGAATA TTTCCATATT ACTTCTTCCA T GGGCCGTC    660
CTCGTCTTGA GTGAAATCGT GATGCCTACT CAAATTAGAC ATTTCCCGTT T CGGTTTAAC   720
TTGTGAATTT GGTAATTGCT TTACGCTCTT GCTAACTGCT TTGTTATAT C TTTTGTTCT    780
TGATGTATTT CGTACTTGTG AAACGGCTAT TGACTTTAGG ACACTTGCAT T GGATACCTT   840
GGTGTTCTTC CCATTTAAGT TATTTATAGG AGCAAAAGCA TACTTTTTTT T CCTCTTAGT   900
TTGCTTAGAT AATATCGCCT TTGAATCATT TTGTATTATT TCTTTTTCCT C TGTCTTCTT   960
CGCAGGTGAA ACAGATATAC TCGCAGACCT CTTGTTCTTC TGTGGCGTTC C GGGCATCCT  1020
GACGATCTCT TCAATTGTCA GTGTTTGCTT GCACAAAATG AGTACTCACT T GAGTATGTT  1080
TTCTCCCAAT TTTG                                                      1094
```

(2) INFORMATION FOR SEQ ID NO: 18:

(i) SEQUENCE CHARACTERISTICS:
        (A) LENGTH: 339 amino acids
        (B) TYPE: amino acid
        (C) STRANDEDNESS: single (D) TOPOLOGY: linear (xi) SEQUENCE DESCRIPTION: SEQ ID NO: 18:

Met Pro Gly Thr Pro Gln Lys Asn Lys Arg Ser Ala Ser Ile Ser Val
1               5                   10                  15

Ser Pro Ala Lys Lys Thr Glu Glu Lys Glu Ile Ile Gln Asn Asp Ser
            20                  25                  30

Lys Ala Ile Leu Ser Lys Gln Thr Lys Arg Lys Lys Lys Tyr Ala Phe
                35                  40                  45

Ala Pro Ile Asn Asn Leu Asn Gly Lys Asn Thr Lys Val Ser Asn Ala
    50                  55                  60

Ser Val Leu Lys Ser Ile Ala Val Ser Gln Val Arg Asn Thr Ser Arg
65                  70                  75                  80

Thr Lys Asp Ile Asn Lys Ala Val Ser Lys Ser Val Lys Gln Leu Pro
                85                  90                  95

Asn Ser Gln Val Lys Pro Lys Arg Glu Met Ser Asn Leu Ser Arg His
                100                 105                 110

His Asp Phe Thr Gln Asp Glu Asp Gly Pro Met Glu Glu Val Ile Trp
        115                 120                 125

Lys Tyr Ser Pro Leu Gln Arg Asp Met Ser Asp Lys Thr Thr Ser Ala
        130                 135                 140

Ala Glu Tyr Ser Asp Asp Tyr Glu Asp Val Gln Asn Pro Ser Ser Thr
145                 150                 155                 160

Pro Ile Val Pro Asn Arg Leu Lys Thr Val Leu Ser Phe Thr Asn Ile
                165                 170                 175

Gln Val Pro Asn Ala Asp Val Asn Gln Leu Ile Gln Glu Asn Gly Asn
                180                 185                 190

Glu Gln Val Arg Pro Lys Pro Ala Glu Ile Ser Thr Arg Glu Ser Leu
            195                 200                 205

Arg Asn Ile Asp Asp Ile Leu Asp Asp Ile Glu Gly Asp Leu Thr Ile
            210                 215                 220

Lys Pro Thr Ile Thr Lys Phe Ser Asp Leu Pro Ser Ser Pro Ile Lys
225                 230                 235                 240

Ala Pro Asn Val Glu Lys Lys Ala Glu Val Asn Ala Glu Glu Val Asp
                245                 250                 255

Lys Met Asp Ser Thr Gly Asp Ser Asn Asp Gly Asp Asp Ser Leu Ile
            260                 265                 270

Asp Ile Leu Thr Gln Lys Tyr Val Glu Lys Arg Lys Ser Glu Ser Gln
            275                 280                 285

Ile Thr Ile Gln Gly Asn Thr Asn Gln Lys Ser Gly Ala Gln Glu Ser
290                 295                 300

Cys Gly Lys Asn Asp Asn Thr Lys Ser Arg Gly Glu Ile Glu Asp His
305                 310                 315                 320

Glu Asn Val Asp Asn Gln Ala Lys Thr Gly Asn Ala Phe Tyr Glu Asn
                325                 330                 335

Glu Glu Asp (2) INFORMATION FOR SEQ ID NO: 19:

(i) SEQUENCE CHARACTERISTICS:
        (A) LENGTH: 2434 base pairs
        (B) TYPE: nucleic acid
        (C) STRANDEDNESS: single
        (D) TOPOLOGY: linear (xi) SEQUENCE DESCRIPTION: SEQ ID NO: 19:

-continued

| | | | | | |
|---|---|---|---|---|---|
| ATCAAATCCC | CTGCAGTTCA | ATGCTGCAAT | GATCTCTAAC | AAATCGAATA A | TAATGATAC | 60 |
| TTCCGCCGCG | CCGGAAAATA | GCTCGTATAT | TGTGATAGGA | AAACAGCATA A | TAACAATAG | 120 |
| TAATAGCACA | GCTATTGCTG | CAACGGCCGA | ATCCAAGCAA | ATAAAAGAAA A | TAACTTGAT | 180 |
| AGACAGGCCA | AACGGAAAGA | AAACCAACAC | TGTTCCTAAA | TCTATGGCTG A | AGCTTTATT | 240 |
| GTTGTATACT | TCTAAAAATG | ATAAAGATGC | TGCAGATGCT | ACTGGTGCCA A | GAAGTCAGC | 300 |
| GGAGCTTTCT | ACGGAGCTTT | CTACGGAGCC | TCCTTCCTCT | TCTTCGGAAG A | TGTCAAAGT | 360 |
| AGGAAAAGAG | GAAGAGGAAG | AGGGTGAAAT | ATTTCATGAG | GCAAGAGACT A | TGTAGAACC | 420 |
| CCGAAAAGCT | AGTTTGAAGG | AACGCGACAA | CGCAGATAAG | GGCGATGGTG A | AGACATCGG | 480 |
| CGAAGACATC | GGTGAAGACA | TCGGTGAAGA | CATCGGTGAA | GACATTGGTG A | AGACATTGG | 540 |
| TGAAAACTTG | GGTTCTCCAT | TAGCAACCAT | TGATGATTCA | TCTAATGAGA A | TGAAAAGGA | 600 |
| AAAAAGAAAG | GAACTGTCTA | CAAGCATTAG | CAGTGATGAC | GAAATAGAAG A | CGACGAGGA | 660 |
| TGAGGATGAC | ATGGATTATG | ATTCTAGTGC | TATGGAAAAA | GAGCTCCCTG A | AGAAGAGGT | 720 |
| GAGCGATTCC | AGCTCCAAAA | TTTCTGAAGG | CGAAAAAAAG | AGTTTATATC A | AGATTTAAT | 780 |
| GGAAAATAGT | ACAGTGGAAG | TAAATCGGTA | CGAACCAGTA | AACAACACCA A | AGAAAATGG | 840 |
| AAACAGGAAT | CCAAAGGGAG | AGGAGGAGGA | AGAAGAGGAA | GAAGAGCTGA A | ACATAAATC | 900 |
| TAGGTCAATC | ACCCCTCCGG | TTACAATATC | AAATCTATCA | AACTTTTACC A | ATTCAATGA | 960 |
| AAATATCAAT | GATCGTGGTT | CTTTAAACTC | TACTAGAATT | GTTAAAAATT G | GGGCGACAA | 1020 |
| ATTCACCAAT | TTGAAGCCTC | GTGGCCTTTT | GAATCATGGT | GTTACTTGTT A | CACAAATGC | 1080 |
| TGCTGTACAG | GCTATGTTAC | ACATTCCTTC | GATCAACAT | TATCTTTTG A | TATACTAAT | 1140 |
| GGGGAAATAC | GATAGCACCA | TCTCAAAAAA | TTCCGTTTCC | TATACTTTAG C | TGAAACAAG | 1200 |
| TAAAAAAATG | TGGTTACCGG | TCTCAAAAAA | CCCTAGAAAG | AACGTTTCAG C | TTCCTACAT | 1260 |
| TAATCCAAAA | CATTTGATTT | CCAGATTGGA | TGACATTAAT | TGTATGATGA G | CGAATGGCA | 1320 |
| GCAGGAAGAT | TCACATGAGT | ACTTCATGTC | TCTGATGTCA | AGATTACAGG A | AGATTCTGT | 1380 |
| TCCCAAGGGT | CATAAACTTA | TAGAATCGAT | AATATATGAC | ATATTCGGTG G | TCTTTTAAA | 1440 |
| GCAGATCGTT | ACTTGCAAAT | CTTGTGGCAG | TATATCTAAA | ACAGAACAAC C | ATTTTACGA | 1500 |
| TTTATCGTTG | CACTTGAAAG | GGAAGAAAAA | ACTTGATCCA | AATTCTGACC T | GTCGAGTGA | 1560 |
| TAGCATTAAC | GGCACTTCAG | CCACCACTTC | TACCACTACC | TCCAATGCTG C | CACAAAACC | 1620 |
| ATCTCTTTCA | TCCTCTTCAT | CTGTCAATTT | AAACAATGGC | TCACCATTTG C | CGCTGCCAG | 1680 |
| TGATTTAAGT | TCAGCCAACC | GCAGATTTTC | TATTGAAAAA | TCAATTAAAG A | TTTCTTCAA | 1740 |
| TCCCGAATTA | ATCAAGGTTG | ACAAGGAGCA | AAAGGGTTAC | GTTTGTGAGA A | GTGTCACAA | 1800 |
| GACCACGAAC | GCCGTGAAGC | ATAGTTCAAT | ATTAAGGGCT | CCTGAAACTT T | ACTTGTGCA | 1860 |
| TCTGAAAAAA | TTCAGATTCA | ATGGCACGTC | CTCATCAAAA | ATGAAGCAAG C | TGTTTCTTA | 1920 |
| TCCTATGTTT | TTAGATTTGA | CGGAATATTG | TGAGAGTAAA | GAGCTACCTG T | CAAATACCA | 1980 |
| ACTATTAAGC | GTGGTGGTTC | ATGAGGGCCG | CTCCCTTTCT | TCAGGTCACT A | CATTGCCCA | 2040 |
| CTGCAAGCAA | CCAGACGGTA | GCTGGGCCAC | TTACGACGAC | GAGTATATTA A | TATAATATC | 2100 |
| TGAAAGGGAC | GTTTTAAAGG | AACCCAACGC | ATATTATCTC | CTATACACGA G | GCTAACTCC | 2160 |
| AAAATCGGTT | CCATTGCCAT | TGGCGAAATC | TGCCATGGCC | ACTGGTAATG T | TACCTCTAA | 2220 |
| ATCCAAACAG | GAACAGGCTG | TTAACGAACC | AAATAACCGC | CCATTGAAGA T | TAATAGCAA | 2280 |
| GAAAAATAAC | AGAAAAAAAT | GGAAAAAAAT | AAAAAAAGGA | AGTTCACCAA A | TGAAAAAAC | 2340 |

```
TCGATATTCC TGGATTTTCC TCTTTTCATA GGCATTTTTA TTAGCATTTC A TTTTTATTA    2400

TACCAAATCA ATATATACAT ATAAAGGCCT TCGT                                 2434
```

(2) INFORMATION FOR SEQ ID NO: 20:

(i) SEQUENCE CHARACTERISTICS:
        (A) LENGTH: 789 amino acids
        (B) TYPE: amino acid
        (C) STRANDEDNESS: single
        (D) TOPOLOGY: linear (xi) SEQUENCE DESCRIPTION: SEQ ID NO: 20:

```
Ser Asn Pro Leu Gln Phe Asn Ala Ala Met I le Ser Asn Lys Ser Asn
1               5                   10                  15

Asn Asn Asp Thr Ser Ala Ala Pro Glu Asn S er Ser Tyr Ile Val Ile
            20                  25                  30

Gly Lys Gln His Asn Asn Asn Ser Asn Ser T hr Ala Ile Ala Ala Thr
        35                  40                  45

Ala Glu Ser Lys Gln Ile Lys Glu Asn Asn L eu Ile Asp Arg Pro Asn
50                  55                  60

Gly Lys Lys Thr Asn Thr Val Pro Lys Ser M et Ala Glu Ala Leu Leu
65                  70                  75                  80

Leu Tyr Thr Ser Lys Asn Asp Lys Asp Ala A la Asp Ala Thr Gly Ala
                85                  90                  95

Lys Lys Ser Ala Glu Leu Ser Thr Glu Leu S er Thr Glu Pro Pro Ser
            100                 105                 110

Ser Ser Ser Glu Asp Val Lys Val Gly Lys G lu Glu Glu Glu Glu Gly
        115                 120                 125

Glu Ile Phe His Glu Ala Arg Asp Tyr Val G lu Pro Arg Lys Ala Ser
    130                 135                 140

Leu Lys Glu Arg Asp Asn Ala Asp Lys Gly A sp Gly Glu Asp Ile Gly
145                 150                 155                 160

Glu Asp Ile Gly Glu Asp Ile Gly Glu Asp I le Gly Glu Asp Ile Gly
                165                 170                 175

Glu Asp Ile Gly Glu Asn Leu Gly Ser Pro L eu Ala Thr Ile Asp Asp
            180                 185                 190

Ser Ser Asn Glu Asn Glu Lys Glu Lys Arg L ys Glu Leu Ser Thr Ser
        195                 200                 205

Ile Ser Ser Asp Asp Glu Ile Glu Asp Asp G lu Asp Glu Asp Asp Met
    210                 215                 220

Asp Tyr Asp Ser Ser Ala Met Glu Lys Glu L eu Pro Glu Glu Glu Glu
225                 230                 235                 240

Ser Asp Ser Ser Ser Lys Ile Ser Glu Gly G lu Lys Lys Ser Leu Tyr
                245                 250                 255

Gln Asp Leu Met Glu Asn Ser Thr Val Glu V al Asn Arg Tyr Glu Pro
            260                 265                 270

Val Asn Asn Thr Lys Glu Asn Gly Asn Arg A sn Pro Lys Gly Glu Glu
        275                 280                 285

Glu Glu Glu Glu Glu Glu Glu Leu Lys His L ys Ser Arg Ser Ile Thr
    290                 295                 300

Pro Pro Val Thr Ile Ser Asn Leu Ser Asn P he Tyr Gln Phe Asn Glu
305                 310                 315                 320

Asn Ile Asn Asp Arg Gly Ser Leu Asn Ser T hr Arg Ile Val Lys Asn
                325                 330                 335

Trp Gly Asp Lys Phe Thr Asn Leu Lys Pro A rg Gly Leu Leu Asn His
```

-continued

```
                340                 345                 350
Gly Val Thr Cys Tyr Thr Asn Ala Ala Val G ln Ala Met Leu His Ile
                355                 360                 365
Pro Ser Ile Gln His Tyr Leu Phe Asp Ile L eu Met Gly Lys Tyr Asp
            370                 375                 380
Ser Thr Ile Ser Lys Asn Ser Val Ser Tyr T hr Leu Ala Glu Thr Ser
385                 390                 395                 400
Lys Lys Met Trp Leu Pro Val Ser Lys Asn P ro Arg Lys Asn Val Ser
                405                 410                 415
Ala Ser Tyr Ile Asn Pro Lys His Leu Ile S er Arg Leu Asp Asp Ile
                420                 425                 430
Asn Cys Met Met Ser Glu Trp Gln Gln Glu A sp Ser His Glu Tyr Phe
                435                 440                 445
Met Ser Leu Met Ser Arg Leu Gln Glu Asp S er Val Pro Lys Gly His
            450                 455                 460
Lys Leu Ile Glu Ser Ile Ile Tyr Asp Ile P he Gly Gly Leu Leu Lys
465                 470                 475                 480
Gln Ile Val Thr Cys Lys Ser Cys Gly Ser I le Ser Lys Thr Glu Gln
                485                 490                 495
Pro Phe Tyr Asp Leu Ser Leu His Leu Lys G ly Lys Lys Leu Asp
            500                 505                 510
Pro Asn Ser Asp Leu Ser Ser Asp Ser Ile A sn Gly Thr Ser Ala Thr
            515                 520                 525
Thr Ser Thr Thr Thr Ser Asn Ala Ala Thr L ys Pro Ser Leu Ser Ser
            530                 535                 540
Ser Ser Ser Val Asn Leu Asn Asn Gly Ser P ro Phe Ala Ala Ala Ser
545                 550                 555                 560
Asp Leu Ser Ser Ala Asn Arg Arg Phe Ser I le Glu Lys Ser Ile Lys
                565                 570                 575
Asp Phe Phe Asn Pro Glu Leu Ile Lys Val A sp Lys Glu Gln Lys Gly
            580                 585                 590
Tyr Val Cys Glu Lys Cys His Lys Thr Thr A sn Ala Val Lys His Ser
                595                 600                 605
Ser Ile Leu Arg Ala Pro Glu Thr Leu Leu V al His Leu Lys Lys Phe
            610                 615                 620
Arg Phe Asn Gly Thr Ser Ser Lys Met L ys Gln Ala Val Ser Tyr
625                 630                 635                 640
Pro Met Phe Leu Asp Leu Thr Glu Tyr Cys G lu Ser Lys Glu Leu Pro
                645                 650                 655
Val Lys Tyr Gln Leu Leu Ser Val Val H is Glu Gly Arg Ser Leu
                660                 665                 670
Ser Ser Gly His Tyr Ile Ala His Cys Lys G ln Pro Asp Gly Ser Trp
            675                 680                 685
Ala Thr Tyr Asp Asp Glu Tyr Ile Asn Ile I le Ser Glu Arg Asp Val
            690                 695                 700
Leu Lys Glu Pro Asn Ala Tyr Tyr Leu Leu T yr Thr Arg Leu Thr Pro
705                 710                 715                 720
Lys Ser Val Pro Leu Pro Leu Ala Lys Ser A la Met Ala Thr Gly Asn
                725                 730                 735
Val Thr Ser Lys Ser Lys Gln Glu Gln Ala V al Asn Glu Pro Asn Asn
            740                 745                 750
Arg Pro Leu Lys Ile Asn Ser Lys Lys Asn A sn Arg Lys Lys Trp Lys
            755                 760                 765
```

```
Lys Ile Lys Lys Gly Ser Ser Pro Asn Glu Lys Thr Arg Tyr Ser Trp
770                 775                 780

Ile Phe Leu Phe Ser
785
```

(2) INFORMATION FOR SEQ ID NO: 21:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (xi) SEQUENCE DESCRIPTION: SEQ ID NO: 21:

```
AGAGAGTTAG AATATCTTCG TTTATCTACA TATATAAAGG GAAGGGTTTG G AATATTTTA      60
CCGATAAGTA CTCCTCTAGA GAAACAAAAA GGGGGTTATT AAACTTCATT C TTCTTTAAA     120
CTTTTCAGCG ACTTCTAAAA CCTCCTTTTT GGCGTCATTT ACACTAACTT C TGGTGATAT     180
CTTAACTCTT TTGAATTTTA ACTTCCCATC AACAAAAATG AAATGCGATC T AATAGAACC     240
AGAAAGTGGC GTTTTTTTGG CTCCTAGCAA CCCAATAAAC TCTCTCTTTG G ATCGCTTAG     300
TAAATGATAT GGCAAATTTT GTTTACTCTG AAACTTTTTC TGGGATGTCA C AGAATCTGC     360
ACTCAGTCCA AAGACAGCAG CATATTTCTT GAGTTCCTGG TAATTGTCAC G AAATCCACA     420
GGCCTGTCTA GTACAACCAG GCGTGCTTGC CCTGGGATAC ACAAAAAACA C CACAACTCT     480
GTTATTTTCG GTGATTTTCT TCAAGGAGAT AGAGTCATTA TCTTCATTTA A AAGACTCAA     540
ATCAGGAATA GGATCGCCTA TCTCTAATTC GTTAACATCA GATGACCTAT T TGCCTCTTG     600
AACTACTGCT TGATTAGCGT TATGTTTAGG ACCCGTCTTG ATTTTCTTCT T AGGCACTTC     660
CGGTGTCGAA ATAGGGGCCA GTTTGGACTC TTCCTCTTCC AACATTCTTT T GGATATTGC     720
AATCCTGGTT GATCTACGTA GTGCTTCACC CATTCTATTA GGAACTTTA A TATTACCTG     780
TATAAAGCTC GTAGTATTAC TTCATCC                                         807
```

(2) INFORMATION FOR SEQ ID NO: 22:

(i) SEQUENCE CHARACTERISTICS:
        (A) LENGTH: 215 amino acids
        (B) TYPE: amino acid
        (C) STRANDEDNESS: single
        (D) TOPOLOGY: linear (xi) SEQUENCE DESCRIPTION: SEQ ID NO: 22:

```
Met Gly Glu Ala Leu Arg Arg Ser Thr Arg Ile Ala Ile Ser Lys Arg
1               5                   10                  15

Met Leu Glu Glu Glu Ser Lys Leu Ala Pro Ile Ser Thr Pro Glu
            20                  25                  30

Val Pro Lys Lys Ile Lys Thr Gly Pro Lys His Asn Ala Asn Gln
        35                  40                  45

Ala Val Val Gln Glu Ala Asn Arg Ser Ser Asp Val Asn Glu Leu Glu
        50                  55                  60

Ile Gly Asp Pro Ile Pro Asp Leu Ser Leu Leu Asn Glu Asp Asn Asp
65                  70                  75                  80

Ser Ile Ser Leu Lys Lys Ile Thr Glu Asn Asn Arg Val Val Val Phe
                85                  90                  95

Phe Val Tyr Pro Arg Ala Ser Thr Pro Gly Cys Thr Arg Gln Ala Cys
            100                 105                 110

Gly Phe Arg Asp Asn Tyr Gln Glu Leu Lys Lys Tyr Ala Ala Val Phe
```

```
                115                 120                 125
Gly Leu Ser Ala Asp Ser Val Thr Ser Gln Lys Lys Phe Gln Ser Lys
            130                 135                 140

Gln Asn Leu Pro Tyr His Leu Leu Ser Asp Pro Lys Arg Glu Phe Ile
145                 150                 155                 160

Gly Leu Leu Gly Ala Lys Lys Thr Pro Leu Ser Gly Ser Ile Arg Ser
                165                 170                 175

His Phe Ile Phe Val Asp Gly Lys Leu Lys Phe Lys Arg Val Lys Ile
            180                 185                 190

Ser Pro Glu Val Ser Val Asn Asp Ala Lys Lys Glu Val Leu Glu Val
                195                 200                 205

Ala Glu Lys Phe Lys Glu Glu
    210                 215

(2) INFORMATION FOR SEQ ID NO: 23:

(i) SEQUENCE CHARACTERISTICS:
        (A) LENGTH: 2117 base pairs
        (B) TYPE: nucleic acid
        (C) STRANDEDNESS: single
        (D) TOPOLOGY: linear (xi) SEQUENCE DESCRIPTION: SEQ ID NO: 23:

CCCATCCTCA GCTACACTCA CTCACTCGTC AGCCACACTC GTCGTCAACA G CTATGTCCA      60

AGAACGAAGC CCAGGAATCT TCGCCCTCTC TGCCAGCTTC CTCTTCATCG T CGACTTCGG    120

CATCGGCATC TGCGTCTTCC AAGAATTCGA GCAAGAACCC TTCCTCTTGG G ACCCTCAAG    180

ATGATCTGCT GCTACGTCAT TTAAAGGAGG TCAAGAAAAT GGGCTGGAAG G ATATTTCGC    240

AATACTTCCC AAACAGGACT CCTAACGCGT GTCAGTTCAG ATGGAGAAGG T TGAAGTCTG    300

GTAACTTGAA GTCGAACAAG ACTGCTTTGA TCGACATCAA CACCTATACG G GCCCACTCA    360

AGATCACCCA CGGCGATGAG ACTGCCAACG CTCAGCAAAA GCCCAGCAAG A AGGTAGAAG    420

AAAACGTATT AACGGAAGAT ACTGCTGAGT TCACTACAAC GTCATCCATC C CGATTCCCT    480

CCAGAAAGAC CTCGTTGCCT TCGTTTCACG CATCGATGTC ATTTTCTCAA T CTCCGTCCA    540

ATGTGACTCC CACTACGATT GTCTCAAACG CTGCTTCTTC CATGCCGTTC G CTCCTCCCA    600

CGCTGCCGGC CGCACTCCCT CATCATCCTC ATCAACACCT ACACCACCAT C CCCATCATA    660

AGACTCTAAA GCCAAGGTCA AACTCTCACT CCTTCACCAA TTCTTTGAAC C AAGACCCCA    720

TCGTTCGGTC TAATGATGAG GAGAAGTATG GATTCATTCC TAAAGTATTC G TTAGATCCA    780

GAAGAAGTTC GTTTGCCTAT CCACAACAGG TAGCAATAAC CACTACTCCG T CTTCTCCAA    840

ACTCTTCGCA TGTCTTACTA AGCTCAAAGT CAAGAAGGGG CTCGCTTGCG A ATTGGTCCA    900

GAAGATCATC GTTAATGTT TCAAGTAACA ACACTTCAAG ACGGTCTTCA A TGATTCTTG    960

CACCAAATTC CGTGTCAAAC ATATTCAATG TCAACAATAG CGGCAGTAAC A CTGCTTCTA   1020

CTTCTAATAC CAACTCAAGA AGGGAATCTG TCATCAAGAA GGAATTTCAG C AAAGATTAA   1080

ACAACTTAAG TAACAGTGGA GGTCCTACCT CCAACAACGG GCCCATTTTC C CCAACTCTT   1140

ATACCTTTAT GGATCTCCCA CATTCTTCAT CGGTGTCATC GTCATCCACT T TGCATAAGT   1200

CTAAACGAGG TTCGTTTTCT GGCCATTCTA TGAAGTCATC GTGTAATCCG A CTAATCTAT   1260

GGTCAAAAGA TGAAGACGCT TTGCTAATGG AAAACAAAAA GAGAAACCTA T CCGTTATGG   1320

AACTATCCAT TCTTTTGCCG CAGAGAACTG AGGTGGAAAT TCAATGGAGA T AAACGCCT    1380

TGTCAAGTGA TGCGGATATG TTGTCTCCTA CACATTCACC TCAAAAAACT C TGTCCAAGA   1440
```

-continued

```
AAACTTGTCC AAGAATGTTC AAAAGTGGTT CTACCACTGA TGATGACAAA G GTAGCGACA      1500

AAGAGGACGT TATGGGTGAT GGTAGTAACG ATGATGACGA AGATAATGTA G ACCCGCTGC      1560

ACCGTGCTAA ACAATCCAGT AACAAGACTG TCTTTTCATC CAGCAGTTCC A ACATATCCT      1620

CCAAAGACGT TTCACCGGAT CCGATCTTTT CACCGGATCC CGCAGATGAT T CATCGAATA      1680

CTTCTGATGC TGGTTCTAGG TGCACCATAA CCTCCGATAC CAGCTCCTCG G CTGCAACCA      1740

TGAATCGCAC CCCTAATTCC AAAAACCCGC AAGATATTGC TTTGTTAAAC A ACTTTCGTT      1800

CTGAAGCCAT TACTCCGAGA CCGAAGCCTT CTTCCACAAC TACATCCATC A CTACCGAAA      1860

CCACCAATAA CATGATAAAC CACTCTAGTT CTACAACTAC TACCACAAAC A ACAGTCCGC      1920

TGCCAAGCAT AAACACTATC TTCAAGGATA TGCTGTGAGG GGAAAACTTA A AATGAAAAA      1980

AAAATAAAAA TAAAAAAATA TCAACAACAA AAAGAAAATG TGAATTTAGC G GGCTTGTTC      2040

ATTAAATTTC TATAGTTTAG CATATTTAAA AGTATAAAAG TTTCTTTGGT T TATATGACG      2100

TATTCATCCA AAAAAA                                                       2117
```

(2) INFORMATION FOR SEQ ID NO: 24:

(i) SEQUENCE CHARACTERISTICS:
        (A) LENGTH: 651 amino acids
        (B) TYPE: amino acid
        (C) STRANDEDNESS: single
        (D) TOPOLOGY: linear (xi) SEQUENCE DESCRIPTION: SEQ ID NO: 24:

```
His Pro Gln Leu His Ser Leu Thr Arg Gln P ro His Ser Ser Thr
 1               5                  10                  15

Ala Met Ser Lys Asn Glu Ala Gln Glu Ser S er Pro Ser Leu Pro Ala
            20                  25                  30

Ser Ser Ser Ser Ser Thr Ser Ala Ser Ala S er Ala Ser Ser Lys Asn
            35                  40                  45

Ser Ser Lys Asn Pro Ser Ser Trp Asp Pro G ln Asp Asp Leu Leu Leu
        50                  55                  60

Arg His Leu Lys Glu Val Lys Lys Met Gly T rp Lys Asp Ile Ser Gln
65                  70                  75                  80

Tyr Phe Pro Asn Arg Thr Pro Asn Ala Cys G ln Phe Arg Trp Arg Arg
                85                  90                  95

Leu Lys Ser Gly Asn Leu Lys Ser Asn Lys T hr Ala Leu Ile Asp Ile
            100                 105                 110

Asn Thr Tyr Thr Gly Pro Leu Lys Ile Thr H is Gly Asp Glu Thr Ala
        115                 120                 125

Asn Ala Gln Gln Lys Pro Ser Lys Lys Val G lu Glu Asn Val Leu Thr
    130                 135                 140

Glu Asp Thr Ala Glu Phe Thr Thr Thr Ser S er Ile Pro Ile Pro Ser
145                 150                 155                 160

Arg Lys Thr Ser Leu Pro Ser Phe His Ala S er Met Ser Phe Ser Gln
                165                 170                 175

Ser Pro Ser Asn Val Thr Pro Thr Thr Ile V al Ser Asn Ala Ala Ser
            180                 185                 190

Ser Met Pro Phe Ala Pro Pro Thr Leu Pro A la Ala Leu Pro His His
        195                 200                 205

Pro His Gln His Leu His His Pro His H is Lys Thr Leu Lys Pro
    210                 215                 220

Arg Ser Asn Ser His Ser Phe Thr Asn Ser L eu Asn Gln Asp Pro Ile
225                 230                 235                 240
```

-continued

```
Val Arg Ser Asn Asp Glu Glu Lys Tyr Gly Phe Ile Pro Lys Val Phe
            245                 250                 255

Val Arg Ser Arg Arg Ser Ser Phe Ala Tyr Pro Gln Gln Val Ala Ile
            260                 265                 270

Thr Thr Thr Pro Ser Ser Pro Asn Ser Ser His Val Leu Leu Ser Ser
            275                 280                 285

Lys Ser Arg Arg Gly Ser Leu Ala Asn Trp Ser Arg Arg Ser Ser Phe
            290                 295                 300

Asn Val Ser Ser Asn Asn Thr Ser Arg Arg Ser Ser Met Ile Leu Ala
305                 310                 315                 320

Pro Asn Ser Val Ser Asn Ile Phe Asn Val Asn Asn Ser Gly Ser Asn
            325                 330                 335

Thr Ala Ser Thr Ser Asn Thr Asn Ser Arg Arg Glu Ser Val Ile Lys
            340                 345                 350

Lys Glu Phe Gln Gln Arg Leu Asn Leu Ser Asn Ser Gly Gly Pro
            355                 360                 365

Thr Ser Asn Asn Gly Pro Ile Phe Pro Asn Ser Tyr Thr Phe Met Asp
            370                 375                 380

Leu Pro His Ser Ser Val Ser Ser Ser Ser Thr Leu His Lys Ser
385                 390                 395                 400

Lys Arg Gly Ser Phe Ser Gly His Ser Met Lys Ser Ser Cys Asn Pro
            405                 410                 415

Thr Asn Leu Trp Ser Lys Asp Glu Asp Ala Leu Leu Met Glu Asn Lys
            420                 425                 430

Lys Arg Asn Leu Ser Val Met Glu Leu Ser Ile Leu Leu Pro Gln Arg
            435                 440                 445

Thr Glu Val Glu Ile Gln Trp Arg Leu Asn Ala Leu Ser Ser Asp Ala
450                 455                 460

Asp Met Leu Ser Pro Thr His Ser Pro Gln Lys Thr Leu Ser Lys Lys
465                 470                 475                 480

Thr Cys Pro Arg Met Phe Lys Ser Gly Ser Thr Thr Asp Asp Asp Lys
            485                 490                 495

Gly Ser Asp Lys Glu Asp Val Met Gly Asp Gly Ser Asn Asp Asp Asp
            500                 505                 510

Glu Asp Asn Val Asp Pro Leu His Arg Ala Lys Gln Ser Ser Asn Lys
            515                 520                 525

Thr Val Phe Ser Ser Ser Ser Asn Ile Ser Ser Lys Asp Val Ser
            530                 535                 540

Pro Asp Pro Ile Phe Ser Pro Asp Pro Ala Asp Asp Ser Ser Asn Thr
545                 550                 555                 560

Ser Asp Ala Gly Ser Arg Cys Thr Ile Thr Ser Asp Thr Ser Ser Ser
            565                 570                 575

Ala Ala Thr Met Asn Arg Thr Pro Asn Ser Lys Asn Pro Gln Asp Ile
            580                 585                 590

Ala Leu Leu Asn Asn Phe Arg Ser Glu Ala Ile Thr Pro Arg Pro Lys
            595                 600                 605

Pro Ser Ser Thr Thr Thr Ser Ile Thr Thr Glu Thr Thr Asn Asn Met
610                 615                 620

Ile Asn His Ser Ser Ser Thr Thr Thr Thr Thr Asn Asn Ser Pro Leu
625                 630                 635                 640

Pro Ser Ile Asn Thr Ile Phe Lys Asp Met Leu
            645                 650
```

(2) INFORMATION FOR SEQ ID NO: 25:

(i) SEQUENCE CHARACTERISTICS:
        (A) LENGTH: 956 base pairs
        (B) TYPE: nucleic acid
        (C) STRANDEDNESS: single
        (D) TOPOLOGY: linear (xi) SEQUENCE DESCRIPTION: SEQ ID NO: 25:

```
GCCACGAAGG CCGGCCTTCG TGGCCTTTTG CTCTTCTTCA TTTTCTTTCT T AGGGGATAG      60
TTTAACTGAT TTATTTTTGT TACTGTTCTC ACGAGAGGAA TAGAGTGTAT T GCTATTTGT     120
ATTCATGGCA GATAAAGCTT TCATGGCTCT TTTCTTTCTT TGGGCCGTCA G TTTGACAAA     180
ATCTATATTC TCGTCATCAG AACTTGTTTC GCTATCACTA TCACTATCAC T TCCGTCATC     240
ATCATCGTCG TCGTCGTCTT CGTCATCATC ATCTTCTTCT TCTTCACTCT C TTCTTCTTC     300
ATTTTCACTC TCTTCGCCAT CTGTTACAGC TTGGTAATCG GATGACTCTG T GCCCTCGTC     360
GTCATTGTCT ATTTGCCTTT GTATAAGTTT ACTTTTTTTT CCTTGGGAAT T ATTTGAAAT     420
GTTCTTTGCT TTTCTTTTAA TTTTATGTGG GTTTGTACTT TTGTTTTTAT C AGAATCAGA     480
TACGTCACTC AAGGATGACT CAGAAGAGTA TAAGGCTA AATCTTCTTG G CCTCGTTGT      540
ACTCAGTGTG GGTGGTGATT GCCTGGACTT TGTATCGGAT TCGCCCTTTT T TATGAGCCT     600
TTTAATATTT GCTGGCAGTT TACCAGAATG TGTACTATGA TTGATCGTAC T TTTTCGAGG     660
ACTTTTTTTG CCTGCCATTT CGTTCTGTTT CCAGTTTGCC GGTTGTTTTT T CCTTATTTG     720
TTTATTTGCT TCCTTGTTGA ATTTCCTTCA ATTTCAACAA GCTTGAAAAT G AATTTCGTA     780
GAATGAATAT TACTAGGTTT GAAATGGTTA TTGCTTATGA TGCTCACCGA A GTTAAAAAA     840
AAATATTATA GGTTTGTCCT ATGTTAGAAT TGTGGAAAGG GAGGAATGTA A TAAATATGC     900
AGTAATTAAA TATAGCCTTT TGAAGAGTTC CTCCTTTTAA TTTCTGGCCT T CGTGG        956
```

(2) INFORMATION FOR SEQ ID NO: 26:

(i) SEQUENCE CHARACTERISTICS:
        (A) LENGTH: 226 amino acids
        (B) TYPE: amino acid
        (C) STRANDEDNESS: single
        (D) TOPOLOGY: linear (xi) SEQUENCE DESCRIPTION: SEQ ID NO: 26:

```
Met Ala Gly Lys Lys Ser Pro Arg Lys Ser T hr Ile Asn His Ser Thr
1               5                  10                  15

His Ser Gly Lys Leu Pro Ala Asn Ile Lys A rg Leu Ile Lys Lys Gly
            20                  25                  30

Glu Ser Asp Thr Lys Ser Arg Gln Ser Pro P ro Thr Leu Ser Thr Thr
        35                  40                  45

Arg Pro Arg Arg Phe Ser Leu Ile Tyr Ser S er Glu Ser Ser Leu Ser
    50                  55                  60

Asp Val Ser Asp Ser Asp Lys Asn Lys Ser T hr Asn Pro His Lys Ile
65                  70                  75                  80

Lys Arg Lys Ala Lys Asn Ile Ser Asn Asn S er Gln Gly Lys Lys Ser
                85                  90                  95

Lys Leu Ile Gln Arg Gln Ile Asp Asn Asp A sp Glu Gly Thr Glu Ser
            100                 105                 110

Ser Asp Tyr Gln Ala Val Thr Asp Gly Glu G lu Ser Glu Asn Glu Glu
        115                 120                 125

Glu Glu Ser Glu Glu Glu Glu Asp Asp A sp Glu Asp Asp Asp Asp
```

```
              130                 135                 140
Asp Asp Asp Asp Gly Ser Asp Ser Asp Ser Asp Ser Glu Thr Ser Ser
145                 150                 155                 160

Asp Asp Glu Asn Ile Asp Phe Val Lys Leu Thr Ala Gln Arg Lys Lys
                165                 170                 175

Arg Ala Met Lys Ala Leu Ser Ala Met Asn Thr Asn Ser Asn Thr Leu
            180                 185                 190

Tyr Ser Ser Arg Glu Asn Ser Asn Lys Asn Lys Ser Val Lys Leu Ser
        195                 200                 205

Pro Lys Lys Glu Asn Glu Glu Glu Gln Lys Ala Thr Lys Ala Gly Leu
    210                 215                 220

Arg Gly
225

(2) INFORMATION FOR SEQ ID NO: 27:

(i) SEQUENCE CHARACTERISTICS:
        (A) LENGTH: 4599 base pairs
        (B) TYPE: nucleic acid
        (C) STRANDEDNESS: single
        (D) TOPOLOGY: linear (xi) SEQUENCE DESCRIPTION: SEQ ID NO: 27:

GATCTACTTG TCTGAGATGG CCTTTGATAA AAAAATCAAT CGAGTACGCA A TAGAGGGGC       60

AGAGACTTTG AAGAGCAAAA AAAAGAAAAA GGAAATTTTC AGTTATTGTT C CGATTTTTC     120

CGTGTGGGGT TCGGGATGCC TAGTTGTTCC GTAATGCGAT TGAAAGATAC A CTTAACTAG    180

GAGGCTGCTA GTACGCGACC CCTACCTACG TATTGCAAAG ATGTTTGAAG T ATCAACGGG    240

TGTAGAACTT TGCAATCAAG CAAAAGCTAG ATAGTTCCAT TATGAATTGT G ACGATGTTA    300

CCCGTACTGC CTACTACATC TCTTTATACG GATTGAAATC TCTAAAGGTT G CCCTGCCCG    360

TCGTTTCTTT TTCGTTGGAA TTCTTTTTTT TTTTTTTTT TTTTCATCT C ATCACTAAA      420

TTGATTTAAA GTACAACTAG GGAAAAGAGA CTAGATAATA GGTGCTTTAC A CGTTTTGAC    480

GTTTAGCTTT TACGGCTCTT TAATTGACTT GCTGTAAGTA TTTGTATAAT C ATTGGTAAT    540

ATTTGAATAC ATTCGAAACA CTTGCTACAA GAAATTAAAA GGAGGAACTC T TCAAAAGGC    600

TATATTTAAT TACTGCTTAT TTATTACATT CCTCCCTTTC CACAATTCTA A CATAGGACA    660

AACCTATAAT ATTTTTTTAA CTTCGGTGAG CATCATAAGC AATAACCATT T CAAACATAG    720

TAATATTCAT TCTACGAAAT TCATTTTCAA GCTTGTTGAA ATTGAAGGAA A TTCAACAAG    780

GAAGCAAATA AACAAATAAG GAAAAACAA CCGGCAAACT GGAACAGAA C GAAATGGCA      840

GGCAAAAAAA GTCCTCGAAA AAGTACGATC AATCATAGTA CACATTCTGG T AAACTGCCA    900

GCAAATATTA AAAGGCTCAT AAAAAAGGGC GAATCCGATA CAAAGTCCAG G CAATCACCA    960

CCCACACTGA GTACAACGAG GCCAAGAAGA TTTAGCCTTA TATACTCTTC T GAGTCATCC   1020

TTGAGTGACG TATCTGATTC TGATAAAAAC AAAAGTACAA ACCCACATAA A ATTAAAAGA   1080

AAAGCAAAGA ACATTTCAAA TAATTCCCAA GGAAAAAAAA GTAAACTTAT A CAAAGGCAA   1140

ATAGACAATG ACGACGAGGG CACAGAGTCA TCCGATTACC AAGCTGTAAC A GATGGCGAA   1200

GAGAGTGAAA ATGAAGAAGA AGAGAGTGAA GAAGAAGAAG AAGATGATGA C GAAGACGAC   1260

GACGACGATG ATGATGACGG AAGTGATAGT GATAGTGATA GCGAAACAAG T TCTGATGAC   1320

GAGAATATAG ATTTTGTCAA ACTGACGGCC CAAAGAAAGA AAAGAGCCAT G AAAGCTTTA   1380

TCTGCCATGA ATACAAATAG CAATACACTC TATTCCTCTC GTGAGAACAG T AACAAAAAT   1440
```

```
AAATCAGTTA AACTATCCCC TAAGAAAGAA AATGAAGAAG AGCAGAAAGA A GAAAAAGAA    1500

AAAGAGAAAG AAGAGCAACA AAAACAACAA GAATCAAACA AAAAAGAAGT A AACGGTTCA    1560

GGCACTACTA CTACACAACA GGCGCTATCG TTTAAATTCA AAAAAGAGGA C GACGGCATT    1620

AGTTTTGGTA ATGGTAATGA AGGCTATAAC GAGGATATAG GTGAAGAAGT C TTGGATTTA    1680

AAAAACAAAG AGAACAATGG TAATGAAGAA GATAAACTGG ATTCTAAGGT G ATGTTAGGT    1740

AACAACGATG AGTTACGATT TCCCAATATT TCAGAGTCAG ATGAATCTGA A TATGATATT    1800

GACCAGGATG CGTACTTTGA CGTGATTAAC AATGAAGATT CTCATGGAGA A ATTGGTACA    1860

GATCTTGAAA CGGGGAAGA CGATCTTCCC ATATTGGAAG AAGAAGAACA A AACATTGTT    1920

TCTGAGCTAC AAAATGACGA CGAACTCTCA TTCGATGGTA GTATACACGA A GAAGGGTCT    1980

GATCCTGTAG AAGATGCTGA AAATAAATTT TTGCAAAATG AATACAATCA A GAAAACGGA    2040

TATGATGAAG AAGATGACGA AGAAGATGAA ATAATGTCTG ATTTTGATAT G CCGTTTTAT    2100

GAAGATCCTA AATTTGCAAA TCTTTATTAT TATGGCGATG GTTCAGAGCC A AAGCTATCC    2160

TTGAGTACAT CTTTACCGTT AATGCTAAAT GATGAAAAAC TATCTAAACT A AAAAAGAAA    2220

GAGGCCAAAA AACGGGAACA GGAAGAAAGG AAACAAAGAC GAAAGCTCTA T AAAAAGACG    2280

CAAAAACCTA GTACGAGAAC AACCTCCAAT GTGGACAATG ATGAGTATAT T TTCAATGTT    2340

TTTTTTCAAT CAGATGATGA AAATAGTGGC CATAAGAGCA AGAAAGGCAG G CATAAATCG    2400

GGCAAAAGTC ATATTGAACA TAAGAATAAA GGCTCGAATT TGATAAAATC C AATGATGAT    2460

CTGGAACCAT CCACTCATAG TACGGTCCTG AATTCCGGGA AATATGATTC T TCTGACGAT    2520

GAATATGATA ACATTTTGTT GGATGTTGCC CATATGCCTT CAGATGATGA A TGCAGTGAA    2580

TCTGAAACGT CCCACGATGC TGACACGGAT GAAGAATTGA GGGCACTAGA T TCAGATAGC    2640

TTAGACATTG GCACAGAACT GGACGACGAT TACGAAGACG ACGACGATGA T TCCAGCGTG    2700

ACAAATGTGT TCATAGACAT CGATGATTTA GATCCAGACT CTTTTTACTT T CATTACGAC    2760

AGCGATGGAT CTTCCTCTTT GATAAGTTCT AACTCAGACA AGAAAAATTC T GATGGATCC    2820

AAAGATTGCA AACATGATCT CTTAGAGACT GTTGTGTACG TTGATGACGA A TCCACAGAT    2880

GAAGATGATA ACCTACCGCC CCCAAGTTCA AGGTCAAAAA ACATTGGCTC A AAAGCAAAG    2940

GAAATCGTAA GTTCAAATGT TGTTGGATTA CGTCCACCAA AATTGGGTAC T TGGGAGACG    3000

GACAACAAAC CTTTTAGTAT TATTGATGGT CTGTCTACTA AATCATTATA C GCCTTAATC    3060

CAAGAACATC AACAGCTTCG CGAGCAACAT CAAAGGGCTC AAACCCCAGA T GTTAAAAGA    3120

GAGGGAAGCT CTAATGGCAA TAACGGTGAC GAATTGACAC TCAATGAGCT G CTAAACATG    3180

AGTGAATTGG AGGATGATTC ACCATCCCAC ACAGACGATA TGGAGAACAA T TACAATGAT    3240

GCAATTAATA GCAAAAGCAC AAATGGCCAT GCTGCAGATT GGTATGAAGT T CCTAAGGTT    3300

CCATTATCTG CATTTAGAAA TAAGGGTATT AATGCCTATG AAGAAGATGA G TACATGATA    3360

CCAGCAAATT CTAACAGAAA AGTTCCCATT GGCTATATTG GTAATGAAAG A ACAAGAAAG    3420

AAGATTGATA AGATGAAAGA GCTACAACGG AAAAAAACTG AAAAAAAAAG G CAGTTAAAG    3480

AAAAAAAAGA AGCTTCTTAA AATAAGAAAG CAAAGACAAA AGGCAATAAA G GAGCAAGAA    3540

ACTATGAATT TACAATTGGG AATCAATGGC CATGAGATCA TCGGTAACAA T AACAGCCAT    3600

AGCGACATAA ATACCGGTAC CGATTTTACA ACCAATGAAA ATACCCCTAT G AATGAACTT    3660

CCCTCTCACG CACCTGAAGA TGCGTCATTA ATACCTCATA ATTCTGATCT T GCCGTGGAC    3720

AGCAATACAA GGAAAAATTC AACAAAAAGT GTTGGTTTAG ATGAAATTCA T GAGATTTTG    3780

GGCAAAGATG AAAATGACTT ACTGTCTGTA GGTGATATTA ACGGTTATGA T GCACAAGAA    3840
```

```
GGTCATGTGA TCGAAGATAC TGACGCCGAT ATCCTAGCAT CGTTAACCGC T CCTGTGCAA      3900

TTCGACAATA CATTAAGCCA TGAAAATAGT AATTCCATGT GGAGAAGAAG G CAAAGTATG      3960

GTGGAAGCAG CGGCTGAAAA TCTTCGTTTC ACTAAAAATG GTTTATTTAG T GAGAGTGCA      4020

TTGGCAGATA TCGAAGGAAT TATGGGCAAT GATGTTAACC ATTCATTCGA A TTCAATGAC      4080

GTCTTACAAT GAGCTATTTT GCATTTTTTT ATGGTTACTA CAATCAAATC A CCTTTCGTT      4140

TACAATATCA TCATCAGTAT GTGACTTTGC CTTATTCTAC TCTGAATTTT G CTTTATCGT      4200

TGGTTGAAAA GAATTACATG TTATTTTTTT ACTTATATAT GCATATTTTT A TAGAAAAAC      4260

ACAATCAATA TTTTTTTTAC TGGTATAATC CGTCCAATCA GACGTATAAA A GTAAATAAG      4320

CCTCAGCAAC CCCATTTGAT GGATTGCCTT ACTCTTCGAC TCTAGTTGAG A TGATAACCT      4380

CATCCACTCT TCTGGCGATT AAGATGGAGC TTCTTAATAT ATCCGTGTAA A GCGACTGAA      4440

AATTTTCTGA AAAATTCAGC TCATCGCTCT CAGATATAAT AGCGGTATGG C ATTAAAGGT      4500

GTGAACCAAC AACATAGTAC TCTCAACGGT AGTAAGCCAT ACTACGTACA A TATGGATCT      4560

GAAAACCTCA TATAAAGGTA TATCGTTAAA CCCTATTTA                             4599
```

(2) INFORMATION FOR SEQ ID NO: 28:

(i) SEQUENCE CHARACTERISTICS:
        (A) LENGTH: 1085 amino acids
        (B) TYPE: amino acid
        (C) STRANDEDNESS: single
        (D) TOPOLOGY: linear (xi) SEQUENCE DESCRIPTION: SEQ ID NO: 28:

```
Met Ala Gly Lys Lys Ser Pro Arg Lys Ser T hr Ile Asn His Ser Thr
  1               5                  10                  15

His Ser Gly Lys Leu Pro Ala Asn Ile Lys A rg Leu Ile Lys Lys Gly
             20                  25                  30

Glu Ser Asp Thr Lys Ser Arg Gln Ser Pro P ro Thr Leu Ser Thr Thr
         35                  40                  45

Arg Pro Arg Arg Phe Ser Leu Ile Tyr Ser S er Glu Ser Ser Leu Ser
     50                  55                  60

Asp Val Ser Asp Ser Asp Lys Asn Lys Ser T hr Asn Pro His Lys Ile
 65                  70                  75                  80

Lys Arg Lys Ala Lys Asn Ile Ser Asn Asn S er Gln Gly Lys Lys Ser
                 85                  90                  95

Lys Leu Ile Gln Arg Gln Ile Asp Asn Asp A sp Glu Gly Thr Glu Ser
            100                 105                 110

Ser Asp Tyr Gln Ala Val Thr Asp Gly Glu G lu Ser Glu Asn Glu Glu
        115                 120                 125

Glu Glu Ser Glu Glu Glu Glu Asp Asp A sp Glu Asp Asp Asp Asp
    130                 135                 140

Asp Asp Asp Asp Gly Ser Asp Ser Asp Ser A sp Ser Glu Thr Ser Ser
145                 150                 155                 160

Asp Asp Glu Asn Ile Asp Phe Val Lys Leu T hr Ala Gln Arg Lys Lys
                165                 170                 175

Arg Ala Met Lys Ala Leu Ser Ala Met Asn T hr Asn Ser Asn Thr Leu
            180                 185                 190

Tyr Ser Ser Arg Glu Asn Ser Asn Lys Asn L ys Ser Val Lys Leu Ser
        195                 200                 205

Pro Lys Lys Glu Asn Glu Glu Glu Gln Lys G lu Glu Lys Glu Lys Glu
    210                 215                 220
```

-continued

```
Lys Glu Glu Gln Gln Lys Gln Gln Glu Ser Asn Lys Lys Glu Val Asn
225                 230                 235                 240

Gly Ser Gly Thr Thr Thr Thr Gln Gln Ala Leu Ser Phe Lys Phe Lys
            245                 250                 255

Lys Glu Asp Asp Gly Ile Ser Phe Gly Asn Gly Asn Glu Gly Tyr Asn
        260                 265                 270

Glu Asp Ile Gly Glu Glu Val Leu Asp Leu Lys Asn Lys Glu Asn Asn
    275                 280                 285

Gly Asn Glu Glu Asp Lys Leu Asp Ser Lys Val Met Leu Gly Asn Asn
290                 295                 300

Asp Glu Leu Arg Phe Pro Asn Ile Ser Glu Ser Asp Glu Ser Glu Tyr
305                 310                 315                 320

Asp Ile Asp Gln Asp Ala Tyr Phe Asp Val Ile Asn Asn Glu Asp Ser
            325                 330                 335

His Gly Glu Ile Gly Thr Asp Leu Glu Thr Gly Asp Asp Leu Pro
        340                 345                 350

Ile Leu Glu Glu Glu Glu Gln Asn Ile Val Ser Glu Leu Gln Asn Asp
    355                 360                 365

Asp Glu Leu Ser Phe Asp Gly Ser Ile His Glu Glu Gly Ser Asp Pro
370                 375                 380

Val Glu Asp Ala Glu Asn Lys Phe Leu Gln Asn Glu Tyr Asn Gln Glu
385                 390                 395                 400

Asn Gly Tyr Asp Glu Glu Asp Glu Glu Asp Glu Ile Met Ser Asp
            405                 410                 415

Phe Asp Met Pro Phe Tyr Glu Asp Pro Lys Phe Ala Asn Leu Tyr Tyr
            420                 425                 430

Tyr Gly Asp Gly Ser Glu Pro Lys Leu Ser Leu Ser Thr Ser Leu Pro
        435                 440                 445

Leu Met Leu Asn Asp Glu Lys Leu Ser Lys Leu Lys Lys Glu Ala
    450                 455                 460

Lys Lys Arg Glu Gln Glu Glu Arg Lys Gln Arg Arg Lys Leu Tyr Lys
465                 470                 475                 480

Lys Thr Gln Lys Pro Ser Thr Arg Thr Ser Asn Val Asp Asn Asp
            485                 490                 495

Glu Tyr Ile Phe Asn Val Phe Phe Gln Ser Asp Asp Glu Asn Ser Gly
            500                 505                 510

His Lys Ser Lys Lys Gly Arg His Lys Ser Gly Lys Ser His Ile Glu
            515                 520                 525

His Lys Asn Lys Gly Ser Asn Leu Ile Lys Ser Asn Asp Asp Leu Glu
    530                 535                 540

Pro Ser Thr His Ser Thr Val Leu Asn Ser Gly Lys Tyr Asp Ser Ser
545                 550                 555                 560

Asp Asp Glu Tyr Asp Asn Ile Leu Leu Asp Val Ala His Met Pro Ser
            565                 570                 575

Asp Asp Glu Cys Ser Glu Ser Glu Thr Ser His Asp Ala Asp Thr Asp
            580                 585                 590

Glu Glu Leu Arg Ala Leu Asp Ser Asp Ser Leu Asp Ile Gly Thr Glu
        595                 600                 605

Leu Asp Asp Asp Tyr Glu Asp Asp Asp Asp Ser Ser Val Thr Asn
    610                 615                 620

Val Phe Ile Asp Ile Asp Asp Leu Asp Pro Asp Ser Phe Tyr Phe His
625                 630                 635                 640
```

```
                            -continued

Tyr Asp Ser Asp Gly Ser Ser Leu Ile Ser Ser Asn Ser Asp Lys
                645                 650                 655

Glu Asn Ser Asp Gly Ser Lys Asp Cys Lys His Asp Leu Leu Glu Thr
            660                 665                 670

Val Val Tyr Val Asp Asp Glu Ser Thr Asp Glu Asp Asp Asn Leu Pro
        675                 680                 685

Pro Pro Ser Ser Arg Ser Lys Asn Ile Gly Ser Lys Ala Lys Glu Ile
    690                 695                 700

Val Ser Ser Asn Val Val Gly Leu Arg Pro Pro Lys Leu Gly Thr Trp
705                 710                 715                 720

Glu Thr Asp Asn Lys Pro Phe Ser Ile Ile Asp Gly Leu Ser Thr Lys
                725                 730                 735

Ser Leu Tyr Ala Leu Ile Gln Glu His Gln Gln Leu Arg Glu Gln His
            740                 745                 750

Gln Arg Ala Gln Thr Pro Asp Val Lys Arg Glu Gly Ser Ser Asn Gly
        755                 760                 765

Asn Asn Gly Asp Glu Leu Thr Leu Asn Glu Leu Leu Asn Met Ser Glu
    770                 775                 780

Leu Glu Asp Asp Ser Pro Ser His Thr Asp Asp Met Glu Asn Asn Tyr
785                 790                 795                 800

Asn Asp Ala Ile Asn Ser Lys Ser Thr Asn Gly His Ala Ala Asp Trp
                805                 810                 815

Tyr Glu Val Pro Lys Val Pro Leu Ser Ala Phe Arg Asn Lys Gly Ile
            820                 825                 830

Asn Ala Tyr Glu Glu Asp Glu Tyr Met Ile Pro Ala Asn Ser Asn Arg
        835                 840                 845

Lys Val Pro Ile Gly Tyr Ile Gly Asn Glu Arg Thr Arg Lys Lys Ile
    850                 855                 860

Asp Lys Met Lys Glu Leu Gln Arg Lys Lys Thr Glu Lys Lys Arg Gln
865                 870                 875                 880

Leu Lys Lys Lys Lys Lys Leu Leu Lys Ile Arg Lys Gln Arg Gln Lys
                885                 890                 895

Ala Ile Lys Glu Gln Glu Thr Met Asn Leu Gln Leu Gly Ile Asn Gly
            900                 905                 910

His Glu Ile Ile Gly Asn Asn Ser His Ser Asp Ile Asn Thr Gly
        915                 920                 925

Thr Asp Phe Thr Thr Asn Glu Asn Thr Pro Met Asn Glu Leu Pro Ser
    930                 935                 940

His Ala Pro Glu Asp Ala Ser Leu Ile Pro His Asn Ser Asp Leu Ala
945                 950                 955                 960

Val Asp Ser Asn Thr Arg Lys Asn Ser Thr Lys Ser Val Gly Leu Asp
                965                 970                 975

Glu Ile His Glu Ile Leu Gly Lys Asp Glu Asn Asp Leu Leu Ser Val
            980                 985                 990

Gly Asp Ile Asn Gly Tyr Asp Ala Gln Glu Gly His Val Ile Glu Asp
        995                 1000                1005

Thr Asp Ala Asp Ile Leu Ala Ser Leu Thr Ala Pro Val Gln Phe Asp
    1010                1015                1020

Asn Thr Leu Ser His Glu Asn Ser Asn Ser Met Trp Arg Arg Arg Gln
1025                1030                1035                1040

Ser Met Val Glu Ala Ala Ala Glu Asn Leu Arg Phe Thr Lys Asn Gly
                1045                1050                1055

Leu Phe Ser Glu Ser Ala Leu Ala Asp Ile Glu Gly Ile Met Gly Asn
```

Asp Val Asn His Ser Phe Glu Phe Asn Asp Val Leu Gln
  1075                1080                1085

(2) INFORMATION FOR SEQ ID NO: 29:

(i) SEQUENCE CHARACTERISTICS:
        (A) LENGTH: 1882 base pairs
        (B) TYPE: nucleic acid
        (C) STRANDEDNESS: single
        (D) TOPOLOGY: linear (xi) SEQUENCE DESCRIPTION: SEQ ID NO: 29:

```
ATCAAGGAGG TCACCAGTAA TTGTGCGCTT TGGTTACATT TTGTTGTACA G TAATGGGCG      60

ATCAAGAAAG TATATCAAAT AATAACTCAG ACTCATTCAT TATGTCGTCC C CCAACTTAG     120

ACTCTCAGGA ATCTTCAATA TCACCTATTG ATGAGAAGAA AGGCACCGAT A TGCAAACCA     180

AGTCGCTTTC AAGCTATTCT AAAGGTACGC TTCTCTCTAA GCAAGTACAA A ATTTATTAG     240

AAGAAGCTAA TAAATACGAT CCAATATATG GGTCATCTTT ACCTCGAGGA T TTTTAAGAG     300

ATAGAAACAC CAAGGGTAAG GATAATGGGT TGGTTCCGCT GGTGGAGAAG G TTATACCTC     360

CCATTCACAA GAAACCAAT AATAGAAACA CAAGGAAGAA GTCATCTACC A CCACGAAGA      420

AGGATGTAAA GAAGCCAAAA GCTGCAAAAG TAAAAGGAAA AAATGGCAGG A CTAACCATA     480

AACATACCCC AATTTCAAAG CAAGAAATAG ATACTGCACG AGAAAAAAAG C CATTGAAAA     540

AAGGTCGGGC AAACAAGAAG AATGATCGCG ATAGTCCTTC ATCAACATTT G TTGATTGGA     600

ATGGCCCGTG TCTACGGTTA CAATATCCAT TATTTGACAT AGAGTACTTA A GATCACATG     660

AAATATATTC TGGAACTCCT ATACAATCCA TTAGTTTAAG AACAAATTCT C CACAGCCAA     720

CGAGCTTGAC ATCAGATAAC GACACTTCCT CAGTAACGAC AGCAAAGTTG C AGAGTATTT     780

TATTTTCAAA TTATATGGAA GAGTACAAAG TCGACTTCAA AAGGTCAACA G CCATTTATA     840

ATCCAATGAG TGAAATTGGT AAATTAATTG AATACAGCTG CCTGGTCTTT T TACCTTCAC     900

CTTATGCTGA ACAATTGAAG GAAACTATAC TACCGGACCT AAATGCATCA T TTGATAACT     960

CTGACACGAA AGGTTTCGTG AATGCTATAA ATTTATACAA CAAAATGATT C GTGAAATTC    1020

CTAGGCAAAG AATAATTGAC CATTTAGAAA CAATTGATAA AATTCCTCGT T CATTCATTC    1080

ATGACTTCTT GCATATCGTC TATACCAGGA GTATCCATCC GCAGGCGAAT A AATTGAAAC    1140

ATTACAAAGC ATTCAGCAAT TATGTTTATG GAGAACTTTT GCCCAATTTC C TATCTGATG    1200

TATATCAACA ATGCCAGTTG AAGAAGGGTG ACACTTTCAT GGATCTCGGT T CGGGAGTAG    1260

GTAATTGCGT AGTACAAGCT GCGTTGGAAT GTGGATGTGC ATTAAGCTTC G GATGTGAAA    1320

TCATGGATGA TGCTAGCGAT TTAACTATAC TGCAGTACGA GGAACTAAAG A AGAGGTGTA    1380

AGTTATATGG GATGCGTTTG AACAACGTGG AGTTTTCATT GAAGAAAGC T TTGTGGACA     1440

ATAACAGGGT CGCTGAACTA ATTCCTCAGT GCGATGTTAT CCTCGTAAAT A ATTTTTTAT    1500

TTGATGAAGA TTTGAATAAA AAAGTCGAAA AGATACTACA AACGGCAAAA G TTGGATGTA    1560

AGATCATAAG TTTGAAAAGT TTAAGAAGCC TCACTTATCA GATCAACTTC T ACAATGTTG    1620

AGAACATCTT CAATAGATTA AAGGTGCAAA GGTATGATCT TAAGGAGGAT A GTGTTTCAT    1680

GGACGCATAG TGGCGGAGAG TATTATATAT CAACAGTGAT GGAGGATGTG G ACGAAAGTT    1740

TATTCAGCCC TGCTGCAAGA GGTAGGAGGA ACAGAGGTAC GCCGGTGAAG T ATACCAGAT    1800

GAGGCACTTT GAACGGCTTT TAACGATGAG TATGAATAAC TAAGTAGAAA T AACATGTAC    1860

ACAAGTGTAA CTTATAAAAA TC                                              1882
```

(2) INFORMATION FOR SEQ ID NO: 30:

(i) SEQUENCE CHARACTERISTICS:
        (A) LENGTH: 1094 base pairs
        (B) TYPE: nucleic acid
        (C) STRANDEDNESS: single
        (D) TOPOLOGY: linear (xi) SEQUENCE DESCRIPTION: SEQ ID NO: 30:

```
CAAAATTGGG AGAAAACATA CTCAAGTGAG TACTCATTTT GTGCAAGCAA A CACTGACAA    60
TTGAAGAGAT CGTCAGGATG CCCGGAACGC CACAGAAGAA CAAGAGGTCT G CGAGTATAT   120
CTGTTTCACC TGCGAAGAAG ACAGAGGAAA AAGAAATAAT ACAAAATGAT T CAAAGGCGA   180
TATTATCTAA GCAAACTAAG AGGAAAAAAA AGTATGCTTT TGCTCCTATA A ATAACTTAA   240
ATGGGAAGAA CACCAAGGTA TCCAATGCAA GTGTCCTAAA GTCAATAGCC G TTTCACAAG   300
TACGAAATAC ATCAAGAACA AAAGATATAA ACAAAGCAGT TAGCAAGAGC G TAAAGCAAT   360
TACCAAATTC ACAAGTTAAA CCGAAACGGG AAATGTCTAA TTTGAGTAGG C ATCACGATT   420
TCACTCAAGA CGAGGACGGC CCCATGGAAG AAGTAATATG GAAATATTCA C CTTTACAAC   480
GAGATATGTC CGACAAAACA ACAAGCGCTG CCGAATACTC TGATGACTAC G AAGATGTCC   540
AAAATCCCTC TTCTACACCT ATAGTCCCTA ATCGACTGAA AACTGTTCTT A GTTTCACAA   600
ATATCCAAGT ACCCAACGCT GACGTAAATC AACTCATTCA AGAAAATGGA A ATGAGCAAG   660
TGCGTCCTAA ACCAGCAGAA ATATCTACCA GGGAGTCTCT CCGTAATATA G ATGATATTC   720
TCGATGATAT AGAGGGCGAT TTAACTATAA AACCGACGAT AACGAAATTC A GCGATTTGC   780
CATCTTCACC CATCAAGGCA CCCAACGTTG AAAAAAAAGC AGAGGTGAAT G CAGAAGAAG   840
TAGATAAAAT GGATTCAACA GGAGATAGCA ACGATGGCGA TGACTCTTTG A TAGATATTT   900
TAACTCAAAA GTATGTTGAG AAACGCAAGA GTGAGAGTCA GATAACAATT C AAGGCAACA   960
CCAATCAAAA AAGTGGAGCC CAGGAAAGTT GTGGGAAGAA TGATAACACA A AATCGAGAG  1020
GAGAAATTGA AGATCATGAA AATGTAGACA ATCAAGCCAA AACAGGCAAT G CATTTTATG  1080
AGAATGAAGA AGAC                                                    1094
```

(2) INFORMATION FOR SEQ ID NO: 31:

(i) SEQUENCE CHARACTERISTICS:
        (A) LENGTH: 807 base pairs
        (B) TYPE: nucleic acid
        (C) STRANDEDNESS: single
        (D) TOPOLOGY: linear (xi) SEQUENCE DESCRIPTION: SEQ ID NO: 31:

```
GGATGAAGTA ATACTACGAG CTTTATACAG GTAATATTAA AGTTCCTTAA T AGAATGGGT    60
GAAGCACTAC GTAGATCAAC CAGGATTGCA ATATCCAAAA GAATGTTGGA A GAGGAAGAG   120
TCCAAACTGG CCCCTATTTC GACACCGGAA GTGCCTAAGA AGAAAATCAA G ACGGGTCCT   180
AAACATAACG CTAATCAAGC AGTAGTTCAA GAGGCAAATA GGTCATCTGA T GTTAACGAA   240
TTAGAGATAG GCGATCCTAT TCCTGATTTG AGTCTTTTAA ATGAAGATAA T GACTCTATC   300
TCCTTGAAGA AAATCACCGA AAATAACAGA GTTGTGGTGT TTTTTGTGTA T CCCAGGGCA   360
AGCACGCCTG GTTGTACTAG ACAGGCCTGT GGATTTCGTG ACAATTACCA G GAACTCAAG   420
AAATATGCTG CTGTCTTTGG ACTGAGTGCA GATTCTGTGA CATCCCAGAA A AAGTTTCAG   480
AGTAAACAAA ATTTGCCATA TCATTTACTA AGCGATCCAA AGAGAGAGTT T ATTGGGTTG   540
```

-continued

```
CTAGGAGCCA AAAAAACGCC ACTTTCTGGT TCTATTAGAT CGCATTTCAT T TTTGTTGAT    600

GGGAAGTTAA AATTCAAAAG AGTTAAGATA TCACCAGAAG TTAGTGTAAA T GACGCCAAA    660

AAGGAGGTTT TAGAAGTCGC TGAAAAGTTT AAAGAAGAAT GAAGTTTAAT A ACCCCCTTT    720

TTGTTTCTCT AGAGGAGTAC TTATCGGTAA AATATTCCAA ACCCTTCCCT T TATATATGT    780

AGATAAACGA AGATATTCTA ACTCTCT                                        807
```

(2) INFORMATION FOR SEQ ID NO: 32:

(i) SEQUENCE CHARACTERISTICS:
        (A) LENGTH: 956 base pairs
        (B) TYPE: nucleic acid
        (C) STRANDEDNESS: single
        (D) TOPOLOGY: linear (xi) SEQUENCE DESCRIPTION: SEQ ID NO: 32:

```
CCACGAAGGC CAGAAATTAA AAGGAGGAAC TCTTCAAAAG GCTATATTTA A TTACTGCAT    60

ATTTATTACA TTCCTCCCTT TCCACAATTC TAACATAGGA CAAACCTATA A TATTTTTTT   120

TTAACTTCGG TGAGCATCAT AAGCAATAAC CATTTCAAAC CTAGTAATAT T CATTCTACG   180

AAATTCATTT TCAAGCTTGT TGAAATTGAA GGAAATTCAA CAAGGAAGCA A ATAAACAAA   240

TAAGGAAAAA ACAACCGGCA AACTGGAAAC AGAACGAAAT GGCAGGCAAA A AAAGTCCTC   300

GAAAAAGTAC GATCAATCAT AGTACACATT CTGGTAAACT GCCAGCAAAT A TTAAAAGGC   360

TCATAAAAAA GGGCGAATCC GATACAAAGT CCAGGCAATC ACCACCCACA C TGAGTACAA   420

CGAGGCCAAG AAGATTTAGC CTTATATACT CTTCTGAGTC ATCCTTGAGT G ACGTATCTG   480

ATTCTGATAA AAACAAAAGT ACAAACCCAC ATAAAATTAA AAGAAAAGCA A AGAACATTT   540

CAAATAATTC CCAAGGAAAA AAAAGTAAAC TTATACAAAG GCAAATAGAC A ATGACGACG   600

AGGGCACAGA GTCATCCGAT TACCAAGCTG TAACAGATGG CGAAGAGAGT G AAAATGAAG   660

AAGAAGAGAG TGAAGAAGAA GAAGATGATG ATGACGAAGA CGACGACGAC G ATGATGATG   720

ACGGAAGTGA TAGTGATAGT GATAGCGAAA CAAGTTCTGA TGACGAGAAT A TAGATTTTG   780

TCAAACTGAC GGCCCAAAGA AAGAAAAGAG CCATGAAAGC TTTATCTGCC A TGAATACAA   840

ATAGCAATAC ACTCTATTCC TCTCGTGAGA ACAGTAACAA AAATAAATCA G TTAAACTAT   900

CCCCTAAGAA AGAAAATGAA GAAGAGCAAA AGGCCACGAA GGCCGGCCTT C GTGGC       956
```

US 6,387,619 B1

TELOMERASE COMPOSITIONS AND METHODS

The present application is a divisional application of U.S. application Ser. No. 08/938,534, filed Sep. 26, 1997 now issued as U.S. Pat. No. 5,916,752, and a divisional application of U.S. application Ser. No. 08/431,080, filed Apr. 28, 1995 now issued as U.S, Pat. No. 5,698,686. is a continuation-in-part of U.S. patent application Ser. No. 08/326,781, filed Oct. 20, 1994, now abandoned the entire text and figures of which disclosure is specifically incorporated herein by reference without disclaimer.

The U.S. Government owns rights in the present invention pursuant to National Institutes of Health Grants GM43893, GM07281 and CA14599 and Army Research Office Grant DAAH04-93-G-0274.

BACKGROUND OF THE INVENTION

A. Field of the Invention

The present invention relates to telomerase compositions and methods connected therewith. Particularly disclosed are genes encoding the template RNA of telomerase in *Saccharomyces cerevisiae* and various telomerase-associated proteins. Methods of using such genes and other related biological components are also provided.

B. Description of the Related Art

DNA polymerases synthesize DNA in a 5' to 3' direction and require a primer to initiate synthesis. These restrictions pose a problem for the complete replication of linear chromosomes (Watson, 1972; Olovnikov, 1973). In the absence of a specialized mechanism to maintain terminal sequences, multiple replication cycles would cause chromosomes to progressively shorten from their ends.

Telomeres are specialized nucleoprotein complexes that constitute the ends of eukaryotic chromosomes and protect them from degradation and end-to-end fusion (Zakian, 1989; Blackburn, 1991; Price, 1991; Henderson & Larson, 1991; Wright et al., 1992; Blackburn, 1994). When telomeres are absent, the instability of non-telomeric chromosomal ends leads to chromosome loss (Sandell & Zakian, 1993). In addition, telomeres are required for the complete replication of chromosomes (Zakian, 1989; Blackburn, 1991; Price, 1991; Henderson & Larson, 1991; Wright et al., 1992; Blackburn, 1993; 1994).

In many eukaryotes, telomeres are composed of simple tandem repeats, with the 3'-terminal strand composed of G-rich sequences (Zakian, 1989; Blackburn, 1991; Price, 1991; Henderson & Larson, 1991; Wright et al., 1992; Blackburn, 1994). Certain insights into the mechanism by which telomeric DNA is maintained has come from the identification of telomerase activity in several species of ciliates, as well as in extracts of Xenopus, mouse, and human cells (Greider & Blackburn, 1985; 1987; 1989; Zahler & Prescott, 1988; Morin, 1989; Prowse et al., 1993; Shippen-Lentz & Blackburn, 1989; Mantell & Greider, 1994).

Telomerase is a ribonucleoprotein enzyme that elongates the G-rich strand of chromosomal termini by adding telomeric repeats (Blackburn, 1993). This elongation occurs by reverse transcription of a part of the telomerase RNA component, which contains a sequence complementary to the telomere repeat. Following telomerase-catalyzed extension of the G-rich strand, the complementary DNA strand of the telomere is presumably replicated by more conventional means.

Germline cells, whose chromosomal ends must be maintained through repeated rounds of DNA replication, do not decrease their telomere length with time, presumably due to the activity of telomerase (Allsopp et al., 1992). In contrast, somatic cells appear to lack telomerase, and their telomeres shorten with multiple cell divisions (Allsopp et al., 1992; Harley et al., 1990; Hastie et al., 1990; Lindsey et al., 1991; Vaziri et al., 1993; Counter et al., 1992; Shay et al., 1993; Klingelhutz et al., 1994; Counter et al., 1994a;b).

Telomerase is believed to have a role in the process of cell senescence (de Lange, 1994; Greider, 1994; Harley et al., 1992). The repression of telomerase activity in somatic cells is likely to be important in controlling the number of times they divide. Indeed, the length of telomeres in primary fibroblasts correlates well with the number of divisions these cells can undergo before they senescence (Allsopp et al., 1992). The loss of telomeric DNA may signal to the cell the end of its replicative potential, as part of an overall mechanism by which multicellular organisms limit the proliferation of their cells.

Due to its role in controlling replication, telomerase has also recently been implicated in oncogenesis (de Lange, 1994; Greider, 1994; Harley et al., 1992). It is thought that late stage tumors probably require the reactivation of telomerase in order to avoid total loss of their telomeres and massive destabilization of their chromosomes. Immortalized cell lines produced from virally transformed cultures have active telomerase and stable telomere lengths (Counter et al., 1992; Shay et al., 1993; Klingelhutz et al., 1994; Counter et al., 1994b). Recently, telomerase activity has also been detected in human ovarian carcinoma cells (Counter et al., 1994a).

Telomerase is thus an important component of eukaryotic cells, the dysfunction of which can have significant consequences. Although present knowledge concerning telomerase is increasing, there is a marked need for individual telomerase components to be isolated and for further analytical methods to be developed. The creation of a system for manipulating telomerase in a genetically tractable eukaryotic organism would be particularly valuable.

SUMMARY OF THE INVENTION

The present invention overcomes these and other drawbacks inherent in the prior art by providing purified telomerase components and systems for isolating further components and for developing agents with the capacity to modify telomerase actions. Particular aspects of-this invention concern the isolation and uses of several telomerase-associated genes from *Saccharomyces cerevisiae*, including the telomerase RNA template gene.

In certain aspects, this invention concerns nucleic acid segments that hybridize to, or that have sequences in accordance with, SEQ ID NO:1, SEQ ID NO:29, SEQ ID NO:30, SEQ ID NO:19, SEQ ID NO:31 or SEQ ID NO:23. SEQ ID NO:1 represents a telomerase RNA template-encoding sequence, also termed TLC1; and each of SEQ ID NO:29, SEQ ID NO:30, SEQ ID NO:19, SEQ ID NO:31 and SEQ ID NO:23 represent sequences that encode telomerase-associated polypeptides, also termed STR sequences (STR1, STR3, STR4, STR5 and STR6, respectively).

Both the gene TLC1 (SEQ ID NO:1 and the complementary sequence, SEQ ID NO:4), and the template RNA, include a CA-rich region. The CA-rich region is represented by SEQ ID NO:3. In the RNA template, the CA-rich region is reversed transcribed to synthesize the GT-rich telomeric repeats. An example of the GT-rich telomeric sequence is represented by SEQ ID NO:2.

The present invention generally concerns non-ciliate eukaryotic telomerase components. These are represented by telomerase components from mammalian cells, including human cells, and telomerase components from other non-ciliate species. One significant contribution of this invention is the development of methods of utilizing telomerase components, which methods are functional in useful eukaryotic cells. "Useful eukaryotic cells" particularly include human cells, as these are directly relevant to the development of diagnostics and therapeutics for human use, and cells of genetically tractable eukaryotic organisms, as these are recognized to have significant value in scientific terms and, ultimately, in drug development. The preferred non-ciliate telomerase components of the invention are thus mammalian, drosophila and yeast telomerase components.

A. DNA Segments and Vectors

The invention thus provides nucleic acid segments that are characterized as nucleic acid segments that include a sequence region that consists of at least 17 contiguous nucleotides that have the same sequence as, or are complementary to, 17 contiguous nucleotides of SEQ ID NO:1, SEQ ID NO:29, SEQ ID NO:30, SEQ ID NO:19, SEQ ID NO:31 or SEQ ID NO:23.

The nucleic acid segments of the invention are further characterized as being of from 17 to about 10,000 nucleotides in length, which nucleic acid segments hybridize to the nucleic acid segment of SEQ ID NO:1, SEQ ID NO:29, SEQ ID NO:30, SEQ ID NO:19, SEQ ID NO:31 or SEQ ID NO:23, or the complement thereof, under standard hybridization conditions.

"Complementary" or "complement", in terms of nucleic acid segments that are complementary to those listed above, or that hybridize to a complement of such nucleic acid segments, means that the nucleic acid sequences are capable of base-pairing to a given sequence, such as the sequences of SEQ ID NO:1, SEQ ID NO:29, SEQ ID NO:30, SEQ ID NO:19, SEQ ID NO:31 or SEQ ID NO:23, according to the standard Watson-Crick complementarity rules. That is, the larger purines will base pair with the smaller pyrimidines to form combinations of guanine paired with cytosine (G:C) and adenine paired with either thymine (A:T), in the case of DNA, or adenine paired with uracil (A:U) in the case of RNA.

Encompassed within the nucleic acid sequences of the invention are full-length DNA sequences or other DNA segments that have a sequence region that encodes a peptide, polypeptide or protein and that may be used, for example, in recombinant expression. Also included within the nucleic acid sequences are DNA and RNA segments for use in nucleic acid hybridization embodiments, such as in cloning.

The smaller nucleic acid segments may be termed probes and primers. The individual sequences of 17, 20, 30, 50 or so nucleotide sequence stretches, for example, may be readily identified by "breaking down" the longer sequences disclosed herein to provide one or more shorter sequences. Using an exemplary length of 17 bases, each of the 17-mer possibilities from the DNA sequences described herein have been defined and are listed in Table 2.

In certain embodiments, the invention provides isolated DNA segments and recombinant vectors that have one or more sequence regions that encode one or more non-ciliate eukaryotic telomerase components, and preferably, those that encode one or more yeast (S. cerevisiae) telomerase components. The creation and use of recombinant host cells, through the application of DNA technology, that express yeast or other non-ciliate eukaryotic telomerase components is also encompassed by the invention.

As used herein, the term "telomerase component" refers to a biological component that is associated with a non-ciliate eukaryotic telomerase complex, such as a mammalian, drosophila or yeast telomerase component. Preferably, the telomerase components will be associated with a yeast telomerase complex. A "telomerase complex" in this sense is a ribonucleoprotein enzyme complex that functions to elongate the G-rich strand of eukaryotic, and preferably yeast, chromosomal termini by adding telomeric repeats. Telomerase components (or telomerase-associated components) therefore include both RNA and polypeptidyl components.

An important component of telomerase is the telomerase RNA template or template sequence. The term "telomerase RNA template", as used herein, refers to a non-ciliate eukaryotic, such as a mammalian, drosophila, or preferably, a yeast telomerase RNA component that includes a sequence that is complementary to the telomere repeat, i.e., that is complementary to the G-rich or GT-rich sequences of chromosomal termini. The telomerase RNA template is thus an isolated RNA component that has a C-rich or CA-rich sequence and that, by interacting with other telomerase components, functions to extend telomeric repeats. The telomerase RNA template may also be defined as the telomerase substrate for reverse transcription.

Further telomerase components are telomerase-associated proteins and polypeptides. The "telomerase-associated proteins and polypeptides" of this invention are proteins, polypeptides or peptides that are required for telomerase function in non-ciliate eukaryotic cells, and preferably, in yeast cells. Such telomerase-associated proteins and polypeptides will generally be physically and functionally associated with the telomerase complex in the nucleus, however, they may also be proteins or polypeptides that only associate with the telomerase complex for certain periods of time, at defined points of the cell cycle, or may be present only in certain cell types of a multicellular organism.

Telomerase-associated proteins, polypeptides and peptides may have either functional or structural roles within the telomerase complex. That is, they may have a catalytic or regulatory role, or may form the scaffolding of the telomerase structure. The telomerase-associated proteins or polypeptides may function only in terms of telomerase activity, i.e., they may be telomerase-restricted; or they may have other biological functions within the cell nucleus, such as in other aspects of chromosome replication and stability, or may even have cytoplasmic functions.

The telomerase DNA segments of the present invention are thus DNA segments isolatable from non-ciliate eukaryotic cells, and preferably, from yeast cells, that are free from total genomic DNA and that include a sequence region that is capable of expressing a telomerase RNA or polypeptide component. The DNA segments may, in certain embodiments, also be defined as those capable of inhibiting the telomerase activity of a cell by over-expression in a cell that previously contained telomerase activity. In further embodiments, the DNA segments may be defined as those capable of conferring telomerase activity to a host cell when incorporated into a cell that has been rendered deficient in such activity.

As used herein, the term "DNA segment" refers to a DNA molecule that has been isolated free of total genomic DNA of a particular species, such as a mammal, drosophila or yeast species. Therefore, a DNA segment that comprises a sequence region that encodes a telomerase-associated component refers to a DNA segment that includes telomerase-associated component coding sequences or regions, yet is isolated away from, or purified free from, total genomic DNA of the species from which the DNA segment is obtained. Included within the term "DNA segment", are DNA segments and smaller fragments of such segments, and also recombinant vectors, including, for example, plasmids, cosmids, phage, viruses, and the like.

Similarly, a telomerase-associated gene is a DNA segment comprising an isolated or purified gene that includes a sequence region that encodes a component associated with a mammalian, drosophila, or preferably, with a yeast telomerase. The term "an isolated gene associated with a non-ciliate eukaryotic telomerase", as used herein, refers to a DNA segment including telomerase RNA or protein coding sequences or regions and, in certain aspects, regulatory sequences, isolated substantially away from other naturally occurring genes or encoding sequences. In this respect, the term "gene" is used for simplicity to refer to a functional RNA, protein, polypeptide or peptide encoding unit or region. As will be understood by those in the art, this functional term includes both genomic sequences, cDNA sequences and smaller engineered gene segments that express, or may be adapted to express, RNA molecules, proteins, polypeptides or peptides.

"Isolated substantially away from other coding sequences" means that the gene of interest, in this case a telomerase-associated gene, forms the significant part of the sequence or coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences that include an isolated gene or sequence region that encodes a non-ciliate eukaryotic telomerase RNA template, such as a mammalian, drosophila, or preferably, a yeast telomerase RNA template. This aspect of the invention is exemplified by DNA segments and genes that encode the S. cerevisiae telomerase RNA template sequence of CAC-CACACCCACACAC (SEQ ID NO:3).

A variety of oligonucleotides, DNA segments and genes that encode the CACCACACCCACACAC (SEQ ID NO:3) telomerase RNA template sequence are made possible by the discovery of the present inventors'. These include sequences from SEQ ID NO:1, and the complementary strand, SEQ ID NO:4. The sequence from SEQ ID NO:1 that includes the template-encoding region of CACCACACCCACACAC (SEQ ID NO:3) is particularly represented by the contiguous DNA sequence from position 468 to position 483 of SEQ ID NO:1. Such DNA segments will have a minimum length of 17 nucleotides, and are exemplified by the contiguous DNA sequences from position 467 to position 483, or from position 468 to position 484, of SEQ ID NO:1.

DNA segments longer than 17 bases are also contemplated, in increments of single integers up to and including the 1301 bases of SEQ ID NO:1, and even longer. The contiguous sequences from SEQ ID NO:1 may be equidistant around the template-encoding region of SEQ ID NO:3, or they may have the SEQ ID NO:3 region located substantially towards the beginning or towards the end of the given sequence. DNA segments may thus have sequences in accordance with the contiguous sequences between about position 450 or 460 and about position 485 of SEQ ID NO:1; between about position 300 or 400 and about position 500, 600 or 700 of SEQ ID No:1; between about position 100 or 200 and about position 800, 900, 1000, 1100 or 1200 of SEQ ID NO:1; or between any of the afore-mentioned ranges and intermediates thereof. DNA segments and isolated genes that include the full-length DNA sequence of SEQ ID NO:1 are also contemplated.

In further embodiments, the invention provides isolated DNA segments, genes and vectors incorporating DNA sequences that encode a non-ciliate eukaryotic telomerase-associated polypeptide, such as a mammalian, drosophila or yeast, telomerase-associated polypeptide, as exemplified by yeast polypeptides that includes within their amino acid sequence a contiguous amino acid sequence from SEQ ID NO:16, SEQ ID NO:18, SEQ ID NO:20, SEQ ID NO:22 or SEQ ID NO:24.

The term "a contiguous amino acid sequence from SEQ ID NO:16, SEQ ID NO:18, SEQ ID NO:20, SEQ ID NO:22 or SEQ ID NO:24" means that a contiguous sequence is present that substantially corresponds to a contiguous portion of one of the afore-mentioned sequences and has relatively few amino acids that are not identical to, or a biologically functional equivalent of, the amino acids of SEQ ID NO:16, SEQ ID NO:18, SEQ ID NO:20, SEQ ID NO:22 or SEQ ID NO:24. The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of SEQ ID NO:16, SEQ ID NO:18, SEQ ID NO:20, SEQ ID NO:22 or SEQ ID NO:24 will be sequences in accordance with the present invention.

The protein-encoding DNA segments, genes and vectors may include within their sequence region a contiguous nucleic acid sequence from SEQ ID NO:29, SEQ ID NO:30, SEQ ID NO:19, SEQ ID NO:31 or SEQ ID NO:23. The term "a contiguous nucleic acid sequence from SEQ ID NO:29, SEQ ID NO:30, SEQ ID NO:19, SEQ ID NO:31 or SEQ ID NO:23" is used in the same sense as described above and means that the nucleic acid sequence substantially corresponds to a contiguous portion of one of the designated sequences and has relatively few codons that are not identical, or functionally equivalent, to the codons of SEQ ID NO:29, SEQ ID NO:30, SEQ ID NO:19, SEQ ID NO:31 or SEQ ID NO:23. The term "functionally equivalent codon" is used herein to refer to codons that encode the same amino acid, such as the six codons for arginine or serine, and also refers to codons that encode biologically equivalent amino acids, as is known in the art and further described herein (see Table 1).

Protein-encoding DNA segments and genes of the present invention may encode a full length telomerase-associated protein or polypeptide, as may be used in expressing the protein. Such DNA segments are exemplified by those that comprise an isolated gene that includes a contiguous DNA sequence substantially as shown between position 54 and position 1799 of SEQ ID NO:29, that encodes a polypeptide substantially as shown in SEQ ID NO:16; or that includes a contiguous DNA sequence substantially as shown between position 78 and position 1094 of SEQ ID NO:30, that encodes a polypeptide substantially as shown in SEQ ID NO:18; or that includes a contiguous DNA sequence substantially as shown between position 2 and position 2368 of SEQ ID NO:19, that encodes a polypeptide substantially as shown in SEQ ID NO:20; or that includes a contiguous DNA sequence substantially as shown between position 55 and position 699 of SEQ ID NO:31, that encodes a polypeptide substantially as shown in SEQ ID NO:22; or that includes a contiguous DNA sequence substantially as shown between position 3 and position 1955 of SEQ ID NO:23, that encodes a polypeptide substantially as shown in SEQ ID NO:24.

For both protein expression and hybridization, the nucleic acid segments used may include the full length versions of any of the telomerase-associated genes disclosed herein, or their biological equivalents, including their complementary sequences where hybridization is concerned. This is exemplified by DNA segments that have, or that comprise a sequence region that has, the 1301 nucleotides of SEQ ID NO:1, the 1882 nucleotides of SEQ ID NO:29, the 1094 nucleotides of SEQ ID NO:30, the 2434 nucleotides of SEQ ID NO:19, the 807 nucleotides of SEQ ID NO:31, the 2117 nucleotides of SEQ ID NO:23, or any substantially equivalent sequences.

Further, the present DNA segments may be used to express protein fragments or peptides, for example, peptides of from about 15 to about 30, about 50 or about 100 amino acids in length. The peptides may, of course, be of any length between or around such stated ranges, with "about" meaning a range of lengths in positive integers between each above-listed reference point and higher, with 12–15 or so being the minimum length. Appropriate coding sequences and regions may be readily identified from any of the regions of SEQ ID NO:29, SEQ ID NO:30, SEQ ID NO:19, SEQ ID NO:31 or SEQ ID NO:23.

The sequence or coding regions of the invention will be a minimum length of 17 nucleotides, and will most often be longer than this, such as upwards of about 40–50 nucleotides in length or so. The maximum length of the DNA segments is not limited by the length of the coding regions themselves, so that DNA segments of about 1,000, about 3,000, about 5,000 and 10,000 or even longer are contemplated. It will be readily understood that all lengths intermediate between the above-quoted ranges are also included.

It will also be understood that amino acid and nucleic acid sequences may include additional residues, such as additional N- or C-terminal amino acids or 5' or 3' sequences, and yet still be substantially as shown in one of the sequences disclosed herein, so long as the sequence meets the criteria set forth above. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 80%; or more preferably, between about 80% and about 90%; or even more preferably, between about 90% and about 99% of nucleotides that are identical to the nucleotides of SEQ ID NO:1, SEQ ID NO:29, SEQ ID NO:30, SEQ ID NO:19, SEQ ID NO:31 or SEQ ID NO:23 will be sequences that are substantially as shown in such sequences. From the inventors' experience, sequences with 70% identity or higher are expected to be telomerase-related sequences.

The nucleic acid segments of the present invention, regardless of the length of any coding sequences themselves, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

As stated above, the invention is not limited to the particular sequences of SEQ ID NO:1, SEQ ID NO:29, SEQ ID NO:30, SEQ ID NO:19, SEQ ID NO:31 or SEQ ID NO:23 (nucleic acid), or SEQ ID NO:16, SEQ ID NO:18, SEQ ID NO:20, SEQ ID NO:22 or SEQ ID NO:24 (amino acid). In terms of expression, recombinant vectors may therefore variously include the telomerase-associated protein coding regions themselves, coding regions bearing selected alterations or modifications in the basic coding region, or they may encode larger polypeptides that nevertheless include such telomerase-associated protein coding regions or may encode biologically functional equivalent proteins or peptides that have variant amino acids sequences.

For protein expression embodiments, the DNA segments may include biologically functional equivalent protein-coding sequences that have arisen as a consequence of codon redundancy and functional equivalency, as is known to occur naturally within biological sequences. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test telomerase mutants in order to examine their activity at the molecular level.

If desired, one may also prepare fusion proteins and peptides, e.g., where the telomerase-associated protein coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which an RNA or protein coding portion of a DNA segment, whether encoding an RNA template, a full length protein or smaller peptide, is positioned under the control of a promoter. The promoter may be in the form of the promoter that is naturally linked to a telomerase-associated gene, as may be obtained by isolating the 5' non-coding sequences located upstream of the coding segment or exon, for example, using recombinant cloning and/or PCR technology, in connection with the compositions disclosed herein.

In other expression embodiments, it is contemplated that certain advantages will be gained by positioning a coding DNA segment or sequence region under the control of a recombinant, or heterologous, promoter. As used herein, a recombinant or heterologous promoter is intended to refer to a promoter that is not normally associated with a telomerase-associated gene in its natural environment. Such promoters may include yeast promoters normally associated with other genes, and/or promoters isolated from any other bacterial, viral, insect or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989). The promoters employed may be constitutive, or inducible, and can be used under the appropriate conditions to direct high level expression of the introduced DNA segment, such as is advantageous in the large-scale production of recombinant proteins or peptides.

Preferred promoter systems contemplated for use in high-level expression in *S. cerevisiae* include, but are not limited to, the GAL1, MET3, and PGK promoter systems. For conditional alleles, as may be used in cellular studies of the RNA template, a chimeric fusion of an RNA template gene may be placed under the regulation of a heterologous promoter. Appropriate promoters include the MET3 promoter, which is repressed in the presence of methionine and induced when methionine is absent from the medium; and the GAL1,10 UAS, as described in Example XI.

B. Nucleic Acid Hybridization

In addition to their use in directing the expression of telomerase-associated RNA and protein components, the nucleic acid sequences disclosed herein also have a variety of other uses, for example, in nucleic acid hybridization embodiments. The ability of nucleic acid probes or primers to specifically hybridize to the telomerase-associated nucleic acid sequences disclosed herein will enable them to be of use in detecting the presence of complementary sequences in a given sample. However, other uses are envisioned, including the use of the sequence information for the preparation of mutant species primers, or primers for use in preparing other genetic constructs.

The present invention thus concerns nucleic acid segments of 17 nucleotides in length, or longer, that hybridize to the telomerase-associated sequences of SEQ ID NO:1, SEQ ID NO:29, SEQ ID NO:30, SEQ ID NO:19, SEQ ID NO:31 or SEQ ID NO:23, or their complements, under standard hybridization conditions. This provides another physical and functional definition for identifying additional sequences in accordance with the invention, as well as defining useful sub-sequences, such as primers.

The nucleic acids that hybridize to the sequences of SEQ ID NO:1, SEQ ID NO:29, SEQ ID NO:30, SEQ ID NO:19, SEQ ID NO:31 or SEQ ID NO:23, may be 17 nucleotides in length or longer, such as about 20, about 25, about 30, about 50, about 75, about 100, about 150, about 200, about 250, about 500, about 750 or about 1,000 nucleotides in length, or even longer. As the length of the nucleic acid segment that hybridizes is not solely a function of the length of the substantially complementary sequence region, these nucleic acid segments may also be about 2,000, about 3,000, about 5,000 or about 10,000 nucleotides in length or longer, so long as the total length does not prevent hybridization under the conditions defined herein.

As with the sequence or coding regions defined hereinabove, it will be readily understood that any intermediate length between the quoted ranges is included, such as 17, 18, 19, 20, 21, 22, 23, etc; 50, 51, 52, 53, etc.; 100, 101, 102, 103, etc.; including all positive integers through the 150–500; 500–1,000; 1,000–2,000; 2,000–5,000; and 5,000–10,000 ranges, up to and including sequences of about 12,001, 12,002, 13,001, 13,002 and the like.

The total size of nucleic acid segment or fragment, as well as the size of the complementary stretch(es), will ultimately depend on the intended use or application of the particular nucleic acid segment. The use of a hybridization probe of about 17 nucleotides in length allows the formation of a duplex molecule that is both stable and selective.

Accordingly, the nucleotide sequences of the invention may be used for their ability to selectively form duplex molecules with complementary stretches of telomerase-associated genes or cDNAs. Depending on the application envisioned, one will desire to employ varying conditions of hybridization to achieve varying degrees of selectivity of probe towards target sequence.

For applications requiring high selectivity, one will typically desire to employ relatively stringent conditions to form the hybrids, e.g., one will select relatively low salt and/or high temperature conditions that tolerate little, if any, mismatch between the probe and the template or target strand. Standard high stringency hybridization conditions are described in the hybridization protocols set forth herein in the detailed description.

Of course, for some applications, for example, where one desires to prepare mutants employing a mutant primer strand hybridized to an underlying template, or where one seeks to isolate telomerase-associated sequences from related species, functional equivalents, or the like, less stringent hybridization conditions are useful to allow formation of the heteroduplex. In these circumstances, one may desire to employ standard low stringency hybridization conditions, which are also described in the hybridization protocols set forth in the detailed description.

Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex, in the same manner as increased temperature. Thus, hybridization conditions can be readily manipulated, and thus will generally be a method of choice depending on the desired results.

Where hybridization probes or primers are to be designed from a consideration of the longer sequences disclosed herein, they may be selected from any portion of any of the nucleic acid sequences. All that is required is to review the sequences and to select any continuous portion of the sequence, from 17 nucleotides in length up to and including the full length sequence.

Once the coding sequence of a telomerase-associated gene has been determined, various primers can be designed around that sequence. Primers may be of any length, but typically, are 17, 20, 25 or 30 bases or so in length. By assigning numeric values to a sequence, for example, the first residue is 1, the second residue is 2, and the like, an algorithm defining all primers is:

$$n \text{ to } n+y$$

where n is an integer from 1 to the last number of the sequence and y is the length of the primer minus one, in the above cases (16, 19, 24, 29), where n+y does not exceed the last number of the sequence. For example, for the TLC1 gene, n is 1 to 1301. Thus, for a 17-mer, the probes correspond to bases 1 to 17, 2 to 18, 3 to 19 . . . up to 1285 to 1301. Table 2 herein sets forth the number of contiguous 17-mer sequences that may be obtained from the sequences of SEQ ID NO:1, SEQ ID NO:29, SEQ ID NO:30, SEQ ID NO:19, SEQ ID NO:31 or SEQ ID NO:23, or their complements.

The choice of probe and primer sequences may be governed by various factors, such as, by way of example only, one may wish to employ primers from towards the termini of the total sequence, or from the ends of any functional domain-encoding sequences, in order to amplify further DNA; one may employ probes corresponding to the entire DNA, or to the RNA template region, to clone template genes from other species or to clone further telomerase template-like or homologous genes from any species including human; one may also design appropriate probes or primers to screen biological samples to identify cells with inappropriate telomerase levels or activity, as may be related to cancer or even to infertility.

The process of selecting and preparing a nucleic acid segment that includes a contiguous sequence from within SEQ ID NO:1, SEQ ID NO:29, SEQ ID NO:30, SEQ ID NO:19, SEQ ID NO:31 or SEQ ID NO:23 may be readily achieved by, for example, directly synthesizing the fragment by chemical means, as is commonly practiced using an automated oligonucleotide synthesizer. Also, fragments may be obtained by application of nucleic acid reproduction technology, such as the PCR technology of U.S. Pat. No. 4,683,202 and U.S. Pat. No. 4,682,195 (each incorporated herein by reference), by introducing selected sequences into recombinant vectors for recombinant production, and by other recombinant DNA techniques generally known to those of skill in the art of molecular biology. Of course, smaller nucleic acid fragments may also be obtained by other techniques such as, e.g., by mechanical shearing or by restriction enzyme digestion.

In certain embodiments, it will often be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In certain embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

C. Further Telomerase Compositions

The present invention further includes isolated RNA segments, of from 17 to about 1,500 nucleotides in length, that comprise a non-ciliate, or preferably, a yeast telomerase RNA template. The isolated RNA segments will be obtained free from total nucleic acids, chromosomes and intact telomerase complexes, and will include a non-ciliate eukaryotic, or preferably, a yeast telomerase RNA template. This is exemplified by RNA segments including the *S. cerevisiae* RNA template sequence of CACCACACCCACACAC (SEQ ID NO:3).

Isolated RNA segments that include the minimum functional mammalian, drosophila or yeast telomerase RNA template coding sequences and the minimum upstream sequences necessary for expression are also contemplated. These may be identified as described herein in Example XI and will be useful in mutant analysis, promoter and expression analysis and creation of conditional mutants.

Isolated RNA segments that have substantially the same secondary structure as the RNA segment encoded by the sequence of SEQ ID NO:1 are also included within the scope of the present invention. This may be assessed by techniques, and computer programs, that predict secondary structure based on the primary sequence of the RNA. The secondary structure predictions are supported by mutant/function analysis, as is well known in the art. That is, given the predicted structure, it is straightforward for the ordinary artisan to accurately predict the effects of certain sets of mutations in the RNA.

Further compositions in accordance with this invention include affinity columns that comprise a deoxyoligonucleotide attached to a solid support, where the deoxyoligonucleotide includes a sequence complementary to a non-ciliate, or preferably, a yeast telomerase RNA template sequence. Such deoxyoligonucleotides and affinity columns will be capable of binding eukaryotic, or preferably, yeast telomerase complexes, enabling their purification. As the template RNA includes the CA-rich template region, an appropriate column-bound bait will be a GT-rich DNA sequence, as represented, by way of example only, by SEQ ID NO:2.

The oligonucleotides may be attached to any one of a variety of solid supports for use in standard column chromatography or in FPLC or HPLC techniques. Oligonucleotides may be attached using a variety of appropriate methods, such as, by way of example, using direct chemical conjugation, or other means such as biotin-avidin linkers, and the like. All such techniques are routine in the art.

Still further embodiments of the present invention concern recombinant host cells that contain or incorporate a DNA segment or recombinant vector that comprises an isolated gene associated with non-ciliate eukaryotic, or preferably, with yeast telomerase. The telomerase-associated components, whether they be cDNA or genomic, may be used in expression systems for the recombinant preparation of RNA templates or telomerase-associated polypeptides.

As used herein, the term "engineered" or "recombinant" cell is intended to refer to a cell into which an exogenous DNA segment or gene, such as a cDNA or gene encoding a telomerase-associated component has been introduced. Therefore, engineered cells are distinguishable from naturally occurring cells that do not contain a recombinantly introduced exogenous DNA segment or gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

The engineering of DNA segment(s) for expression in prokaryotic or eukaryotic systems is performed using techniques known to those of skill in the art, and further described herein in detail. It is believed that virtually any prokaryotic or eukaryotic host cell system may be employed in the expression of one or more telomerase-associated components, with yeast systems being preferred in certain embodiments. Telomerase-associated polypeptides may also be as fusions with, e.g., β-galactosidase, ubiquitin, *Schistosoma japonicum* glutathione S-transferase, and the like.

To achieve expression, one would position the telomerase coding sequences adjacent to and under the control of a promoter. It is understood in the art that to bring a coding sequence under the control of such a promoter, one positions the 5' end of the transcription initiation site of the transcriptional reading frame of the protein between about 1 and about 50 nucleotides or so "downstream" of (i.e., 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

The recombinant host cells of the invention will effectively expresses a DNA segment to produce a telomerase RNA template or a polypeptide associated with telomerase. The invention thus further includes recombinant gene products that are prepared by expressing a eukaryotic, or preferably, a yeast telomerase-associated gene in a recombinant host cell and purifying the expressed gene product away from total recombinant host cell components. The gene products include telomerase RNA templates, proteins, polypeptides and peptides associated with telomerase, and combinations and equivalents thereof.

The preparation of such recombinant gene products is preferably achieved by using a DNA segment of the invention in the preparation of a recombinant vector in which a telomerase-associated gene is positioned under the control of a promoter. The recombinant vector is then introduced into a recombinant host cell, which is cultured under conditions effective, and for a period of time sufficient, to allow expression of the telomerase-associated gene, which thus allows the expressed gene product to be collected, giving a purified preparation.

The invention further concerns recombinant RNA segments that include non-ciliate telomerase RNA templates, such as mammalian, drosophila, or preferably, yeast telomerase RNA templates; and recombinant protein and polypeptide compositions, free from total cell components, that comprise one or more purified non-ciliate, or preferably, yeast telomerase-associated components. These are exemplified by polypeptides that include a contiguous amino acid sequence from SEQ ID NO:16, SEQ ID NO:18, SEQ ID NO:20, SEQ ID NO:22 or SEQ ID NO:24.

The terms "purified telomerase-associated polypeptide and RNA template", as used herein, refer to telomerase-associated polypeptide or RNA template compositions, isolatable from eukaryotic, or preferably, from yeast cells, wherein the polypeptide or RNA is purified to any degree relative to its naturally-obtainable state, e.g., relative to its purity within a cellular extract. More preferably, "purified" refers to telomerase-associated polypeptide or RNA template compositions that have been subjected to fractionation to remove various non-telomerase components. "Substantially purified" native and recombinant telomerase RNA templates and polypeptides are also preparable using the methods of the invention.

To prepare a purified telomerase-associated component in accordance with the present invention one would subject a composition to fractionation to remove various non-telomerase-associated components. Various techniques suitable for use in RNA and protein purification will be well known to those of skill in the art. Protein purification techniques include, for example, precipitation with ammonium sulphate, PEG, antibodies, and the like, or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

Specific examples of purification schemes for use in the present invention are those including initial separation of nuclear proteins, followed by gradient centrifugation methods (equilibrium and sedimentation velocity), column chromatography and gel electrophoresis, as described in Example XV. Specific binding to RNA or DNA segments related to the telomerase template sequences, including affinity column binding embodiments, is also envisioned to be particularly useful.

For assays of intact or relatively intact telomerase complexes, deoxyoligonucleotide substrates, representing 3' G-rich telomere tails, are incubated in cellular extracts containing telomerase with $^{32}$P-labeled dNTP's (typically dGTP or dTTP). The products of telomerase elongation on the input deoxyoligonucleotide substrate may then be detected by, e.g., gel electrophoresis and autoradiography. A series of substrates is also preferably used, as described in Example XV.

Although preferred for use in certain embodiments, there is no general requirement that the RNA or proteins always be provided in their most purified state. Indeed, it is contemplated that less substantially purified telomerase-associated components, which are nonetheless enriched relative to their natural state, will have utility in certain embodiments. These include, for example, certain binding assays, screening protocols, titration of components, and the like. Inactive protein fractions also have utility, for example, in antibody generation.

In further embodiments, the invention also provides polyclonal or monoclonal antibodies that bind to a non-ciliate, and preferably, to a yeast telomerase-associated polypeptide, as exemplified by an antibody that has binding affinity for a protein or peptide that includes a contiguous amino acid sequence from SEQ ID NO:16, SEQ ID NO:18, SEQ ID NO:20, SEQ ID NO:22 or SEQ ID NO:24. Cross-reactive antibodies are also encompassed by the invention, as may be identified by employing a competition binding assay, such as an ELISA or RIA, as are well known in the art.

Particular techniques for preparing antibodies in accordance with the invention are disclosed herein, which methods generally comprise administering to an animal a composition comprising an immunologically effective amount of a telomerase-associated component protein, peptide or other epitopic composition. By "immunologically effective amount" is meant an amount of a telomerase-associated protein or peptide composition that is capable of generating an immune response in the recipient animal, and particularly, in this case, generating an antibody or B cell response.

Any of the DNA, RNA, proteins, polypeptides and antibodies of this invention may also be linked to a detectable label, such as a radioactive, fluorogenic, biological, chromogenic or even a nuclear magnetic spin resonance label. Biolabels such as biotin and enzymes that are capable of generating a colored product upon contact with a chromogenic substrate will be preferred in certain embodiments. Exemplary enzyme labels include alkaline phosphatase, hydrogen peroxidase, urease and glucose oxidase enzymes.

In still further embodiments, the invention concerns molecular biological and immunodetection kits. The labelled nucleic acid segments, proteins or antibodies may be employed to detect other telomerase-associated nucleic acid, protein or antibody components in extracts, cells or biological samples, as may be used in the detection of telomerase in clinical samples, or in the purification of telomerase-associated components, as appropriate. The kits will generally include a suitable telomerase-associated nucleic acid segment or antibody together with an detection reagent, and a means for containing the telomerase-associated component and reagent.

The detection reagent will typically comprise a label associated with the telomerase nucleic acid segment or antibody, or even associated with a secondary binding ligand. Exemplary ligands include secondary antibodies directed against a first antibody. The kits may contain telomerase-associated nucleic acid segments or antibodies either in fully conjugated form, in the form of intermediates, or as separate moieties to be conjugated by the user of the kit.

Kits for use in molecular biological tests to identify telomerase-associated components may also contain one or more unrelated nucleic acid probes or primers for use as controls, and optionally, one or more further molecular biological reagents, such as restriction enzymes or PCR components. The components of the kits will preferably be packaged within distinct containers.

The container means for any of the kits will generally include at least one vial, test tube, flask, bottle, syringe or other container means, into which the nucleic acid or antibody may be placed, and preferably suitably aliquoted. Where a second component, e.g., a binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

D. Telomerase-Associated Methods

The invention further provides methods for detecting non-ciliate eukaryotic, and preferably, yeast telomerase-associated genes or nucleic acid segments in samples, such as cells, cellular extracts, partially purified telomerase compositions and other biological and even clinical samples. Such methods generally comprise obtaining sample nucleic acids from a sample suspected of containing a telomerase-associated gene; contacting the sample nucleic acids with a telomerase-associated nucleic acid segment as described herein under conditions effective to allow hybridization of substantially complementary nucleic acids; and detecting the hybridized complementary nucleic acids thus formed.

A variety of hybridization techniques and systems are known that can be used in connection with the telomerase detection aspects of the invention. For example, in situ hybridization, Southern blotting, Northern blotting and PCR technology. In situ hybridization describes the techniques wherein the target nucleic acids contacted with the probe sequences are located within one or more cells, such as cells within a clinical sample or cells grown in culture. As is well known in the art, the cells may be prepared for hybridization by fixation, e.g. chemical fixation, and placed in conditions that allow for the hybridization of a detectable probe with nucleic acids located within the fixed cell.

Alternatively, target nucleic acids may be separated from a cell or clinical sample prior to contact with a probe. Any of the wide variety of methods for isolating target nucleic acids may be employed, such as cesium chloride gradient centrifugation, chromatography (e.g., ion, affinity, magnetic), phenol extraction and the like. Most often, the isolated nucleic acids will be separated, e.g., by size, using electrophoretic separation, followed by immobilization onto a solid matrix, prior to contact with the labelled probe. These prior separation techniques are frequently employed in the art and are generally encompassed by the terms "Southern blotting", that detects DNA and "Northern blotting", that detects RNA. Virtually of the methods may be adapted for clinical or diagnostic assays, including diagnostic PCR technology.

In general, the "detection" of telomerase sequences is accomplished by attaching or incorporating a detectable label into the nucleic acid segment used as a probe and "contacting" a sample with the labeled probe. In such processes, an effective amount of a nucleic acid segment that comprises a detectable label (a probe), is brought into direct juxtaposition with a composition containing target nucleic acids. Hybridized nucleic acid complexes may then be identified by detecting the presence of the label, for example, by detecting a radio, enzymatic, fluorescent, or chemiluminescent label.

These detection methods may be employed to detect telomerase-associated genes, whether RNA- or protein-encoding, in both clinical and laboratory samples, e.g., as may be used in telomerase purification, analysis, mutagenesis and the like. In cells or cellular extracts obtained from an animal or human patient, the detection of telomerase may have particular relevance, for example, in the diagnosis or detection of tumor cells within a sample suspected of containing such cells. This is supported by recent findings linking telomerase to oncogenesis and various late stage tumors and tumor cells (Harley et al., 1992; Counter et al., 1992, 1994a; Shay et al., 1993; Klingelhutz et al., 1994; de Lange, 1994; Greider, 1994). The differential detection and diagnosis of malignant tumors as opposed to benign tumors is also contemplated.

Further clinical samples that may be analyzed for the presence of telomerase-associated genes, as described above, include those suspected of containing a pathogen. As telomerase activity is only present in dividing cells, testing a sample of somatic cells of an animal or human for the presence of telomerase may indicate the presence of an invading unicellular organism within the sample. This may allow disease diagnosis alone, or in combination with other methods. The diagnosis of yeast infections, for example, is an immediate application of the present invention. The development of species-specific markers for other opportunistic infections is also contemplated.

Diagnostic methods for identifying various conditions associated with infertility in animals and humans are also provided by the invention. For example, as telomerase activity is required in germ cells, including human sperm and ova, testing samples from animals and humans suspected of having a condition connected with reproductive failure would provide useful information. A negative test would likely indicate a defect in the reproductive capacity of sperm or egg cells within a given sample.

In further embodiments, the invention concerns methods based upon suppression of "telomeric silencing" for use in identifying non-ciliate, and preferably, yeast telomerase-associated genes or active fragments thereof. Such methods generally comprise, initially, preparing a cell containing a chromosome that contains a genetic marker located proximal to a telomere, wherein the telomere represses the expression of the marker. Next, one would contact the cell with a composition comprising a candidate gene and identify any gene, or portion thereof, that allows expression of the marker. "Genes" identified in this way may be wild type genes or fragments that may disrupt the telomere function due to over-expression, or they may be mutant or truncated genes that simply do not function correctly.

Appropriate cells for use in such assays include those cells that contain an active telomere, such as eukaryotic cells that are capable of dividing, as exemplified by yeast cells, drosophila cells, and certain human cells, such as sperm, egg and cancer cells. The novel technology developed by the inventors is contemplated for use in any organism in which the telomeres cause a transcriptional repression (silencing) of nearby genes. For ease of operation, yeast and *Drosophila melanogaster* (fruit flies) are currently preferred. However, the use of human cells is also contemplated.

The genetic markers that are added in the vicinity of a telomere may be any marker gene that gives a readily identifiable phenotype upon expression. Such markers are also often termed "reporter genes". Generally, the marker or reporter genes encode a polypeptide not otherwise produced by the cell which is detectable by analysis, e.g., by visual inspection or by fluorometric, radioisotopic or spectrophotometric analysis. One example is *E. coli* beta-galactosidase, which produces a color change upon cleavage of an indigogenic substrate; a further example is the enzyme chloramphenical acetyltransferase (CAT), which may be employed with a variety of substrates that give detectable products; and still further examples are firefly and bacterial luciferases.

Still further marker genes for use herewith are those capable of transforming the host cell to express unique cell surface antigens, e.g., viral env proteins such as HIV gp120 or herpes gD, which are readily detectable by immunoassays. The polypeptide products of this type of marker gene are secreted, membrane bound polypeptides, or polypeptides adapted to be membrane targeted, allowing ready detection by antibodies. However, antigenic reporters are not currently preferred because, unlike enzymes, they are not catalytic and thus do not amplify their signals.

Yeast markers, when expressed, may result in a colored phenotype or result in a specific nutrient independence (prototrophy), or even in a nutrient requirement, or such like. Exemplary genetic markers that may be used in yeast include genes that are required for the biosynthesis of specific amino acids, such as HIS3, TRP1, LYS2, and LEU2. Genes that confer sensitivity to drugs, such as the CAN1 gene that confers sensitivity to canavinine are also contemplated for use. Currently preferred marker genes for use in yeast are ADE2 and URA3.

Many suitable genetic markers are also available for use in human cell systems. These include the markers based upon color detection or antigen detection, as above, and also marker genes that encode polypeptides, generally enzymes, that render the host cells resistant against toxins. These include the neo gene that protects host cells against toxic levels of the antibiotic G418; the dihydrofolate reductase genes that confer resistance to methotrexate; and the HSV tk gene that is used in conjunction with ganciclovir. Currently preferred examples are the markers neo and hprt, which are routinely used in the art.

The cells used in such assays may contain two distinct genetic markers, and each genetic marker may be located on a distinct chromosome if desired. The combined use of ADE2 and URA3 in yeast cells is currently a particularly preferred system.

As described hereinabove, human telomerase RNA template and polypeptide-encoding genes that have substantial sequence homology to the yeast sequences throughout, or in certain sequence regions, may be isolated by nucleic acid hybridization, i.e., standard cloning techniques (Sambrook et. al., 1989). However, even if the human sequences are not directly homologous, RNA template and other telomerase genes may still be isolated using the advantageous methods disclosed herein.

One suitable method for identifying a human telomerase-associated gene, is to apply the suppression of telomeric silencing protocol to a human nucleic acid library using a yeast cell system. Such methods generally comprise preparing a yeast cell containing a chromosome that contains a genetic marker located proximal to a telomere, where the telomere represses the expression of the marker; contacting the cell with a composition comprising a candidate human gene; and identifying a human gene that allows expression of the marker.

Further suitable methods for identifying human telomerase-associated genes are those based entirely upon human cells, which methods presuppose the lowest level of homology between the yeast and human cell systems. These methods comprise preparing a human cell that contains a chromosome having a genetic marker located proximal to a telomere, where the telomere represses the expression of the marker; contacting the cell with a composition comprising a candidate human gene; and identifying a human gene that allows expression of the marker.

Another method for isolating genes that encode products that interact with telomerase RNA is that which assays for genes that re-establish telomeric silencing when the template RNA is overexpressed, as described in Example XIV. Here, initially the RNA template is presumed to interact with a limiting telomerase component to form a non-functional complex. Increasing the concentration of a limiting component, by over-expression, thus re-establishes telomeric silencing. Preferably, RNA template levels that are minimally suppressive are used.

Still more approaches for identifying components that interact with telomerase RNA are described in Example XIV, which are based upon isolating mutations that enhance or suppress the phenotypes of conditional telomerase template alleles.

Further elements of this invention are non-ciliate eukaryotic, and preferably, yeast genes that are identified by any of the foregoing methods. One such gene is disclosed herein, termed TLC1, that encodes a telomerase RNA template. Other such genes are also disclosed herein, termed STR genes, that encode telomerase-associated polypeptides. Particular examples of such genes of the invention are thus TLC1, STR1, STR3, STR4, STR5 and STR6, and other non-ciliate eukaryotic, and preferably, yeast nucleic acid segments that have the physical and functional characteristics of any of the foregoing genes.

Active fragments of genes and RNA components, such as TLC1 RNA, may also be identified using the present methods. Titration assays based upon those used for the original identification of TLC1 may be used to define the minimum functional region. It is contemplated that relatively small regions of the RNA (about 50 bp) that suppress silencing will be identified. Conditional mutations made in regions of the RNA that are evolutionarily conserved, or that may interact with a limiting factor, as suggested by the titration analysis, will identify functionally important region of the telomerase RNA. Active regions of telomerase genes and RNA components may also be identified using methods for dissecting small nuclear RNAs (snRNAs), as described in Example XIII.

In still further embodiments, the invention provides methods for use in identifying candidate substances that bind to yeast and other non-ciliate eukaryotic telomerase components. These methods generally include preparing an isolated telomerase component; contacting the isolated telomerase component with a composition comprising a candidate substance under conditions effective and for a period of time sufficient to allow binding; and detecting the presence of a telomerase component-candidate substance bound complex.

It will be understood that such methods are similar in principle to the nucleic acid hybridization methods described hereinabove. Indeed, the "candidate substances" to be detected may be nucleic acids, including human nucleic acid segments, that are detected by binding to eukaryotic, and preferably, to yeast telomerase RNA or DNA components, and preferably to a defined small functional region of the template that suppress silencing, under the high or low hybridization conditions described above. However, other components that bind to telomerase may be identified by binding to the isolated RNA, DNA or polypeptide components of the present invention. These components may include proteins, polypeptides, peptides, antibodies, small molecules, cofactors and the like.

Accordingly, the present invention provides binding assays, including high throughput binding assays using recombinant expression products, for use in identifying compounds capable of binding to telomerase or to a telomerase-associated component. The binding assays will preferably use the smaller RNA fragments identified in titration or other functional assays described herein.

Further methods for identifying compounds that bind to telomerase-associated components include those based upon cellular assays. One method for identifying a candidate substance that modifies telomerase activity comprises the following steps:

preparing a eukaryotic, or preferably, a yeast cell containing a chromosome that contains a genetic marker located near to, or in the vicinity of, a telomere, the telomere capable of repressing the expression of the marker;

contacting the cell with a composition comprising a candidate substance; and identifying a candidate substance that allows expression of the marker or that further represses the expression of the marker.

This method is most suitable for identifying candidate inhibitory substances that allow expression of the marker. However, it can also be used to identify candidate stimulatory substances that allow further repression of the marker.

To identify a compound that inhibits telomerase activity, one generally prepares a cell with a genetic marker that is substantially repressed by the telomere. Here, the marker gene is located proximal, i.e., immediately adjacent, to the telomere. Substantial repression is defined by repression to at least about 50%, or preferably, to about 25%, 10% or about 1%. However, the expression of the marker may be repressed to even about 0.01%. The inhibitory substance is then detected by detecting greater expression of the marker.

To identify a compound that activates telomerase activity, one would generally prepare a cell with a genetic marker that is either not repressed at all or that is not substantially or maximally repressed. One would then select a candidate activator by identifying a substance that establishes or allows repression or more substantial repression. This is based upon the concept that stimulating telomerase to synthesize longer than normal telomeres will result in an increase in silencing of a marker gene. To detect the increase requires that a system initially be established in which the marker gene is only minimally repressed, or even not repressed at all. This is readily achieved by inserting the marker gene in the location or vicinity of the telomere, but further away from the telomere rather than immediately adjacent to it. An increase in repression, i.e., a decrease in marker gene expression, indicates a positive candidate substance.

Still further methods for identifying compounds that functionally interact with telomerase or telomerase-associated components are those based upon the telomerase "healing of broken chromosomes" assay described herein. This method is conducted as generally described in Example XII and FIG. 8, using a modified Haber-based assay (Kramer & Haber, 1993). Other useful telomerase functional assays are those that analyze telomere length and cell viability with increased age of a culture (Lundblad & Blackburn, 1989), and those in vitro systems described herein based on the addition of labelled nucleotides to a telomeric-like sequence.

Any of the cellular or activity-based telomerase assays may be adapted to screen for candidate substances that modify telomerase activity. To achieve this, one would first conduct the assay in the absence of the test candidate substance to obtain an activity value in its absence. One would then add the candidate substance to the telomerase composition or cell and conduct the assay under the same conditions. Candidate substances that reduce or promote telomerase activity can thus be readily identified.

Useful telomerase-modifying compounds are not believed to be limited in any way to protein or peptidyl compounds or oligonucleotides. In fact, it may prove to be the case that the most useful pharmacological compounds identified through application of a screening assay will be non-peptidyl in nature. Accordingly, in such screening assays, it is proposed that compounds isolated from natural sources, such as animals, bacteria, fungi, plant sources, including leaves and bark, and marine samples, may be assayed for the presence of potentially useful pharmaceutical agents. It will be understood that the pharmaceutical agents to be screened could also be derived from chemical compositions or man-made compounds.

The invention thus further encompasses components that bind to telomerase and that are capable of modifying telomerase activity, as may be identified by any of the foregoing binding and/or functional or cellular assay methods. This results in compositions of telomerase activators or inhibitors, including pharmaceutically acceptable compositions, and methods for modifying telomerase activity.

In yet still further embodiments, the present invention thus also provides methods for modifying the replicative capacity of a cell, which methods comprise contacting a telomerase-containing cell with an amount of a component or substance effective to modify telomerase activity. "Modifying" in this context includes both compositions and methods for inhibiting telomerase activity, as may be used, e.g., in inhibiting or killing a tumor cell or a pathogen; and compositions and methods for stimulating telomerase activity, as may be used in embodiments connected with promoting the replication of a cell, such as in treating infertility.

Where the telomerase-containing cells are located within an animal, a pharmaceutically acceptable composition of the telomerase activator or inhibitor may be administered to the animal in an amount effective to modify the telomerase activity of the target cell. In terms of inhibiting telomerase activity in tumor cells, this is contemplated to be an effective mechanism by which to treat cancer that will have very limited side effects. Similarly, effective antimicrobial treatments are contemplated, as are applications in treating age-related disorders such as atherosclerosis and osteoporosis. Further, gene therapy using functional telomerase-associated genes is envisioned to be of use in treating telomerase dysfunction, as could provide a treatment for infertility in humans and other animals.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 1A, Viability on medium lacking uracil was measured for S. cerevisiae strains containing URA3 either at telomere VII-L (UCC3505) or at HML (UCC3515), and overexpressing either vector alone (pTRP, down sloping hatched bar), a representative TLC1 cDNA clone (pTRP6, upward sloping hatched bar), or a SIR4 cDNA clone (pTRP10, white bar) (Kyrion et al., 1993). In FIG. 1B, ADE2 expression, as assayed by colony color, was examined in cells containing ADE2 placed near telomere V-R (UCC3505), and containing the vector (pTRP). In FIG. 1C, ADE2 expression, as assayed by colony color, was examined in cells containing ADE2 placed near telomere V-R (UCC3505), and containing another representative TLC1 cDNA clone (pTRP61). The medium contained 3% galactose and lacked tryptophan. The median value for viability in the absence of uracil is marked by the height of each column, and the upper extreme is indicated by the error bar. The strains were pregrown for four days on solid synthetic medium without tryptophan (to maintain selection for the plasmid) that contained 3% galactose (to induce the GAL1 promoter controlling expression of the cDNA inserts). Colonies were then diluted in water, and serial dilutions were plated on 3% galactose medium without tryptophan and uracil. Cells were also plated on medium containing uracil, to determine overall cell viability. Five independent transformants of each strain were tested.

FIG. 3A shows the membrane probed with a 1.25 kb TLC1 antisense probe (made from the pTRP61 insert) and exposed to film. Phosphor-imaging analysis determined that there is approximately 12-fold more TLC1 RNA in the overexpressing strain (lane 4) than in the vector-containing wild-type strain grown under the same conditions (lane 3). FIG. 3B displays the ethidium bromide-stained gel prior to blotting, with the sizes of the rRNA species (25S and 18S) indicated on the right. The wild-type and tlc1 strains shown in lanes 1 and 2 were derived from sporulation of UCC3508 (Aparicio et al., 1991). The yeast strain transformed with the pTRP and pTRP61 plasmids, shown in lanes 3 and 4, is UCC3505.

In FIG. 5A, is shown a model by which the TLC1 RNA anneals to the single-stranded G-rich overhanging strand at the end of the chromosome and templates its elongation via a reverse transcription reaction. The bold-type DNA bases represent newly synthesized sequence. FIG. 5B, shows that, accordingly, mutating the putative template motif of TLC1, creating the TLC1-1(HaeIII) allele, results in the incorporation of the altered sequence into telomeric DNA.

DETAILED DESCRIPTION OF THE PREFERRED EMBODIMENTS

Figure 1A:
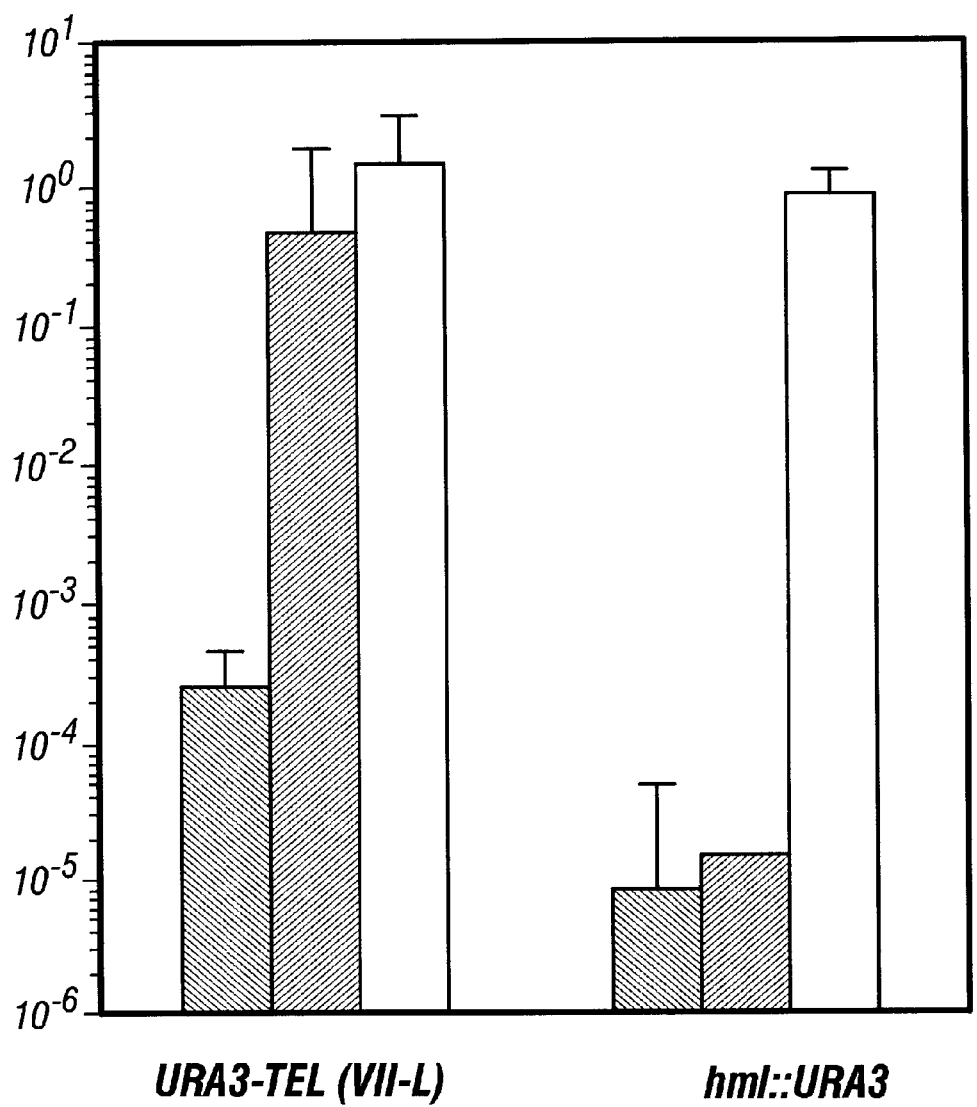
FIG. 1A, FIG. 1B and FIG. 1C. Overexpression of TLC1 suppresses transcriptional silencing at telomeres, but not at the HML locus.

Telomeres, the natural ends of linear eukaryotic chromosomes, are essential for chromosome stability. Because of the nature of DNA replication, telomeres require a specialized mechanism to ensure their complete duplication. This is controlled by telomerase activity. Due to its role in controlling replication, changes in telomerase activity have been linked to disturbances in cell proliferation, as can lead to a cancerous phenotype (de Lange, 1994; Greider, 1994; Harley et al., 1992).

The evolutionary conservation of telomere structure suggested to the present inventors that the study of telomerase in genetically tractable organisms, such as the budding yeast *Saccharomyces cerevisiae*, would yield important information directly applicable to telomere studies in eukaryotic and mammalian cells. The existence of an *S. cerevisiae* telomerase was suggested by studies in which double-strand breaks were introduced into yeast chromosomes in vivo, after which healed chromosomes with new telomeric tracts were formed (Kramer & Haber, 1993). Specific 13-bp motifs (GTGTGTGGGTGTG; SEQ ID NO:2), or subsets thereof, were found at the junction between the break site and the new telomeric tracts, suggesting that this sequence is added de novo (Kramer & Haber, 1993).

However, prior to the present invention, little was known about the molecular machinery that could be involved in telomeric replication in *S. cerevisiae*. Previously, the only candidate as a component of the telomere replication apparatus was the protein encoded by the EST1 gene (Lundblad & Szostak, 1989). Its role in telomere replication was suggested by the finding that est1 cells display progressive telomere shortening, accompanied by a gradual loss of chromosome stability and cell viability. The direct function of Est1p still remains to be elucidated.

The inventors discovered that *S. cerevisiae* telomeres repress, or silence, expression of genes located nearby (Example I). Silencing of telomeric genes is due to a structurally distinct chromatin domain whose formation initiates at the telomere (Example III). Evidence for this specialized chromatin structure includes: identification of mutations in the histone H3 and H4 genes which relieve telomeric silencing (Example II), the finding that telomere-adjacent chromatin contains histone H4 in a hypoacetylated state compared to H4 in actively transcribed chromatin (Braunstein et al., 1993), and the relative inaccessibility of telomere-proximal DNA to in vivo modification by the *E. coli* dam methyltransferase protein (Gottschling, 1992). At least six additional gene products, including the telomere DNA binding protein, RAP1, are required for telomeric silencing (Aparicio et al., 1991; Kyrion et al., 1993).

In order to identify genes in *S. cerevisiae* that are important for telomere function, the inventors developed and used a novel screening method to identify genes that, when expressed at high levels, suppress telomeric silencing. This screen lead to the identification of the gene TLC1 (telomerase component 1), one of the components of the present invention, along with several other novel genes.

TLC1 encodes the template RNA of telomerase, a ribonucleoprotein required for telomere replication in a variety of organisms. The discovery of TLC1 is the first clear evidence that shows telomerase exists in *S. cerevisiae*. This finding will facilitate further telomerase studies and screening assays to identify activators or inhibitors with potential for modulating telomerase activity, as may ultimately be used in a clinical setting.

The present discoveries may be utilized in conjunction with certain techniques that are well-known in the biological arts and that are further described in the following sections.

A. Biological Functional Equivalents

Modification and changes may be made in the structure of telomerase-associated polypeptides and still obtain molecules having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules, receptors, RNA molecules, chromosomal ends and the like. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, the same considerations may be employed to create a protein or polypeptide with countervailing (e.g., antagonistic) properties. It is thus contemplated by the inventors that various changes may be made in the sequences of the telomerase-associated proteins or peptides disclosed herein (or their underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where smaller peptides are concerned, it is contemplated that relatively few amino acids may be changed within a given peptide. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites or key binding regions, such residues may not generally be exchanged.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. Thus, it is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein (Table 1) for use in such embodiments, as well as for other uses, such as in the design of probes and primers and the like.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

U.S. Pat. No. 4,554,101 (Hopp, incorporated herein by reference) also teaches the identification and preparation of epitopes from primary amino acid sequences on the basis of hydrophilicity. Through the methods disclosed in Hopp one of skill in the art would be able to identify epitopes from within the telomerase-associated amino acid sequences disclosed herein. Such regions would also be referred to as "epitopic core regions".

Numerous scientific publications have been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101. Moreover, computer programs are currently available to assist with predicting antigenic portions and eptiopic core regions of proteins. Examples include those programs based upon the Jameson-Wolf analysis (Jameson & Wolf, 1998; Wolf et al., 1988), the program PepPlot® (Brutlag et al., 1990; Weinberger et al., 1985), and other new programs for protein tertiary structure prediction (Fetrow & Bryant, 1993). The identification of epitopic regions from within the telomerase-associated sequences allows the ready generation of specific antibodies.

B. Site-Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes a telomerase-associated component. An oligonucleotide primer bearing the desired mutated sequence is prepared, this primer is then annealed with the single-stranded vector, and subjected to DNA polymerizing enzymes such as $E.$ $coli$ polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as $E.$ $coli$ cells, and clones are selected which include recombinant vectors bearing the mutated sequence arrangement.

The preparation of sequence variants of the selected telomerase-associated gene using site-directed mutagenesis is provided as a means of producing potentially useful species and is not meant to be limiting as there are other ways in which sequence variants may be obtained. For example, recombinant vectors encoding a desired telomerase-associated gene may be treated with mutagenic agents to obtain sequence variants, as used in the mutagenesis of plasmid DNA using hydroxylamine.

C. Nucleic Acid Hybridization

In Southern analysis, membrane-bound, denatured DNA fragments are hybridized to a labeled DNA probe. Following this hybridization, the membrane is washed in order to remove nonspecifically bound probe, leaving only probe that is specifically base-paired to the target DNA. By controlling the stringency of the washing conditions, different levels of probe-target DNA complementarity may be detected.

High stringency conditions are useful in order to identify DNA fragments with little mismatch, even close to and including 100% complementarity to the probe DNA. Low stringency conditions are used to identify sequences that are related, though not identical, to the probe DNA, e.g., members of a multigene family, or a single gene in a different organism.

Preferred hybridization conditions are, currently, those that use a buffer of 5×SSC, 0.5%(w/v) blocking reagent, 0.1%(w/v) N-lauroylsarcosine, Na-salt, 0.02% (w/v) SDS and 50%(w/v) formamide, with hybridization at 42° C. overnight. The high stringency washing conditions involve washing the blot twice for 5 minutes with Blot Wash #1 (2×SSC, 0.1%(w/v) SDS), and then washing twice for 15 minutes with Blot Wash #2 (0.1×SSC, 0.1%(w/v) SDS) at 55° C.

For low stringency hybridization, the hybridization conditions remain using 5×SSC, 0.5%(w/v) blocking reagent, 0.1%(w/v) N-lauroylsarcosine, Na-salt, 0.02%(w/v) SDS and 50% (w/v) formamide, with hybridization at 42° C. overnight. The low stringency washing conditions involve using Blot wash #2 as 0.2×SSC, 0.1%(w/v) SDS at 45° C. In the low stringency protocols, a certain limited variation in the conditions may be necessary to achieve optimal conditions, on a case-by-case basis. Such optimization is standard and routinely practiced by those of skill in the art.

D. Protein Expression

To express a recombinant telomerase-associated RNA or protein component in accordance with the present invention one would prepare an expression vector that comprises the telomerase-associated component under the control of one or more promoters. The "upstream" promoters stimulate transcription of the DNA and promote expression of the encoded recombinant protein or RNA unit. This is the meaning of "recombinant expression" in this context.

Many standard techniques are available to construct expression vectors containing the appropriate nucleic acids and transcriptional/translational control sequences in order to achieve RNA or protein expression in a variety of host-expression systems. Cell types available for expression include, but are not limited to, bacteria, such as $E.$ $coli$ and $B.$ $subtilis$ transformed with recombinant bacteriophage DNA, plasmid DNA or cosmid DNA expression vectors.

Certain examples of prokaryotic hosts are $E.$ $coli$ strain RR1, $E.$ $coli$ LE392, $E.$ $coli$ B, $E.$ $coli$×1776 (ATCC No. 31537) as well as $E.$ $coli$ W3110 (F-, lambda-, prototrophic, ATCC No. 273325); bacilli such as $Bacillus$ $subtilis$; and other enterobacteriaceae such as $Salmonella$ $typhimurium$, $Serratia$ $marcescens$, and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, $E.$ $coli$ is often transformed using pBR322, a plasmid derived from an $E.$ $coli$ species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392. Further useful vectors include pIN vectors; and pGEX vectors, for use in generating glutathione S-transferase (GST) soluble fusion proteins for later purification and separation or cleavage.

Those promoters most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling a skilled worker to ligate them functionally with plasmid vectors.

Naturally, in certain embodiments, yeast (e.g., Saccharomyces, Pichia) transformed with recombinant yeast expression vectors containing telomerase-associated RNA or protein coding sequences will be preferred in certain embodiments.

For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In yeast, any plasmid vector containing a yeast-compatible promoter, an origin of replication, and termination sequences is suitable. However, preferred recombinant expression vectors include pYPGE-2, as described by Brunelli & Pall (1993).

In addition to microorganisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the telomerase-associated coding sequences.

In a useful insect system, *Autograph californica* nuclear polyhidrosis virus (AcNPV) is used as a vector to express foreign genes. The virus grows in *Spodoptera frugiperda* cells. The telomerase-associated protein or RNA coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Patent No. 4,215,051 (Smith)).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used.

Expression vectors for use in such cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and often desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing telomerase-associated RNA or proteins in infected hosts.

Specific initiation signals may also be required for efficient translation of telomerase-associated component coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in phase (or in-frame) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

For long-term, high-yield production of recombinant proteins, stable expression is preferred. For example, cell lines that stably express constructs encoding telomerase-associated components may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosophoribosyltransferase, in tk-, hgprt- or aprt-cells, respectively. Also, antimetabolite resistance can be used as the basis of selection for dhfr, that confers resistance to methotrexate; gpt, that confers resistance to mycophenolic acid, neo, that confers resistance to the aminoglycoside G-418; and hygro, that confers resistance to hygromycin.

E. Monoclonal Antibody Generation

Means for preparing and characterizing antibodies are well known in the art (See, e.g., Antibodies: A Laboratory Manual, Cold Spring Harbor Laboratory, 1988; incorporated herein by reference).

The methods for generating monoclonal antibodies (MAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified telomerase-associated protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

A molecular cloning approach may also be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Position Effect at S. Cerevisiae Telomeres

Position effect is a term used to describe phenomena in which a gene's behavior is affected by its location on the chromosome (Lima-de-Faria, 1983b). The change in behavior can be manifested in a variety of ways, such as a difference in phenotype, transcription level, recombination frequency, or replication timing. Although position effects have been reported in insects, plants, and mice, most studies have been carried out in Drosophila, where euchromatic genes translocated near or within centromeric heterochromatin come under a position effect, typically exhibiting phenotypic repression (Spofford, 1976). More recently, in S. cerevisiae the silent mating type loci, HML and HMR, have been shown to exert a position effect on the transcription of nearby genes (Brand et al., 1985; Mahoney and Broach, 1989; Schnell and Rine, 1986).

Telomeric DNA in ciliates, humans, and probably other eukaryotes, facilitates the complete replication of linear DNA molecules by serving as substrates for telomerase (Zakian, 1989; Blackburn, 1990). Telomeres act as chromosome "caps"; in contrast to ends generated by chromosome breakage, telomeres are protected from exonucleolytic degradation and end-to-end fusions. Telomeres are also implicated in establishing nuclear organization by engaging in associations with other telomeres and with the nuclear envelope (Agard and Sedat, 1983; Lima-de-Faria, 1983a).

In S. cerevisiae, the simple DNA repeat ($TG_{1-3}$) is found at the ends of all linear chromosomes (Shampay et al., 1984;

Walmsley et al., 1984). The repeated sequence is necessary and sufficient in cis to provide telomere function in vivo (Wellinger and Zakian, 1989): telomeric repeats are required at each end of a DNA molecule in order for it to be maintained in a linear form in yeast (Lundblad and Szostak, 1989; Pluta and Zakian, 1989). Examination of chromosomal ends reveals a heterogeneity in the number of ($TG_{1-3}$) repeats at individual telomeres both within and between strains, with an average of ~300 bp (Shampay and Blackburn, 1988; Walmsley and Petes, 1985). In addition to the ($TG_{1-3}$) repeats at the ends of chromosomes, most yeast telomeres bear middle repetitive elements called telomere associated sequences (Chan and Tye, 1983a; Chan and Tye, 1983b).

In S. cerevisiae there are two types of telomere associated sequences: Y' is a highly conserved sequence that exists in a long (~6.7 kbp) and short form (5.2 kbp), whereas X is less well conserved and ranges in size from 0.3 to 3.8 kbp. The sequences can occur in tandem arrays near the ends of the chromosome, where they are separated from one another by tracts of ($TG_{1-3}$) 50–130 bp in length (Walmsley et al., 1984). It is unclear whether the X and Y' sequences serve a particular function, since they are absent from some telomeres (Jager and Philippsen, 1989; Zakian and Blanton, 1988); however in humans and Drosophila telomere associated sequences have been implicated in meiotic chromosome pairing and the establishment of heterochromatin (Ellis et al., 1989; Young et al., 1983).

In order to understand better the properties of telomeres, the inventors began an investigation to map in vivo protein-DNA interactions at chromosomal termini in S. cerevisiae. The inventors chose to examine a single telomere by introducing a unique marker adjacent to the tract of ($TG_{1-3}$) DNA at the end of a chromosome. However, early in the course of such investigations it was realized that the transcription of the gene used to mark the telomere was altered. In this example, the inventors demonstrate that in S. cerevisiae, telomeres without an X or Y' exert a position effect on the expression of genes located nearby.

When URA3, TRP1, HIS3, or ADE2 was located near a telomere, the gene's transcription was repressed. However, the expression of each gene was reversible between states of repressed and active transcription. Both transcriptional states were inherited mitotically in a semi-stable manner. Switching between the states appears to be under epigenetic control. At a locus ~20 kbp from the telomere, transcription of URA3 was not repressed, even when an 81 bp tract of ($TG_{1-3}$) sequence was located adjacent to the gene. However, the internal 81 bp tract spontaneously became a telomere at a frequency of ~$10^{-6}$, and in so doing repressed the expression of the URA3 gene. This example therefore provides genetic methods for analyzing telomere structure, and formation of new telomeres from internal telomeric DNA sequences.

A. Material & Methods

1. Construction of Plasmids

Plasmid pVII-L URA3-TEL was constructed in two steps, beginning with the plasmid pYTCA-1. Plasmid pYTCA-1 has the 125 bp Hae III-Mnl I fragment from pYt103, that contains 81 bp of ($TG_{1-3}$) sequence derived from a yeast telomere, in the Sma I site of pUC9 (Runge and Zakian, 1989; Shampay et al., 1984). The ($TG_{1-3}$) sequence is oriented such that digestion of pYTCA-1 with Eco RI will yield an end that is a substrate for telomere formation in yeast. Plasmid pYTCA-1 was digested with Hind III and Hinc II and a 1.1 kbp Hind III-Sma I DNA fragment that contains the URA3 gene was ligated between these sites (Rose et al., 1984) to form pURA3-TEL. Plasmid YA4-2 (obtained from V. Williamson) contains the ADH4 gene on an Eco RI-Bgl II fragment inserted within the Eco RI-Bam HI sites of pUC8 (Walton et al., 1986; Williamson and Paquin, 1987). Plasmid pURA3-TEL was digested with Hind III and the 1.2 kbp Hind III fragment of pYA4-2 was ligated within, such that the Sal I site of the inserted fragment was positioned away from the URA3 gene. This results in plasmid pVII-L URA3-TEL.

Plasmid adh4::URA3-TEL was also constructed in two steps. First, pVII-L URA3-TEL was digested with Bam HI, the DNA ends were made blunt by treatment with T4 DNA polymerase and dNTPs, and the plasmid was recircularized. Next, this new plasmid, pVII-L URA3-TEL (-Bam HI), was digested with Eco RI, the ends were made blunt as before, and ligated to the blunt-ended 1.8 kbp Hind III-Eco RI fragment of YA4-2. Plasmids with the Bam HI site furthest from the ($TG_{1-3}$) sequence have the correct orientation of the insert.

Plasmid adh4::URA3 was constructed by digesting pVII-L URA3-TEL with Bam HI, making the ends blunt, then treating the plasmid with Eco RI; the 1.8 kbp Hind III-Eco RI fragment of YA4-2 with only its Hind III end made blunt, was ligated into the plasmid.

Plasmid V-R URA3-TEL was made by digesting pVII-L URA3-TEL with Hind III and replacing the ADH4 derived sequence with the 2.8 kbp Hind III fragment of plasmid B6-10H, such that the Eco RI site of the insert was furthest from the URA3 gene. Plasmid B6-10H (obtained from C. Newlon) contains ~19 kbp of unique DNA sequence from the region adjacent to the subtelomeric Y' repeat on the right arm of chromosome V (Chan and Tye, 1983b; McCarroll and Fangman, 1988). The 2.8 kbp Hind III fragment from B6-10H used in this study is unique sequence ~5.5 kbp from the Y' repeat.

Plasmid pULA was constructed in a two step process. First, the 1.1 kbp Hind III-URA3 fragment was inserted into the Hind III sit of a pUC9 derivative, in which the Pst I site has been deleted. The resulting plasmid was digested with Pst I and Nsi I; the coding sequence of URA3 was removed and replaced with a 4 kbp Pst I fragment containing LEU2 isolated from YEP13 (Broach et al., 1979).

Plasmids pADHIS3(+), pADHIS3(-), pADADE2(+), pADADE2(-), pADTRP1(+), and pADTRP1(-) were all constructed by inserting the wild-type HIS3, ADE2, or TRP1 genes in either orientation, into the Bam HI site in the vector VII-L URA3-TEL. For HIS3: A 1.85 kbp Bam HI fragment from plasmid pHIS3 (Struhl, 1985; obtained from K. Runge) was inserted into the Bam HI site of VII-L-URA3-TEL. Two plasmids are formed: pADHIS3(+), in which the HIS3 gene is in the same transcriptional orientation as the URA3 gene, and pADHIS3(-) which has the HIS3 gene in the opposite orientation.

For ADE2, a 3.6 kbp Bam HI fragment in plasmid pL909 (obtained from R. Keil), was inserted into the Bam HI site of the vector VII-L URA3-TEL. The resulting plasmids were designated pADADE2(+), indicating ADE2 transcription in the same direction as the adjacent URA3 gene, or pADADE2(-) for ADE2 transcription in the opposite direction.

For TRP1, 0.85 kbp Eco RI-Bgl II fragment from plasmid YRp7 (Struhl et al., 1979) was blunt-ended with T4 DNA polymerase and inserted into the Bam HI site in VII-L URA3-TEL which also had the Bam HI ends filled-in with T4 DNA polymerase. The plasmid with the TRP1 gene in the same transcriptional orientation as URA3 was denoted pADTRP1(+), while the plasmid in which TRP1 transcription was in the opposite direction as URA3 transcription was pADTRP1(-).

Plasmid TRP1/RS306 was made by inserting the Eco RI-Bgl II fragment of TRP1 into the Eco RI-Bam HI site of pRS306 (Sikorski and Hieter, 1989).

E. coli strain MC1066 (r⁻ m⁻, trpC9830, leub600, pyrF::Tn5, lacΔX74, strA, galU, galk) was used as a host for all plasmids (Casadaban et al., 1983). LB medium with ampicillin (100 μg/ml) and M9 medium supplemented with appropriate amino acids were prepared as described by Maniatis et al. (Maniatis et al., 1982). Complementation of MC1066 mutations by the homologous yeast genes was used when applicable.

2. Yeast Strains & Methods

Media used for the growth of S. cerevisiae were based on synthetic complete media as described by Sherman et al. (Sherman et al., 1986) to which uracil (35 mg/l), tyrosine and lysine (60 mg/l), and leucine and isoleucine (80 mg/l) had been added. One gram of 5-FOA per liter of media was added to determine resistance to 5-FOA. Medium for ADE2 red/white sectored colony growth was as described (Klapholz and Esposito, 1982) except arginine was 50 mg/l and threonine was 100 mg/l. Colonies were grown for three days at 300, then incubated for 1–2 weeks at 4° for full color development. S. cerevisiae transformation was performed using the lithium acetate procedure (Ito et al., 1983).

To delete the URA3 gene, strain 1GA2 (MATα ade2 ade5 leu2-3,112 lys5 cyh2$^r$ can1$^r$; made in this study) was transformed with Hind III digested pULA (see above), and Leu+ colonies were isolated. The structure of the chromosome from which URA3 was deleted was checked by Southern analysis in Leu+ isolates that also tested Ura⁻. DG20 is the ura3Δ::LEU2 derivative of 1GA2. Strains DG26, DG27, DG28, and DG30 were constructed by transforming DG20 with different DNA fragments: DG26 with plasmid adh4::URA3-TEL cleaved by Bam HI and Sal I, DG27 with plasmid adh4::URA3 cleaved by Bam HI and Sal I, DG28 with plasmid VII-L URA3-TEL cleaved by Sal I and Eco RI, and DG30 with plasmid V-R URA3-TEL cleaved by Eco RI. All transformants were selected as being both Ura⁺ and Leu⁺. The expected structure for each transformant was verified by Southern analysis. In each case, total genomic DNA was cleaved twice, once by Bgl II and once by Pst I. The Southern blots of DG26, DG27, and DG28 were hybridized with a series of DNA probes which included: the 1.1 kbp Hind III URA3 gene, the proximal ADH4 probe, and the distal ADH4 probe. The structure of DG30 was verified in a similar manner using probes from plasmid B6-10H.

Strains UCC41, UCC42, UCC45, UCC61, UCC62, UCC63, UCC81, UCC82, and UCC83 were derived from strain 4-1 (MATα lys2 his4 trp1Δ ade2 leu2-3,112 ura3-52 made in this study), by transforming strain 4-1 with different DNA fragments and selecting for Ura⁺ colonies: UCC41 with pADADE2(+) cut with Sal I and Not I, UCC42 with pADADE2(−) cut with Sal I and Not I, UCC45 with pL909 cut with Bam HI, UCC61 by pADTRP1(+) cut with Sal I and Eco RI, UCC62 with pADTRP1(−) cut with Sal I and Eco RI, UCC81 with VII-L URA3-TEL cut with Sal I and Eco RI, UCC82 with adh4::URA3 cut with Bam HI and Sal I, UCC83 with pUCU (contains the 1.1 kbp Hind III fragment containing the URA3 gene in pUC9) cut with Hind III, and UCC63 with pTRP1/RS306 digested with Nde I.

Strains UCC51, UCC52, UCC53, UCC74, UCC75, and UCC76 were derived from strain 3482-16-2 (MATa, met2, his3D-1, leu2-3,112, trp1-289, ura3-52, obtained from L. Hartwell), by transforming strain 3482-16-2 with different DNA fragments, again selecting for Ura⁺ colonies: UCC51 by pADHIS3(+) cut with Sal I and Eco RI, UCC52 with pADHIS3(−) cut with Sal I and Eco RI, UCC53 with pHIS3 cut with Bam HI, UCC74 with VII-L URA3-TEL cut with Sal I and Eco RI, UCC75 with adh4::URA3 cut with Bam HI and Sal I, and UCC76 with pUCU cut with Hind III. The expected chromosome structure of each transformant was verified by Southern analysis.

3. Selection for 5-FOA$^R$ Colonies

Cells were grown into colonies for 2–3 days at 30° on YC plates or plates that lacked uracil. Colonies were picked and resuspended in 1.0 ml H$_2$O, serial dilutions were made and an appropriate amount of cell suspension was spread to produce ~200 colonies/plate. Cells were spread onto 5-FOA$^R$ plates for selection, and YEPD, YC, or synthetic complete media plates to determine the total number of colony forming cells. The number of colonies on a plate was determined after 3–4 days of growth at 30°.

4. Analysis of Nucleic Acids from S. Cerevisiae

S. cerevisiae cells were grown in 5 ml of YEPD to stationary phase, and total genomic DNA was isolated by disrupting cells with glass beads as described (Runge and Zakian, 1989). Methods for cleavage of total genomic DNA with restriction enzymes, gel electrophoresis, and Southern hybridizations have been previously described (Gottschling and Cech, 1984; Runge and Zakian, 1989). For rehybridization studies, probes were removed from blots with boiling water.

Cells were grown to a density of 0.5–2×10$^7$ cells/ml and total RNA was isolated as described (Sherman et al., 1986), except that the nucleic acids were precipitated with 2 vol. ethanol and resuspended in water at a concentration of 1–10 mg/ml. RNA concentration was determined by UV spectroscopy. Ten or twenty μg of total RNA was separated by electrophoresis on a 1.5% agarose-formaldehyde-MOPS gel and transferred to nitrocellulose or nylon membrane as described (Ogden and Adams, 1987; Wahl et al., 1987). Strand specific RNA probes were made by in vitro transcription of linearized plasmids with T7 polymerase in the presence of [α-$^{32}$P] CTP (~600 Ci/mmole) (Wahl et al., 1987).

Plasmids used for transcription were derivatives of pVZ1 (Eghtedarzadeh and Henikoff, 1986); the URA3 probe contained the Pst I-Nco I fragment of the gene, the HIS3 probe contained the Bam HI-Kpn I fragment of the gene, the TRP1 probe contained the Hind III-Bgl II fragment of the gene. Northern hybridization was performed as described (Wahl et al., 1987). Multiple exposures of autoradiograms were scanned with an LKB Ultroscan XL densitometer to determine the relative levels of URA3 or HIS3 mRNA.

B. Results

1. Marking a Telomere with URA3

URA3, which is required for uracil biosynthesis, is normally found near the centromere on chromosome V. The entire gene, including the cis elements required for its normal regulation, is located on a 1.1 kbp Hind III-Sma I fragment (Rose et al., 1984). This fragment was used in all of the URA3 constructs described in this example. Studies were carried out in haploid yeast strains that contained either of two non-reverting ura3⁻ alleles: ura3-52, which contains a Ty transposon insertion within the URA3 coding sequence (Rose and Winston, 1984) (UCC series), or ura3Δ::LEU2, in which the entire coding region of URA3 on chromosome V has been replaced by the LEU2 gene (DG series).

ADH4 is the most distal gene on the left arm of chromosome VII (Walton et al., 1986). Fragment mediated transformation (Rothstein, 1983) was used to introduce URA3 onto the left arm of chromosome VII, to create the haploid strain DG28. In DG28, a portion of ADH4 and the DNA distal to it are deleted and replaced with URA3 and an 81 bp stretch of ($TG_{1-3}$). After transformation into yeast, the 81 bp are extended to ~300 bp of ($TG_{1-3}$), a length typical of all other telomeres in this strain. Transcription of the URA3 gene is towards the telomere, with its promoter ~1.3 kbp from the end of the chromosome.

2. Position Effect at Yeast Telomeres

The chemical 5-fluoro-orotic acid (5-FOA) can be used in the negative selection of URA3 expression; 5-FOA is converted into a toxic substance by the URA3 gene product (Boeke et al., 1987). The constitutive level of URA3 expression in a cell is normally sufficient to yield cells sensitive to 5-FOA (5-$FOA^S$). Resistance to 5-FOA (5-$FOA^R$) can be used as a method to select for cells that have lost or mutated the wild type URA3 gene. Therefore, sensitivity to 5-FOA was used as a means to determine URA3 expression as a function of chromosomal location.

The frequency of a spontaneous 5-$FOA^R$ allele arising at the normal URA3 locus is ~$10^{-7}$ (1GA2; Boeke et al., 1984). Since 5-$FOA^R$ cells derived in this way have mutations in the URA3 gene, they are Ura$^-$ (i.e. unable to grow in the absence of uracil). In contrast, when cells with URA3 at the telomere (DG28) were pre-grown in media containing uracil (no selection for URA3 expression) and then plated for single colonies onto 5-FOA, 33% of the cells gave rise to 5-$FOA^R$ colonies (DG28). Moreover, when these 5-$FOA^R$ colonies were replica-plated to media that lacked uracil, cells were able to grow. That is, the cells were still URA3$^+$. These results suggested that the 5-$FOA^R$ exhibited by these cells was not due to an inordinately high mutation rate in or loss of the URA3 gene, but rather that URA3 expression at the telomere was reduced below the killing threshold of 5-FOA. Nonetheless, cells in an 5-$FOA^R$ colony still had the ability to produce sufficient URA3 gene product to overcome a lack of uracil in the medium.

When DG28 cells were pre-grown in medium lacking uracil (selecting for URA3 expression), one out of $10^5$ cells produced a colony on plates containing 5-FOA. Once again, each of these 5-$FOA^R$ colonies was still URA3$^+$. Taken together these results suggested that under non-selective growth conditions expression of the URA3 gene in about one-third of the DG28 cells was sufficiently repressed to allow growth on 5-FOA, but that under selection, expression of the telomere-linked URA3 gene is still possible in many or all of the cells. The resistance to 5-FOA of cells with URA3 at the VII-L telomere has been observed in a number of strains. While there have been strain specific differences in the fraction of 5-$FOA^R$ cells when cells were pre-grown under non-selective conditions, these values (0.10–0.90) were all within an order of magnitude of one another (UCC74 & UCC81), and indicate that repression of a telomere-linked URA3 gene on VII-L is a general phenomenon.

This unexpected behavior of the URA3 phenotype (colonies that were 5-$FOA^R$ yet still Ura$^+$) caused the inventors to examine the steady state levels of URA3 mRNA in cells with the gene either at its normal chromosomal position or at the telomere of VII-L. RNA was isolated from cells grown under either selective or non-selective conditions for URA3 expression. Consistent with earlier studies, cells with URA3 at its normal chromosomal locus had a modest increase in URA3 mRNA levels (~1.4-fold) when grown under selective conditions compared to growth under non-selective conditions (strain 1GA2) (Bach et al., 1979; Lacroute, 1968; Rose and Botstein, 1983). However, a major difference in URA3 mRNA levels was observed in cells with the URA3 gene at the telomere. RNA levels in DG28 cells grown under non-selective conditions were one-fifth that of cells with URA3 at its normal locus (DG28 & 1GA2).

In contrast, under selective conditions, RNA levels in cells with URA3 at the telomere were equivalent to the level in cells with URA3 at its normal locus (strains DG28 & 1GA2, INDUC). Thus consistent with the 5-$FOA^R$ phenotype, the constitutive level of URA3 RNA is significantly reduced when the gene is located next to the telomere at VII-L compared to when it is at its normal chromosomal locus. Yet under selection, the level of URA3 RNA at the telomeric locus in DG28 cells is virtually the same as when URA3 is at its normal chromosomal locus.

In order to determine whether repression occurs at telomeres other than VII-L, strain DG33 was constructed. This strain has the URA3 gene inserted near the telomere on the right arm of chromosome V (V-R), in a manner similar to that for URA3 on VII-L in strain DG28. Determination of the fraction of 5-$FOA^R$ colonies and analysis of mRNA levels in strain DG33 indicates that constitutive expression of URA3 is also repressed at this telomere. The difference in the fraction of 5-$FOA^R$ cells between the two strains (0.33 for DG28, 0.04 for DG33) presumably reflects differences between individual telomeres in terms of their specific chromosomal environments.

URA3 was also repressed when positioned near the telomere of a telocentric version of chromosome IV or of a 60 kbp artificial linear chromosome. Thus the ability to repress the expression of a nearby URA3 gene appears to be a general property of S. cerevisiae telomeres.

3. Repression by Proximity to Telomeres Occurs for Other Genes

In general, a region of the chromosome that exerts a position effect does so in a gene non-specific manner. Therefore the inventors examined whether genes other than URA3 were repressed by proximity to a telomere. The TRP1, HIS3, or ADE2 gene was inserted between URA3 and the telomere DNA sequence at the Bam HI site of plasmid 'VII-L URA3-TEL'. Each gene was inserted in both orientations. These constructs were then used to introduce TRP1, HIS3, or ADE2 adjacent to the VII-L telomere, by selecting for URA3 expression. In selecting only for URA3 expression during strain construction, no selective pressure was placed upon the telomeric TRP1, HIS3, or ADE2 genes.

In strains bearing a telomere-linked copy of TRP1, and grown under non-selective conditions, TRP1 RNA was undetectable by Northern analysis, regardless of the gene's orientation at the telomere (UCC61 & UCC62). By examining very long exposures of the autoradiograms the inventors estimated that the RNA level from the telomeric TRP1 was ≦1% of the RNA level when the same TRP1 fragment was located at an internal chromosomal site within the normal URA3 locus on chromosome V.

Colonies of cells with TRP1 at the telomere or at an internal locus were grown on non-selective medium and then plated in serial dilution to medium that lacked tryptophan. All of the cells with TRP1 at an internal site on the chromosome (UCC63) formed colonies on plates lacking tryptophan. However, those with TRP1 at the telomere showed a reduction in colony forming ability on plates lacking tryptophan (UCC61 & UCC62). Only $10^{-2}$ cells with TRP1 oriented such that transcription was directed towards the telomere formed colonies in the absence of tryptophan (UCC61). When TRP1 transcription was away from the telomere, ~$10^{-3}$ cells formed colonies (UCC62). In addition, the UCC61 cells formed robust colonies in three days, while the UCC62 colonies were smaller.

The telomeric TRP1 RNA levels and plating efficiency data indicate that under non-selective growth conditions the majority of cells with TRP1 near the telomere had very low or no TRP1 expression. In all three TRP1 constructs described, a portion of the UAS/promoter elements found at the normal TRP1 locus was missing (Kim et al., 1986). While these missing elements have no apparent effect on the ability of cells to grow without tryptophan when TRP1 is at an internal locus, their absence may explain why TRP1 expression was more severely repressed at the telomere compared to the expression of URA3 at the telomere.

When HIS3 was placed at the telomere and its transcription was directed away from the telomere, there was a detectable reduction in RNA levels compared to when the gene was at its normal chromosomal locus (UCC52). When the direction of transcription at the telomere was reversed, there was a slight increase in RNA levels (UCC51). Phenotypically, there was a modest (less than ten-fold) reduction in plating efficiency on media lacking histidine for UCC52, but no effect on UCC51, a result consistent with the relative RNA levels.

4. Transcriptional Repression at Telomeres is Reversible and Inherited in a Semi-Stable Fashion As shown above, when the URA3 gene was telomere-linked (DG28), cells from colonies that were 5-FOA$^R$ could still grow when placed on medium lacking uracil. Conversely, cells grown in the absence of uracil were able to form colonies when placed on medium containing 5-FOA. These results suggested that a telomere-linked URA3 gene could switch between repressed and active transcriptional states. The ADE2 gene provides a convenient color assay for determining whether the gene is expressed; ADE2$^+$ colonies are white, whereas ade2$^-$ colonies are red (Roman, 1956). Thus, expression of a telomere-linked ADE2 gene can be monitored by determining the color of colonies produced by cells carrying this marked telomere.

When the ADE2 gene was placed at the telomere such that ADE2 transcription was directed towards the telomere (UCC41), all colonies contained red and white sectors. This sectored phenotype indicated a switch between the repressed and active transcriptional states of ADE2 during colony development. The colonies displayed a wide range of sectoring phenotypes. Some colonies were primarily white (active) and gave rise to red (repressed) sectors near the periphery. An equal number of colonies were primarily red with white sectors near the periphery. Intermediate levels of sectoring between these two extremes were also readily visible.

In some colonies multiple switches between transcriptional states can be inferred. For example, a predominantly red colony has a large white sector. Within this white portion, red sectors are clearly visible. The reversibility was further demonstrated by isolating cells within a white (or red) sector and plating them for single colonies. Each new colony contained red and white sectors. In contrast with the results in UCC41, when ADE2 transcription was directed away from the telomere (UCC42), no red sectors were observed in a colony.

These results demonstrate that the expression of a telomere-linked ADE2 gene can switch between an active and repressed state, and that the expression state is semi-stable during mitotic growth. Based on the results with URA3, TRP1, and HIS3, the inventors infer that the control of ADE2 expression is at the transcriptional level. However, it was not possible to determine the level of RNA produced at the telomere-linked ADE2, because an identical sized transcript was made by the ade2 allele at its normal chromosomal locus.

The probability of a telomere-linked ADE2 gene (UCC41) being in an active (repressed) transcriptional state was estimated from the fraction of predominantly white (red) colonies. Five colonies of UCC41 cells grown on non-selective medium, were plated for single colonies onto non-selective medium. Approximately equal numbers of colonies were found that had primarily red centers giving rise to white sectors, and primarily white centers that gave rise to red sectors. This result indicates that a telomere-linked ADE2 gene on VII-L has an about equal probability of being in an active or repressed transcriptional state.

However, when five colonies of UCC41 were pre-grown in the absence of adenine (selecting for ADE2 expression) and then plated onto non-selective plates, there were up to nine times as many colonies with white centers than with red centers. Closer examination of colonies with white centers revealed that red sectors generally did not appear until very close to the periphery of the colony. This observation suggested that the active expression state of ADE2 was stable for many generations. The distance from the center of these colonies to the points at which multiple red sectors appeared was measured. This value was used to compute the fraction of the total colony volume (assuming a half sphere geometry for a colony) that comprised the non-sectored center of the colony. The number of cells within this region of the colony was calculated (assuming there are ~$10^8$ cells in a colony), and this value was used to derive the number of cell divisions required to produce the quantity of white cells from a single progenitor. From these calculations the inventors estimate that the active transcriptional state of ADE2 is inherited for 15–20 generations in these colonies.

The phenotypic switching displayed by ADE2 at a telomere was also observed with the URA3 gene using a single cell analysis. Freshly budded cells grown on medium containing 5-FOA were moved by micromanipulation to a region of the plate where they could develop into full colonies. The majority (81/119) of the cells formed colonies, but 8% (9/119) of the cells formed microcolonies consisting of 4–8 cells. Microcolonies were not detected in a control study in which no 5-FOA was present in the medium. Therefore the microcolonies presumably represent cells arrested in growth on the 5-FOA due to the URA3 gene being switched to an actively expressing state after budding. The cells that did not form colonies may have been progeny of cells that had switched to an actively expressing state prior to budding, or were inviable as a result of the micromanipulation method. A rough value for the switching of URA3 from a repressed to an active state in DG28 cells was calculated by dividing the number of cells that formed microcolonies (9) by the total number of colony forming cells (9+81), which yields an estimated switch rate of $10^{-1}$ per division.

5. The Distance Over which Telomeres Exert a Position Effect on URA3 Expression

In order to obtain an estimate of the distance over which the telomere exerted a position effect, the URA3 gene was placed ~20 kbp from the end of the left arm of chromosome VII by insertion within the ADH4 locus (DG27). Based on both RNA analysis and the frequency of 5-FOA$^R$ colony formation, cells with URA3 inserted within ADH4 had levels of URA3 expression comparable to cells with URA3 at its normal locus, under either selective or non-selective growth conditions. Thus on the left arm of chromosome VII the telomeric repression was no longer detectable when URA3 was ~20 kbp from the telomere.

In order to determine whether repression occurred over distances less than 20 kbp from the telomere, the constructs described above, in which TRP1, HIS3, or ADE2 was inserted between URA3 and the telomere DNA sequence, were analyzed for URA3 expression. The inserted genes increased the distance between URA3 and the telomere by 0.85, 1.8, or 3.6 kbp, respectively.

Cells with each of the constructs were pre-grown in complete synthetic medium, thus no selection for the expression of URA3 or the inserted gene was introduced. The cells were then plated to medium containing 5-FOA and the fraction of 5-FOA$^R$ colonies was determined. The analysis revealed that as the distance between URA3 and the telomere was increased, the level of repression decreased. For instance, insertion of the 0.85 kbp TRP1 fragment yielded 5-FOA$^R$ colonies at a frequency of 0.02–0.14 (UCC61 and UCC62), while insertion of the 3.6 kbp ADE2 fragment yielded $\leq 10^{-5}$ 5-FOA$^R$ cells (UCC41 and UCC42). However, the level of URA3 expression was also influenced by the orientation of the inserted DNA fragment.

This conclusion was best demonstrated by the result with the HIS3 fragment: when transcription of the HIS3 gene was towards the telomere (UCC51), ~$10^{-4}$ cells were 5-FOA$^R$; when HIS3 transcription was away from the telomere (UCC52), 0.26 of the cells were 5-FOA$^R$. The orientation of TRP1 and ADE2 had smaller, but detectable effects on URA3 expression. Thus further studies on the level of URA3 expression as a function of distance from the telomere must take into account both the composition and orientation of the DNA sequences located between the telomere and URA3.

6. Internal Tracts of $(TG_{1-3})$ Do Not Cause Repression, but they Can Become Chromosome Ends and Consequently Cause Position Effect Internal tracts of $(TG_{1-3})$ sequence occur naturally between the telomere associated elements X and Y' and between tandem Y' elements (Chan and Tye, 1983a; Chan and Tye, 1983b). Internal $(TG_{1-3})$ tracts range from 50 to 130 bp in length (Walmsley et al., 1984). In order to determine whether these internal $(TG_{1-3})$ sequences might also exert a position effect, 81 bp of $(TG_{1-3})$ were introduced adjacent to the telomeric side of URA3, within the ADH4 locus (DG26).

RNA levels in these cells were somewhat higher than in cells with URA3 at its normal locus or at the ADH4 locus without $(TG_{1-3})$ (DG26, DG27, & 1GA2). This elevated transcription was true for both constitutive and induced URA3 gene expression. These elevated mRNA levels are probably explained by an enhancer-like activity associated with $(TG_{1-3})$ repeat sequences when they are adjacent to a gene in a non-telomeric location (Runge and Zakian, 1990). Whatever the mechanism responsible for elevated expression, the internal tract of 81 bp of $(TG_{1-3})$ at the ADH4 locus clearly does not cause repression of constitutive expression. These data demonstrate that $(TG_{1-3})$ sequences are not sufficient to cause position effect: the URA3 gene must be positioned near a telomere (or alternatively, near a $(TG_{1-3})$ tract >81 bp) in order for transcription to be repressed.

Consistent with the high level of URA3 expression seen in the RNA analysis, the fraction of 5-FOA$^R$ colonies from cells with URA3 next to the internal tract of $(TG_{1-3})$ and grown in uracil was ~$10^{-6}$ (DG26 CONST). Although this value was low compared to cells with a telomere-linked copy of URA3, it is an order of magnitude greater than the fraction of 5-FOA$^R$ colonies in cells with URA3 at its normal locus (strains 1GA2 & DG26). Replica-plating of the 5-FOA$^R$ colonies derived from DG26 cells revealed that they were all still Ura$^+$ (in contrast to 5-FOA$^R$ colonies arising from cells with URA3 at its normal locus, which were typically Ura$^-$). This phenotype is identical to that seen for the cells with URA3 at the telomere (i.e. DG28), suggesting that the internal $(TG_{1-3})$ sequences might have become telomeric in those cells able to form colonies on 5-FOA.

This hypothesis was confirmed by Southern analysis. In four out of four independent isolates in which DG26 cells gave rise to 5-FOA$^R$ colonies, the URA3 sequences were on a restriction fragment of the size expected for a telomeric location. In addition, Southern hybridization demonstrated that sequences immediately distal to the internal $(TG_{1-3})$ tract were no longer detectable in the 5-FOA$^R$ cells. These results show that internal tracts of $(TG_{1-3})$ sequence can spontaneously become chromosomal ends by a mechanism that results in the deletion of sequences distal to the internal $(TG_{1-3})$ tract. In addition, the results provide independent evidence that the repressed expression of URA3 at the telomere is neither an artifact of transformation, nor a mutation within the URA3 gene or one of its trans activating factors.

C. Discussion

1. Position Effect at Yeast Telomeres

A position effect was demonstrated at the telomeres of *S. cerevisiae* chromosomes. The effect resulted in reduced gene expression of telomere-linked genes as assayed both by amount of stable mRNA and by phenotype. For instance, cells with a telomere-linked URA3 gene were able to grow in the presence of 5-FOA, behavior consistent with a ura3$^-$ phenotype. When ADE2 was telomere-linked many cells produced predominantly red colonies as is characteristic of ade2$^-$ cells. The position effect altered the expression of four out of four Pol II genes: ADE2, HIS3, TRP1, and URA3. In addition the effect was observed at four out of four telomeres, including an artificial linear chromosome. Therefore, it can be concluded that the position effect is a general phenomenon of *S. cerevisiae* telomeres.

The position effect acted upon the URA3 promoter at distances of at least ~4.9 kbp from the telomere, but at ~20 kbp from the left end of chromosome VII the effect was not observed. In addition the influence of distance on position effect strongly depended upon the specific DNA sequences located between URA3 and the telomere and probably other factors that are not yet well understood. For example, the transcriptional activity of ADE2, HIS3, and URA3 was dependent upon the gene's orientation with respect to the telomere. In the process of generating artificially fragmented linear chromosomes, Hegemann et al. report a "leaky" 5-FOA$^R$ phenotype for a URA3 gene located 6–8 kbp from the telomere (Hegemann et al., 1988). In these constructs, most of the 6–8 kbp was the subtelomeric middle repetitive element Y'. The inventors postulate that the reported "leaky" phenotype is due to a telomeric position effect and suggest that telomeric repression can act at a distance of at least 6 kbp, and through a Y' element.

The telomeric position effect appears to be a result of proximity to the end of the chromosome and not simply due to the telomeric DNA sequence $(TG_{1-3})$. Eighty-one base pairs of $(TG_{1-3})$ sequence ~20 kbp from the telomere did not repress URA3 expression. While longer lengths of $(TG_{1-3})$ were not tested at internal loci, one of several strains that were tested for telomeric position effect contained the tel1 mutation. In the tel1 strain, the telomere adjacent to URA3 had a $(TG_{1-3})$ tract of 95–120 bp, yet the level of 5-FOA$^R$ in this strain was similar to that for all other strains tested. Taken together these results argue that the telomere itself, not simply $(TG_{1-3})$ repeats are responsible for telomeric position effect in *S. cerevisiae*.

The repressed state conferred by the telomere was mitotically inherited over a number of generations, but the genes could escape from repression and switch to a state of active transcription. This reversibility was visually demonstrated by the red and white sectored colonies of cells with ADE2 near the telomere (UCC41), and was also supported by the single cell analysis of DG28 cells on 5-FOA. The transcriptional state of a gene, whether repressed or active, appeared to be stable over many generations.

The switching between active and repressed transcriptional states for genes at telomeres is not due to genetic alteration, but rather to an epigenetic switch. Several lines of evidence support this interpretation: 1. The repression was readily reversible, in the presence or absence of selection. 2. There were no differences in DNA structure or copy number of the telomeric genes, as judged by Southern analysis, regardless of whether these haploid cells were grown under conditions that were non-selective, or that selected for expression or repression of the genes. 3. The telomeric position effect was gene non-specific.

Epigenetic variation of gene expression has been observed in plants, insects, mammals, and *S. cerevisiae*. In Drosophila, position effect variegation is observed when a euchromatic gene is moved within or near a heterochromatic region of the chromosome (Eissenberg, 1989; Spofford, 1976). Heterochromatin is a portion of the chromosome which remains visibly condensed throughout interphase of the cell cycle. In contrast, euchromatin decondenses after telophase and appears diffuse during interphase. When the white gene is located near some types of heterochromatin, a 'salt-and-pepper' mosaicism in eye color is observed (Spofford, 1976). This mosaicism is visually analogous to the sectored colonies produced by cells with ADE2 at the telomere, and it could be inferred that similar mechanisms are at work in the two organisms.

In *S. cerevisiae*, epigenetic switching has been reported at the silent mating type locus, HML (Pillus and Rine, 1989). In a wild type cell HMLα is not expressed. However in a sir1 strain, HMLα switches between repressed and expressed states. Current models for the HML switch favor a change in chromatin conformation between the two phenotypic states. Besides changes in chromatin structure, postulated mechanisms of epigenetic variation in plants and mammals include changes in DNA methylation, topology, and nuclear locale (Pedoroff et al., 1989; Holliday, 1987; Monk, 1990; Weintraub, 1985).

Cytological observations in plants, insects, and mammals indicate that telomeres occupy specific regions within the nucleus and are frequently associated with the nuclear envelope (Lima-de-Faria, 1983a; White, 1973). In addition, telomeres are usually packaged as heterochromatin (Fussell, 1975; Traverse and Pardue, 1989). In the single-celled eukaryotes, Oxytricha, Dictyostelium, and Tetrahymena, the DNA adjacent to the chromosome termini are packaged in an orderly array of phased nucleosomes, which is consistent with the presence of a highly ordered chromatin structure (Budarf and Blackburn, 1986; Edwards and Firtel, 1984; Gottschling and Cech, 1984). In Drosophila, P element-mediated transposition of the white gene near the 3R telomere results in mosaic expression of the gene, indicative of a position effect caused by proximity to the heterochromatin observed at this telomere (Hazelrigg et al., 1984; James et al., 1989; Levis et al., 1985).

It is noted that *S. cerevisiae* telomeres have two of the classic features of heterochromatin: telomeres replicate late in S phase (McCarroll and Fangman, 1988), and as shown here, they exert position effect on the expression of nearby genes. The inventors propose that the phenotypic switching of telomere-linked genes in yeast is the result of a competition between the formation of a stable active transcriptional complex and the normal telomeric chromatin structure that prevents gene expression. Such a chromatin structure must originate from the end of the chromosome. In Oxytricha the molecular ends of macronuclear mini-chromosomes are recognized by a heterodimeric protein complex (Gottschling and Zakian, 1986; Price and Cech, 1989). Similar proteins in yeast may form a telomeric structure that is important in establishing the position effect.

The semi-stable, reversible repression (or expression) at yeast telomeres may be analogous to a primitive developmental switch. When cells with a telomere-linked copy of ADE2 were pre-grown under selection for ADE2 expression, most (~80%) subsequently gave rise to colonies of primarily white (transcriptionally active) cells under non-selective growth conditions. The active transcriptional state of ADE2 can be inherited for at least 15–20 generations after removal of selection. This primitive control mechanism for gene expression may be exploited by some organisms to allow developmentally controlled expression of telomere-linked genes. In Trypanosomes, telomeres are the exclusive genomic expression sites for surface antigen genes (reviewed in (Pays and Steinert, 1988). Many telomeres within a cell can carry transcriptionally competent genes, yet only one such gene is expressed at a time. Perhaps the other telomere-linked genes are kept repressed, albeit reversibly, by telomeric position effect.

2. New Telomere Formation

The inventors found that internal tracts of ($TG_{1-3}$) sequence can spontaneously become chromosomal ends. Since the DNA distal to the ($TG_{1-3}$) tract is deleted, it seems unlikely that telomere formation occurred by reciprocal recombination between the internal ($TG_{1-3}$) sequence and another telomere. New telomere formation may have occurred through intrachromosomal recombination between the internal ($TG_{1-3}$) sequence and the telomere with a resulting deletion of intervening sequences (as has been postulated for deletion of the subtelomeric repeat Y' (Horowitz and Haber, 1985)), by unequal sister chromatid exchange or conversion, or by a distal chromosome break followed by telomere "healing" at the ($TG_{1-3}$) sequence.

New telomere formation in conjunction with deletion of all terminal sequences has been observed cytologically, and has been an area of intense interest because of its implications for chromosome breakage at fragile sites and for the generation of chromosomal abnormalities in cancer cells (Le Beau, 1988; Sutherland and Hecht, 1985). Recently it has been postulated that a subclass of such sites might in fact be regions of the chromosome which contain internal stretches of telomeric DNA sequences (Hastie and Allshire, 1989). In this example the inventors find that internal tracts of telomeric DNA do indeed spontaneously become chromosomal termini, albeit at a low frequency (~$10^{-6}$).

EXAMPLE II

Modifiers of Position Effect are Shared Between Telomeric and Silent Mating-Type Loci in *S. Cerevisiae*

The inventors have shown that Pol II-transcribed genes succumb to a position effect when placed near the ends of chromosomes in *S. cerevisiae* (Gottschling et al., 1990; Example I), reflecting observations made in other eukaryotes that the chromosomal location of a gene can affect its expression (Eissenberg, 1989; Henikoff, 1990; Lima-de-Faria, 1983; Spofford, 1976; Spradling and Karpen, 1990; Wilson et al., 1990). The position effect is manifested as the stable but reversible transcriptional repression of each gene examined.

The mechanism by which this repression occurs is unclear, but it is likely due to a structural attribute of *S. cerevisiae* telomeres. Cytological observations in plants, insects, and mammals indicate that telomeres are heterochromatic; in addition, the telomeres in these organisms and in Trypanosomes occupy unique locations within the nucleus, typically being associated with the nuclear envelope (Chung et al., 1990; Fussell, 1975; Hochstrasser et al., 1986; Lima-de-Faria, 1983; Rawlins and Shaw, 1990; Traverse and Pardue, 1989; White, 1973).

HML and HMR are two other loci in *S. cerevisiae* where a position effect on transcription has been observed (Klar et al., 1981; Nasmyth et al., 1981). The mating-type genes, which are expressed when present at the MAT locus, are maintained transcriptionally silent when present at HML and HMR even though all cis-acting sequences required for full expression at MAT are present. Other Pol II- or Pol III-transcribed genes are also repressed when inserted within or near the HM loci (Brand et al., 1985; Mahoney and Broach, 1989; Schnell and Rine, 1986).

DNA sequences known as 'silencers' flank both HM loci and are required for transcriptional repression (Abraham et al., 1984; Brand et al., 1985; Feldman et al., 1984; Mahoney and Broach, 1989). The silencers (denoted "E" and "I") have been genetically dissected into smaller functional elements, which are recognition sites for DNA binding proteins; these include an ARS (Autonomous Replicating Sequence) element, and ABF1 and RAP1 binding sites (Brand et al., 1987; Buchman et al., 1988; Mahoney and Broach, 1989; Mahoney et al., 1991; Shore and Nasmyth, 1987; Shore et al., 1987). The RAP1 protein also binds to the yeast telomeric sequence $(TG_{1-3})_n$ (Buchman et al., 1988; Longtine et al., 1989). RAP1 is apparently involved in repression of HM, since HMR is derepressed when RAP1 temperature sensitive mutant cells are shifted to the nonpermissive temperature (Kurtz and Shore, 1991).

At least seven additional genetic loci play a role in HM silencing. The products of four genes, SIR1, SIR2 (MAR1), SIR3 (MAR2, CMT), and SIR4 (Silent Information Regulator), are required for complete silencing at both the HM loci (Haber and George, 1979; Hopper and Hall, 1975; Ivy et al., 1985; Ivy et al., 1986; Klar et al., 1979; Rine et al., 1979; Rine and Herskowitz, 1987). The molecular mechanism by which the SIR genes act to repress transcription is unclear; none of the SIR proteins have been demonstrated to bind silencer sequence DNA (Buchman et al., 1988; Shore et al., 1987).

A null allele of either NAT1 (N-terminal AcetylTransferase) or ARD1 (ARrest Defective) causes several phenotypes, one of which is derepression of the silent mating type locus HML (Mullen et al., 1989; Whiteway et al., 1987). NAT1 and ARD1 appear to encode an N-terminal acetyltransferase, however it is not known whether the acetyltransferase activity acts directly in silencing at HML.

*S. cerevisiae* harbors two copies of genes encoding histone H4 (HHF1 and HHF2), either of which alone is sufficient for viability (Kim et al., 1988). In strains with deletions of HHF1 (hhf1::HIS3), single point mutations in any of four consecutive amino acids (residues 16–19) near the N-terminus of histone H4 (HHF2) relieve transcriptional silencing at HML, with no other apparent phenotypic consequence (Johnson et al., 1990; Megee et al., 1990; Park and Szostak, 1990). These results directly implicate chromatin in HM silencing. Further evidence for the involvement of chromatin in silencing is suggested by the inaccessibility of HML and HMR to the HO endonuclease in vivo (Strathern et al., 1982; Kostriken et al., 1983). Additionally, in vitro nuclease sensitivity analysis of HML and HMR suggests that the HM loci exist in a distinct chromatin structure that is refractory to transcription in a SIR dependent manner (Nasmyth, 1982).

The characteristics of position effect and RAP1 binding sites shared by telomeres and the HM loci prompted the inventors to test whether the SIR, HHF2, NAT1, and ARD1 genes play a role in transcriptional repression at yeast telomeres. The results of this Example show that in addition to their roles in silencing at the HM loci, the SIR2, SIR3, SIR4, NAT1, ARD1, and HHF2 genes are required for the telomeric position effect in *S. cerevisiae*.

Mutations in any of these genes relieves transcriptional repression of either URA3 or ADE2 at two different telomeres. In contrast, mutations in SIR1 did not alter repression at telomeres. These results suggest that telomeres in *S. cerevisiae* exist in a heterochromatin-like structure; a structure composed of proteins which also function at similar chromosomal domains such as the HM loci. Based on the differences in silencing between telomeres, HML, and HMR, the inventors suggest a hierarchy of chromosomal silencing exists within the yeast genome.

A. Materials and Methods

1. Plasmid Constructions

Plasmid pADE2 contains the ADE2 gene on a 3.6 kbp chromosomal BamHI fragment from plasmid pL909 (obtained from R. Keil). Plasmid pΔADE2 was constructed by replacing the internal 2.2 kbp HindIII fragment (contains all but the six C-terminal residues of the ADE2 open reading frame; (Stotz and Linder, 1990) of plasmid pADE2 with the 3.8 kbp BamHI-BglII fragment of pNKY51 which contains two direct repeats of the Salmonella hisG gene flanking URA3 (Alani et al., 1987). The HindIII and BamHI ends, and the HindIII and BglII ends were blunt-ended with T4 DNA polymerase and ligated together, resulting in the destruction of these particular restriction sites Thus, pAADE2 contains a 5.2 kbp BamHI fragment with about 700 bp of homology to sequences upstream and downstream of the ADE2 gene flanking the 3.8 kbp BamHI-BglII (hisG-URA3-hisG) fragment from pNKY51.

A 2.4 kbp HindIII fragment from plasmid pJR104 (obtained from J. Rine) which contains the 5' end of the SIR3 gene was inserted into pVZ1 to yield plasmid pH3SIR3. Plasmid pH3SIR3 was digested with BglII to excise a 600 bp fragment in the SIR3 coding sequence, which was replaced with a 1.8 kbp BamH1 fragment containing the HIS3 gene. The resulting plasmid was pΔSIR3::HIS3.

2. Yeast Strains and Methods

Media used for the growth of *S. cerevisiae* were described previously (Gottschling et al., 1990; Example I). *S. cerevisiae* were transformed by the lithium acetate procedure (Ito et al., 1983) or by electroporation in the presence of sorbitol (Becker and Guarente, 1991).

The URA3 gene was placed adjacent to the telomere sequence $(TG_{1-3})_n$ on the left end of chromosome VII (UCC1–UCC5, UCC16, UCC18, UCC25, UCC128, UCC2031–UCC2036), or the right end of chromosome V (UCC31–UCC35); no telomere associated sequences (i.e.: X and Y' elements (Chan and Tye, 1983a; Chan and Tye, 1983b)) were present. Alternatively, the ura3-52 or ura3-1 allele (at the normal URA3 locus on chromosome V in the parent strains) was converted to URA3+ (UCC6–UCC10, and UCC129), or URA3 was inserted into the ADH4 locus about 20 kbp from the telomere on VII-L (UCC11–UCC15).

Strains UCC5, UCC6, UCC12, and UCC35 were derived from DBY703; UCC1, UCC7, UCC11, and UCC31 were derived from JRY1705; UCC2, UCC8, UCC13, and UCC32 were derived from JRY1706; UCC3, UCC9, UCC14, and UCC33 were derived from JRY1264; UCC4, UCC10, UCC15, and UCC34 were derived from JRY1263. Strain UCC18 was derived from W303-1a; UCC16 was derived from AMR1; UCC25 was derived from JRM5. UCC128 and UCC129 were derived from YDS73; strain UCC2031 was derived from LJY153, UCC2032 from LJY405I, UCC2033 from LJY412I, UCC2034 from LJY421I, UCC2035 from LJY305TR1, UCC2036 from LJY305T. Plasmids and methods for these constructions are described in Example I and Gottschling et al. (1990).

Strains UCC46 (SIR$^+$), UCC47 (sir1), and UCC48 (sir4), which were derived from strains DBY703, JRY1705, and JRY 1263, respectively, harbor an ade2Δ. The ade2Δ was made by transformation of strains DBY703, JRY1705, and JRY1263 with plasmid pAADE2 digested with BamHI, followed by selection for URA$^+$ transformants. In these transformants the ADE2 open reading frame has been replaced (all but the six C-terminal residues were deleted) with a DNA fragment containing two direct repeats of the Salmonella hisG gene flanking URA3. Loss of URA3 by recombination between the two hisG repeats within the ade2 locus was screened for by 5-FOAR (Alani et al., 1987).

Strains UCC84, UCC86, and UCC88, derived from UCC46, UCC47, and UCC48, respectively, and strains UCC97, UCC98 and UCC99, derived by transformation of strains W303-1a, AMR1, and JRM5, respectively, have a functional ADE2 gene located adjacent to the chromosome VII-L telomere (ADE2-TEL) (Example I); no telomere associated sequences (i.e.: X and Y' elements (Chan and Tye, 1983a; Chan and Tye, 1983b)) were present. Strains UCC2037–UCC2042, derived from strains LJY153, LJY405I, LJY412I, LJY421I, LJY305T, and LJY305TR1, respectively, were constructed in the same manner to place ADE2 adjacent to telomere VII-L.

Strain UCC121 was derived from W303-1a by transformation with a 3.6 kbp BamH1 ADE2$^+$ fragment and selection for ADE$^+$ transformants. Strain UCC120 was constructed by introduction of plasmid pJR531 (Kimmerly and Rine, 1987) which had been digested with SphI and EcoRV into UCC97, and selection for HIS$^+$ transformants. Strain UCC131 was constructed by introduction of pΔSIR3::HIS3 which had been digested with EcoRI into UCC84, and selection for HIS$^+$ transformants.

Strains UCC122–UCC125, UCC138, and UCC139 were constructed by transformation of strains UCC16, UCC18, UCC19, UCC21, UCC128, and UCC129, respectively, with plasmid PKL1. Plasmid PKL1 contains the SIR1 gene on a 2μ-based vector which contains TRP1 for selection (Stone et al., 1991).

The expected structures of the various chromosomal constructs were confirmed by gel electrophoresis followed by DNA blot hybridization analyses. The sir$^-$ phenotypes of strains UCC120 and UCC131 were confirmed by their inability to mate (Sprague, 1991).

3. Quantification of 5-FOA Resistance Cells from isolated colonies grown on rich medium for 2–3 days at 30° were inoculated into liquid medium containing (100 mg/L) uracil. When these cultures reached mid-log phase, serial dilutions were plated onto synthetic complete medium or medium containing 5-FOA (Example I; Gottschling et al., 1990). 5-FOA resistance was determined as the average ratio of colonies formed on 5-FOA medium to colonies formed on complete medium, from a minimum of three independent trials, using different colony isolates for each trial. The number of colonies on a plate was determined after 3–4 days of growth at 30° C. Alternatively, colonies of strains grown on rich medium two to three days were suspended in H$_2$O, and ten-fold serial dilutions were plated as described above. For some strains, selection for TRP$^+$ was required to maintain episomal plasmids; these strains were grown on synthetic medium lacking tryptophan three to four days and colonies were suspended in H$_2$O, serially diluted, and plated as above on synthetic medium lacking tryptophan or on 5-FOA medium lacking tryptophan.

4. Analyses of Nucleic Acids from *S. Cerevisiae*

Preparation and analyses of nucleic acids were as in Example I, except that some DNA blot hybridization analyses were carried out using the Genius system from Boehringer Mannheim following the manufacturer's procedures.

B. Results

1. SIR2, SIR3, and SIR4 Maintain Transcriptional Repression at Telomeres

An isogenic set of sir$^-$ strains with the URA3 gene located at one of four different chromosomal sites was constructed: adjacent to telomere VII-L or V-R, at its normal chromosomal location, or at a second non-telomeric site (ADH4, ~20 kbp from telomere VII-L). URA3 expression was measured by two criteria: resistance to 5-fluoroorotic acid (5-FOA$^R$), and URA3 mRNA levels as determined by RNA blot hybridization analysis. 5-FOA is converted into a toxic metabolite by the URA3 gene product, such that cells expressing normal levels of the URA3 gene product are killed on media containing 5-FOA, whereas ura3$^-$ cells are resistant to 5-FOA (5-FOA$^R$) (Boeke et al., 1987). Cells with URA3 near a telomere form colonies on 5-FOA medium, yet cells within these 5-FOA$^R$ colonies can grow in the absence of uracil, indicating that genetically identical cells can switch from a clonally inherited repressed state to a transcriptionally active state (Gottschling et al., 1990).

Consistent with these earlier results, when the URA3 gene was located adjacent to either the VII-L or V-R telomere in a SIR$^+$ strain, a significant fraction of cells were resistant to 5-FOA (0.62 for UCC5, 0.15 for UCC35), and cells from 5-FOA$^R$ colonies retained the ability to form colonies on medium lacking uracil. Similar results were obtained with the sir1 strain, indicating that expression of the telomeric URA3 gene is repressed in a subset of cells in these strains, and that the SIR1 gene product is not required for repression.

In contrast, a telomeric URA3 gene was not repressed in cells that were sir2, sir3, or sir4. The frequency of 5-FOA$^R$ colonies arising from these strains (~10$^{-7}$) was equivalent to that seen for all strains with URA3 at its normal chromosomal locus or at the ADH4 locus. Mutations in the SIR genes had no effect on the 5-FOA resistance of cells having URA3 at either of these non-telomeric loci.

RNA blot hybridization analysis shows that sensitivity to 5-FOA as a result of the sir mutations was a reflection of mRNA levels from the telomeric URA3 gene. No URA3 mRNA was detectable in SIR$^+$ or sir1 strains which had URA3 at the telomere and were grown under non-selective conditions ("uracil +"), even when the autoradiograph was greatly overexposed. URA3 mRNA was only detectable in the SIR$^+$ or sir1 strains when they were grown to select for telomeric URA3 expression ("uracil –"), though this level was significantly lower than when URA3 was at its normal chromosomal locus.

In sharp contrast, the telomeric URA3 gene produced high levels of mRNA in sir2, sir3, and sir4 strains. These levels were comparable to those from URA3 at its normal chromosomal locus. The sir mutations had no effect on URA3 expression at its normal chromosomal locus or when inserted within the ADH4 locus. These data indicate that the telomeric position effect on URA3 expression mediated by SIR2, SIR3, and SIR4 is at the level of transcription.

To demonstrate that the SIR requirement for the telomeric position effect was not gene specific, sir strains were constructed with the ADE2 gene located at the VII-L telomere, or at its normal locus. The ADE2 gene provides a visual color assay for its expression; ADE2$^+$ strains form white colonies, while ade2$^-$ strains form red colonies (Roman, 1956). Example I shows that a SIR$^+$ strain containing a single copy of ADE2 at a telomeric locus exhibited phenotypic variegation of ADE2, manifested as red-and-white sectored colonies. Here it was found that strains with the telomeric ADE2 that were SIR$^+$ or sir1 formed red and white variegated colonies, indicating that ADE2 was repressed in a subset of the cells within these colonies. The sir2, sir3, and sir4 strains formed entirely white colonies, demonstrating that the telomeric ADE2 gene was not repressed (for sir2 and sir3). These results confirm that the SIR2, SIR3, and SIR4 genes are required for maintaining transcriptional repression at telomeres, in addition to silencing the HM loci (Rine and Herskowitz, 1987).

2. Single Point Mutations in Histone H4 Relieve Transcriptional Repression at Telomeres Single point mutations in any of four consecutive amino acids (residues 16–19) near the N-terminus of histone H4 (HHF2) relieve transcriptional silencing at HML (Johnson et al., 1990; Megee et al., 1990; Park and Szostak, 1990). URA3 or ADE2 was placed at the VII-L telomere in isogenic strains that carried a single copy of either the wild-type histone H4 (HHF2), or a mutated copy of HHF2. Three such point substitution mutations, all of which derepress HML, were tested: a change of lys-16 to either gly-16 or gln-16, and a change of arg-17 to gly-17.

Each strain that contained one point mutation in histone H4 exhibited derepression of telomeric URA3 transcription as shown by their inviability on 5-FOA. When ADE2 was near the telomere in strains with these same histone H4 mutations, colonies were completely white, once again indicating derepression of the telomeric gene. Thus single point mutations at residues 16 or 17 in histone H4 which replace the wild-type basic amino acid with an uncharged residue, result in relief of the telomeric position effect.

There is genetic evidence that SIR3 interacts with histone H4 to silence genes at HML (Johnson et al., 1990). Alleles of sir3 (e.g. sir3R1) have been identified that can partially suppress the HML silencing defect caused by certain point mutations in histone H4 (e.g.: lys-16 to gly-16). URA3 was introduced at the VII-L telomere in an isogenic pair of strains which were either HHF2-gly16, SIR3$^+$ (UCC2036) or HHF2-gly16, sir3R1 (UCC2035). No suppression by sir3R1 was observed at the telomere as judged by complete sensitivity to 5-FOA. Equivalent strains with ADE2 at the telomere produced no red sectored colonies, supporting the conclusion that the sir3R1 allele could not restore repression at the telomere in an HHF2-gly16 strain.

3. NAT1 and ARD1 are Required for the Telomeric Position Effect

A null mutation of either NAT1 or ARD1 causes derepression of the silent mating-type locus HML (Mullen et al., 1989; Whiteway et al., 1987). URA3 or ADE2 was introduced at the VII-L telomere into each member of a set of isogenic strains that was either nat1, ard1, or wild-type for both genes. The sensitivity to 5-FOA of nat1 and ard1 strains was equivalent to that observed for sir2, sir3, and sir4 and the point mutants in histone H4. Thus no position effect was observed for a telomeric URA3 gene in nat1 or ard1 cells. Likewise, the telomeric ADE2 gene was not repressed in the nat1 and ard1 strains as these strains formed entirely white colonies.

4. Overexpression Of SIR1 does not Restore Position Effect at Telomeres

Overexpression of SIR1 partially suppresses the mating defects of MATa strains containing nat1 or ard1 mutations, or certain sir3 or HHF2 alleles by re-establishing silencing at HMLα (Stone et al., 1991). The inventors tested whether SIR1 overexpression could restore silencing of a telomere-linked gene in a nat1 or sir3::LEU2 strain. Plasmid pKL1 (Stone et al., 1991) which contains SIR1 on a 2$\mu$-based vector was transformed into strains which were nat1, sir3, or wild-type and have URA3 located at telomere VII-L or at the normal URA3 locus. As expected, a significant fraction of cells of strain UCC123 (wild-type, URA3-TEL/pKL1) were resistant to 5-FOA. However, the nat1 and sir3 strains which have URA3 at telomere VII-L and harbor pKL1 continue to be sensitive to 5-FOA, as are the strains with URA3 at its normal chromosomal locus. Thus the overexpression of SIR1 does not restore silencing at telomeric loci in nat1 or sir3 strains These results are consistent with the results presented above, indicating that SIR1 plays no role in transcriptional silencing at telomeres.

C. Discussion

1. Similarities and Differences in Position Effects at Telomeres and the HM loci This example shows that the SIR2, SIR3, SIR4, HHF2, NAT1, and ARD1 genes are required for the position effect at telomeres in S. cerevisiae. Consequently, it implies that these gene products constitute a general mechanism for silencing chromosomal domains in S. cerevisiae. In view of the results presented here, it is interesting to note that both HML and HMR are located quite close to the termini of chromosome III, ~12 kbp (Button and Astell, 1986) and ~25 kbp (Yoshikawa and Isono, 1990), respectively. When HML is present on a circular plasmid or a ring chromosome III derivative, deletion of HMLE or HMLI results in derepression of HML (Feldman et al., 1984; Strathern et al., 1979). However, these mutated HML loci are fully silenced when present at the normal telomeric HML locus (Mahoney and Broach, 1989) suggesting the proximity of HML to the telomere may facilitate full repression of this locus.

There was no detectable change in the telomere-specific position effect in sir1 strains or in strains with SIR1 on a high copy plasmid. Since both of these genotypes have an effect on HML and HMR, the inventors conclude that SIR1 function is specific to silencing of the HM loci. Single-cell analysis of sir1 strains indicates that a mixed population of cells exists with ~20% of cells being transcriptionally silent at HML and the remainder being transcriptionally active at HML; the transcriptional state is clonally inherited, though cells switch between transcriptionally active and repressed states at a low frequency (Pillus and Rine, 1989).

The inventors have found that epigenetic switching between transcriptional states occurs at telomeres in SIR$^+$ (and sir1) strains, analogous to that observed at HML in sir1 mutants (Example I; Pillus and Rine, 1989). The inventors therefore propose that SIR1 provides complete silencing at HML and HMR by preventing switching from the silent to the active transcriptional state. The HM loci is thus proposed to contain elements through which SIR1 acts, which are absent from chromosomal termini (e.g.: the A and B elements (Brand et al., 1987)). In support of this, a recent study has identified deletions at HMLE which result in epigenetic switching of transcriptional states at HML (Mahoney et al., 1991).

A number of differences have been observed between silencing at telomeres, HML, and HMR, which may yield insights into the functional organization of the silent loci. As indicated above, the epigenetic switching of HML expression in sir1 strains is very similar to the expression of a telomeric gene in a $SIR^+$ (or sir1) strain, indicating that elements through which SIR1 can act to fully silence HML are present at HML (and probably HMR) but not at telomeres. Also, while a sir1 mutation has only a slight effect at either HM locus, and a mutation in nat1 alone derepresses HML but not HMR (Mullen et al., 1989), the sir1, nat1 double mutant is completely derepressed at HMR, suggesting that additional mechanisms of silencing exist at HMR compared to HML (or telomeres) (Stone et al., 1991). Deletion of NAT1 or ARD1 results in significant derepression of HML but not HMR (Whiteway et al., 1987); however, deletion of the RAP1 binding site at HMRE results in derepression of HMR in nat1 or ard1 strains (Stone et al., 1991), again indicating that redundant silencing mechanisms exist at HMR compared to HML and telomeres.

Lastly, sir3R1 partially restores HML silencing in a HHF2-gly16 strain (mating efficiency is restored from $\sim 10^{-5}$ to $\sim 10^{-1}$; (Johnson et al., 1990)), but does not restore telomeric silencing. This may be explained if suppression of HHF2-gly16 by sir3R1 is facilitated by the presence of a redundant silencing mechanism(s), such as that mediated by SIR1. Thus the inventors suggest that telomeres exhibit a basal level of transcriptional repression, and that silencing at HML and HMR is based on the same mechanism(s), but is strengthened and regulated by the presence of additional silencer elements.

2. How does the Telomeric Position Effect Occur?

Little is known about the specific mechanism by which the SIR, HHF2, NAT1, and ARD1 gene products act in transcriptional silencing, however the available evidence suggests that they modify chromatin structure (Nasmyth, 1982). Single point mutations in histone H4 completely relieve the telomeric position effect and thus provide the best evidence that chromatin structure is intimately involved in telomeric silencing. Mutations in any of four contiguous amino acids (residues 16–19) in the N-terminus of histone H4 result in derepression at HML (Johnson et al., 1990; Megee et al., 1990; Park and Szostak, 1990); these four positively charged amino acids are conserved throughout eukaryotes, and are sites of post-translational modifications (van Holde, 1989). Significantly, correlative studies note that the modifications (e.g. acetylation and phosphorylation) on histone H4 are associated with the transcriptional status of the chromatin (van Holde, 1989).

In yeast, suppressors of the histone H4 point mutations, which restore silencing, map as compensatory changes in the SIR3 gene, thus providing evidence that SIR3 interacts with chromatin (Johnson et al., 1990). In addition, SIR2 has been shown to suppress intrachromosomal recombination between rDNA repeats, supporting the idea that SIR2 may play a general role in chromatin organization (Gottlieb and Esposito, 1989).

NAT1 and ARD1 apparently encode two subunits of a yeast N-terminal acetyltransferase which acetylates histone H2B along with at least twenty other proteins (Mullen et al., 1989) which may play a direct role in silencing by acetylation of H2B.

It has been reported that SIR4 shares sequence similarity with the coiled-coil domains of human nuclear lamins A and C (Diffley and Stillman, 1989). These domains facilitate polymerization of lamins into the lamina, which lines the nuclear envelope. Taking into account the cytological observations in interphase nuclei which indicate telomeres are located at the nuclear periphery it is plausible that the putative polymerization domain of SIR4 is associated with the nuclear lamina and might therefore mediate binding of telomeres to the nuclear envelope. Since the SIR4 gene product is believed not to bind DNA directly (Buchman et al., 1988; Shore et al., 1987), an interaction between SIR4 and a telomere binding protein (e.g. RAP1) may enable an association between telomeres and the nuclear envelope. It is noteworthy that purified mammalian nuclear lamins A and C bind in vitro to synthetic oligonucleotides containing mammalian telomere repeat sequences (Shoeman and Traub, 1990). Thus attachment of telomeres, as well as other chromosomal loci or regions, to the nuclear envelope may be a component of nuclear organization, and might therefore affect local gene expression (Alberts et al., 1989; Blobel, 1985).

The position effect at S. cerevisiae telomeres may reflect a general feature of eukaryotic telomeres. In Drosophila, stable transposition of the white gene to a position near a telomere results in a mottled eye color phenotype (Levis et al., 1985), which is consistent with transcriptional repression of white in some cells. Cytological studies in a number of organisms indicate that telomeres are organized into heterochromatin (Lima-de-Faria, 1983; Traverse and Pardue, 1989). While heterochromatin is defined cytologically as a region of the chromosome which remains condensed in interphase, it also displays two distinctive traits: late DNA replication, and the ability to repress transcription of euchromatic genes placed nearby (Eissenberg, 1989; Henikoff, 1990; Spofford, 1976; Spradling and Karpen, 1990). S. cerevisiae telomeres possess both of these hallmarks of heterochromatin (Example I; McCarroll and Fangman, 1988). The SIR2, SIR3, SIR4, HHF2, NAT1, and ARD1 products may be intimately involved with the organization of regions of yeast chromosomes into heterochromatin or heterochromatin-like structures. Because telomeres and histones are highly conserved structurally and functionally among eukaryotes, it seems quite likely that the mechanism of transcriptional repression functioning in S. cerevisiae is also utilized in multi-cellular eukaryotes.

EXAMPLE III

Silent Domains are Assembled Continuously from the Telomere and are Defined by Promoter Distance and Strength and SIR3 Dosage The eukaryotic genome is organized into regions distinct in their structure and function. Heterochromatin, which defines one such structural region, is condensed throughout the cell cycle, while its counterpart, euchromatin, is more diffuse in appearance during interphase (Heitz, 1928, as cited in Brown, 1966). Chromosomal regions also differ functionally since the expression of a eukaryotic gene can be profoundly affected by its chromosomal position. This phenomenon, chromosomal position effect, is observed in many eukaryotes (Lima-de-Faria, 1983) and has been extensively studied in Drosophila melanogaster (Lewis, 1950; Baker, 1968; Spofford, 1976). When genetic rearrangements place euchromatic segments of the genome into or near heterochromatin, the expression of a translocated euchromatic gene is altered in a population of cells: some cells express the gene, while others do not. Thus a mosaic or variegated phenotypic pattern is produced.

Chromosomal position effects phenomena can spread over great distances in the genome; e.g., in Drosophila, genes located as far away as 80 chromosome polytene bands (~2000 kbp) are still subject to position-effect variegation (PEV) (Demerec, 1940). This spreading effect is thought to reflect the dynamic nature of assembly of heterochromatin over a locus (Zuckerkandl, 1974; Spofford, 1976). When heterochromatin assembles far enough to include a locus, the gene within it is inactivated.

In *Saccharomyces cerevisiae*, chromosomal domains have been identified that exert position effect: the cryptic mating-type loci, HML and HMR, and telomeres (Laurenson and Rine, 1992; Sandell and Zakian, 1992). Genes located near or within these domains may be transcriptionally silenced and exhibit phenotypic variegation (Klar et al., 1981; Nasmyth, et al. 1981; Schnell and Rine, 1986; Mahoney and Broach, 1989; Example I). At least six modifiers of position effect are shared between the HM loci and telomeres. A mutation in SIR2, SIR3, SIR4, NAT1, ARD1, or HHF2 (which encodes histone H4) reduces or abolishes silencing at telomeres, HML, and HMR (Hopper and Hall, 1975; Haber and George, 1979; Klar et al., 1979; Klar et al., 1981; Ivy et al., 1986; Rine and Herskowitz, 1987; Whiteway et al., 1987; Kayne et al., 1988; Mullen et al., 1989; Megee et al., 1990; Park and Szostak, 1990; Example II; Aparicio et al., 1991).

The involvement of histone H4, and the observation that the HM loci and telomeres are refractory to DNA modifications in vivo in a SIR-dependent manner, point to chromatin structure as being involved in silencing the HM loci and telomeres. Specifically, this chromatin structure is thought to hinder access of transcription factors to these loci (Nasmyth, 1982; Kostriken et al., 1983; Klar et al., 1984; Gottschling, 1992; Singh and Klar, 1992).

Spreading of position effect also occurs in yeast (Abraham et al., 1984; Feldman, et al. 1984). Genes located up to ~4.9 kbp from a telomere still are subject to position effect, whereas no silencing is detected at loci ~20 kbp from the chromosome end (Gottschling et al., 1990). Additionally, insertion of a 30 kbp Ty-array between the E and I sites (cis-elements required for silencing) at HMLa relieves silencing at this locus. However silencing is re-established when this array is reduced to a single 7 kbp Ty (Mastrangelo et al., 1992). Thus there is a limit to the size of silenced domains at both HM loci and telomeres.

Telomeric silencing in yeast provides an excellent opportunity to study the spread of position effect in a eukaryote, particularly because the initiation site of position effect is known to be the end of the chromosome (Example I). In this Example, a quantitative method to examine telomeric position effect was used to identify parameters that modulate spreading. The results provide a molecular and mechanistic insight into the propagation of silencing in yeast, as well as the functional organization of silent chromosomal domains.

A. Methods

1. Construction of Plasmids

The set of plasmids used to insert the URA3 gene at various positions along V-R was constructed as follows, starting with plasmid pB610H (obtained from C. Newlon). Plasmid pHSS6TG carries a telomeric repeat sequence (derived from pYTCA-2; Example I) inserted between the EcoRI and BamHI restriction sites of plasmid pHSS6 (Seifert et al., 1986). Orientation of the telomeric sequence is such that digestion of pHSS6TG with EcoRI will yield an end that is a substrate for telomere formation in yeast. A 7.3 kbp BamHI fragment from plasmid pB610H was ligated into the BamHI site of pHSS6TG. Next, a 7.4 kbp NotI fragment of this new plasmid, carrying unique V-R sequences adjacent to a telomeric $(TG_{1-3})_n$ repeat, was cloned into the NotI site of pVZ1 (Henikoff and Eghtedarzadeh, 1987), generating pSC1. Plasmids pVURAH2(+) and pVRURAH2(−) were constructed by inserting a 1.2 kbp HindIII fragment containing URA3 into the "$H_2$" site of pSC1 partially digested with HindIII. URA3 transcriptional orientation is denoted (+) when transcription is toward the telomere and (−) when toward the centromere. URA3 was cloned in a similar way into the "$H_3$" and "$H_4$" HindIII restriction sites, generating plasmids pVURAH3(+), pVURAH3(−), pVURAH4(+) and pVURAH4(−), respectively.

The HIS3 gene was isolated from plasmid pHIS3 (Struhl, 1985; Example I) by amplification using the polymerase chain reaction (Innis et al., 1990), using the following primers: 5' oligo 5' CC<u>GGATCC</u>TGCCTCGGTAATGATTTCATTTTTT 3' (SEQ ID NO:13); 3' oligo 5' CC<u>GGATCC</u>TCTCGAGTTCAAGAGAAAAAAAAGAAA 3' (SEQ ID NO:14). Restriction sites for BamHI, which were placed at the ends of the oligonucleotides for convenient cloning, are underlined. Hence, the inventors refer to this DNA segment as "HIS3 BamHI fragment".

Plasmids used to test for discontinuity of silenced chromosomal domains along V-R were created as follows: pH1.5HIS3(+) and pH1.5HIS3(−) were constructed in two steps. First, a 1.5 kbp HindIII fragment of V-R chromosomal DNA was inserted into the HindIII site of pHSS6 to generate plasmid pHSS6(1.5). pHSS6(1.5) was then digested with KpnI, blunt-ended, and ligated with the HIS3 BamHI fragment which had its ends filled-in. A two-step process was also required to construct plasmids pVRUH2(−)HR1(+) and pVRUH2(−)HR1(−). Plasmid pVURAH2(−) was cut with XhoI and SalI, and recircularized by ligation; a blunt-ended HIS3 BamHI fragment was ligated into this plasmid which had been partially digested with EcoRI and blunted with T4 DNA polymerase. Plasmids pVRUH2(+)HR1(+) and pVRUH2(+)HR1(−) were constructed following the same procedure. Plasmids pYAHIS4-2(−) were made by cloning the HIS3 BamHI fragment into the BamHI site of pYA4-2 (Walton et al., 1986).

Plasmid pDPPR1-HIS3 was constructed by replacing a 0.7 kbp BglII fragment containing the promoter region of PPR1 (Kammerer et al., 1984), in plasmid pUC8-PPR1 (obtained from R. Losson), with a 1.85 kbp BamHI fragment from plasmid pHIS3. In plasmid pDPPR1::LYS2 the same BglII fragment was replaced by a blunt-ended 4.8 kbp HindIII-XbaI fragment containing LYS2, isolated from pDP6 (Fleig et al., 1986).

Plasmid pVZ1DGCN4::TRP1 carries a deletion in the translation initiation region of GCN4. Plasmid pB238 (a derivative of plasmid p164 (Hinnebusch, 1985)) was digested with BamHI and BglII, and a 0.8 kbp BamHI fragment containing TRP1 from YDpW (Berben et al., 1991) was ligated into it. A SalI-EcoRI 3.2 kbp fragment of the resulting plasmid was then ligated into pVZ1 previously digested with EcoRI and SalI, to create pVZ1DGCN4::TRP1.

The plasmid pVZJL38TRP1(+)ADE2(−) was used to insert TRP1 and ADE2 between ADH4 and telomere VII-L. Plasmid pUC19-JL3 contains a 0.4 kbp EcoRI-HindIII fragment including the JL3 region from VII-L (Walton et al., 1986). This plasmid was digested with EcoRI, its ends were made blunt, and the linearized plasmid was treated with HindIII. The JL3 region was ligated into plasmid pVZ1 previously digested with HincII and HindIII. Plasmid pVZJL38 was constructed by digesting the resulting plasmid, pVZJL3, with SmaI and EcoRI; an ~0.8 kbp EcoRI-HindIII fragment from plasmid pUC19-JL8 (Walton et al., 1986), with only its HindIII end made blunt, was ligated into the plasmid. A 1.45 kbp EcoRI fragment from plasmid YRp7 containing the TRP1 gene (Struhl et al., 1979), was then inserted into this new plasmid, pVZJL38. The resulting plasmid, pVZJL38TRP1(+), was digested with BglII and a 3.6 kbp BamHI fragment containing ADE2 was inserted (Gottschling et al., 1990). Plasmid pVZJL38TRP1 (+)ADE2(−) has ADE2 inserted in the opposite transcriptional orientation as TRP1.

YEpSIR3 (pKAN63) carries a ~7 kbp BamHI genomic insert containing SIR3 and flanking chromosomal sequences (Ivy et al., 1986), cloned into YEp13 (Broach et al., 1979). CEN-SIR3 (pHR62-16) contains a 3.7 kbp HpaI fragment of plasmid pKAN63, encompassing SIR3 and its putative transcriptional regulatory elements (Shore et al., 1984), inserted into the SmaI restriction site of plasmid pRS314 (Sikorski and Hieter, 1989). Plasmid-23 (2m-SIR3) carries the same SIR3 fragment cloned into pHR59-33 (2m), a derivative of pRS424 (Christianson et al., 1992) in which the ClaI site was deleted.

Plasmid pHR49-1 was constructed by inserting a 1.2 kbp BamHI fragment containing HIS3 from YDpH (Berben et al., 1991) into the BglII site of pRS316-SIR1 (obtained from Lorraine Pillus), which contains SIR1 and flanking genomic sequences. All other plasmids used for strain construction have been described previously (Ivy et al., 1986; Kimmerly and Rine, 1987; Examples I and II).

DNA manipulations were performed as previously reported (Sambrook et al., 1989; Example I). $E.\ coli$ strains MC1066 (r⁻ m⁻ trpC9830 leuB600 pyrF::Tn5 lacDX74 strA galU galK) (Casadaban et al., 1983), JF1754 (r⁻m⁻ leuB metB hisB) (Himmelfarb et al., 1987) and TG1 (supE hsdD5 thiD(lac-proAB) F'[traD36 proAB⁺ lacI$^q$ lacZDM15]) (Sambrook et al., 1989) were used as plasmid hosts. Media for bacterial strains were prepared as described (Sambrook et al., 1989). Complementation of bacterial mutations by homologous yeast genes was used when applicable.

2. Yeast Strains and Methods

Media used for the growth of *S. cerevisiae* were described in Example I; all cultures were grown at 30° C. Yeast transformation was performed by electroporation in the presence of sorbitol (Becker and Guarente, 1991) or the lithium acetate procedure (Schiestl and Gietz, 1989). 5-FOA resistance (5-FOA$^R$) was determined as described in Example II. Yeast strains manipulations were carried out as described (Rose et al., 1990).

Strains UCC500–505 were constructed by transformation of YPH250 (Sikorski and Hieter, 1989) with BamHI-digested plasmids pVURAH2(+), pVURAH2(−), pVURAH3(+), pVURAH3(−), pVURAH4(+), and pVURAH4(−), respectively. Strains UCC506–511 were constructed by transformation of strain YPH250 with the same plasmids digested with NotI. In both cases, Ura⁺ colonies were selected. ppr1⁻ derivatives of these strains were constructed by transformation with EcoRI digested pDPPR1-HIS3, and selection for His⁺ transformants.

URA3 was inserted into the ADH4 locus (about 20 kbp from telomere VII-L) of YPH250 to yield UCC1003, as described (Gottschling et al., 1990). UCC3248, UCC3249 and UCC3250 are derivatives of UCC1001 (Gottschling, 1992) that are sir2::HIS3, sir3::HIS3 and sir4::HIS3, respectively, and were created by transformation as described (Kimmerly and Rine, 1987; Example II). A sir1::HIS3 derivative of UCC1003 (UCC3243) was constructed by transforming UCC1003 with ClaI and SmaI digested pHR49-1.

Plasmid ph1.5HIS3(+) was digested with NotI and transformed into UCC506 and UCC507 to make UCC2515 and 2517, respectively. ph1.5HIS3(−) was transformed in the same way into UCC506 and UCC507, to generate UCC2516 and UCC2518, respectively. Strains UCC2524–2527 were derived from YPH250 after transformation with the various pVRUH2(+/−)HR1(+/−) constructions digested with SphI and NotI. UCC1005 is derived from YPH250 (Sikorski and Hieter, 1989) by transformation with pVRURA3TEL, as described (Gottschling et al., 1990). UCC1005 was transformed with pYAHIS4-2(−) that had been digested with EcoRI and SalI, yielding strain UCC2509. Strain UCC2528 carries a telomeric URA3 at the VII-L telomere; it was created by transformation of YPH500 (Sikorski and Hieter, 1989) with pVII-L URA3-TEL (Example I).

The UCC2535 strain was created by transforming YPH250 with pVRUH2(−)HR1(+), selecting for His⁺ transformants, and then screening for Ura⁻ cells. URA3 was integrated at the ADH4 locus of UCC2535 by transformation with padh4::URA3, as described (Gottschling et al., 1990), generating strain UCC2585. UCC2536, a meiotic segregant of a cross between UCC2528 and UCC2535, carries HIS3 on V-R and URA3 on VII-L. ppr1⁻ gcn4⁻ derivatives of the strains UCC2515–2518, 2524–2527, 2509, 2536 and 2585 were constructed by transformation with EcoRI digested pDPPR1::LYS2, and selection for Lys⁺ colonies; next, the GCN4 locus was disrupted by transformation with pVZ1DGCN4::TRP1 digested with NotI and SalI, yielding UCC2580–2583, 2576–2579, and 2589–2591.

The gamma-deletion method (Sikorski and Hieter, 1989) was used to introduce TRP1 and ADE2 between the JL3 and JL8 regions on VII-L (Walton et al., 1986). Plasmid pVZJL38TRP1(+)ADE2(−) was digested with BamHI and transformed into UCC1003 to yield strain UCC1035. The expected structures of the various chromosomal constructs were confirmed by Southern analysis as described in Examples I and II. All other strains have been described in Example I.

B. Results

1. Silencing of URA3 Decreases with Increased Distance From the Telomere

In Example I, the inventors detected telomeric position effect (TPE) in *S. cerevisiae* 4.9 kbp from the left end of a modified chromosome VII (VII-L) by measuring the level of transcriptional repression of a telomere-proximal URA3 when various yeast genes were inserted between URA3 and the telomere. However, the effect of each inserted sequence on URA3 expression was not exclusively dependent on the size of the insert. To better characterize the spread of TPE in *S. cerevisiae*, the inventors examined the expression of URA3 as a function of its distance from a representative telomere, without introducing any new sequences between URA3 and the end of the chromosome.

A set of isogenic strains was created with URA3 placed at various distances from the right end of chromosome V (V-R); the normal chromosomal copy of URA3 is non-functional in each strain. At each site of insertion, URA3 was positioned in either transcriptional orientation. This set of strains may be divided into two groups: those that maintained the original ~6.7 kbp telomere-associated Y' element of V-R, and those in which the Y' and some adjacent sequences were replaced with a new terminus of $(TG_{1-3})_n$. These Y' elements are middle-repetitive DNA sequences found proximal to some but not all yeast telomeres; their function is unknown (Olson, 1991).

Transcriptional repression as a function of distance from the chromosome end was analyzed by determining the level of URA3 silencing in each strain. The level of silencing in a population of cells is quantified by determining the fraction of cells capable of forming colonies on 5-fluoroorotic acid (5-FOA) medium; 5-FOA is lethal to cells expressing the URA3 gene product (Boeke et al., 1987). In the inventors' analysis, the ability of a cell to give rise to a colony on 5-FOA ($5\text{-FOA}^R$) indicates that when it was plated onto the medium, the cell contained little or no URA3 gene product. Thus when URA3 is telomeric, telomere-mediated transcriptional repression enables the cell to grow on 5-FOA (Gottschling et al., 1990).

Quantification of TPE spreading showed that, when the fraction of $5\text{-FOA}^R$ cells is plotted versus the distance of the URA3 promoter from the telomere, a continuous gradient in frequency of silencing is observed, with the highest frequency occurring at the most telomere-proximal position. Repression was no longer detected when the URA3 promoter was located 3.5 kbp away from the telomere. The steady decrease in frequency of repression with respect to promoter distance from the telomere suggested that the position of the URA3 promoter was the key element in determining repression; transcriptional orientation with respect to the telomere did not appear to be significant in regulating URA3 expression. Finally, in strains with a Y' element between the URA3 gene and the V-R telomere (UCC500–505), no repression was detected at the tested distances of 10 kbp to 16 kbp from the telomere.

2. Absence of a Transactivator Increases the Extent of TPE Spreading

If promoter distance from the telomere is a primary determinant for governing TPE spreading, then weakening the promoter might result in an increase in spreading. To test this, $ppr1^-$ derivatives of the strains described above, with URA3 at various distances from the telomere, were created. PPR1 is a transactivator protein that enhances expression of the URA3 gene (Loison et al., 1980; Roy et al., 1990). Repression was more frequent at each location of URA3, and detectable over a greater distance from the telomere in $ppr1^-$ than in $PPR1^+$ strains. Thus the range over which TPE spreads seems to be inversely related to the promoter strength of the gene being assayed. Similarly, deleting GCN4, the HIS3 transactivator (Hope and Struhl, 1985; Hinnebusch, 1988), reduced the ability of strains carrying a telomeric copy of HIS3 to form colonies on medium lacking histidine, indicating that this effect is not specific to URA3.

In the $ppr1^-$ strains with the Y' element present at V-R, a small fraction of $5\text{-FOA}^R$ cells were reproducibly observed in the two strains in which the URA3 promoter is about 11 and 12 kbp from the telomere. Southern analysis revealed no change in chromosome structure between URA3 and the telomere in these strains. These results contrast with the data for strains lacking the Y' element on V-R (UCC518–523), in which no repression was detected beyond ~6 kbp from the V-R telomere. Thus it seems that 6.7 kbp of Y' sequence has a greater ability to sustain telomere-dependent silencing than the same length of unique V-R sequence.

3. Overexpression of SIR3 Enhances TPE Spreading

The gene products of SIR2, SIR3, and SIR4 are required for TPE, and it has been postulated that one or more of them is a structural component of silent yeast chromatin (Nasmyth, 1982; Ivy et al., 1986; Marshall et al., 1987; Rine and Herskowitz, 1987; Alberts and Sternglanz, 1990; Johnson et al., 1990; Example II; Stone et al., 1991). To examine whether the normal cellular level of SIR2, SIR3, or SIR4 limits the range of silent telomeric domains, the inventors tested whether introduction of multiple copies of the SIR2, SIR3, or SIR4 genes would increase the spread of TPE. Only raising SIR3 copy number enhanced position-effect spreading on telomere-adjacent genes. No phenotype was observed in strains transformed with a multicopy plasmid carrying SIR2. Increasing SIR4 dosage relieved silencing on telomeric genes; a similar effect has been previously observed at a weakened HMR (Sussel and Shore, 1991).

The effect of SIR3-overexpression was quantified in the previously described sets of strains. Increased dosage of SIR3 raised the frequency of URA3 silencing in each strain. In $ppr1^-$ strains overexpressing SIR3 on a high-copy plasmid (YEpSIR3), URA3 was frequently silenced 16 kbp from the telomere (with a Y'), while in cells with vector alone (YEp13) no significant silencing was detectable beyond 4 kbp. Similar results were obtained in $PPR1^+$ strains transformed with YEp13 or YEpSIR3, although as expected from the data presented in the previous section, URA3 transcription was somewhat less frequently repressed than in the $ppr1^-$ strains. Again, the presence of a Y' element appeared to facilitate TPE spreading over longer distances than unique chromosomal sequences.

Extrapolation of the "YEpSIR3 with Y'" curve suggested that TPE spreading should extend inward ~25 kbp from the end of chromosome V-R in the SIR3-overexpressing strains. Consistent with this estimate, URA3 was repressed at 22 kbp from the VII-L telomere when SIR3 was overexpressed, but URA3 expression was not affected at its normal locus, ~120 kbp from telomere V-L (Mortimer et al., 1992). No increase in telomeric silencing was detected in strains transformed with plasmids carrying mutant alleles of SIR3, indicating that propagation of telomeric silencing is dependent on functional SIR3. These results are consistent with SIR3 being a limiting component required to assemble repressive telomeric chromatin.

If SIR3 is indeed limiting, the spread of TPE should be very sensitive to SIR3 gene dosage. This hypothesis was tested in $ppr1^-$ strains transformed with SIR3 carried either on a centromeric (CEN-SIR3) or a multicopy plasmid (2m-SIR3), or with the vectors alone. With a single-copy plasmid (CEN-SIR3), the spreading effect was indeed less enhanced than with a high-copy plasmid (2m-SIR3), but greater than with either vector alone. Hence, the results indicate that SIR3 dosage limits the spread of yeast telomeric position-effect.

4. Increased SIR3 Dosage Cannot Suppress the Requirements of SIR2, SIR4, NAT1, ARD1, and Histone H4 for TPE In addition to SIR3, the gene products of SIR2, SIR4, NAT1, ARD1 and HHF2 (histone H4) are required for transcriptional silencing at telomeres (Example II). The inventors tested whether the increased dosage of SIR3 could restore TPE in cells deficient for these other proteins. Strains containing URA3 adjacent to the VII-L telomere and defective in each of the aforementioned genes, were transformed with a high-copy SIR3 plasmid. In no case did increased levels of SIR3 restore telomeric silencing.

Mutations in SIR1 do not relieve silencing at telomeres, suggesting that SIR1 is not involved in controlling TPE (Example II). Consistent with this idea, SIR3-overexpression in $sir1^-$ strains enhanced TPE spreading, as observed in wild-type strains. Since the SIR3 dosage-dependent enhancement of TPE cannot suppress the requirements for SIR2, SIR4, NAT1, ARD1, and histone H4, it appears that the SIR3-effect operates through the normal mechanism of telomeric silencing, rather than introducing a novel mechanism of silencing.

5. Silenced Chromosomal Domains Spread Continuously from the Telomere

The results presented above suggest that the silenced telomeric domain spreads inward along the chromosome in a continuous fashion. To further test this idea, two genes were placed adjacent to one another near the same telomere, and the transcriptional state of the centromere-proximal gene was examined when the telomere-proximal gene was transcriptionally active. If the silenced domain is indeed spread continuously along the chromosome, then the centromere-proximal gene should always be derepressed when the telomere-proximal gene is active. However, if the repressed domain is discontinuous, then the centromere-proximal gene may be in a repressed state even when the telomere-proximal gene is active.

Both the URA3 and HIS3 genes were inserted near the V-R telomere without a Y' element present; each of the eight possible permutations of URA3 and HIS3 located near the V-R telomere was constructed. In addition, three strains were created in which URA3 and HIS3 were located on two different chromosomes (V-R and VII-L), either with both genes adjacent to a telomere (UCC2590), or URA3 at a telomere and HIS3 non-telomeric (UCC2589), or the converse situation (UCC2591). In order to improve the sensitivity of the spreading assay, the promoters of URA3 and HIS3 were weakened by deleting PPR1 and GCN4, the genes which encode their respective transactivators, in each strain. All strains grew in the absence of histidine, indicating that HIS3 was capable of being expressed at each chromosomal position, although expression was compromised at some telomeric locations (e.g. UCC2577, colony size was small and plating efficiency was reduced on "-his"). All strains carrying a telomeric URA3 gave rise to colonies which grew on fully-supplemented 5-FOA medium, reflecting transcriptional repression of URA3.

In the four strains with both URA3 and HIS3 located near the V-R telomere, and HIS3 as the telomere-proximal marker (UCC2576–2579), no growth was detected on "FOA-his" medium. That is, when HIS3 was nearer to the telomere and transcriptionally active, URA3 was never transcriptionally repressed. In contrast, when URA3 was telomere-proximal (UCC2580–2583) colonies were obtained on FOA-his, indicating that it was possible for URA3 to be repressed while HIS3 was active. Thus TPE spreads continuously inward from the telomere. These results also suggest that the spread of silencing can be blocked by transcription of an intervening gene.

Of the four strains with URA3 in the telomere-proximal location, UCC2581 showed conspicuously poor growth on FOA-his. In this strain, the URA3 and HIS3 promoters are separated by only ~0.5 kbp. In such close proximity it might be difficult to open the HIS3 chromatin structure without also disrupting the silencing apparatus over URA3. Another notable result was observed when URA3 and HIS3 were located at different telomeres (UCC2590); robust colonies grew on "FOA-his", indicating repression at one telomeric locus while the other telomeric marker was expressed. This result indicates that telomeric silencing is locus-specific.

The inventors then examined whether the increased spread of silencing mediated by SIR3-overexpression was also continuous. TRP1 and URA3 were inserted ~12.5 and 22 kbp, respectively, from the VII-L telomere. 5-FOA$^R$ colonies were observed only when the cells were transformed with YEpSIR3; however, no 5-FOA$^R$ was detected if TRP1 was simultaneously expressed in these cells. TRP1 expression by itself was only modestly impaired in YEpSIR3-transformants, as demonstrated by their high efficiency of plating on "-trp-leu". Similar results were obtained when ADE2 (inserted ~9 kbp from the same telomere) replaced TRP1 in this study. Taken together, these observations suggest that SIR3 propagates silencing continuously from the telomere.

C. Discussion

The inventors have carried out a systematic characterization of the spreading of telomeric position effect (TPE) in *Saccharomyces cerevisiae*. The telomeric position effect in yeast can be considered as a gradient of transcriptional silencing along the chromosome. The inventors postulate that this gradient reflects the limited assembly of a silent chromatin (heterochromatic-like) structure that initiates at the telomere and proceeds continuously inward along the chromosome. In the inventors' analysis, the fraction of 5-FOA$^R$ cells provided an estimate of the frequency at which a telomeric URA3 was located within this repressive structure.

Transcriptional inactivation of a telomeric locus may be viewed as the final product of a reaction in which subunits of silent chromatin are assembled. In a simple model, silencing of a URA3 gene six kbp from the telomere would require six times as many subunits than that needed to silence a URA3 gene located one kbp away. If the assembly of telomeric repressive chromatin were a first-order reaction, then the occurrence of a repressed URA3 gene at one kbp from the telomere would be expected six times as frequently as when URA3 is six kbp away. This Example shows that this is not the case. An exponential function more aptly describes the relationship between frequency of silencing and distance from the telomere. Rather the data suggest that telomeric silencing results from the cooperative assembly of subunits, and/or assembly of multiple components. A multimeric representation of silent chromatin is expected to involve the four core histones plus additional components (Eissenberg, 1989; Henikoff, 1990; Spradling and Karpen, 1990; Grigliatti, 1991), as quantitated in vivo in this Example.

It has been proposed that specific terminator sequences along the chromosome act as barriers to heterochromatic spreading (Tartof et al., 1984). No such regions were detected on the telomere-proximal 16 kbp of V-R, nor over 20 kbp of a modified VII-L, although these data do not rule out the existence of such sites in yeast.

Cells carrying URA3 and HIS3 located near the V-R telomere, with HIS3 telomere-proximal, were unable to form colonies on FOA-his media. Since this medium selects for cells in which both URA3 is repressed and HIS3 is active, this result demonstrates that silent telomeric domains are continuously propagated from the end of the chromosome in yeast. Since a telomeric gene can be induced to become active Example I, the inventors suggest that transcription may actively block silent chromatin propagation. Alternatively, transcription may not act as a barrier to the spread of silencing per se, but rather reflect that the silent telomeric domain assembled only a short distance from the telomere, thus never encompassing the HIS3 (or URA3) gene. The distinction between these two models should be considered in thinking about gene regulation within chromosomal domains.

1. The Role of the Promoter in TPE Spreading

The presence of silent chromatin structures over a telomeric locus appears to impede the access of sequence-specific DNA-binding proteins to the DNA within, thereby generating a TPE (Examples I and II; Gottschling, 1992). These data show a steady decrease in the frequency of silencing compared to the distance of the URA3 promoter from the telomere. This result strongly suggests that a gene's promoter is a major determinant in cis for effective transcriptional repression near telomeres. Combined with the finding that silencing of URA3 does not appear to be dependent on the transcriptional orientation of URA3, the inventors propose that repression is primarily exerted on the gene's promoter, and therefore blocks initiation rather than elongation.

Two important points about position effect are provided by the studies in which PPR1 was deleted. As with most transactivator proteins, PPR1 appears to modulate transcription through the promoter (Roy et al., 1990). Hence, the increased frequency of telomeric silencing of URA3 in ppr1⁻ strains supports the result that promoter occlusion is critical in achieving position effect repression. These results also suggest that spreading of position effect is a function of promoter strength of the gene being assayed.

A position effect on timing of replication has been detected at ~35 kbp from the V-R telomere (Ferguson et al., 1991; Ferguson and Fangman, 1992), while position effect on URA3 transcription is not detected beyond ~13 kbp from the same terminus. At present the inventors cannot resolve whether this apparent discrepancy reflects differences between the two assays being used, or inherent distinctions between the mechanisms of initiating replication and transcription.

2. Effect of Y' Elements on the Spread of Telomeric Silencing

It has been suggested that Y' elements overcome telomere position effect (Greider, 1992), since genes embedded into Y's are not transcriptionally repressed (Carlson et al., 1985; Louis and Haber, 1990). However, these data argue that Y's do not block the spread of telomeric repression per se; the inventors find that a 6.7 kbp Y' element sustains a greater frequency of silencing than an equal length of unique chromosomal sequences. It is unclear whether Y's are involved in propagation or reinitiation of silencing, or if Y's simply lack elements present in unique chromosomal DNA which suppress the spreading of telomere-dependent transcriptional inactivation. Nevertheless, the presence of a Y' element adjacent to a telomere results in a more extensive silent chromosomal domain. Perhaps this trait is important in maintaining the unique telomeric presence of Y' elements.

3. SIR3 Enhances Position Effect in Yeast

Overexpression of SIR3 enhances position-effect variegation of telomeric genes; this SIR3-effect was also detected within and adjacent to the HM loci. Thus the modulation by SIR3 of position-effect repression is likely to occur at other places in the genome where an initiation site for SIR3-dependent silencing resides.

The slope of the observed gradient in frequency of URA3 silencing along V-R is altered by overexpressing SIR3 in the cell, suggesting that, in contrast to the effect of a ppr1 mutation, SIR3-overexpression affects silent chromatin rather than an intrinsic property of URA3. In addition, the increase in telomeric silencing is sensitive to SIR3 gene dosage, indicating that SIR3 is limiting in the cell. These data suggest that SIR3 may be a structural component of yeast repressive chromatin, or a factor directly required for its assembly. Alternatively, SIR3 may act indirectly by regulating the level or activity of structural or assembly constituents of silent chromosomal domains.

SIR3 bears no significant similarity to any known enhancers of position effects, such as the Drosophila Su(var)2–5 (HP-1) or Su(var)3–7 proteins (Alberts and Sternglanz, 1990), nor does it harbor a detectable chromodomain motif, which is thought to mediate the packaging of heterochromatin by the Su(var) 2–5 and Polycomb gene products (Paro and Hogness, 1991; Messmer et al., 1992). Extragenic suppressor analysis of HML silencing indicates a physical interaction between SIR3 and histone H4 (Johnson et al., 1990). Thus the inventors favor the model that SIR3 directly interacts with yeast nucleosomes to facilitate the compaction of chromatin into a higher-order structure responsible for silenced regions of the yeast genome. In this light, SIR3 may be a functional equivalent of histone H1, mediating supra-nucleosomal organization of the genome (Weintraub, 1984).

In addition to histone H4, telomeric silencing requires the products of SIR2, SIR4, NAT1 and ARD1. The roles of SIR2 and SIR4 in transcriptional repression are not yet clear. NAT1 and ARD1, which are subunits of an N-terminal acetyltransferase (Park and Szostak, 1992), presumably modify chromatin component(s) to facilitate assembly of repressed chromosomal states (Mullen et al., 1989; Park et al., 1992).

The ability of telomeric silencing to spread along the chromosome raises the question as to whether a cell can control the size of silenced domains. This issue is particularly critical for *S. cerevisiae*, in which inappropriate regional silencing might have immediate deleterious effects, due to the high density of genes along the chromosome (Olson, 1991). A cis-element can act as a chromosome-specific barrier against the spread of silent domains [e.g. active transcription units (this work), or homologues of the Drosophila scs sequences (Kellum and Schedl, 1992)]. On a cellular scale, limiting the amount of SIR3 in the cell could prevent excessive transcriptional inactivation of the entire genome. Since the SIR3 gene is itself located near a telomere (Ivy et al., 1985), and no essential gene has been found between SIR3 and the telomere (Basson et al., 1987; Brisco et al., 1987; Dietzel and Kurjan, 1987; Mortimer et al., 1992), position-effect repression of the SIR3 locus would provide a plausible negative feedback mechanism for control of position-effect spreading in yeast. If telomeric chromatin spread as far as the SIR3 locus, transcription of SIR3 would be repressed, thus limiting further spreading of the repressive chromatin. In apparent contrast to the yeast genome, larger eukaryotic genomes are extensively heterochromatic. This may be due to the presence of more abundant functional homologue(s) of SIR3. Extensive but carefully controlled heterochromatization of chromosomes may play a major role in control of cellular differentiation and development in complex eukaryotes.

This Example shows that the spread of telomeric position effect in *S. cerevisiae* is modulated by numerous factors, including promoter distance from the telomere, promoter strength, transcriptional status of telomere-proximal genes, presence of Y' elements, and intracellular concentration of the SIR3 gene product.

EXAMPLE IV

A Transactivator Competes to Establish Gene Expression in a Cell Cycle Dependent Way In multicellular eukaryotes, chromosomal position effects generally involve the repression of a euchromatic, wild-type gene when it has been placed in or near heterochromatin as the result of a chromosomal rearrangement (Lima-de-Faria, 1983). In a population of cells with such a rearrangement, the gene may escape repression; consequently, the resulting phenotype is variegated, exhibiting patches of normal and mutant tissue. A classic example of this phenomenon is the mosaic red-and-white eye of Drosophila in which the white gene has been translocated within centromeric heterochromatin (Eissenberg, 1989; Henikoff, 1990; Spradling and Karpen, 1990).

When a wild-type gene is located near a telomere in the budding yeast *Saccharomyces cerevisiae*, it too is subject to position-effect variegation (Example I). For instance, when yeast cells with the ADE2 gene placed near a telomere form a colony on solid medium, the colony is composed of sub-populations in which the ADE2 gene is either expressed (white sectors) or repressed (red sectors). The different phenotypes of the sectors in a colony reflect the ability of genetically identical cells to switch between phenotypic states. The fact that large sectors are phenotypically uniform reflects the ability of each state to be heritably propagated for multiple generations.

Similarly, yeast cells with a telomeric URA3 gene can form colonies on medium containing 5-FOA, a drug lethal to cells expressing URA3 (Boeke et al., 1987), indicating that the cells are phenotypically ura3⁻. However, these 5-FOA resistant cells can form colonies when placed on medium lacking uracil, thus the cells are able to switch their phenotypic status and induce expression of the telomeric URA3 gene (Example I).

Silencing of telomeric genes in S. cerevisiae is likely due to a structurally distinct chromatin domain that initiates at the telomere. Evidence for this specialized chromatin structure includes: identification of mutations in the histone H3 and H4 genes which relieve telomeric silencing (Example II) the finding that telomere-adjacent chromatin contains histone H4 in a hypoacetylated state compared to H4 in actively transcribed chromatin regions of the genome (Braunstein et al., 1993), and the relative inaccessibility of telomere-proximal DNA to in vivo modification by the E. coli dam methyltransferase protein (Gottschling, 1992).

In addition, the frequency with which a gene is silenced decreases with increasing distance from the telomere, suggesting that the structure nucleates at the telomere and the extent of its inward assembly along the chromosome varies between cells (Example III; Renauld et al., 1993). The extent of this assembly is proportional to the cellular concentration of SIR3, a gene product required for silencing at telomeres and the silent mating loci, HML and HMR (Example II; Laurenson and Rine, 1992; Example III). These results suggest that SIR3 is rate-limiting for assembly of the silent chromatin structure, and implicate SIR3 as a component of the silent structure.

Questions that arise in the study of position effect variegation are how does a gene switch between phenotypic states and, once a state is determined, how is it heritably propagated (Brown, 1984; Weintraub, 1985). With respect to position-effect variegation and the first question, two models of regulation that involve a role for chromatin structure have evolved (Felsenfeld, 1992). Both models propose that transcription of a gene is inhibited by assembly of its DNA into chromatin. Furthermore, one or more transcriptional activator proteins (transactivators) bind in a sequence-specific manner to DNA located in proximity to the gene and facilitate transcription of that gene, thus overcoming the chromatin's repressive nature. Where the models differ is that in one case chromatin prevents the transactivator from gaining access to the DNA, in essence keeping the gene 'irreversibly' repressed. However, during DNA replication the chromatin structure of the gene is perturbed and the transactivator has the opportunity to gain access and establish transcription, before re-assembly of the chromatin is completed. In the second case, the transactivator can induce gene transcription at anytime in a replication-independent manner, effectively disrupting the repressive nature of the chromatin.

At its normal locus, URA3, like many biosynthetic pathway genes, is constitutively expressed at a basal level, but can be induced to higher levels of expression (Lacroute, 1968). URA3 induction is contingent upon binding of an activated form of the transactivator PPR1 to the Upstream Activating Sequence (UAS) of the gene (Losson and Lacroute, 1981; Roy et al., 1990). Interestingly, when URA3 is located adjacent to a telomere its basal level of expression may be repressed, since the cells are phenotypically ura3⁻ (Example I).

This Example concerns how a gene located near a telomere overcomes silencing. Specifically, the inventors examined the role of PPR1 in the expression of a telomeric URA3 gene. The results show that silent telomeric chromatin inhibits basal expression of URA3 and prevents the transcriptional activation by PPR1 of the telomeric URA3 gene in $G_1$ and early S phases of the cell cycle, in addition to when cells are arrested in $G_0$. Furthermore, this suggests that upon replication of the telomeric DNA, a competition takes place between assembly of a silent chromatin structure and assembly of a PPR1-mediated transcriptionally active gene.

A. Methods

1. Plasmid Constructions

Plasmid FAT-PPR1 was constructed by ligating a 4.4 kbp EcoRI fragment containing the PPR1 gene (from pUC8-PPR1, obtained from R. Losson) into plasmid YEpFAT10 (referred to as "FAT"; 2μ ARS, TRP1, leu2-d, obtained from K. Runge; Runge and Zakian, 1989). A 3.7 kbp HindIII-SphI fragment containing the entire PPR1-1 allele (from plasmid pFL11; Losson and Lacroute, 1983) was inserted into plasmid pVZ1 (Henikoff and Eghtedarzadeh, 1987). The resulting plasmid (pVZPPR1-1) provided a 3.7 kbp HindIII-BamHI fragment containing PPR1-1 which was ligated into pRS425 (Sikorski and Hieter, 1989) to yield plasmid pRS4-PPR1-1.

Plasmids pRS305-GALPPR1-1 and pRS305-GALppr1-1 were constructed in a series of steps. A 685 bp EcoRI-BamHI fragment containing the GAL1,10 promoter (Johnston and Davis, 1984, from pBM150) was ligated into EcoRI-BamHI digested pRS314 (Sikorski and Hieter, 1989), the resulting plasmid (pRS314GAL) was digested with ApaI-EcoRI and a 2.8 kbp ApaI-EcoRI fragment containing the 3' portion of PPR1-1 from plasmid pRS4-PPR1-1 was inserted yielding pRS3GAL3'PPR1-1. Next, a 500 bp fragment containing the 5' portion of the PPR1-1 allele was produced by PCR amplification (Innis et al., 1990). The primers were designed to introduce an EcoRI site 28 bp upstream of the PPR1 ATG initiation codon and to include the EcoRI site within the PPR1-1 coding sequence (PPR1-ATG oligo, 5'-CCG GAATTCATACGAAGATGATGATTAAATC-3', SEQ ID NO:6, the new EcoRI site is underlined; PPR1-n650 oligo, 5'-GGCTTGCCATAGACTTGCTCG-3', SEQ ID NO:7). The fragment was digested with EcoRI and inserted between the GAL1,10 promoter and the 3' PPR1-1 sequence in pRS3GAL3'PPR1-1; one orientation of the insert yielded pGALPPR1-1 which has the GAL1,10 promoter fused to the entire PPR1-1 coding sequence (GALPPR1-1), while the other orientation of the insert yielded pGALppr1-1 which has the 5' portion of the PPR1-1 allele inverted resulting in a mutated gene fusion (GALppr1-1). The 3.5 kbp ApaI-BamHI fragments containing GALPPR1-1 and GALppr1-1 from PGALPPR1-1 and pGALppr1-1 respectively, were inserted into pRS305 (Sikorski and Hieter, 1989) yielding pRS305-GALPPR1-1 and pRS305-GALppr1-1.

Plasmid pVZADH4 contains the ADH4 locus on a 3.1 kbp EcoRI-SalI fragment (Example I). A 4.8 kbp HindIII-XbaI fragment containing the LYS2 gene from plasmid pDP6 (Fleig et al., 1986) was inserted into XbaI-HindIII digested pVZADH4 creating pVZadh4::LYS2. The UASGAL-URA3 allele was produced by sequential PCR amplification steps (Ausubel et al., 1989). The primers were designed to replace the PPR1 binding site (UAS$_{URA}$, 5'-TTCGGTAATCTCCGAA-3', SEQ ID NO:8 (Roy et al., 1990)) with a GAL4 binding site (URA3-GAL-5' oligo, 5'-CGGACGACTGTCGTCCGTCAAAAAAATTTCAAGG-AAACCG, SEQ ID NO:9, URA3-GAL-3' oligo, 5'-CGGACGACAGTCGTCCGCAGAAGGAAGAACGAA-GGAA, SEQ ID NO:10, the GAL4 binding sequence is underlined (Verdier, 1990)).

The UAS$_{GAL}$-URA3 PCR product was digested with SalI and BamHI and inserted into pRS315(-PstI) producing pRS315(-PstI)-GALURA3; the PstI site in pRS315 was previously deleted by digestion of pRS315 (Sikorski and Hieter, 1989) with PstI, making the ends blunt with T4 DNA polymerase, and religating the plasmid. Plasmid pRS315(-PstI)-GALURA3 was digested with HindIII and SmaI and religated, resulting in the UAS$_{GAL}$-URA3 fragment being inverted in the vector to yield pRS315(-PstI)-GALURA3-flip.

This plasmid provided a 1.1 kbp HindIII-BamHI fragment containing UAS$_{GAL}$-URA3 which was inserted into pVII-L URA3-TEL (Example I) to produce pADH4GALURA3TEL; the same 1.1 kbp HindIII-BamHI UAS$_{GAL}$-URA3 fragment was inserted into HindIII-BamHI digested pVZADH4 resulting in plasmid pΔadh4::GALURA3. A 1.2 kbp HindIII-NotI fragment (made blunt-ended with T4 DNA polymerase, from pVII-L URA3-TEL) was ligated into HindIII (made blunt ended with T4 DNA polymerase) digested pVZadh4::LYS2 producing pURA3-TEL-LYS2. A 1.5 kbp PstI fragment (from pADH4GALURA3TEL) containing the UAS$_{GAL}$-URA3 promoter was inserted into PstI digested pURA3-TEL-LYS2 to replace the wild-type URA3 promoter; the resulting plasmid was pGALURA3-TEL-LYS2.

A 1.35 kbp BamHI fragment containing the entire URA1 gene (Roy, 1992) produced by PCR amplification of genomic DNA (5'URA1 oligo, 5'-CGAAC GGATCCCCTTCAGCCACTACAGCCTACTT-3', SEQ ID NO:11; 3'URA1 oligo, 5'-CGAAG GGATCCGCCAATTGCGAATGCACTCACCG-3', SEQ ID NO:12, the BamHI sites are underlined) was inserted into pVZ1 to yield plasmid pVZURA1. A 1.1 kbp HindIII-BamHI URA3 fragment was ligated into HindIII-BamHI digested plasmid YDpK (Berben et al., 1991), yielding plasmid YDpK-URA3. Plasmid p5'URA3 contains a 415 bp HindIII-EcoRV 5' URA3 fragment ligated into HindIII-EcoRV digested pVZ1. Plasmid CY807+TRP1 (bar1::TRP1) was constructed by inserting a 723 bp BamHI fragment containing TRP1, from YDp-W (Berben et al., 1991), into the BglII site in the BAR1 sequence in plasmid CY807 (obtained from S. Honigberg).

Plasmids pBM292 (GAL4-wild-type, 881 amino acids), pBM430 (GAL4, C-term. amino acid 292), pBM433 (GAL4, C-term. amino acid 684), pBM789 (GAL4, C-term. amino acid 174), and pBM1268 (GAL4, C-term. amino acid 383) are CEN, TRP1 plasmids, as described by Johnston (1988). Plasmids pBD57 and pJM206 were obtained from F. Cross, and plasmid pPL9 was obtained from R. Surosky (1992).

2. Yeast Methods and Strains

*S. cerevisiae* were grown at 30° C.; liquid cultures were agitated during incubation at 180 RPM. All studies in liquid culture were carried out with mid-log phase cells unless otherwise indicated. Plating efficiency analysis and synthetic media have been described previously (Example I), except for α-aminoadipate containing medium which was prepared as described in (Sikorski and Boeke, 1991). Studies involving galactose control employed YEP-3% raffinose, and 0.3% galactose for induction unless otherwise indicated.

For studies involving drug or α-factor washout, cells were pelleted by centrifugation for three minutes at 1500×g and washed and/or resuspended in prewarmed medium (30°). Cells were arrested with 20 nM α-factor for three hours, and 50 mM pthalic acid (pH=5.5) was included in the medium. For release from α-factor arrest, 1 mg/ml pronase E was included in the fresh resuspension media, except for one study where one water wash of the pellet was carried out and pronase E was not included in the resuspension medium. Cells were arrested with 10 μg/ml nocodazole (from a 1000× stock solution in DMSO) for three hours. Hydroxyurea was dissolved directly in medium immediately before use to a final concentration of 400 mM, except in one study where it was dissolved directly in the cultures. Cells were fixed and stored in 10 mM Tris, 100 mM EDTA, pH=8.0, 3.7% formaldehyde, and sonicated before microscopy to assess cell morphology.

*S. cerevisiae* were transformed using the lithium acetate procedure (Ito et al., 1983). The URA3 gene was placed adjacent to the telomere sequence $(TG_{1-3})_n$ on the left end of chromosome VII (UCC2013), or inserted at the ADH4 locus about 20 kbp from the telomere on VII-L (UCC432), as described in Example I. UCC2013 was derived from YPH499, UCC432 was derived from UCC431.

Strains UCC111, UCC113, UCC115, UCC412, and UCC2014 were constructed by transformation of strains UCC1001, UCC1003, YPH250, UCC411, and UCC2013 respectively, with plasmid pΔAPPR1::HIS3 and selection for HIS$^+$ transformants; this plasmid was described in Example III. Strains UCC116, UCC117, and UCC151 were derived from strains UCC1001, UCC1003, and YPH250 respectively, by transformation with plasmid pFAT-PPR1 and selection for TRP$^+$ cells; strains UCC238, UCC152, and UCC153 were derived from strains UCC1001, UCC1003, and YPH250 respectively, by transformation with plasmid YEpFAT10 (FAT) and selection for TRP$^+$.

Strain UCC411 was derived from YPH499 by transformation with HpaI digested YDpK-URA3 and selection for LYS$^+$ cells. UCC413 and UCC2016 were derived from UCC412 and UCC2014 respectively, by transformation with plasmid CY807+TRP1 digested with ClaI. Strain UCC431 was a 5-FOA$^R$ (ura$^-$, lys$^-$) derivative of UCC413. Strains UCC409, UCC433, and UCC435 were derived from strains UCC2016, UCC431, and UCC432 respectively, by transformation with HpaI digested pRS305-GALPPR1-1; strains UCC410, UCC434, and UCC436 were derived from strains UCC2016, UCC431, and UCC432 respectively, by transformation with HpaI digested pRS305-GALppr1-1.

In order to place UAS$_{GAL}$-URA3 (or another non-selectable marker) adjacent to telomere VII-L, a method was developed based on the phenomenon of new telomere formation at internal telomeric sequences (Example I). Plasmid pGALURA3-TEL-LYS2 was used to integrate within the ADH4 locus: UAS$_{GAL}$-URA3 adjacent to 81 bp of telomere repeat sequence followed by LYS2 as the selectable marker (centromere-proximal to centromere-distal). At a frequency of ~10$^{-6}$, loss of chromosomal sequences distal to the 81 bp internal telomeric sequence (including LYS2) resulted in formation of a new and stable telomere having the UAS$_{GAL}$-URA3 gene adjacent to it.

Cells that were transformed with pGALURA3-TEL-LYS2, and were LYS$^+$ and had the correct sequences inserted within the ADH4 locus (verified by DNA blot hybridization analysis), were grown non-selectively for about 25 generations. Cells which had lost LYS2 were selected for survival on medium containing α-aminoadipate; the expected structure of telomere VII-L in the resulting lys⁻ strain was verified by DNA hybridization analysis.

UCC418 was derived from YM725 by transformation with NotI-SalI digested plasmid pGALURA3-TEL-LYS2 and selection for LYS⁺ transformants; UCC420 was an α-aminoadipate resistant (lys⁻) derivative of UCC418 which has $UAS_{GAL}$-URA3 adjacent to telomere VII-L. UCC419 was derived from YM725 by transformation with EcoRI-SalI digested plasmid pDadh4::GALURA3 and selection for URA⁺ transformants. Strains UCC419 and UCC420 were transformed with plasmids pBM292, pBM430, pBM433, pBM789, and pBM1268, to yield strains UCC421–UCC425 respectively, for the UCC419 parent, and strains UCC426–UCC430 respectively for the UCC420 parent. The expected structures of the various chromosomal constructs were confirmed by DNA blot hybridization analysis.

3. Analysis of Nucleic Acids

RNA was isolated from mid-log phase cells, unless otherwise indicated, as described in Example I. RNA hybridization analyses were performed as described in Example I, except that 15 or 20 μg of total RNA was denatured in the presence of 20 μg/ml ethidium bromide and separated by electrophoresis on a 1.2% agarose-5% formaldehyde (37% stock)-MOPS gel. Immediately following electrophoresis the gel was photographed and washed twice for 15 minutes in H₂O, 15 minutes in 10×SSC and transferred to nylon (MSI, Westboro, Mass.). Photography of the gel following transfer verified that complete transfer of the rRNA had occurred.

RNA was immobilized on the nylon membrane by UV irradiation (120 mJ) of the damp membrane, followed by prehybridization of the membrane. Prehybridization and hybridization solutions contained 5×SSC, 50% formamide, 5× Denhardt's solution, 0.2 mg/ml denatured and degraded herring sperm DNA, 0.2% SDS; hybridization solution also contained 10% dextran sulfate and was filtered through a 45 μm membrane to remove particulates. Prehybridization (1–6 hr) and hybridization (18–30 hr) were carried out at 42° C. for DNA probes and 53° C. for RNA probes.

Blots were washed five minutes at 23° C. in 2×SSC, 0.1% SDS, followed by two 15 minutes washes at 55° C. in 0.1×SSC, 0.1% SDS for DNA probes, or three 20 minute washes at 60° C. in 0.1×SSC, 0.1% SDS for RNA probes, and exposed to film. The relative levels of URA3 and URA1 RNAs were quantified on a Radioanalytic Imaging System (Ambis, San Diego, Calif.). For rehybridization studies, probes were removed from the blots with three 20 minute washes with boiling 0.2% SDS.

RNA antisense probes were labeled with $^{32}$P-CTP or $^{32}$P-UTP (3000 Ci/mmol) by in vitro transcription of linearized plasmids with T7 RNA polymerase or SP6 RNA polymerase (Sambrook et al., 1989). DNA probes were labeled with $^{32}$P-dCTP (3000 Ci/mmol) by random oligonucleotide priming as described (Sambrook et al., 1989). Plasmid p5'URA3 (T7) was the template for the URA3 RNA probe. Plasmid pPL9 (SP6) was the template for the ACT1 RNA probe. The URA3 DNA probe was a 1.1 kbp HindIII fragment containing the entire coding sequence, the URA1 probe was a 1.3 kbp BamHI fragment containing the entire URA1 gene in plasmid pVZURA1, the SWI5 probe was a 3.3 kbp HindIII fragment from pBD57, and the CLN2 probe was a 640 bp HindIII-SpeI fragment in pJM206.

B. Results

1. The URA3 Transactivator, PPR1, Is Required for Overcoming Telomeric Silencing of URA3

In order to test the idea that the transactivator, PPR1, plays a role in overcoming silencing of a telomere-linked URA3 gene, the PPR1 gene was deleted from a strain in which URA3 was located adjacent to telomere VII-L (UCC1001). To determine whether deletion of PPR1 had a specific effect on URA3 expression at a telomere, PPR1 was also deleted in a strain with URA3 inserted at an internal chromosomal position, the ADH4 locus which is about 20 kbp from telomere VII-L (UCC1003). PPR1 was also deleted in a strain lacking URA3 (ura3-52; YPH250).

URA3 expression was measured by two methods: plating viability assays on medium containing 5-fluoro-orotic acid (5-FOA) and on medium lacking uracil (-URA), and RNA blot hybridization analysis. 5-FOA is converted into a toxic metabolite by the URA3 gene product, such that cells expressing normal levels of the URA3 gene product are sensitive to 5-FOA, while cells that lack it are resistant to 5-FOA (Boeke et al., 1984).

For the RNA analysis, transcript levels were analyzed from URA3, URA1, and ura3-52 (Rose and Winston, 1984, in this allele the URA3 transcript is truncated) each of which is regulated by the PPR1 protein (Losson and Lacroute, 1981). Thus, URA1 and ura3-52 RNA levels reflect the in vivo level of PPR1 activity as a transcriptional activator in each experimental sample.

PPR1 was found to be required for overcoming silencing of the telomeric URA3 gene. Wild type (PPR1⁺) cells with URA3 near a telomere, formed colonies on 5-FOA medium and medium lacking uracil. This reflects the ability of the telomeric URA3 gene to switch between transcriptionally repressed and active states. Deletion of PPR1 abolished the ability of cells with a telomeric URA3 gene to grow in the absence of uracil. Deletion of the PPR1 binding site within the URA3 gene promoter had the same effect as deletion of PPR1, indicating that specific binding of PPR1 at the URA3 UAS was required for overcoming silencing. Thus, in this telomeric context, PPR1 is required for the transcriptional activation of the URA3 gene.

The very small colonies which arose on -URA medium from the ppr1⁻ strain with a telomeric URA3 gene had acquired trans-acting mutations or local chromosomal rearrangements which permitted expression of URA3. Therefore, essentially no URA3 gene product was produced from this telomeric site when PPR1 was absent from the cell. In contrast, deletion of PPR1 had no effect on 5-FOA or -URA viability when URA3 was located at an internal chromosomal locus. This result suggests that at an internal location transcription of URA3 still occurs, independently of PPR1, and is consistent with URA3 regulation at its normal chromosomal locus (Losson et al., 1985). As expected, PPR1 deletion had no effect on the plating viability of cells lacking a functional URA3 gene.

Telomeric URA3 mRNA was undetectable when PPR1 was deleted. However, PPR1⁺ cells with a telomeric URA3 maintained the ability to activate URA3 transcription. Deletion of PPR1 had little or no effect on expression of an internal copy of URA3, or on expression of URA1.

Both the plating viability on -URA medium and the RNA analysis indicate that the constitutive or basal (PPR1-independent) expression of URA3 at telomere VII-L is repressed by the telomeric silencing machinery. However, the transactivator, PPR1, is able to circumvent the telomeric repression, thus facilitating URA3 expression.

2. Increased PPR1 Dosage Prevents Silencing of a Telomeric URA3

Since a telomeric URA3 could exist in either an active or repressed state, and because PPR1 was required for the active state, the inventors postulated that PPR1 might compete against the assembly of a repressed state. If this hypothesis were true, then increasing the dosage of PPR1 should increase the frequency with which an active state is established.

To test this hypothesis, PPR1 was expressed from a multi-copy plasmid (FAT-PPR1, FAT is the vector alone) in strains with URA3 absent, URA3 at a telomeric, or URA3 at an internal chromosomal locus. Cell viability of the resulting strains was quantified on 5-FOA medium and medium lacking uracil. Increase of PPR1 protein concentration from FAT-PPR1 (verified by ura3-52 and URA1 RNA levels and quantitative electrophoretic mobility shift analyses) resulted in complete 5-FOA-sensitivity of cells with URA3 at the telomeric locus, along with improved growth on -URA. As expected, viability was not affected by overproduction of PPR1 when URA3 was at the internal locus or absent. Thus, high levels of PPR1 compete against telomeric silencing to perpetually maintain the URA3 gene in an active state. These results also suggest that in a wild type cell, the concentration of PPR1 is limiting for telomeric URA3 expression.

3. GAL4 Can Overcome Telomeric Silencing

To determine if the ability of PPR1 to overcome telomeric silencing on URA3 transcription was a general characteristic of transcriptional activator proteins, the PPR1 binding site upstream of the URA3 gene was replaced with a binding site for the GAL4 transactivator protein (Verdier, 1990). This modified URA3 gene ($UAS_{GAL}$-URA3) was placed next to telomere VII-L (UCC420) or within the ADH4 locus (UCC419) in strain YM725 (gal4$^-$, gal80$^-$, ura3$^-$). The gal80 mutation relieves negative regulation of the GAL4 protein so that activity of GAL4 is proportional to its concentration (Johnston, 1987). $UAS_{GAL}$-URA3 was silenced when placed at telomere VII-L, as the cells were 5-FOA-resistant and Ura$^-$, but $UAS_{GAL}$-URA3 was not repressed when internally located on the chromosome since cells were 5-FOA-sensitive and URA$^+$.

The wild-type GAL4 protein or a series of C-terminal truncations of the GAL4 protein were expressed in the strains with $UAS_{GAL}$-URA3 located at the telomere or at the internal locus. The C-terminal truncation derivatives of GAL4 maintain the N-terminal DNA binding domain and bind to $UAS_{GAL}$ in vitro, but are defective in transcriptional activation in vivo (Johnston and Dover, 1988). Expression of wild-type GAL4, from a single copy centromeric plasmid, completely reversed silencing of the telomeric $UAS_{GAL}$-URA3, as indicated by the sensitivity of this strain to 5-FOA, and robust growth on -URA medium. None of the truncated GAL4 derivatives were able to activate $UAS_{GAL}$-URA3 adjacent to the telomere. Expression of GAL4 or its derivatives had no effect on 5-FOA-sensitivity, or -URA viability, of strains with $UAS_{GAL}$-URA3 located internal on the chromosome. It appears that the activation domain of GAL4 is required to compete for telomeric gene expression. These results suggest that the ability to overcome telomeric silencing is a general function of transactivators.

4. Modulating the Dosage of PPR1C Reveals that its Accessibility to the Telomeric URA3 Gene is Limited The finding that PPR1 dosage has a demonstrable effect on telomeric URA3 expression, but not for internal URA3 expression, suggested that the telomeric URA3 gene is relatively resistant to transcriptional activation by PPR1 compared to when URA3 gene is located non-telomerically.

To investigate this, a chimeric gene, GALPPR1-1, was constructed with the coding sequence of the PPR1-1 allele under control of the GAL1,10 promoter (Johnston and Davis, 1984). The PPR1-1 allele encodes a constitutively active protein, PPR1$^c$; thus, the level of PPR1$^c$ activity as a transactivator is directly proportional to its total cellular concentration (Losson and Lacroute, 1983). The GAL1,10 promoter permitted precise regulation of PPR1$^c$ protein concentration within the cell (Durrin et al., 1991), since the intracellular level of PPR1$^c$ was proportional to the level of galactose in the medium (based on ura3-52 RNA levels and quantitative electrophoretic mobility-shift analyses). As a control, a non-functional version of the gene fusion (GALppr1-1), which contains an inversion within the PPR1-1 coding sequence, was also created. These gene fusions were inserted at the leu2 locus in isogenic ppr1$^-$ strains containing URA3 at a telomeric (UCC2016) or internal chromosomal locus (UCC431) or in which URA3 was absent (UCC432).

The resulting strains were tested for viability on 5-FOA and -URA medium that also contain galactose. Expression of the GALPPR1-1 fusion, but not the mutated GALppr1-1 fusion, effectively overcame silencing of the telomeric URA3 in all cells of the population; the cells were URA$^+$ and 5-FOA-sensitive. Expression of GALPPR1-1 or GALppr1-1 had no effect on the 5-FOA sensitivity or the -URA viability of strains with URA3 at the internal locus or absent.

Levels of mRNA were analyzed from these strains grown in rich medium containing 3% raffinose and 0.25% galactose, which induced expression of GALPPR1-1 or GALppr1-1. Expression of GALPPR1-1 strongly activated transcription from URA3, URA1, and ura3-52, although compared to expression of the internal URA3 gene, expression of the telomeric URA3 was reduced. Equivalent levels of PPR1$^c$ activity (based on URA1 and ura3-52 mRNA levels, and electrophoretic mobility-shift analyses) were present in the GALPPR1-1 strains. This result supports the idea that, compared to the internal URA3, the telomeric URA3 gene is relatively resistant to transcriptional activation at this concentration of PPR1$^c$.

The inventors compared the relative expression levels of the telomeric URA3 gene and the internal URA3 gene when different concentrations of PPR1 protein were expressed. The level of ura3-52 RNA was used as a standard for PPR1$^c$ concentration in vivo in comparing the two URA3 loci; ura3-52 has the same upstream sequences as URA3 and is responsive over a wide range of PPR1$^c$ concentrations. The level of GALPPR1-1 expression was varied by growing cells with different concentrations of galactose in the medium; levels of ura3-52 RNA confirmed that higher concentrations of galactose did in fact result in higher intracellular PPR1$^c$ protein concentrations.

The results show that URA3 at the telomeric locus was less responsive to low levels of the transactivator than URA3 at an internal locus. In addition, while both loci can achieve the same maximum level of expression, a higher PPR1$^c$ concentration was required for the telomeric URA3 compared to the internal URA3. These results suggest that there is a competition for binding at the telomeric URA3 promoter between PPR1$^c$ and silent chromatin.

5. PPR1$^c$ Activation of a Telomeric URA3 Gene is Cell Cycle Regulated

The studies described above were performed on actively dividing cells. Hence, the cells were transiting through the cell cycle during the analysis. Keeping this in mind, two simple models can be set forth to explain the competition between PPR1 and telomeric chromatin for expression of the URA3 gene. In the first model, the competition only occurs within specific periods of the cell cycle. During part of the cell cycle the telomeric URA3 gene is resistant to activation by PPR1 if the silent chromatin state has been established. Only when the silent chromatin is weakened or disassembled, which might occur during DNA replication of the telomeric region, does PPR1 have the opportunity to activate the gene. In the second model, PPR1 competes with equal fervor throughout the cell cycle.

To test and distinguish between these models, cells were grown in rich medium containing 3% raffinose and no galactose. Thus PPR1$^c$ was not present and the telomeric URA3 gene was maintained in a silent state. The cells were then synchronously arrested by treatment with either α-factor pheromone, to arrest them late in $G_1$ (Pringle and Hartwell, 1981), or nocodazole, an inhibitor of microtubule assembly (Pillus and Solomon, 1986).

In many eukaryotes, nocodazole produces a synchronous arrest at metaphase. Nocodazole also produces a very synchronous arrest in yeast, however it is unclear whether the arrest occurs late in $G_2$ or at metaphase. By the criterion of spindle pole body separation the cells appear to be in $G_2$ (Jacobs et al., 1988); however recent studies suggest that the chromosomes may be condensed as expected for a metaphase arrest (Guacci et al., 1994). In light of this uncertainty, the arrest is referred to as $G_2$/metaphase. Once arrested, galactose was added to induce expression of PPR1-1, and half of the culture was released from the arrest, while arrest was maintained in the other half.

Expression of the telomeric URA3 gene and the internal URA1 and ura3-52 genes was compared. The transcript levels of CLN2 and SWI5 were also analyzed to monitor the progress of cells through the cell cycle. CLN2 is transiently expressed in late G1 near the time of START (Wittenberg et al., 1990), and SWI5 is transiently expressed beginning sometime in S, through $G_2$, and on into M (Nasmyth et al., 1987).

The telomeric URA3 was not activated by PPR1$^c$ during α-factor arrest. The analysis clearly shows that while cells were arrested with α-factor, the telomeric URA3 gene remained repressed. The increase in URA1 and ura3-52 mRNA levels indicate that PPR1$^c$ was active in these cells. Following release from the α-factor arrest, PPR1$^c$ was able to activate the telomeric URA3 gene. The analysis of the SWI5 transcript and microscopic analysis of cell morphology were consistent with the cell-cycle arrest imposed by α-factor, and release thereafter. The low level of telomeric URA3 transcript seen late during the continued α-factor arrest correlated with the small fraction of cells (~5%) that escaped from the arrest.

In striking contrast to the repressed state of telomeric URA3 during α-factor arrest, the telomeric URA3 gene in $G_2$/metaphase, nocodazole arrested, cells was effectively activated by PPR1$^c$. In the absence of functional PPR1$^c$, "GALppr1-1"), no activation of the telomeric URA3 or the internal URA1 and ura3-52 genes occurred. In fact, not even basal expression of the telomeric URA3 was seen in the absence of PPR1$^c$. Analyses of CLN2 and SWI5 expression, as well as microscopic analyses of cell morphology, confirmed the successful arrest with nocodazole and the release that followed.

To determine whether the effects of the α-factor and nocodazole treatments were due to the specific cell cycle arrests and not to other physiological effects of the treatments, the inventors tested the effect of α-factor on telomeric gene expression in cells arrested in $G_2$ with nocodazole, and conversely, the effect of nocodazole on telomeric gene expression in cells arrested in $G_1$ with α-factor.

The α-factor treatment did not prevent the expression of the telomeric URA3 gene in cells previously arrested with nocodazole, and nocodazole treatment did not result in expression of the telomeric gene in cells previously arrested with α-factor. Thus, it appears that the effects on telomeric gene transcription by α-factor and nocodazole were due to the specific cell cycle arrests. These results suggest that the ability of a transactivator (PPR1$^c$) to function in a telomeric domain is cell cycle regulated. The inventors propose that a transactivator is inaccessible to the telomeric domain in $G_1$ phase and becomes accessible by the time the cells are in $G_2$/metaphase.

To more accurately determine the period of the cell cycle in which PPR1$^c$ activation of a telomeric URA3 could occur, cells were arrested in S phase with hydroxyurea, an inhibitor of DNA replication (Slater, 1973). Yeast cells with a telomeric URA3 and the integrated GALPPR1-1 fusion were pregrown in medium lacking galactose, to maintain repression of the telomeric URA3 gene, and arrested with α-factor. Galactose was added to the α-factor arrested cells to induce expression of PPR1-1, and the cells were released from the α-factor arrest; half of the culture was released into medium containing hydroxyurea.

Cells treated with this α-factor/hydroxyurea protocol arrest very early in S phase, significantly before telomeric regions replicate (Hartwell, 1976; McCarroll and Fangman, 1988). Hydroxyurea prevented the activation of the telomeric URA3, but did not affect transcriptional activation of the internal URA1 and ura3-52 genes. Telomeric URA3 and SWI5 expression following release from the hydroxyurea arrest, indicated that the arrest was reversible. Additionally, hydroxyurea did not prevent activation of the telomeric URA3 gene in cells which were previously arrested in $G_2$/metaphase with nocodazole, indicating that the presence of hydroxyurea itself does not prevent telomeric URA3 expression. These results indicate that early in S phase the transactivator can not gain access to the telomeric URA3, and taken together with the results above, suggest that progression through S phase is required for the establishment of the transcriptionally active state in the telomeric domain.

Temperature sensitive alleles of CDC (Cell Division Control) genes represent another method commonly used to arrest yeast cells at a specific point in the cell cycle (Pringle and Hartwell, 1981). Cells are typically shifted from a permissive growth temperature (~23°) to a non-permissive temperature (37°) to cause arrest. The inventors began to use temperature sensitive alleles of CDC genes to define the cell cycle period in which PPR1 activation occurred. However, it was discovered that PPR1$^c$-induced expression of a telomeric URA3 was severely compromised at 37° in wild type (CDC$^+$) cells (Aparicio, 1993). This finding precluded the use of temperature sensitive alleles in dissecting the period of activation in the cell cycle. The effect appeared to be telomere specific, since the ura3-52 locus was activated. It is not clear if the effect of temperature on telomeric URA3 activation was specific to PPR1$^c$ (e.g. a reduction in the effective concentration of PPR1$^c$), or reflects a general strengthening of telomeric repression.

6. Telomeric Silencing is Irreversible When Cells Are in Stationary Phase ($G_0$)

An additional means to synchronously arrest a population of yeast cells is to maintain a culture in stationary phase (Werner-Washburne et al., 1993, for a review). Stationary phase cells of *S. cerevisiae* arrest in a state referred to as $G_0$; the cells are unbudded and their genomes are unreplicated. Cells enter $G_0$ by exiting from $G_1$ phase, and general transcriptional repression occurs upon entry to stationary phase (Choder, 1991).

Strains with URA3 at a telomeric or a nontelomeric locus and an integrated GALPPR1-1 were grown to stationary phase in rich medium containing 3% raffinose, so that PPR1$^c$ was absent and hence the telomeric URA3 gene was silenced. Cells were determined to be in stationary phase when the optical density of the culture had not increased during the previous 24 hour period, and greater than 98% of cells were unbudded. Expression of GALPPR1-1 was induced in the stationary cells by adding 0.3% galactose to the cultures. Incubation was continued as aliquots were collected for RNA analysis.

While the internal URA3 gene, as well as the URA1 and ura3-52 genes were transcriptionally activated by PPR1$^c$ in the stationary cells, the telomeric URA3 gene was not activated. Only after 48 hours of induction was a telomeric URA3 transcript observed, just slightly above limits of detection. Thus, silencing of a telomeric gene in stationary phase cells is essentially irreversible. As expected, basal levels of transcription decreased in the stationary cells. Moreover, the SWI5 transcript was not detected in Go cells, confirming that cells were not progressing through the mitotic cell cycle. In this study, galactose was added to cultures about 48 hours after mid-log phase; equivalent results were obtained when the study was performed with seven day old cultures.

C. Discussion

In this Example, the inventors examined the ability of transactivator proteins to overcome silencing of a telomere-adjacent gene in *S. cerevisiae*. It was found that the transactivator protein, PPR1, is absolutely required for expression of a URA3 gene located immediately adjacent to the left telomere of chromosome VII. In contrast, when URA3 is at a non-telomeric location, PPR1 merely provides a modest increase in expression (Roy et al., 1990). Two conclusions may be drawn from these results: telomeres inhibit basal transcription, and transactivators have a mechanism to circumvent this inhibition.

It is likely that the basal transcription apparatus of URA3 is prevented from accessing the gene's promoter due to steric occlusion by silent telomeric chromatin. This is supported by the observation that other DNA binding proteins, such as E. coli dam methylase, are excluded from telomere-proximal DNA regions in vivo (Gottschling, 1992). Note that basal expression of URA3, as with most housekeeping genes in yeast, requires not only a TATA element but additional sequences upstream that bind PPR1-independent factors (Roy et al., 1990).

These results show that, first, PPR1 cannot activate transcription of the telomeric URA3 gene in $G_1$, early S, or $G_0$ cells. Only in a $G_2$/metaphase arrest is activation observed. Second, the cellular concentration of PPR1 dramatically affects the frequency with which telomeric URA3 expression is established. Third, the complete activation domain of a transactivator is essential for its efficacy. While a telomeric gene with a GAL4 UAS can be activated in the presence of wild type GAL4, the gene remains silenced when the wild type GAL4 is replaced by derivatives which remove the GAL4 transcriptional activation domain.

The inventors propose a replication-dependent model to explain how a telomeric gene can overcome silencing to become transcriptionally active. In $G_1$ of the cell cycle, a silenced telomeric gene is packaged in a repressive chromatin structure which is relatively "static" and prevents interactions of the DNA with other DNA binding proteins such as basal transcription factors and transactivators. However, the telomeric chromatin loses its static structure, as a result of the DNA replication process or some other coordinate cellular event. Alternatively, one of the two newly replicated sister chromatids retains the silent chromatin while the other is essentially 'naked' DNA and awaits assembly into chromatin.

Regardless of which pathway occurs, upon completion of replication, two distinct assembly processes compete to establish the transcriptional state of a telomeric gene. Assembly of silent chromatin initiates at the telomere and propagates inward along the DNA. This process requires not only the histones but a number of additional factors, such as RAP1, SIR2, SIR3, and SIR4 (Example II; Kyrion et al., 1993). The competing process involves the binding of the transactivator protein to the telomeric gene and assembly of an active transcription complex. The competition ends when one of the two processes is fully established at the promoter region of the telomeric gene. In the absence of competition from the transactivator, the silent chromatin eventually assembles into its static structure. The moment that this silent structure forms, defines the end of the cell cycle period in which the transactivator has an opportunity to compete.

Having a limited period in the cell cycle during which a transcriptional state is established has several ramifications. Environmental or genetic changes that alter the length of the silent chromatin assembly process could dramatically affect the frequency of establishing a state. Such changes may be direct. For instance, the SIR3 gene product appears to be a component of silent chromatin that is rate-limiting in its assembly (Johnson et al., 1990; Example III). Thus increasing SIR3 concentration increases the frequency of establishing repression (Example III). Alternatively, changes that extend periods of the cell cycle in which silent chromatin assembly occurs, such as $G_2$, provide a transactivator greater opportunity to establish an active state. Conversely, a shorter $G_2$ would favor establishment of a silent state. In essence, such changes can dictate the amount of phenotypic variegation within a population of cells.

The assembly of silent telomeric chromatin may consist of several distinct, sequential steps rather than an 'all-or-none', concerted process. In nocodazole-arrested cells, telomeric URA3 expression was rapid when PPR1 was present (GALPPR1). However, basal, or PPR1-independent (GALppr1), expression of the telomeric URA3 was not detected, even after a lengthy arrest (~5 hr); while basal expression at internal loci was normal. These results suggest that at the nocodazole-arrest point silent chromatin is assembled up to a stage that precludes basal expression, yet does not prevent PPR1-induced expression.

This postulated intermediate of silent chromatin assembly may not be locked into a fully static structure, yet it is still more recalcitrant to gene expression than other areas of the genome. The static chromatin structure likely requires several contributions: binding of the core histones by accessory proteins such as SIR3 (Example III) modifications of telomeric histones such as hypoacetylation (Braunstein et al., 1993), and localization of the structure to the nuclear periphery (Palladino et al., 1993). Any of these contributions may be absent at an intermediate stage.

These results extend observations made at the yeast silent mating type loci, HML and HMR (Miller and Nasmyth, 1984). Telomeres and the HM loci share a number of silencing factors (e.g. SIR2, SIR3, and SIR4) and Nasmyth determined, using temperature sensitive alleles of SIR3 and SIR4, that establishment of silencing at the HM loci requires passage through S phase, and thus presumably DNA replication. Their conclusion is consistent with the model the inventors propose, that the competition for assembly occurs after replication. Furthermore, the inventors show that, at least in the case of the VII-L telomeric locus, assembly of silencing is not completed until sometime after $G_2$/metaphase (nocodazole-arrest).

Miller and Nasmyth also found that inactivating the SIR3 or SIR4 gene product at any time in the cell cycle resulted in gene expression at the HM loci. Here, the inventors show that passage through S phase is required for activation of a telomeric gene. Thus, dismantling of the repressive chromatin, either by artificially compromising it with a defective SIR3 or SIR4 allele, or in every cell cycle during passage through S phase, allows a renewal of the competition between establishment of active and silent states.

As the result of a telomeric location, URA3 can be much more highly regulated than at its normal locus. When URA3 is at a non-telomeric location, the presence of $PPR1^c$ produces a three to seven-fold induction over basal expression (Liljelund et al., 1984). However, with URA3 near a telomere, an equivalent amount of PPR1 induces expression about 100-fold. The inventors suggest that the genomes may have evolved to take advantage of this type of telomeric regulation. For example, Trypanosomes depend upon the highly regulated expression of the telomeric VSG (Variable Surface Glycoprotein) genes (Borst, 1991, Cross, 1990).

When cells were in $G_0$, essentially no amount of transactivator protein was sufficient to overcome telomeric silencing, while at an internal non-silenced position the transactivator readily induced expression. Interestingly, general transcriptional repression, apparently mediated by chromatin changes, occurs upon entry to stationary phase (Choder, 1991). In fact, stationary phase chromosomes display different sedimentation properties than $G_1$ phase chromosomes, suggesting that chromosomes assume a distinct compact structure in $G_0$ cells (Pifion, 1978). It is possible that the same machinery and mechanism of telomeric silencing in $G_1$ extends to other regions of the genome in $G_0$, thus facilitating the more global compaction and transcriptional repression.

Whatever the nature of the silent telomeric chromatin, it contrasts with the chromatin structure of the PHO5 gene in yeast. While this locus is transcriptionally repressed by nucleosomes upstream of the transcription initiation site, it can be induced rapidly at anytime in the cell cycle or in $G_0$ arrested cells (Schmid et al., 1992). The induction involves the displacement of a nucleosome by the gene's transcriptional activator protein. In contrast, overcoming telomeric silencing requires that the nucleosomes be modified or removed by passage through S phase before the transactivator protein can have its effect. This emphasizes that telomeric chromatin is inherently different than chromatin at PHO5 or most other regions of the yeast genome.

EXAMPLE V

Identification of Genes that Suppress Telomeric Silencing

Genes located near *S. cerevisiae* telomeres are subject to transcriptional silencing by a repressive chromatin structure that initiates at the telomeres (Gottschling et al., 1990; Gottschling, 1992; Renauld et al., 1993; Examples I through IV). The inventors hypothesized that the telomeric structure responsible for silencing is likely to be a multimeric complex that would be sensitive to the stoichiometric imbalance of its components. Therefore, in order to identify genes involved in telomere structure or function, the inventors carried out a screen for gene products that, when expressed at high levels, would suppress telomeric silencing.

A yeast strain was constructed with genetic markers located at two telomeric loci. The ADE2 gene, which is required for adenine biosynthesis, was placed adjacent to the telomere at the right arm of chromosome V (V-R), and URA3, a gene required for uracil biosynthesis, was located adjacent to the telomere at the left arm of chromosome VII (VII-L).

More specifically, the strain used for transformation with the library was UCC3505 (MATa ura3-52 lys2-801 ade2-101 trp1-Δ63, his3-Δ200 leu2-Δ1 ppr1::HIS3 adh4::URA3-TEL DIA5-1). DIA5-1 refers to the directed integration of ADE2 adjacent to telomere V-R. UCC3505 was constructed by successively transforming YPH499 (Sikorski & Hieter, 1989) with pVII-L URA3-TEL (Gottschling et al., 1990), pΔPPR1-HIS3 (Renauld et al., 1993), and pHR10-6. Plasmid pHR10-6, obtained from H. Renauld, was constructed by inserting a 2.8 kb Hind III fragment from plasmid pV-R URA3-TEL (Gottschling et al., 1990), containing sequences from the subtelomeric region of chromosome arm V-R, into the Hind III site of pYTCA-2 (Gottschling et al., 1990), such that the Eco RI site of the insert was furthest from the Bam HI site of the vector, thus creating pHR9-9. Into the Bam HI site of pHR9-9 was inserted the 3.4 kb Eco RI-Bam HI fragment containing the ADE2 gene from pL909 (Gottschling et al., 1990), thus creating pHR10-6. The ADE2 gene is oriented with its promoter proximal to the V-R sequences. pHR10-6 was cleaved with Eco RI for use in fragment-mediated transformation of yeast.

Normally, colonies expressing ADE2 are white, while those not expressing it (ade2) are red (Roman, 1956). Due to the semi-stable nature of telomeric silencing of most genes, switching between silenced and transcriptionally active states may occur every few generations, giving rise to different phenotypic populations. In the case of strains with ADE2 near a telomere, these different populations are seen as red and white sectors within a single colony (Gottschling et al., 1990). A URA3 gene located at telomere VII-L also normally switches between transcriptional states (Gottschling et al., 1990). However, the telomeric URA3 was caused to be completely silenced by deleting its transactivator, PPR1 (Aparicio & Gottschling, 1994). The cells were therefore unable to grow in the absence of uracil.

To identify genes or gene fragments whose overexpression could disrupt silencing, the strain was transformed with a high-expression *S. cerevisiae* cDNA library. The pTRP plasmid expression library used in this study was created with cre-lox site-directed recombination from the XTRP library (obtained from S. J. Elledge, Baylor College of Medicine, Houston). The pTRP vector contains a 2μ origin of replication and the TRP1 selectable marker. The cDNA inserts were cloned into a Xho I site of the pTRP vector, placing them under the control of the GAL1 promoter. The creation of similar libraries is described in Elledge et al. (1991).

By the nature of its synthesis, a cDNA library typically contains both full length and truncated versions of RNA transcripts. Thus high level expression from a cDNA library has two means of causing a stoichiometric imbalance: by expression of a normal gene product or a defective one (Herskowitz, 1987). In the library used in this study, the expression of cDNA inserts was controlled by the GAL1 promoter, which is strongly induced by the presence of galactose in the medium (Johnston & Davis, 1984). Of the 330,000 yeast transformants obtained, 48 displayed a galactose-dependent decrease in telomeric silencing. That is, when grown on media containing galactose, the cells were able to grow in the absence of uracil (Ura+) and gave rise to predominantly white colonies (Ade+). On the basis of restriction mapping, DNA blotting (Southern) analysis, and DNA sequencing, it was determined that these 48 clones represented ten independent genes.

EXAMPLE VI

Isolation of TLC1, a Telomere-Specific Suppressor of Silencing

Figure 1B:
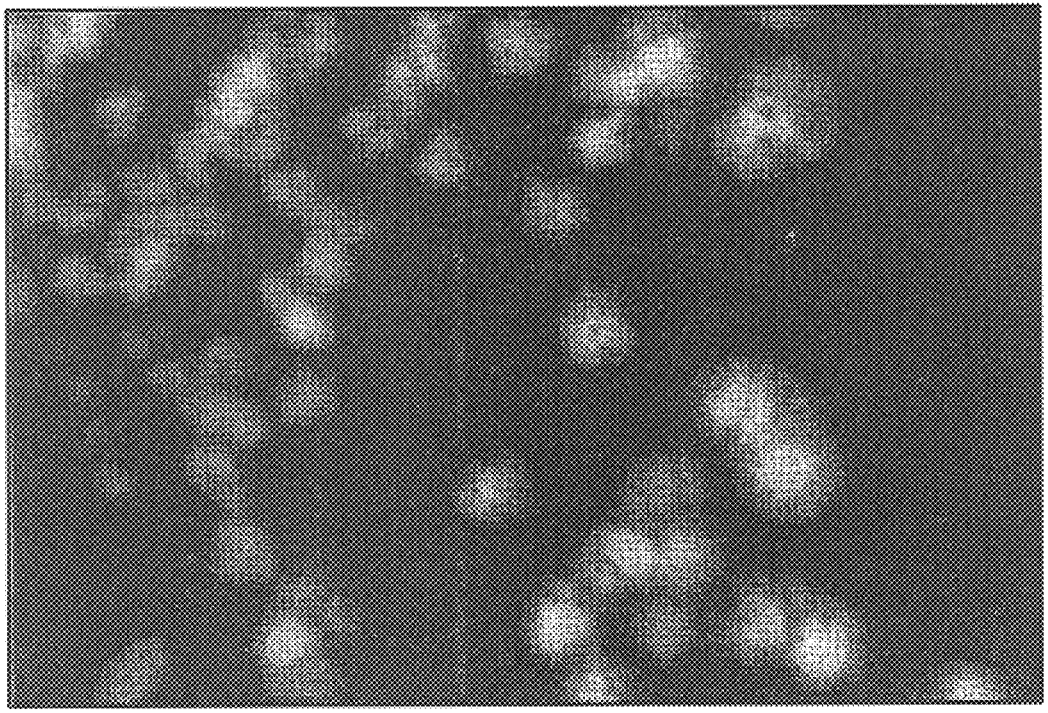
Figure 1C:
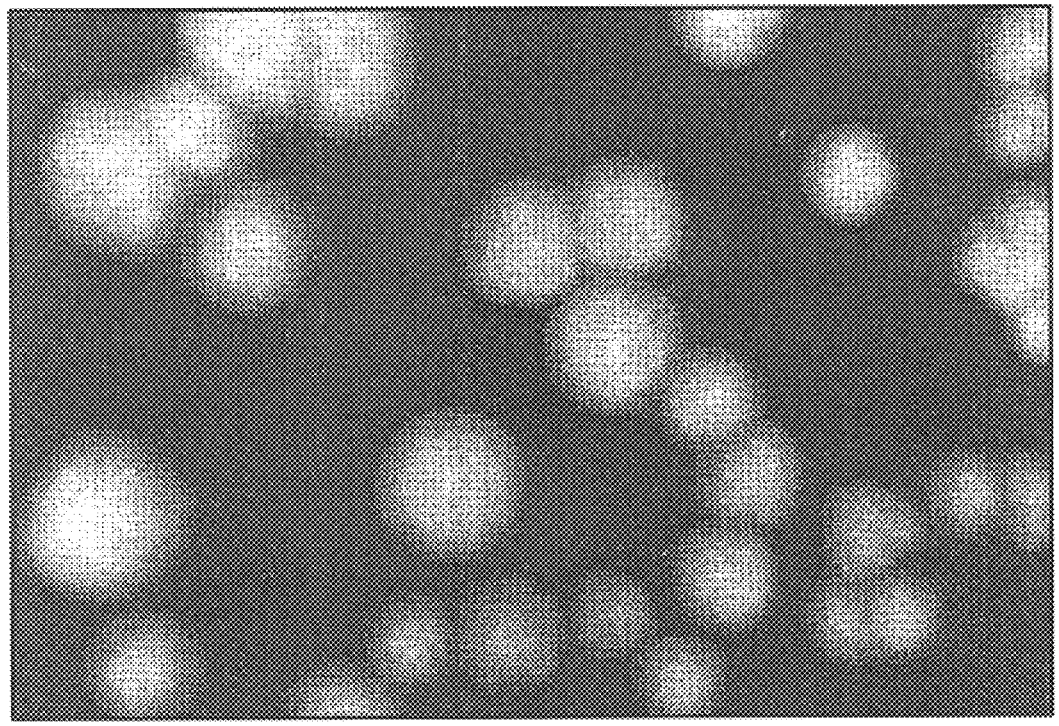

The genes known to be required for telomeric silencing are also involved in transcriptional silencing at two internal chromosomal sites, the HML and HMR loci, which harbor the unexpressed copies of the mating type genes in *S. cerevisiae* (Aparicio et al., 1991). To determine whether the newly isolated suppressors of telomeric silencing also affect silencing at HML, the expression plasmids were introduced into a strain in which the URA3 gene was inserted into the HML locus. The strain used for assaying silencing at the HML locus was UCC3515 (MATα lys2-801 ade2-101 trp1-Δ63 his3-Δ200 leu2-Δ1 ura3-52 hml::URA3). The hml::URA3 construct is the same as that described for strain GJY5 (Mahoney & Broach, 1989). Overexpression of one of the novel genes identified, TLC1, had no effect on silencing at HML, but strongly suppressed telomeric silencing of URA3 and ADE2 (FIG. 1A, FIG. 1B and FIG. 1C). The SIR4 gene, whose overexpression disrupts silencing both at telomeres and at HML (Marshall et al., 1987), was also isolated in the present screen and derepressed both of these loci in this assay (FIG. 1A, FIG. 1B and FIG. 1C).

Figure 2:
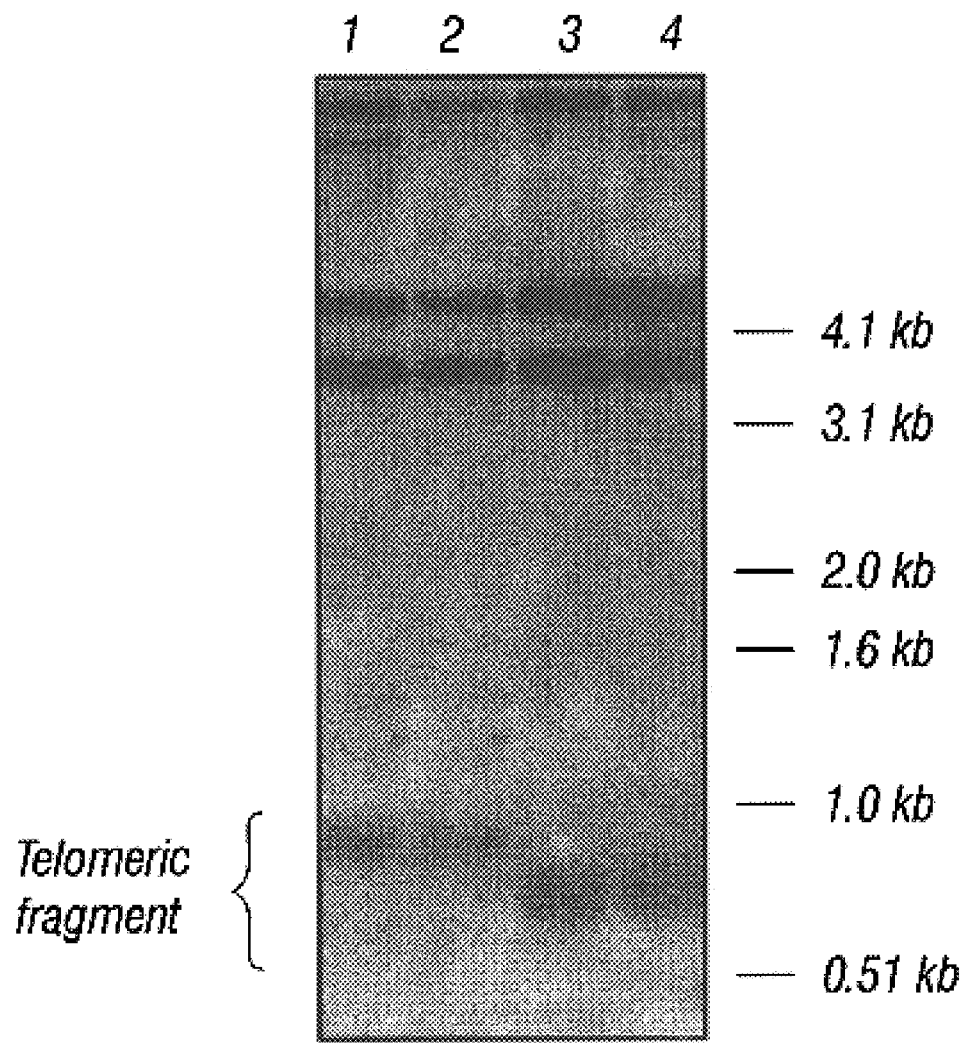
FIG. 2. Overexpression of TLC1 causes a decrease in telomeric tract length. Yeast strain UCC3505 carrying either vector (pTRP, lanes 1 and 2) or a TLC1 cDNA clone (pTRP6, lanes 3 and 4) were pregrown for approximately 60 generations on medium containing 3% galactose without tryptophan. Genomic DNA was prepared from two independent transformants of each strain, digested with Apa I and Xho I, separated by electrophoresis on a 1% agarose gel, and blotted onto a nylon membrane. The membrane was probed with a 1.1 kb Hind III-Sma I URA3 fragment. The URA3 gene in this strain is located adjacent to telomere VII-L. The higher molecular weight (non-telomeric) URA3 fragments represent sequences of the telomeric URA3 that are centromere-proximal to the URA3 Apa I site, and sequences from the ura3-52 allele at the normal chromosomal locus of URA3. The Southern blot was also probed with an 81 bp labeled $(TG)_{1-3}TG_{2-3}$(telomeric sequence) riboprobe, to determine the telomere length of chromosomes with Y' elements (Walmsey et al., 1984). These telomere-associated sequences are at the ends of multiple yeast chromosomes and generally have Xho I sites at their telomere-proximal ends (Louis & Haber, 1990). Y'-containing chromosomes showed a decrease of telomere length upon overexpression of the TLC1 cDNA clone similar to that seen for telomere VII-L.

Further evidence for the specific association of TLC1 with telomere structure came from examination of telomere length in strains overexpressing a TLC1 cDNA clone. In the absence of the TLC1 overexpression plasmid, the telomeric sequences at VII-L averaged 330 base pairs (bp) in length. Upon overexpression of TLC1, the average telomere length at VII-L decreased between 90 and 220 bp (FIG. 2). The alteration of telomere length upon overexpression of TLC1, together with the loss of telomeric silencing, suggested that this gene is specifically involved in telomere structure.

Of the 48 cDNA clones isolated in the present screen as suppressors of telomeric silencing, nine represented TLC1. The inventors sequenced one of the TLC1 cDNA clones in its entirety (pTRP61, 1248 bp), as well as the ends of the other eight TLC1 clones. These sequence data overlapped to yield a contiguous sequence of 1301 bp, although no single clone included the entire sequence. The combined sequence of the TLC1 cDNA clones has been submitted to GenBank and assigned the accession number U14595.

The span of each of the cDNA clones with respect to the entire 1301 bp fragment is as follows: pTRP6 (1-1248), pTRP61 (54-1301), pTRP14 and pTRP47 (54-1263), pTRP33 and pTRP39 (54-1269), pTRP55 (54-1264 or 1265), pTRP59 (39-1250), pTRP60 (270-1264 or 1265), and pTRP61 (54-1301). Four of the TLC1 cDNA sequences (in clones pTRP55, pTRP60, pTRP33 and pTRP39) are followed by short stretches (5–20 nts) of adenines. It is not yet clear whether these adenines reflect authentic in vivo polyadenylation of the TLC1 transcripts, or are by-products of cDNA synthesis.

For reference, both the TLC1 gene and the RNA template include the CACCACACCCACACAC (SEQ ID NO:3) template sequence that ultimately allows the GTGT-GTGGGTGTG sequence (SEQ ID NO:2) to be inserted into the telomere. The TLC1 gene sequence CACCACACCCA-CACAC (SEQ ID NO:3) spans the region 468–483 of SEQ ID NO:1. In the complementary strand, SEQ ID NO:4, this region is 819–834.

Physical mapping localized TLC1 to a single site on chromosome II, immediately adjacent to CSG2. TLC1 was mapped by hybridizing the labeled cDNA clone (1.25 kb Xho I insert from pTRP6) to a filter grid containing λ phage clones representing over 96 percent of the yeast genome. The filter set was obtained from the American Type Culture Collection (Olson et al., 1986; Link & Olson, 1991; Beeler et al., 1994). Subsequent to the present work, the sequence of chromosome II was entered into the EMBL database. The chromosome II-R sequences have the EMBL accession number X76078. These data matched the present sequence obtained from the cDNAs.

Figure 3A:
FIG. 3A and FIG. 3B. TLC1 encodes a 1.3 kb RNA. TLC1 transcript levels were analyzed in yeast strains containing a wild-type TLC1 gene (lane 1), or a tlc1::LEU2 disruption allele (lane 2), and in wild-type cells carrying either vector (pTRP, lane 3) or a TLC1 cDNA clone (pTRP61, lane 4). Total RNA was isolated from mid-log phase cells grown in rich medium (for strains lacking plasmids) or synthetic medium without tryptophan but with 3% galactose (for the plasmid-containing strains). 20 μg of RNA from each strain was electrophoretically separated on a 0.9% agarose formaldehyde gel and transferred to a nylon membrane.
Figure 3B:
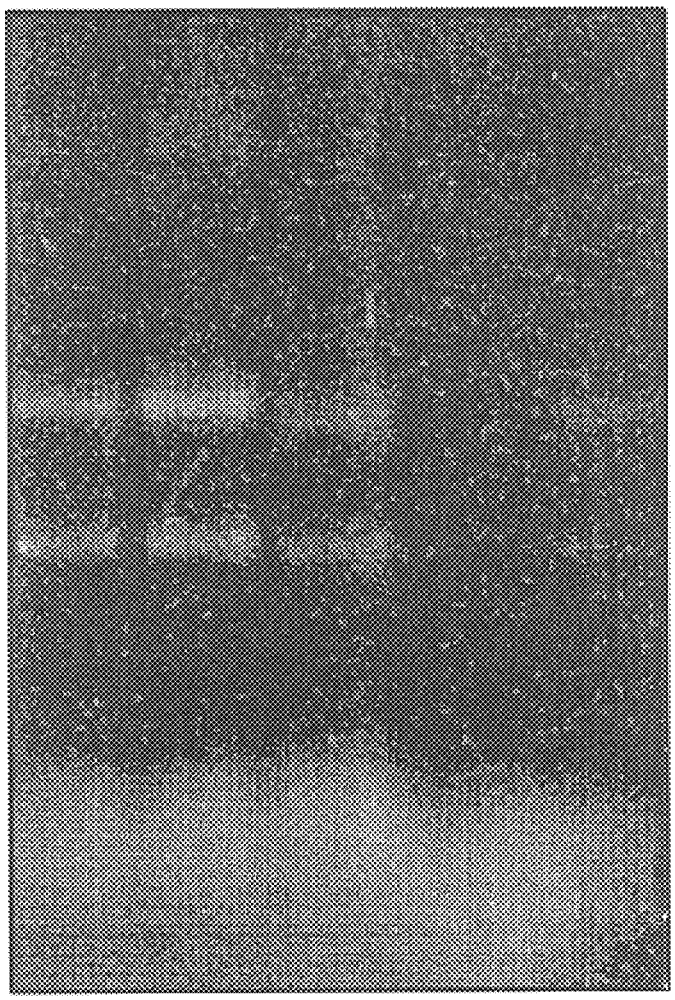

RNA blot (Northern) analysis confirmed that a wild-type strain contained a relatively abundant RNA that hybridized to a TLC1 probe and was approximately 1.3 kilobases (kb) in length (FIG. 3A and FIG. 3B).

EXAMPLE VII

TLC1 Encodes the Telomerase RNA

The TLC1 sequence has two notable features. The gene is unlikely to encode a protein since it does not contain a large open reading frame (ORF). The longest ORF that begins with an ATG codon is only 43 amino acids in length. This finding suggested that the functional TLC1 gene product might be the RNA itself. Moreover, TLC1 contains the sequence CACCACACCCACACAC (SEQ ID NO:3), which includes the motif predicted to template *S. cerevisiae* telomeres (Kramer & Haber, 1993). These results suggested to the inventors that TLC1 encodes the putative yeast telomerase RNA.

To confirm that the TLC1 gene product is indeed the telomerase RNA, the TLC1 gene was disrupted. The inventors predicted that this would cause incomplete replication of telomeres and result in progressive telomere shortening with each cell division. A TLC1 gene disruption was created in which a large part of TLC1, including the predicted telomere-templating region, was removed and replaced with a marker gene.

For the gene disruption, the TLC1 cDNA clone in plasmid pTRP61 was excised away from pTRP vector sequences as a 1.25 kb Xho I fragment, and inserted into the Xho I site of pBluescript II KS(–) (Stratagene; La Jolla, Calif.), creating pBlue61. The disruption of TLC1 was created by replacing the 693 bp Nco I-Nsi I fragment of pBlue61 with a blunt-ended Bam HI 1.6 kb LEU2 clone from plasmid YDp-L (Berben et al., 1991), creating pBlue61::LEU2. This construct was digested with Xho I and transformed into the diploid strain UCC3507, selecting for Leu+ transformants, to produce UCC3508 (UCC3507 TLC1/tlc1::LEU2). Southern blot analysis confirmed that UCC3508 was heterozygous for the disruption at the TLC1 locus.

Nineteen out of nineteen tetrads sporulated from UCC3508 yielded 2:2 segregation of the tlc1::LEU2 allele. The genotype of UCC3507 is: MATa/MATα ura3-52/ura3-52 lys2-801/lys2-801 ade2-101/ade2-101 his3-Δ200/his3-Δ200 trp1-Δ1/TRP1 leu2-Δ1/leu2-Δ1 adh4::URA3-TEL/adh4::URA3-TEL DIA5-1/DIA5-1 ppr1::HIS3/ppr1::LYS2. The haploid strains crossed to create UCC3507 were derived from YPH250 and YPH102 (Sikorski & Hieter, 1989). The introduction of changes into the genotypes of these haploids all utilized plasmids described above, except allele ppr1::LYS2, which was introduced using plasmid pΔPPR1::LYS2 (Renauld et al., 1993).

Figure 4A:
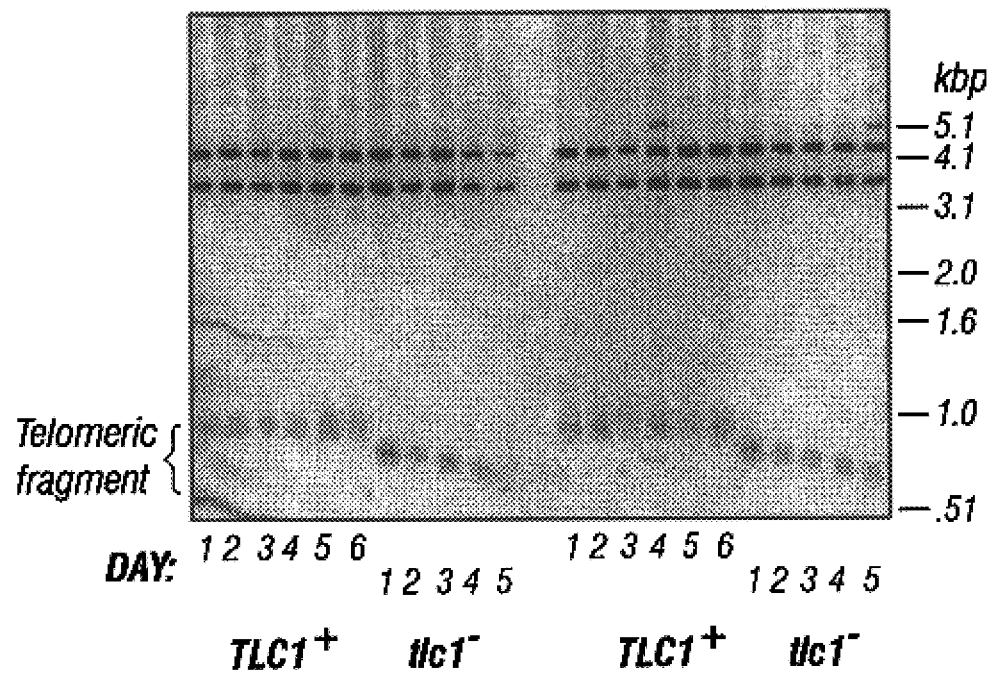
FIG. 4A. Disruption of TLC1 causes progressive telomere shortening and a gradual decrease in growth rate and viability. A TLC1/tlc1::LEU2 diploid (UCC3508) was sporulated and the resulting tetrads dissected and germinated on rich medium. Colonies representing the four spore products from a tetrad were inoculated into 5.5 ml of rich medium and grown at 30° C. Every 24 hours, 5 ml of the culture were used for the preparation of genomic DNA, and 5 μl were used to inoculate 5.5 ml of fresh medium. The genomic DNA was digested with Apa I, electrophoresed on a 1% agarose gel, transferred to a nylon membrane and hybridized to a 1.1 kb URA3 probe. The URA3 gene is located adjacent to telomere VII-L in these strains. In a similar study, genomic DNA from TLC1 and tlc1 cultures was digested with Xho I, as well as Apa I, in order to examine Y'-containing telomeres using the Southern blotting method described in FIG. 2 with the 81 bp labeled telomeric sequence riboprobe (Walmsey et al., 1984). The size of this population of telomeres decreased in size at the same rate as the URA3-labeled telomere VII-L.

The disrupted gene was introduced into a wild-type diploid strain to create a TLC1/tlc1 heterozygote, which was then sporulated, giving rise to two mutant and two wild-type haploid strains. Northern analysis confirmed that in the TLC1-disrupted spore products, there was no detectable TLC1 RNA (FIG. 3A and FIG. 3B). The spore colonies were inoculated into rich medium and grown for several days by diluting the cultures into fresh medium every 24 hours. In all cases examined (eight tetrads), TLC1 strains maintained a normal telomere length after 6 days of growth. In contrast, the tlc1 strains displayed shortened telomeres. In the cases where DNA samples were collected daily (three tetrads), the tlc1 telomeres were found to shorten progressively, at an approximate rate of 3 bp per generation (FIG. 4A).

Figure 4B:
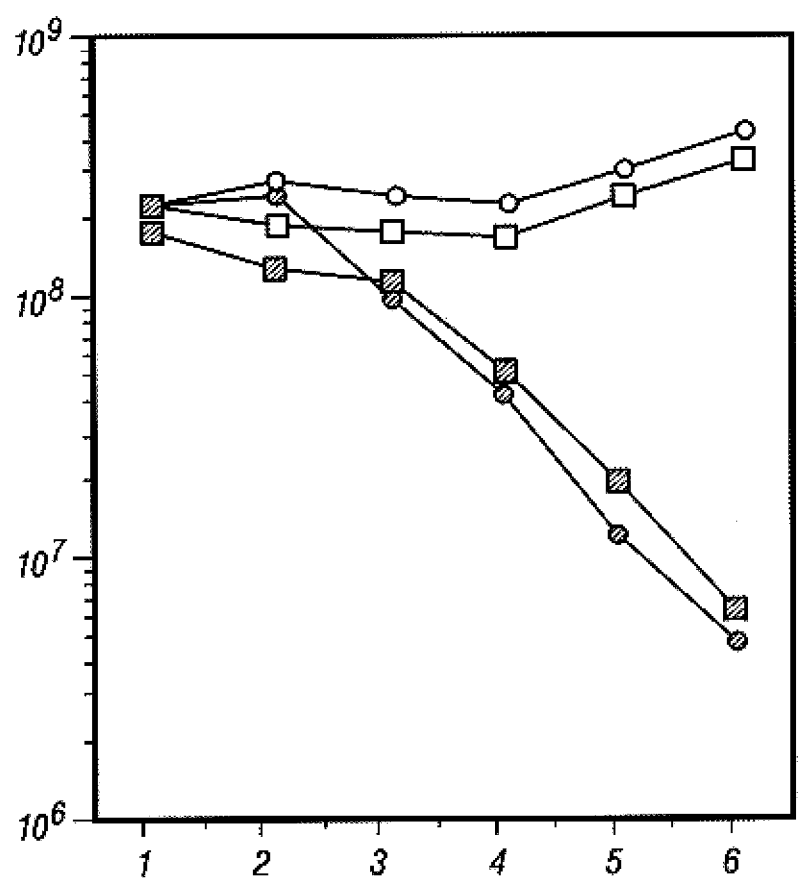
FIG. 4B. Disruption of TLC1 causes progressive telomere shortening and a gradual decrease in growth rate and viability. In a study similar to that of FIG. 4A, UCC3508 spore products were grown continuously in rich medium. Every 24 hours the cell density was determined and each culture was diluted to $3 \times 10^5$ cells/ml in 5.5 ml of fresh medium for further growth. The cell density at each time point is plotted for the two TLC1 (white circle and square) and tlc1 (hatched ○ and □) spore products of a tetrad.

In conjunction with the shortening telomere phenotype, older tlc1 cultures displayed a gradual increase in generation time. Through the first 40 generations after sporulation of a TLC1/tlc1 strain, all four spore products were able to regrow approximately one thousand-fold in rich medium within 24 hours, indicating a generation time of less than 2.4 hours (FIG. 4B). This growth rate was maintained in TLC1 strains for up to 80 generations.

In contrast, the tlc1 strains, by 65 generations after germination, the growth rate had slowed to about 3.3 hours/generation. After 75 generations, the doubling time of the tlc1 cultures was 5.7 hours. This decrease in growth rate was accompanied by a 50% drop in viability in the tlc1 strains after 75 generations. This general pattern was clear in all 14 tetrads examined, although there was some variation in the period at which the decrease in growth rate occurred. However, as was reported for est1 strains (Lundblad & Blackburn, 1993), the dying tlc1 cultures were overwhelmed within approximately 100 generations by faster-growing cells, which presumably contained suppressor mutations.

Figure 5A:
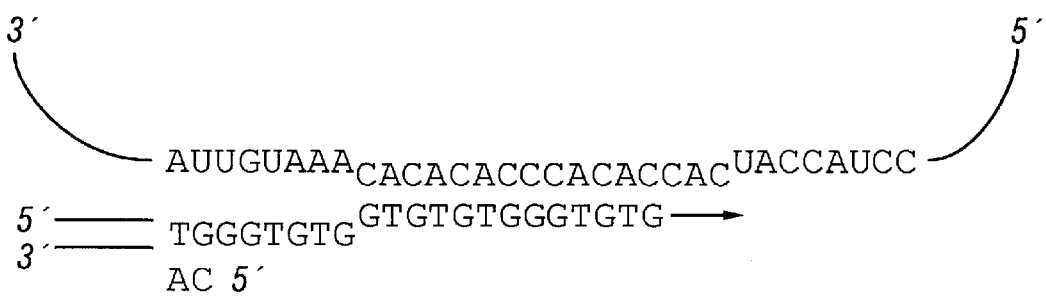
FIG. 5A and FIG. 5B. The TLC1 gene encodes an RNA that functions as a templating component of telomerase, an enzyme that elongates the G-rich strand of S. cerevisiae telomeres.
Figure 5B:
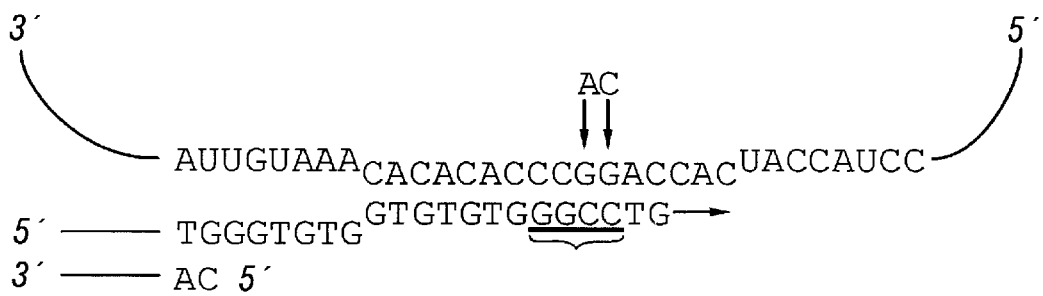

To demonstrate that the TLC1 gene product was the *S. cerevisiae* telomerase template RNA, it was necessary to confirm that TLC1 sequences encoded telomeric tract repeats. Earlier studies with Tetrahymena thermophila showed that when a mutated telomerase RNA is introduced into a cell, the altered sequence may then be templated into the cell's telomeres (Yu et al., 1990). A candidate motif for the telomere template within TLC1 was the sequence CAC-CACACCCACACAC (SEQ ID NO:3) (FIG. 5A). The inventors constructed a TLC1 allele, designated TLC1-1 (Hae III), in which two base pairs of this motif were changed to create a recognition site for the restriction enzyme Hae III (FIG. 5B).

The mutant TLC1-1(Hae III) allele was used to replace one of the normal TLC1 genes in a diploid strain as follows: Plasmid pVZ61b was constructed by inserting the 1.25 kb Xho I fragment containing the TLC1 cDNA clone from pTRP61 into the Sal I site of plasmid pVZ1 (Henikoff & Eghtedarzadeh, 1987). The TLC1-1(Hae III) mutant allele was generated using two oligonucleotides, Hpa I primer (5'-TCCAGAGTTAACGATAAGATAGAC-3') and Hae III primer (5'-TAATTACCAT GGGAAGCCTA CCATCACCA GGCCCACACAC AAATG-3'; SEQ ID NO:5 [Greider and Blackburn, 1985, 1987, 1989; Zahler and Prescott, 1988; Morin, 1989; Prowse et al., 1993; Shippen-Lentz and Blackburn, 1989; Mantell and Greider, 1994; de Lange, 1994; Greider, 1994; Harley et al., 1992]) to PCR-amplify a 232-bp fragment from plasmid pVZ61b.

The PCR product was then cleaved with Nco I and Hpa I, to create a 213 bp fragment that was used to replace the 213-bp Nco I-Hpa I fragment of pBlue6l, to create pBlue6l-Hae III. The 213 bp fragment was sequenced from the pBlue61 plasmid to verify that the PCR amplification did not introduce additional mutations into the sequence.

The TLC1-1(Hae III) allele, contained in a 1.25 kb Xho I fragment, was then cleaved from pBlue6l-Hae III and inserted into the Xho I site of pRS306 (Sikorski & Hieter, 1989), to create the integrating plasmid pRS306-TLCl-1 (Hae III). This latter construct was digested with Afl II and used to transform YPH501 (Sikorski & Hieter, 1989), with selection for Ura⁺ transformants, thus creating the heterozygous strain UCC3520. UCC3522 (YPH501 TLC1-1(Hae III)/TLC1) was isolated as a 5-fluoro-orotic acid-resistant derivative of UCC3520 in which the pRS306-TLC1 plasmid had recombined out of the TLC1 locus, which left the TLC1-1(Hae III) allele in the chromosome (Scherer & Davis, 1979), as confirmed by Southern blot analysis.

Figure 6A:
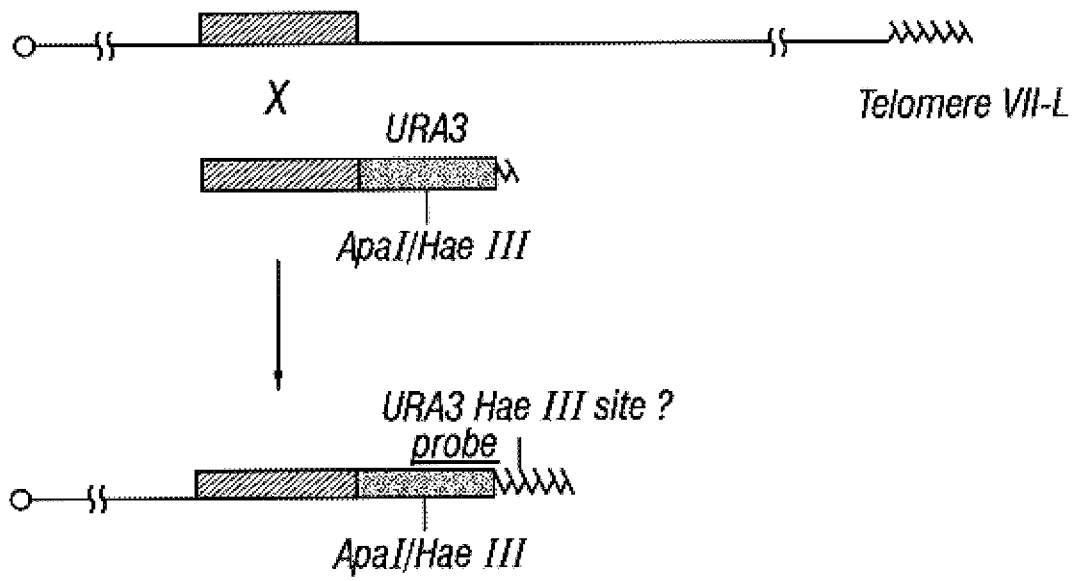
FIG. 6A. Altering the putative telomere-templating region of TLC1 results in the incorporation of the mutant sequence into telomeric tracts. Fragment-mediated transformation of TLC1/TLC1 and TLC1-1(HaeIII)/TLC1 diploid strains was used to replace the terminal sequences of the left arm of one of the chromosome VII homologs with a URA3 gene and a short telomeric tract sequence. The most telomere-proximal Apa I and Hae III sites in the fragment used in the transformation overlap and are located 0.75 kb from the telomeric end of the fragment.

In addition to functioning at the very ends of normal telomeres, telomerase is also believed to play an important role in the healing of broken chromosomes and the extension of unusually short telomeric tracts (Kramer & Haber, 1993). In this latter capacity, the activity of a mutant telomerase would be most easily detected. Therefore, fragment-mediated transformation was used to remove the sequence distal to the ADH4 locus on the left arm of chromosome VII, and replace it with a URA3 gene and a short tract of telomeric sequence to act as a seed for in vivo telomere elongation (FIG. 6A).

This transformation was done in both homozygous wild-type (TLC1/TLC1) and heterozygous TLC1-1(Hae III)/TLC1 strains. The ADH4-URA3-TG$_{1-3}$ fragment used to replace the left arm of chromosome VII was generated by Not I-Sal I digestion of plasmid AD3ARUGT-IV. This plasmid was constructed by the following set of steps: the 1.1 kb Hind III-Sma I DNA fragment containing URA3 (Rose et al., 1984) was inserted into the Hinc II site of pYTCA-2 by blunt-end ligation, with the promoter of URA3 proximal to the TG$_{1-3}$ sequences of the vector, creating plasmid p3ARUCA. The 1.2 kb Hind III fragment of pYA4-2, containing ADH4 (Lundblad & Szostak, 1989; Williamson & Paquin, 1987), was then inserted into the Hind III site of p3ARUCA, with the Sal I site of the insert distal to the URA3 gene in the vector, creating plasmid pAD3ARUCA. Finally, the Sal I-EcoR I fragment containing the composite insert (ADH4-URA3-TG$_{1-3}$) from pAD3ARUCA was cloned into pVZ1, creating AD3ARUGT-IV.

The yeast strains that were transformed with the ADH4-URA3-TG$_{1-3}$ fragment were YPH501 (TLC1/TLC1) and UCC3522 (TLC1-1(HaeIII)/TLC1). These studies were repeated with the transforming ADH4-URA3-TG$_{1-3}$ DNA liberated from the pAD3ARUGT-IV plasmid as a Sal I-EcoR I fragment, and results similar to those reported in FIG. 6B were obtained.

Figure 6B:
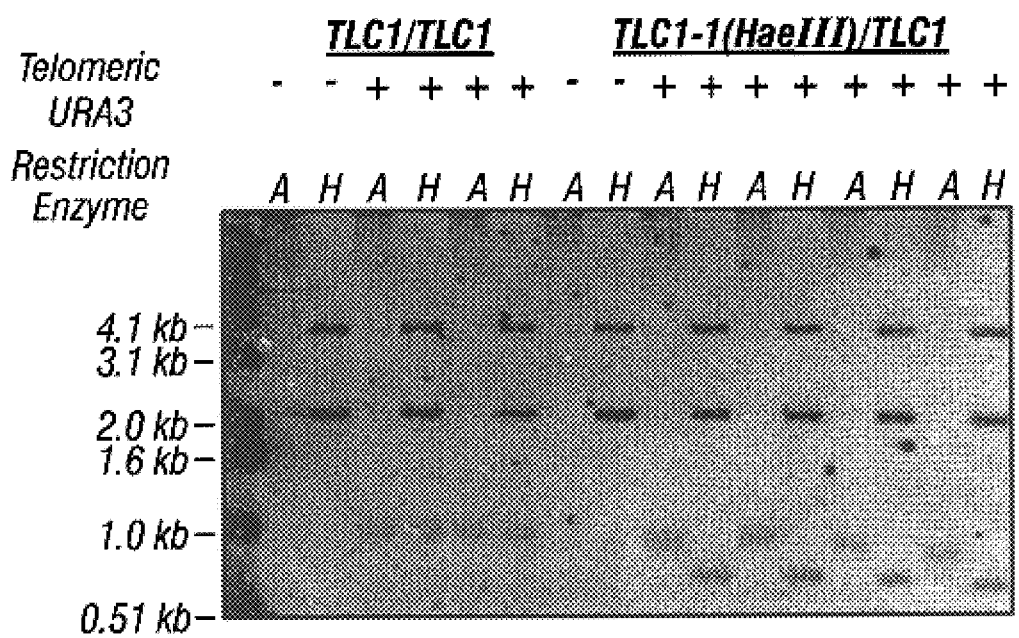
FIG. 6B. Altering the putative telomere-templating region of TLC1 results in the incorporation of the mutant sequence into telomeric tracts. Restriction digests of genomic DNA from transformed strains were used to determine whether Hae III sites were introduced into the new telomere VII-L upon its elongation in vivo. Genomic DNA from TLC1/TLC1 and TLC1-1(HaeIII)/TLC1 yeast strains, either transformed with URA3TEL (Telomeric URA3+) or not (Telomeric URA3−), was digested with Apa I (A) or Hae III (H). The DNA fragments were separated by electrophoresis on a 1.25% agarose gel, transferred to a nylon membrane, and probed with a labeled 0.6 kb URA3 probe (Apa I-Hind III fragment), as depicted in FIG. 6A. Each Telomeric URA3+ strain represents an independently isolated transformant.

Southern analysis was performed on genomic DNA from the transformed strains to determine the structure of the new telomeres at VII-L (FIG. 6B). Digestion with Apa I, whose most distal site in the new VII-L arm occurs within the URA3 gene, demonstrated that in both the wild-type (TLCL/TLC1) and heterozygous TLC1-1(Hae III)/TLC1 transformants, the new chromosomal end was extended in vivo to several hundred base pairs. The new telomeres in the TLC1-1(Hae III)/TLC1 strain were slightly shorter and more heterogeneous in length than those added in the TLC1/TLC1 strain.

In all twelve TLC1/TLC1 independent transformants tested, digestion with Hae III, which cuts at the same site in URA3 as Apa I, indicated that no Hae III sites were introduced during telomere elongation in vivo. In contrast, in all eight TLC1-1(Hae III)/TLC1 independent strains examined, Hae III sites were incorporated into the newly formed telomere. It can thus be concluded that the mutated sequence in the TLC1-1(Hae III) gene served as a template for the addition of telomeric repeats, which indicates that the TLC1 gene indeed encodes the *S. cerevisiae* telomerase RNA.

EXAMPLE VIII

TLC1 Compared to Other Telomerase RNAs

In these studies the inventors demonstrated the existence of an *S. cerevisiae* telomerase and identified the gene that encodes its RNA component (Examples V through VII). These above findings support the proposal that the telomerase mechanism of replicating the ends of chromosomes is widespread among eukaryotes. However, the TLC1 RNA is much larger (1.3 kb) than the known ciliate telomerase RNAs, which are 160 to 200 nucleotides (nt) in length (Blackburn, 1993). This discrepancy in gene size is reminiscent of the 1175 nt *S. cerevisiae* U2 snRNA, which is almost 1 kb larger than the mammalian U2 snRNA (Ares, 1986). The conserved secondary structure that is shared among the ciliate telomerase RNAs is not apparent in the sequences surrounding the TLC1 template region (Romero & Blackburn, 1991; ten Dam et al., 1991), though the large size of the transcript may allow homologous structures to form that are not obvious at this time. TLC1 also lacks a short primary sequence adjacent to the template region that is conserved among the ciliate telomerase RNAs (Lingner et al., 1994).

While telomeric DNA in most organisms is comprised of sequences repeated in a regular fashion, e.g. mammalian $(T_2AG_3)$, Tetrahymena $(T_2G_4)$, the telomeric sequence of *S. cerevisiae* is irregular $[(TG)_{1-3}TG_{2-3}]$ (Zakian, 1989). However, this irregularity can be fully explained by the telomere-templating sequence in TLC1. Telomerase RNAs are thought to synthesize the G-rich strand of telomeres by multiple rounds of hybridization to a short sequence at the end of a telomeric tract, elongation of the DNA by a limited reverse transcription of the RNA, and disengagement (Blackburn, 1993). In vitro, the Tetrahymena telomerase RNA appears to use as few as three nucleotides for the hybridization step (Autexier & Greider, 1994).

The telomere template region of TLC1 (CACCACACCCACACAC; SEQ ID NO:3) suggests that the telomerase RNA may be able to align with a telomere terminus at a number of different points within the RNA, especially if CAC is all that is required for hybridization. It is also possible that the telomerase could abort a round of reverse-transcription at several different positions along the RNA. If a terminal DNA sequence such as GTG is left, then alignment with the CAC RNA motif in the next round of elongation can readily occur. Either alone or in combination, these different alignment and termination possibilities can account for the heterogeneity observed in the *S. cerevisiae* telomeric tracts.

EXAMPLE IX

Telomeric Silencing and Telomerase

Overexpression of the TLC1 cDNA clones identified in the present studies (Examples V through VIII) both disrupts telomeric silencing and causes a shortening of telomeres. One model to explain these results is that overexpression of the cDNAs causes limiting telomerase components to be titrated into incomplete and nonfunctional complexes, thereby reducing the total telomerase activity in the cell and resulting in shorter telomeres. The length of the telomere may relate to its ability to bind silencing proteins; shorter telomeres simply have fewer binding sites, and thus may silence telomeric genes less efficiently (Kyrion et al., 1993). Alternatively, the telomerase RNA itself, or one of the factors it binds, may be an integral component of the complex that is required for silencing at telomeres. Overexpression of TLC1 may perturb the stoichiometry of this complex, and thus interfere with its assembly. It is noteworthy that of the nine TLC1 cDNAs isolated in the present screen, none appear to be full length. Thus it is formally possible that only an incomplete (non-functional) TLC1 RNA can produce the effects detected.

The telomere shortening and growth defects observed when the telomerase RNA was disrupted are very similar to those described for estl strains, supporting the prediction that EST1 is a constituent of telomerase (Lundblad & Szostak, 1989). Moreover, the genetic link discovered here between telomeric silencing and telomerase suggests future approaches for identifying other telomerase components, which so far have been elusive.

EXAMPLE X

Other Genes Identified by Telomeric Silencing

Using the telomeric silencing protocol described herein, the inventors isolated 48 clones. On the basis of restriction mapping, DNA blotting (Southern) analysis, and DNA sequencing, it was determined that these 48 clones represented ten independent genes. Of the these ten genes, four have been sequenced and identified previously. These genes are the SIR4 (Marshall et. al., 1987); ASF1 (Le and Sternglanz, Genbank Accession Number 107593); RPL32 (Dabeva and Warner, 1987); and RRP3 (Cherel and Thuriaux, Genbank Accession Number z29488).

Figure 7A:
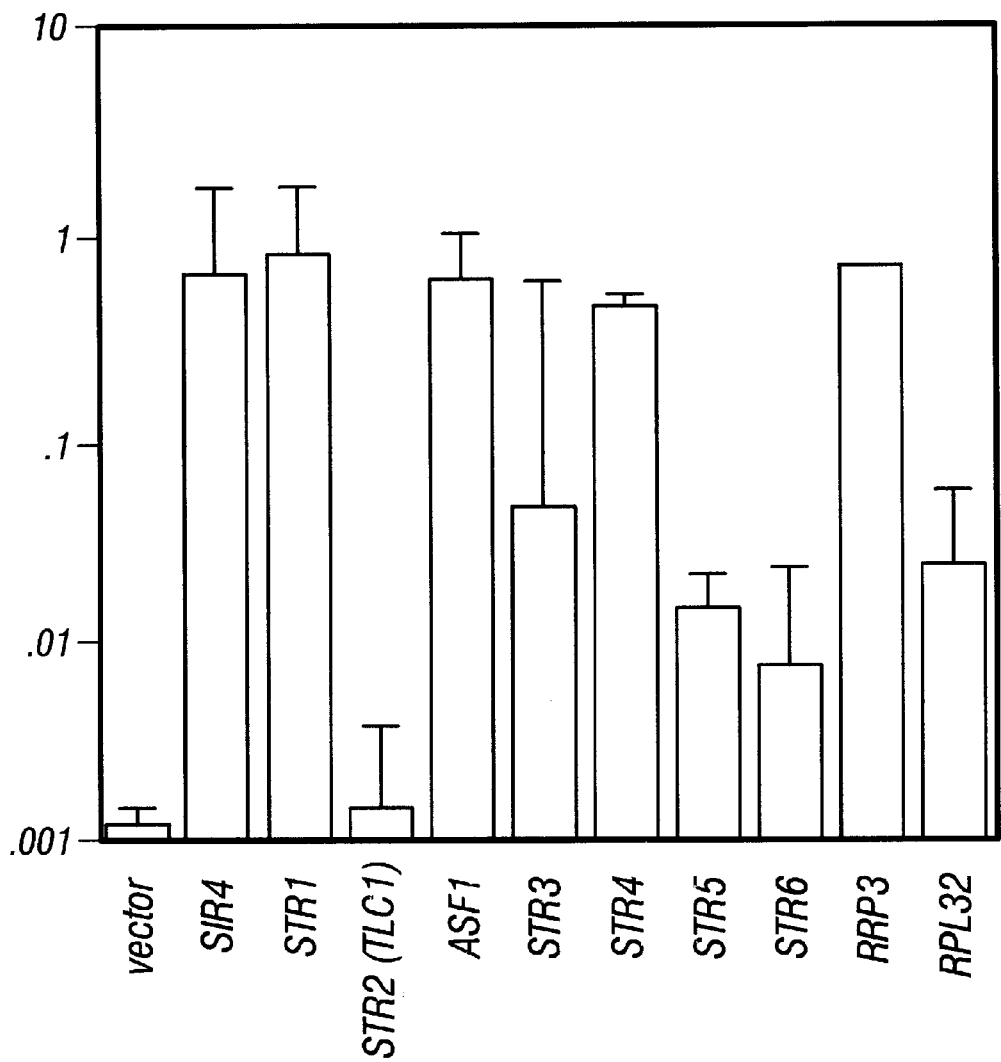
FIG. 7A. Quantitative suppression of telomeric silencing by various different genes. This was assessed by viability in the absence of uracil for the strains that contained the telomeric URA3 gene and each of the 10 highly expressed genes of Example X. All the genes suppressed silencing of the telomeric URA3, although a hierarchy of suppression was observed.
Figure 7B:
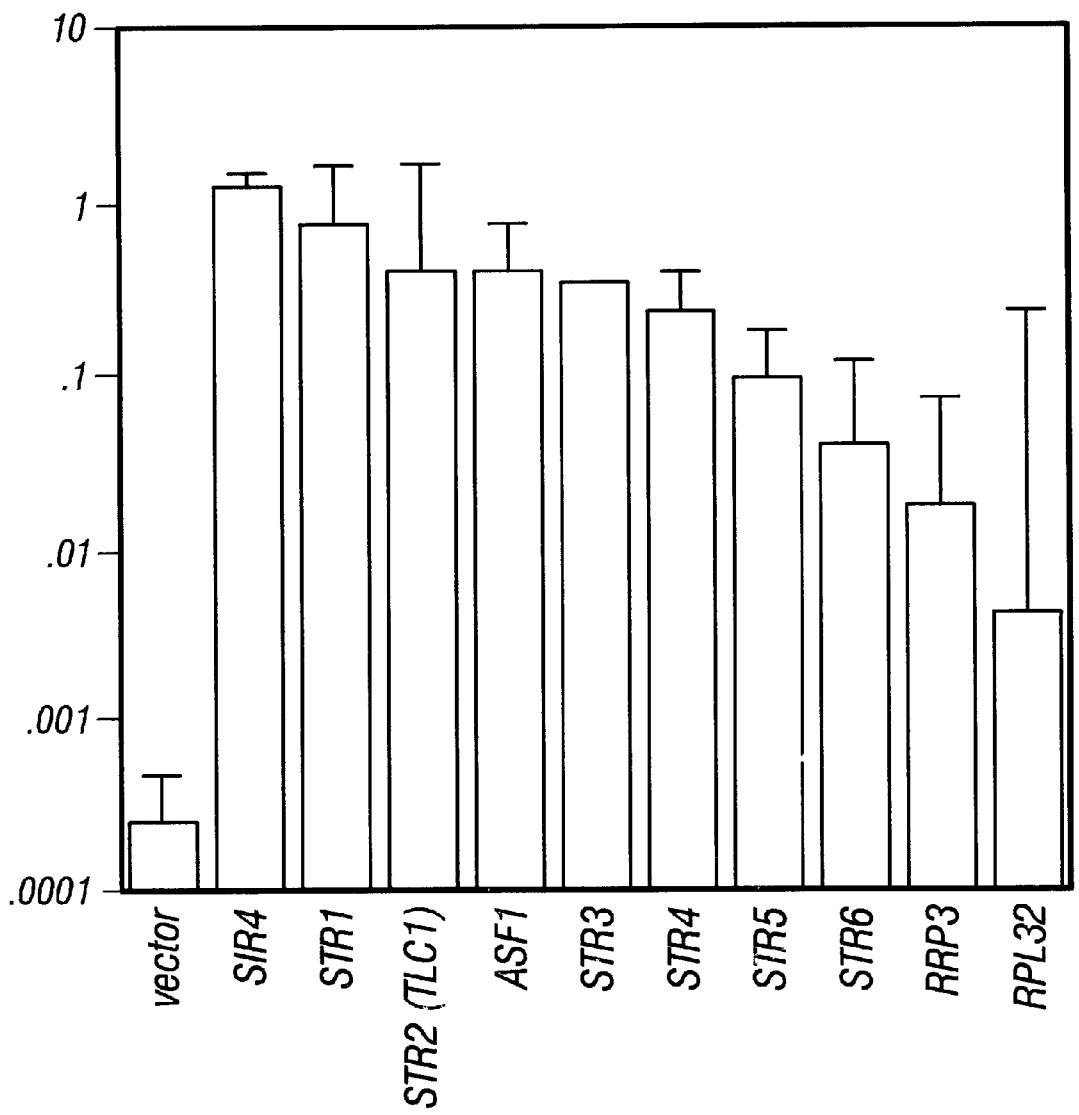
FIG. 7B. Effect of genes on silencing at HML. The expression plasmids containing each of the 10 genes of Example X were introduced into a strain in which the URA3 gene was inserted into the HML locus (Mahoney & Broach, 1989). Overexpression of TLC1 (STR2) had no effect on silencing at HML, but strongly suppressed telomeric silencing of URA3 and ADE2. The SIR4 and ASF1 genes derepressed HML very well, as did the STR1, STR4, and RRP3 genes. Overexpression of RPL32, STR3, STR5 and STR6 had intermediate effects at HML.

The new genes are herein termed STR genes, Suppressors of Telomeric Repression. Initially, seven STR genes were designated, although STR7 was later found to correspond to part of the sequence for RRP3. STR2 has been renamed TLC1 following its functional characterization, as shown in FIG. 7A and FIG. 7B.

The DNA and predicted amino acid sequences, where relevant, of the STR genes are as defined in Table 2.

TABLE 2

| Gene | DNA SEQ ID NO: | Complementary Strand SEQ ID NO: | Polypeptide SEQ ID NO: | Probes & Primers Projected SEQ ID NOS: |
|---|---|---|---|---|
| STR1 | 15 | 29† | 16 | 5837-7702 |
| TLC1 (STR2) | 1 | 4 | * | 33-1317 |
| STR3 | 17 | 30† | 18 | 7703-8780 |
| STR4 | 19† | | 20 | 1318-3735 |
| STR5 | 21 | 31† | 22 | 8781-9571 |
| STR6 | 23† | | 24 | 3736-5836 |
| STR7 | 25 | 32† | 26 | |
| RRP3 | 27\ | | 28 | |

*Encodes RNA Template - SEQ ID NO:3
554 Denotes strand with protein-encoding open reading frame Table 2 shows the DNA and amino acid sequences of seven of the STR genes. STR2, renamed TLC1, encodes the RNA template component, rather than a polypeptide species. Both SEQ ID NO;1 and SEQ ID NO:4 are provided for TLC1. STR7 (SEQ ID NO:25, DNA; and SEQ ID NO:26, amino acid) was found to be a partial sequence of RRP3, the full length sequences of which are also included herein (SEQ ID NO:27, DNA; and SEQ ID NO:28, amino acid).

Table 2 also provides information concerning the numbers of 17-mer probes and primers from SEQ ID NO:1 and from each of the polypeptide-encoding DNA sequences of the present invention. Naturally, the number of 17-mers from each of the complementary strands could be readily made. Given that 32 separate sequences are already disclosed herein, should the 17-mer probes and primers from the claimed sequences be specifically identified and numbered, they would start with SEQ ID NO:33.

The projected SEQ ID NO designations in Table 2 refer to the individual sequences that could be readily predicted from the given information. For example, the sequence AATAAAACTAGAGAGGA, residues 1 to 17 of SEQ ID NO:1, would be assigned SEQ ID NO:33; the sequence ATAAAACTAGAGAGGAA, residues 2 to 18 of SEQ ID NO:1, would be assigned SEQ ID NO:34. On this basis, SEQ ID NO:100 would be ATTTTTTTTTTTTCAG, residues 68 to 84 of SEQ ID NO:1; SEQ ID NO:1000 would be GATCAAGAACGTAATTT, residues 968 to 984 of SEQ ID NO:1; SEQ ID NO:5000 would be AAAAGATGAAGACGCTT, residues 1265 to 1281 of SEQ ID NO:23; and SEQ ID NO:9571 would be AGATATTCTAACTCTCT, residues 791 to 807 of SEQ ID NO:31.

The start and stop site locations for the major open reading frames (ORFs) of each of the STR sequences are presented in Table 3. The ORFs for STR4 and STR6 are presented with respect to the DNA strand originally sequenced. It was noted that certain of the DNA sequences had ORFs oriented in the opposite direction to the original DNA strand sequence, so that the ORF starts at a high position in the DNA, and ends at a low position. Namely, the STR1 ORF was located between nucleotides 1829–84; the STR3 ORF was located between nucleotides 1017–1; and the STR5 ORF was located between nucleotides 753–109. Although this phenomenon is well known, the complementary DNA strand of STR1, STR3, STR5 and STR7 are also included herein (SEQ ID NO:29, SEQ ID NO:30, SEQ ID NO:31 AND SEQ ID NO:32, respectively; Table 2 and Table 3), and the ORFs listed in ascending numbers for instant recognition.

TABLE 3

| Gene | Strand SEQ ID NO: | Complementary Strand SEQ ID NO: | ORF Starts at (bp #) | Original ORF Ends at (bp#) | Length of ORF (Amino Acid Residues) |
|---|---|---|---|---|---|
| STR1 | 15 | 29\ | 54 | 1799 | 582 |
| STR3 | 17 | 30\ | 78 | 1094 | 339 |
| STR4 | 19\ | 2 | 2368 | 789 | |
| STR5 | 21 | 31\ | 55 | 699 | 215 |
| STR6 | 23\ | 3 | 1955 | 651 | |
| STR7 | 25 | 32\ | 279 | 956 | 226 |

†Denotes strand with open reading frame (ORF)

To determine how strongly each gene suppressed telomeric silencing, viability in the absence of uracil was quantified for the strains that contained the telomeric URA3 gene and each of the highly expressed genes. All the genes suppressed silencing of the telomeric URA3, although a hierarchy of suppression was observed (FIG. 7A).

All previously identified genes known to be required for telomeric silencing are also known to be involved in transcriptional silencing at two internal chromosomal sites, the HML and HMR loci, which harbor the unexpressed copies of the mating type genes in S. cerevisiae (Aparicio et al., 1991). To determine whether the newly isolated suppressors of telomeric silencing also affect silencing at HML, the expression plasmids were introduced into a strain in which the URA3 gene was inserted into the HML locus (Mahoney & Broach, 1989).

Overexpression of the novel gene TLC1 (STR2) had no effect on silencing at HML, but strongly suppressed telomeric silencing of URA3 and ADE2 (FIG. 7B). The SIR4 and ASF1 genes, whose overexpression was previously known to disrupt silencing both at telomeres and at HML (Marshall et al., 1987), as well as STR1, STR4, and RRP3 genes, derepressed HML very well (FIG. 7B). Overexpression of RPL32, STR3, STR5 and STR6 had intermediate effects at HML (FIG. 7B).

EXAMPLE XI

Detailed Analysis of the TLC1 Gene and RNA

To define the components of telomerase activity, the telomerase template RNA from S. cerevisiae is used in conjunction with classical and molecular genetic techniques to identify the previously elusive telomerase proteins.

Telomere length in S. cerevisiae is normally under tight genetic control; telomeres do not grow infinitely long, nor do they become drastically shortened. In addition, a 3' tail is detected at the end of yeast chromosomes late in S-phase. Taken together these observations suggest that telomerase activity is regulated, most likely being limited to late S-phase of the cell cycle. There are numerous mechanisms to explain the proposed modulation of telomerase activity in a cell. At a first level of evaluation the models can be divided into those in which (1) the RNA is regulated (the RNA is the limiting component), (2) a different component of telomerase activity (mostly likely a protein) is regulated, or (3) that telomerase activity is constitutive and access to its substrate (the 3' end of the chromosome) is regulated. Validity of these models concerning telomerase regulation is determined as follows.

A. Fine structure Analysis of the TLC1 RNA

To determine the 5' and 3' ends of the telomerase RNA, standard techniques, such as Si and ribonuclease protection (for both the 5' and 3' ends), and primer extension (for the 5' end) are used (Sambrook et al., 1989). By using this combination of methods, the physical ends of the RNA are identified.

Typically, non-translated RNAs do not have a polyA$^+$ tail. However, of the nine TLC1 cDNA clones isolated in the earlier genetic selection/screen, four had adenine tracts of 5–20 nucleotides at their 3' ends. A recently published method is available for determining the precise sequence of 3' ends of messages, irrespective of whether they have a long, a short or no poly-A tail (Liu & Gorovsky, 1993). The method uses T4 RNA ligase to attach a DNA oligonucleotide to the 3' end of RNA molecules, followed by cDNA synthesis, PCR amplification, cloning and sequencing. This method is capable of detecting a poly-A$^+$ transcript if it is represented in only a few percent of the TLC1 RNA population.

The inventors currently believe that the yeast telomerase RNA is not poly-adenylated, but that the subset of TLC1 cDNAs with poly-A tracts that the inventors isolated represent a by-product of the cDNA synthesis. However, if the telomerase RNA is polyadenylated in *S. cerevisiae*, it may represent another level of control. For instance, genes involved in poly-A$^+$ addition, degradation and message localization have been identified in yeast, and may be important in regulating TLC1 activity (Muhlrad & Parker, 1992).

B. TLC1 RNA Expression and Cell-Cycle

A simple mechanism for limiting telomerase activity to a specific period of the cell cycle, is to regulate the presence of the telomerase RNA. Therefore the steady-state levels of the TLC1 RNA through the cell cycle are determined. Methods are available to bring a culture of yeast cells into a synchronized progression through the cell cycle, or to arrest the cells at specific stages (Aparicio & Gottschling, 1994). For instance, MATa cells are arrested in late G1 with α-factor or a conditional cell-cycle arrest mutation. Steady state RNA levels are then isolated and analyzed. In addition, the cells are later released from the arrest and allowed to progress synchronously through the cycle, with RNA samples being taken at various times after release. The cell cycle position of the cell population is determined by examining cell morphology and RNA levels of genes known to be cell-cycle regulated (e.g. CLN2 and SWI5). During the analysis of the TLC1 RNA, any changes in transcript length, particularly if a fraction of the RNA is modified, such as by poly-adenylation, is noted. A cell-cycle change may be the result of cell-cycle regulated transcription or a post-transcriptional event such as RNA degradation.

C. Characterizing the TLC1 Gene

The inventors verified that the cDNA clones of TLC1 isolated are identical to the genomic sequences. Thus, it does not appear that any major sequence modifications occur to the telomerase RNA after transcription, such as RNA splicing or editing (Moore et al., 1993; Bass, 1993), although the possibility of post-transcriptional modifications, such as methylation (Reddy & Busch, 1988), cannot presently be ruled out.

The precise positioning of TLC1 within the genome, and the sequences of the gene's transcriptional control elements, was also determined by the inventors. The 3' ends of TLC1 and CSG2 converge from opposite directions. The CSG2 gene has a predicted ORF that terminates within 50 bp of the 3' end of the TLC1 cDNA sequences. On the opposite side of TLC1, PDX3 has a divergent transcript with an ORF beginning ~650 bp from the 5' end of the TLC1 cDNA sequences. Analysis of this intervening 650 bp, particularly in the region within 200 bp of the predicted TLC1 5' end, reveals matches or very near matches to TATA elements, GCN4 (Hill et al., 1986) and HOMOL1 (Rotenberg & Woolford, Jr., 1986) consensus binding sites (both are transcriptional activators that bind to Upstream Activating Sequences (UAS)), and to A block and B block sites (Geiduschek & Tocchini-Valentini, 1988, RNA Polymerase III control elements). Thus at this point, TLC1 may be transcribed by either Pol II or Pol III.

In order to determine which polymerase transcribes the gene, the steady state level of the TLC1 message in strains containing a conditional temperature sensitive allele of either Pol II or Pol III is examined, after the cells have been shifted to a non-permissive temperature (Gudenus et al., 1988; Kolodziej & Young, 1991). This analysis, in concert with 5' deletion analysis, allows the RNA polymerase that transcribes the gene to be determined. Sequences for two known cell-cycle specific control elements, an Mlu I site or SWI4/SWI6 consensus binding site (Nasmyth, 1993; Primig et al., 1992), are not present upstream of TLC1. Thus it is unlikely that TLC1 transcription is regulated by either of these cell-cycle dependent pathways.

The minimum extent of the sequences, both 5' and 3' of TLC1, that are required on a single-copy CEN plasmid to complement the chromosomal null mutation tlc1::LEU2 are determined using, e.g., the plasmid PAZ1 (obtained from Teresa Dunn, Beeler et al., 1994), which contains a 5.5 kbp Sal I fragment that encodes all of CSG2 and TLC1, and most of PDX3. Using restriction enzymes and exonucleases the essential sequences are determined. The reduced size of the gene fragment will greatly facilitate further mutant analysis, and the 5' deletion analysis will determine which UAS-promoter elements are essential for expression, thereby facilitating the creation of a conditional mutant with a heterologous UAS/promoter.

D. Constructing an Allele of TLC1 that is Regulated by a Heterologous Promoter

In order to facilitate in vivo studies on TLC1, a conditional allele of the gene is useful. A chimeric fusion of the TLC1 gene placed under the regulation of a heterologous promoter/UAS is contemplated. Based on data from the TLC1 DNA sequence, the 5' end of the TLC1 RNA, and determining what sequences at the 5' end of the gene are essential for TLC1 expression, the TLC1 upstream region is then replaced with the control elements of the MET3 gene (Cherest et al., 1987). The MET3 promoter is repressed in the presence of methionine and induced when methionine is absent from the medium. MET3 transcriptional fusions to a number of RNA Pol II transcribed genes have been described. The GAL1,10 UAS may also be used (Johnston & Davis, 1984). If TLC1 is transcribed by Pol III, the bacterial tetracycline repressor-operator system may be used to regulate the TLC1 gene. A Pol III-transcribed gene has been shown to be regulated by this system when the tetO operator sequence was introduced near the 5' end of the gene in *S. cerevisiae* (Dingermann et al., 1992).

The plasmid shuffle technique (Sikorski & Boeke, 1991) and conditional alleles may also be used in place of heterologous promoters.

EXAMPLE XII

The Role of TLC1 in Additional in vivo Processes

A. Telomerase RNA and Single-Strand $TG_{1-3}$ Tails

A single-strand $TG_{1-3}$ tail at the ends of yeast telomeres is transiently detected late in S phase (Wellinger et al., 1993). This tail may be the result of elongation of the 3' strand at chromosome ends by telomerase activity. Tail formation in a tlc1 strain (Welinger et al., 1993) is thus examined. The $TG_{1-3}$ tails are detected by using a Southern hybridization method in which yeast DNA is never denatured, and then hybridized with a $C_{1-3}A$ probe. When the tails are $\geq 65$ nucleotides long, the probe efficiently hybridizes to the single-strand of $TG_{1-3}$. The analysis is performed on cells that are synchronously progressing through S phase after release from an α-factor arrest (late G1), or a cdc7 arrest (G1-S boundary). In a wild type (TLC1) cell the same results as previously observed are expected, but in a tlc1$^-$strain, no tail detection is contemplated. However, if a single-strand tail is still observed in a tlc1$^-$strain, then the tail is likely to be formed by a telomerase-independent mechanism. For instance, the tail may be formed by loss of terminal 5' $C_{1-3}A$ strand sequences, the result of a cell-cycle controlled exonuclease activity. The tlc1 allele used in this study is a conditional allele placed under a heterologous promoter. Alternatively, young (<50 generations old) haploid cells, the spore products of a TLC1/tlc1 diploid strain, are used.

The role of EST1 in tail formation (Lundblad & Szostak, 1989) is also examined. If tail formation is dependent upon both TLC1 and EST1, it lends support that EST1 is part of telomerase, or regulates its activity. Alternatively, if the tail is only dependent upon TLC1, it suggests that EST1 may be important in another aspect of telomere replication, perhaps in synthesis of the 5' strand.

B. Telomerase RNA and Healing Broken Chromosome Ends

When a chromosome is broken, two non-telomeric DNA ends are generated; these ends are unstable. One mechanism for stabilizing ends is to 'heal' them by the addition of telomeric sequences. Telomerase activity may provide a major mechanistic pathway for healing by adding telomere DNA de novo to the broken ends (Kramer & Haber, 1993; Harrington & Greider, 1991). An alternative pathway, which has been documented in S. cerevisiae and Drosophila, utilizes recombinational mechanisms (Biessmann & Mason, 1992).

To test telomere healing, a Haber-based assay is used (Kramer & Haber, 1993). In this system, a recognition sequence for the HO endonuclease is located at a unique site in the genome of a diploid cell (on only one of the homologues), with markers genes on either side of it. The HO endonuclease is then conditionally expressed (it is under control of a galactose-dependent promoter) and results in cleavage of the single homologue. The strain is rad52⁻, which eliminates the major mitotic recombination pathway in yeast, thus preventing repair of the broken chromosome by gene conversion from the uncut homologue, or telomere healing by the recombination pathway (Lundblad & Blackburn, 1993). By selecting for cells that retain a marker centromere proximal to the cut site, and loss of a marker telomere proximal to the cut, healed chromosomes are identified. A diploid cell is required in this system, because essential genes are lost distal to the cut site; these gene functions are provided by the uncut homologue.

Figure 8:
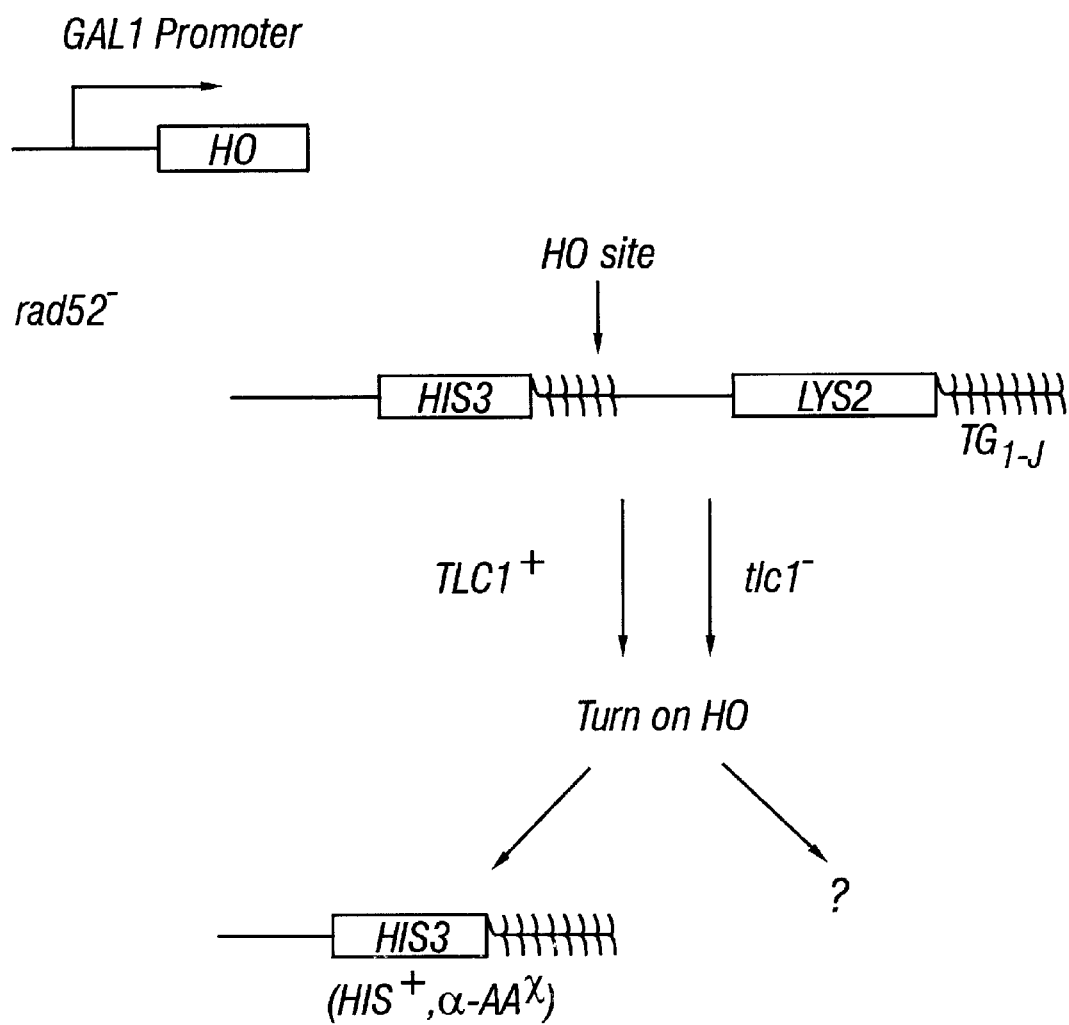
FIG. 8. Schematic representation of the new genetic system to test telomere healing, as described in Section 2 of Example XII.

The inventors have designed a new genetic system, improved (FIG. 8) in several important ways: (1) The unique HO cleavage site is introduced at the ADH4 locus into a haploid strain. ADH4 and the sequences distal to it are non-essential for haploid growth; thus, they may be lost without apparent consequence (Gottschling, 1990). The haploid nature of the strain is of particular use in genetic identification and analyses of recessive mutations. (2) A short tract of $TG_{1-3}$ is placed centromere-proximal of the HO cleavage site. This sequence serves as a 'seed' for the healing event, thus increasing the probability that a stable chromosome will be recovered. Correlative evidence from healed chromosomes in both yeast and humans indicate that normal occurrences of such sequences at internal chromosomal loci are the major sites of de novo telomere addition (Kramer & Haber, 1993; Harrington & Greider, 1991). (3) The LYS2 gene is located on the telomere-proximal side of the HO site, and HIS3 is located on the centromere-proximal side of the $TG_{1-3}$ sequence. The combination of these two genes provides a strong genetic selection for the healing event. The loss of LYS2, and hence loss of the region distal to the cut site, is selected by growth on α-aminoadipate (α-AA) (Zaret & Sherman, 1985). Simultaneous selection for HIS3 (growth in the absence of histidine) ensures that sequences centromere-proximal to the cleavage site are still present (Aparicio & Gottschling, 1994).

The strain contains one additional difference, the TLC1 gene is a conditional allele, under control of the MET3 promoter. Loss of TLC1 function is accomplished by turning off the MET3 promoter (by the addition of methionine to the media), thus allowing the requirement for TLC1 function in telomere healing to be tested.

It is expected that when HO endonuclease is expressed (by the presence of galactose in the medium) in TLC1⁺ cells, the VII-L chromosome will be cleaved at the HO site. Those cells that have formed a new telomere at or near the $TG_{1-3}$ 'seed' sequences, and have lost the distal LYS2 gene (presumably to nuclease degradation, inability to replicate, or missegregation) 5 will be selected on −his +α-AA plates. The selection will be imposed on the cells several generations after HO cleavage. This is to avoid phenotypic lag during α-AA selection, due to the initial presence of the LYS2 gene product.

It is expected that HO endonuclease cleavage will occur in nearly 100% of the cells in the population (FIG. 8), and that at least 1/1000 cells will heal at the $TG_{1-3}$ 'seed' (Kramer & Haber, 1993). Those chromosomes that do not heal at the 'seed' may form a new telomere at a more centromere-proximal chromosomal position, or be completely lost. In the event an essential gene or the entire chromosome is lost, the cell is inviable; if a new telomere is formed at a viable chromosomal location, the cell will be His⁻. To verify that the telomere has indeed healed as expected, Southern analysis of the chromosome in this region is performed. When the study is repeated in the absence of functional TLC1 gene product, it is expected that no growth will be observed on −his +α-AA media. In fact, the process of HO cleavage in tlc1⁻ cells may result in complete inviability, as the lack of telomerase activity to 'heal' the broken chromosome end may result in chromosome loss. If growth on −his +α-AA media is observed in tlc1 cells, it may be the result of a loss of function mutation in the LYS2 gene in a small subset of cells where cleavage did not occur (this is determined by Southern analysis).

Of course, the original diploid system developed by Haber may be used in this analysis. The assays used to characterize loss of TLC1 and EST1 function in vivo, namely a decrease in telomere length and cell viability with increased age of a culture (in a rad52strain), can also be used for further analysis (Lundblad & Blackburn, 1989).

EXAMPLE XIII

Genetic Dissection of TLC1 RNA

The telomerase RNA molecule is dissected to identify regions that are essential for telomerase activity and to define regions that interact with other telomerase components. Two different genetic approaches are used. First, the technique that resulted in the original identification of TLC1, namely, overexpression of TLC1 cDNAs to suppress telomeric silencing. Limited sequences within the RNA that are responsible for the suppression are defined. These regions will interact with other telomerase components and are useful in identifying these components.

Second, methods used to dissect small nuclear RNAs (snRNAs) and their function in yeast (Parker, 1989: Guthrie & Patterson, 1988) are adapted. Here mutants of TLC1 are constructed and tested for in vivo functions, such as the ability to 'heal' broken chromosomes or form single-stranded tails late in S phase. Again, important regions of the RNA are identified and used to isolate interacting components.

Methods to identify important regions of snRNAs include phylogenetic comparisons of each type of RNA (e.g. U1, U2, etc.) (Miraglia et al., 1991; Ares, Jr., 1986; Ares, Jr., & Igel, 1990). Conserved sequences and secondary structures in the RNA molecules of different species have been analyzed. Comparisons between telomerase RNAs from a variety of ciliates have suggested conserved secondary structures, while little conservation at the primary sequence level is detected (Lingner et al., 1995; Romero & Blackburn, 1991). So far, conserved sequences or structures between the 1.3 kb TLC1 RNA and the much smaller ciliate RNAs (the largest is 200 nucleotides) have not been identified, but continued analyses may yield useful information. While a similar size difference is seen between the long U2 snRNA from *S. cerevisiae* and the smaller U2's in vertebrates, conserved primary sequences between U2 RNAs facilitated structural alignments that identified critical stems and loops in the RNA.

A. Minimal Sequence Elements in TLC1 RNA that Suppress Telomeric Silencing

The same strains and expression vector used to identify TLC1 cDNAs are used to identify limited regions of the telomerase RNA that suppress telomeric silencing. The full length telomerase RNA is examined to determine whether it has the ability to suppress silencing at high levels. While this molecule is expected to suppress very well, it is possible that only truncated, non-functional telomerase RNAs have this phenotype when overexpressed (a dominant-negative phenotype) (Herskowitz, 1987). Nonetheless, the full length RNA serves as the starting point for creating 5' and 3' deletion derivatives, as well as derivatives that either delete internal segments or retain a single internal element. It is contemplated that relatively small regions of the RNA (perhaps 50 bp) that suppress silencing will be identified. By reducing the size, an assured interaction of a single component and the RNA fragment is determined. This increases the likelihood of identifying the component.

It is believed that overexpression of TLC1 causes suppression of telomeric silencing because the RNA titrates away a limited component in the cell. To determine whether the limited component is part of telomerase, part of the telomeric silencing machinery, or plays a role in both complexes, each of the TLC1 overexpression derivatives are tested in other assays, e.g., in particular, the telomere 'healing' assay that can be performed quantitatively. The derivatives that have the strongest effect in reducing the frequency of healing are the best candidates for a telomerase-specific interaction.

This titration assay is contemplated for use in identifying telomerase RNA structures that are conserved between species. For instance, the telomerase RNA from a ciliate such as Oxytricha may act to suppress telomeric silencing when expressed at high levels, if the Oxytricha RNA is able to interact with a conserved telomerase component in yeast. If such structural conservation occurs, this assay is then useful for isolating telomerase RNAs from species in which the RNA has not yet been isolated, such as from humans.

B. Creating TLC1 Mutants

A second method to identify important regions of the TLC1 RNA that may interact with other telomerase components involves making loss of function mutations in the RNA, excluding the template region. With an RNA as large as the TLC1 transcript, such mutations are relatively easy to isolate and, indeed, specific regions of the RNA will be mutated. Either site-directed or limited random mutations to regions of TLC1 for which there is evidence of a conserved secondary structure, or for interaction with other telomerase components, are thus made. Such regions of TLC1 RNA include those that can suppress telomeric silencing when overexpressed, or contain predicted secondary structures that are conserved between TLC1 RNA and telomerase RNAs from other species. These mutations may define dominant, semi-dominant, or recessive alleles of TLC1.

Screening for recessive mutations is first advised because they can be more easily manipulated. Conditional alleles that are sensitive to temperature or moderate structural perturbations, such as low concentrations of formamide or $D_2O$, typically are of greater utility identifying interacting proteins than mutations which are complete loss of function (Huffaker et al., 1987; Bartel & Varshavsky, 1988). These alleles are isolated by a "plasmid shuffle" scheme (Sikorski & Boeke, 1991): One centromere plasmid that contains both the URA3 and wild type TLC1 genes is introduced into a strain deleted for the normal chromosomal copy of TLC1 and containing the required genotype for the telomere 'healing' assay. A second centromere plasmid, with a different selectable marker such as TRP1, carries a mutated TLC1 gene. The mutagenized plasmid(s) are then transformed in the appropriate yeast strain, and a screen for conditional alleles of TLC1 is carried out.

Mutants of interest are those that allow a transformant to "heal" telomeres on –trp +FOA medium (losing the wild type TLC1-URA3 plasmid and retaining the mutant version, which still functions) only when grown at the permissive temperature. At the nonpermissive temperature, such strains are unable to heal telomeres in the presence of FOA because healing is dependent on wild-type TLC1 RNA (growth on FOA can only occur in the absence of the URA3 gene product (Boeke et al., 1987). The relative ability of these alleles to function in the healing assay is quantified by determining the frequency of chromosome healing. The quantitative analysis is useful in classifying the alleles and isolating either suppressors or enhancers. The TLC1 alleles are also screened in other assays, such as formation of single-strand tails, to determine if there are mechanistic differences between the alleles.

EXAMPLE XIV

Isolation of Genes that Interact with TLC1

Based on the two types of TLC1 derivatives created, genetic screens are carried out to isolate genes whose products interact with the telomerase RNA.

A. Genes that Re-Establish Telomeric Silencing when TLC1 RNAs are Overexpressed

This approach is based on the model that when parts of the TLC1 RNA are overexpressed, they interact with a limiting telomerase component to form a non-functional complex. This reduces the level of telomerase activity in the cell, causing reduced telomere length, and the reduction in telomere length decreases the frequency with which telomeric silencing complexes are assembled. Thus, if the concentration of the component is increased such that it is no longer limiting, telomeres become longer and telomeric silencing is re-established.

In this approach, the small TLC1 fragment(s) are expressed at a level that is only slightly higher than necessary for suppression of telomeric silencing. This way, only a small amount of the limiting component is needed to re-establish silencing. The threshold concentration for the GAL1-TLC1 RNA fragment to suppress telomeric silencing is determined by decreasing the concentration of galactose in the medium; expression from this promoter is modulated by galactose concentration. The actual threshold is determined by measuring steady-state RNA levels as a function of telomeric silencing. If a threshold concentration is achieved, the construct is integrated into the genome to help keep the TLC1 RNA fragment level constant.

Once a suitable concentration of the TLC1 fragment is established, the gene encoding the limiting telomerase component is isolated by identifying an overexpression plasmid that, when introduced into this strain, re-establishes silencing. Yeast plasmid libraries that may be used include high copy genomic libraries and cDNA libraries, e.g., driven by the ADH1 promoter (obtainable from S. Elledge).

Candidate plasmids are isolated by a reversal of the selection procedure used to originally identify TLC1. The starting strain contains the construct that expresses the TLC1 fragment at high levels in addition to having two telomeres marked, one with ADE2 the other with URA3. In this strain, telomeric silencing is suppressed by the expression of the TLC1 fragment; the cells are sensitive to growth on FOA (URA3$^+$), and are white (ADE2$^+$). When silencing is re-established, the cells are able to grow on FOA (FOA$^R$; ura3) and form red/white sectored colonies (red=ade2). After the library plasmids are transformed into the strain, re-establishment of silencing is selected/screened by growth of red/white colonies on FOA. In addition to components that interact with TLC1, some plasmids may be isolated that affect the expression level of the GAL1-driven TLC1 fragment. This class is identified by examining the steady state level of the TLC1 RNA fragment. This class may represent genes that negatively regulate GAL1 transcription, or genes that regulate RNA stability.

However, it is also possible that more than one gene product may be limiting in the titration; for example the RNA fragment may be bound by a dimeric complex, with the two components at low concentration in the cell. The limiting factor may be lethal to yeast cells at high concentration, "fouling" an essential cellular function. Therefore, the TLC1 RNA fragment may be used to probe a lgtll yeast cDNA expression library. An in vitro synthesized $^{32}$P-labeled RNA, identical to that defined in vivo, is used to probe a set of filters containing phage plaques. Those plaques that contain a cDNA expressing a TLC1 interacting protein are isolated by virtue of their ability to bind the radioactive probe.

For those plasmids that are candidates for encoding a TLC1 interacting component, the DNA necessary for the effect is determined and subjected to sequence analysis. Putative genes are then subjected to the same analyses used to identify TLC1 as a telomerase component. That is, examining telomere length and cell viability in a strain with a null mutation of the gene and the gene is characterized in biochemical analyses.

B. Modifiers of Conditional TLC1 Mutations

A more classical approach for identifying components that interact with telomerase RNA may be used, e.g., by isolating mutations that enhance or suppress the phenotypes of conditional alleles of TLC1 (as created above). This genetic approach has been successfully utilized in identifying components from many complex biological systems, including proteins that interact with snRNAs involved in splicing (Parker, 1989; Guthrie & Patterson, 1988).

Mutations that suppress the defect of telomere healing in conditional alleles of tlc1 under non-permissive conditions are isolated. The starting strain includes the "healing" set-up in addition to a specific conditional allele of tlc1. At non-permissive temperatures, this strain is unable to grow on –his+α-AA medium after HO endonuclease induction (or as noted, induction may be lethal), the result of a defect in telomere healing. This strain is then mutagenized and mutations that permit 'healing' to occur (growth on –his+α-AA medium) are isolated. The strains containing the suppressors are back-crossed to a parent strain (congenic with the starting strain except the opposite mating type) and the resulting diploid is sporulated and tetrads dissected. After several such backcrosses to isolate the suppressor mutation from other mutations that may have been introduced during mutagenesis, the suppression phenotype is checked to see that it segregates 2:2. Once isolated, the suppressor is crossed to strains containing other tlc1 alleles to determine if it acts specifically on the allele from which it was isolated. If there is allele specificity, then the suppressor mutation interacts with TLC1 RNA in vivo (Huffaker et al., 1987). If not, there is still a high probability that the suppressor interacts with TLC1. Possible suppressor linkage to tlc1 mutations are also determined.

The strategy to isolate the gene encoding the suppressor depends on whether the mutation is dominant, semi-dominant, or recessive, and whether the mutation has additional phenotypes that may be followed. Dominant mutations are currently preferred. A centromere-based genomic DNA library made from the strain containing the suppressor is used to transform the non-mutated 'healing', tlc1 strain. Those plasmids that permit telomere healing, as described above, and do not encode the wild type TLC1 gene, carry the suppressor gene.

An alternative method is to isolate genes that suppress a mutation when in high dosage (Bender & Pringle, 1991). Suppressors can thus be screened for by transforming with a high copy genomic library and isolating plasmids that suppress the telomere healing defect.

Enhancers of the conditional TLC1 alleles grown at permissive or semi-permissive temperatures may also be isolated, as has been successful in identifying interacting components within many biological processes of yeast (Frank et al., 1994).

C. Continued Characterization of the STR Genes

Two of these genes, STR5 and STR6 have a much stronger affect on telomeric silencing than on silencing at HML though not as strikingly as TLC1 does (Example X; FIG. 7A, FIG. 7B). If null mutations of these genes have similar effects on telomeres as those seen in tlc1$^-$-strains, they are excellent candidates for being components of telomerase.

EXAMPLE XV

Biochemical Approaches to Telomerase

Telomere DNA binding proteins from Oxytricha have been isolated and characterized (Gottschling & Zakian, 1986). In vitro transcription assays with yeast extracts and proteins have also yielded low abundance transcription factors (Parthun & Jaehning, 1992). Therefore, protein elements of telomerase are isolatable.

A. Biochemical Characterization of the Ribonucleoprotein Complex Associated with TLC1 RNA To examine the physical association of genes with TLC1, procedures used to isolate small nuclear ribonucleoprotein particles (snRNPs) are adapted (Luhrmann, 1988). The approximate steady state concentration of TLC1 RNA within cells is first determined, by comparing the amount of the RNA isolated from a given number of cells with a dilution series of in vitro transcribed TLC1 RNA. The information obtained from this analysis indicates how much telomerase activity and associated protein is in a cell, and serves as an indicator for enrichment of the TLC1 ribonucleoprotein complex during fractionation procedures.

The first fractionation step separates the nucleus and the cytoplasm, using procedures described for other ribonucleoprotein complexes in yeast (Hopper et al., 1990). It is expected that all TLC1 RNA will be localized to the nucleus, however a cytoplasmic location is not excluded. In the event TLC1 RNA is in the cytoplasm, the fractionation is performed on cells that are arrested at various points in the cell cycle (with pheromone, CDC mutations, or chemicals).

Next, with RNA in the nucleus, a nuclear extract is made and fractionated to give a TLC1 RNA associated particle e.g., by a combination of gradient centrifugation methods (equilibrium and sedimentation velocity), column chromatography steps, including gel-filtration, ion-exchange, hydrophobic/ion-exchange, and agarose beads linked to dyes and other ligands, and gel electrophoresis (Luhrmann, 1988). In addition, buffer and ion conditions are carefully monitored as they can affect the stability of the particle (Roth et al., 1991). An affinity column for TLC1 RNA is also contemplated, e.g., as is created by synthesizing a biotinylated DNA oligonucleotide that is complementary to the RNA's template sequence. The oligonucleotide, which will hybridize to the RNA in the particle, is then tethered to streptavidin beads (Kijas et al., 1994).

As a first use of the fractionation, the fate of EST1 may be followed using protein anti-EST1 antibodies (available from Dr. V. Lundblad) as genetic evidence suggests that it may be part of or regulate telomerase (Lundblad & Szostak, 1989). It is contemplated that extracts from two different mutants that both have 'defective' particles will be combined to generate a fully assembled particle, thus allowing insights into the particle's biogenesis.

Reagents, such as antibodies, to proteins identified in the genetic screens are also contemplated.

B. In vitro Assay for Telomerase Activity from *S. cerevisiae*

Telomerase activity has been biochemically identified from several ciliates and vertebrates, including human cells. However, prior to the present invention, telomerase activity had not been biochemically detected in *S. cerevisiae*. Now assays are available, based partly on those previously described (Greider & Blackburn, 1985; Mantell & Greider, 1994; Prowse et al., 1993; Autexier & Greider, 1994; Greider & Blackburn, 1987), in which a DNA oligonucleotide substrate, representing the 3' G-rich telomere tail, is incubated in extracts with $^{32}$P-labeled dNTP's (typically dGTP or dTTP). The products of telomerase elongation on the input oligonucleotide substrate are then detected by gel electrophoresis and autoradiography.

Identifying the TLC1 RNA and its sequence will likely assist in isolating the activity. To identify telomerase activity in yeast, buffer conditions that have been successful in other systems are used and damaging nucleases are removed. In addition, extracts from strains that are deficient in several of the major proteases (Jones, 1991), and use cocktails of protease inhibitors that have been successfully used for in vitro transcription (Parthun & Jaehning, 1992) are employed.

A series of substrates, ones that are perfectly complementary to the template, are truncated on their 3' end by one or a few nucleotides, or are simply alternating tracts of $(GT)_n$ are used in isolation studies, and very short oligonucleotide products are also analyzed. As telomerase activity in yeast may be very tightly regulated, and limited to only a brief period of the cell cycle, (Wellinger et al., 1993), extracts from cells isolated in a synchronous population late in S phase are also to be used.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abraham, "Regulation of mating-type information in yeast: negative control requiring sequences both 5' and 3' to the regulated region", *J. Mol. Biol.*, 176:307–331, 1984.

Agard & Sedat, "Three-dimensional architecture of a polytene nucleus", *Nature*, 302:676–81, 1983.

Alani et al., "A method for gene disruption that allows repeated use of URA3 selection in the construction of multiply disrupted yeast strains", *Genetics*, 116:541–545, 1987.

Alberts & Sternglanz, "Chromatin contract to silence", *Nature*, 344:193–194, 1990.

Alberts et al., "Molecular Biology of the Cell", (New York: Garland Publishing Inc.), 1219, 1989.

Allsopp et al., "Telomere Length Predicts Replicative Capacity of Human Fibroblasts," *Proc. Natl. Acad. Sci. U.S.A.*, 89(21):10114–10118, 1992.

Aparicio et al., "Modifiers of Position Effect Are Shared Between Telomeric and Silent Mating-Type Loci in *S cerevisiae*", *Cell*, 66:1279–1287, 1991.

Aparicio, "Telomeric Position Effect in *S. cerevisiae*: A Model for the Establishment of Alternative Transcriptional States Under Epigenetic Control", Ph.D. thesis. The University of Chicago, 1993.

Aparicio & Gottschling, "Overcoming telomeric silencing: a trans-activator competes to establish gene expression in a cell cycle-dependent way," *Genes Dev.*, 8:1133–1146, 1994.

Ares, "U2 RNA from yeast is unexpectedly large and contains homology to vertebrate U4, U5, and U6 small nuclear RNAS," *Cell*, 47(1):49–59, 1986.

Ares & Igel, "Mutations define essential and nonessential U2 RNA structures," *Mol Biol Rep*, 14(2–3):131–132, 1990.

Ausubel et al., "Current Protocols in Molecular Biology", 1989.

Autexier & Greider, "Functional reconstitution of wild-type and mutant Tetrahymena telomerase," *Genes Dev.*, 8(5):563–575, 1994.

Bach, "Evidence for transcriptional regulation of orotidine-5'-phosphate decarboxylase in yeast by hybridization of mRNA to the yeast structural gene cloned in *Escherichia coil*", *Proc Natl Acad Sci U S A*, 76:386–90, 1979.

Baker, "Position-effect variegation", *Adv. Genet.*, 14:133–169, 1968.

Bartel & Varshavsky, "Hypersensitivity to heavy water: a new conditional phenotype," *Cell*, 52(6):935–941, 1988.

Bass, "RNA Editing: New Uses for Old Players in the RNA World," In: The RNA World, Gesteland & Atkins, Eds., Cold Spring Harbor Press, p. 383–418. 1993.

Basson et al., "Identifying mutations in duplicated functions in *Saccharomyces cerevisiae*: recessive mutations in HMG-CoA reductase genes", *Genetics*, 117:645–655, 1987.

Becker & Guarente, "High-efficiency transformation of yeast by electroporation", *Meth. Enzymol.*, 194:182–187, 1991.

Beeler et al., "A novel protein, CSG2, is required for Ca2+ regulation in *Saccharomyces cerevisiae*," *J. Biol. Chem.*, 269(10):7279–7284, 1994.

Bender & Pringle, "Use of a screen for synthetic lethal and multicopy suppressed mutants to identify two new genes involved in morphogenesis in *Saccharomyces cerevisiae*," *Mol Cell Biol*, 11(3):1295–1305, 1991.

Berben et al., "The YDp plasmids: a uniform set of vectors bearing versatile gene disruption cassettes for *Saccharomyces cerevisiae*", *Yeast*, 7:475–477, 1991.

Berman et al., "Identification of a telomer-binding activity from yeast," *Proc. Natl. Acad. Sci. U.S.A.*, 83(11):3713–3717, 1986.

Biessmann & Mason, "Genetics and molecular biology of telomeres," *Advances in Genetics*, 30:185–249, 1992.

Blackburn, "Telomeres: structure and synthesis", *J Biol Chem*, 265:5919–21, 1990.

Blackburn, "Structure and Function of Telomeres", *Nature*, 350:569–573, 1991.

Blackburn, "Telomerase," In: The RNA World, Gesteland & Atkins, Eds., Cold Spring Harbor Laboratory Press, pp. 557–576, 1993

Blackburn, *Cell*, 77:621, 1994.

Blobel, "Gene gating: A hypothesis", *Proc. Natl. Acad. Sci. U.S.A.*, 82:8527–8529, 1985.

Boeke et al., "A positive selection for mutants lacking orotidine-5'-phosphate decarboxylase activity in yeast: 5-fluoro-orotic acid resistance", *Mol Gen Genet*, 197:345–6, 1984.

Boeke et al., "5-Fluoroorotic acid as a selective agent in yeast molecular genetics", *Methods Enzymol*, 154:164–75, 1987.

Boeke et al., "A positive selection for mutants lacking orotidine-5'-phosphate decarboxylase activity in yeast: 5-fluoro-orotic acid resistance", *Mol Gen Genet*, 197:345–6, 1984.

Borst, "Molecular genetics of antigenic variation", *Immunol Today*, 12:A29–33, 1991.

Brand, "Characterization of a 'silencer' in yeast: a DNA sequence with properties opposite to those of a transcriptional enhancer", *Cell*, 41:41–8, 1985.

Brand et al., "A yeast silencer contains sequences that can promote autonomous plasmid replication and transcriptional activation", *Cell*, 51:709–19, 1987. Braunstein et al., "Transcriptional silencing in yeast is associated with reduced nucleosome acetylation", *Genes Dev.*, 7:592–604, 1993.

Brisco et al., "Cloning, disruption and chromosomal mapping of yeast LEU3, a putative regulatory gene", *Genetics*, 115:91–99, 1987.

Broach, "Transformation in yeast: development of a hybrid cloning vector and isolation of the CAN1 gene", *Gene*, 8:121–133, 1979.

Brown, "The role of stable complexes that repress and activate eukaryotic genes", *Cell*, 37:359–365, 1984.

Brown, "Heterochromatin", *Science*, 151:417–425, 1966.

Brunelli, J. P. and M. L. Pall, *Yeast*, 9:1299-, 1993.

Brutlag, D. L. et al. (1990) *CABIOS*, 6:237–245.

Buchman et al., "Two DNA-binding factors recognize specific sequences at silencers, upstream activating sequences, autonomously replicating sequences, and telomeres in *Saccharomyces cerevisiae*", *Mol Cell Biol*, 8:210–25, 1988.

Budarf & Blackburn, "Chromatin structure of the telomeric region and 3'-nontranscribed spacer of Tetrahymena ribosomal RNA genes", *J Biol Chem*, 261:363–9, 1986.

Button & Astell, "The Saccharomyces cerevisiae chromosome III left telomere has a type X, but not a type Y', ARS region", *Mol Cell Biol*, 6:1352–6, 1986.

Campbell, in Monoclonal Antibody Technology, Laboratory Techniques in Biochemistry and Molecular Biology Vol. 13, Burden and Von Knippenberg, Eds. pp. 75–83, Amsterdam, Elseview, 1984

Carlson et al., "Evolution of the dispersed SUC gene family of Saccharomyces by rearrangements of chromosome telomeres", *Mol. Cell. Biol.*, 5:2894–2902, 1985.

Casadaban et al., "b-Galactosidase gene fusions for analyzing gene expression in *Escherichia coli* and yeast", *Meth. Enzymol.*, 100:293–308, 1983.

Chan & Tye, "A family of *Saccharomyces cerevisiae* repetitive autonomously replicating sequences that have very similar genomic environments", *J Mol Biol*, 168:505–23, 1983a.

Chan & Tye, "Organization of DNA sequences and replication origins at yeast telomeres", *Cell*, 33:563–73, 1983b.

Cherest et al., "The *Saccharomyces cerevisiae* MET3 gene: nucleotide sequence and relationship of the 5' non-coding region to that of MET25," *M&GG*, 210(2):307–313, 1987.

Choder, "A general topoisomerase I-dependent transcriptional repression in the stationary phase of yeast", *Genes Dev.*, 40 5:2315–2326, 1991.

Chou and Fasman, "Prediction of Protein Conformation," *Biochemistry*, 13(2):222–245, 1974a.

Chou and Fasman, "Conformational Parameters for Amino Acids in Helical, $\beta$-Sheet, and Random Coil Regions Calculated from Proteins," *Biochemistry*, 13(2):211–222, 1974b.

Chou and Fasman, "Prediction of the Secondary Structure of Proteins from Their Amino Acid Sequence," *Adv. Enzymol. Relat. Areas Mol. Biol.*, 47:45–148, 1978a.

Chou and Fasman, "Empirical Predictions of Protein Conformation," *Ann. Rev. Biochem.*, 47:251–276, 1978b.

Chou and Fasman, "Prediction of $\beta$-Turns," *Biophys. J.*, 26:367–384, 1979.

Christianson et al., "Multifunctional yeast high-copy-number shuttle vectors", *Gene*, 110:119–122, 1992.

Chung et al., "Architectural organization in the interphase nucleus of the protozoan *Trypanosoma brucei*: location of telomeres and mini-chromosomes", *Embo J*, 9:2611–9, 1990.

Counter et al., "Telomere shortening associated with chromosome instability is arrested in immortal cells which express telomerase activity," *EMBO J.*, 11(5):1921–1929, 1992.

Counter et al., "Telomerase activity in human ovarian carcinoma," *Proc. Natl. Acad. Sci. U.S.A.*, 91(8):2900–2904, 1994a.

Counter et al., "Stabilization of short telomeres and telomerase activity accompany immortalization of Epstein-Barr virus-transformed human B lymphocytes," *J. Virol.*, 68(5):3410–3414, 1994b.

Cross, "Cellular and genetic aspects of antigenic variation in trypanosomes", *Annu Rev Immunol*, 8:83–110, 1990.

Dabeva and Warner, *J. Biol. Chem.*, 262:16055- , 1987.

Demerec, "Genetic behavior of euchromatic segments inserted into heterochromatin", *Genetics*, 25:618–627, 1940.

de Lange, "Activation of telomerase in a human tumor," *Proc. Natl. Acad. Sci. U.S.A.*, 91(8):2882–2885, 1994.

Dietzel & Kurjan, "Pheromonal regulation and sequence of the *Saccharomyces cerevisiae* SST2 gene: a model for desensitization to pheromone", *Mol. Cell. Biol.*, 7:169–4177, 1987.

Diffley & Stillman, "Transcriptional silencing and lamins", *Nature*, 342:24, 1989.

Dingermann et al., "RNA polymerase III catalyzed transcription can be regulated in *Saccharomyces cerevisiae* by the bacterial tetracycline repressor-operator system," *Embo Journal*, 11(4):1487–1492, 1992.

Durrin et al., "Yeast histone H4 N-terminal sequence is required for promoter activation in vivo", *Cell*, 65:1023–31, 1991.

Edwards & Firtel, "Site-specific phasing in the chromatin of the rDNA in Dictyostelium discoideum", *J Mol Biol*, 180:73–90, 1984.

Eissenberg, "Position effect variegation in Drosophila: towards a genetics of chromatin assembly", *Bioessays*, 11:14–7, 1989.

Elledge et al., "Lambda YES: a multifunctional cDNA expression vector for the isolation of genes by complementation of yeast and *Escherichia coli* mutations," *Proc. Natl. Acad. Sci. U.S.A.*, 88(5):1731–1735, 1991.

Ellis et al., "The pseudoautosomal boundary in man is defined by an Alu repeat sequence inserted on the Y chromosome", *Nature*, 337:81–4, 1989.

Fauvargue & Dura, "Polyhomeotic regulatory sequences induce developmental regulator-dependent variegation and targeted P-element insertions in Drosophila", *Genes Dev*, 7:1508–20, 1993.

Fedoroff et al., "Mutations, epimutations, and the developmental programming of the maize Suppressor-mutator transposable element", *Bioessays*, 10:139–44, 1989.

Feldman et al., "Identification of sites required for repression of a silent mating type locus in yeast", *J. Mol. Biol.*, 178:815–834, 1984.

Felsenfeld, "Chromatin as an Essential Part of the Transcriptional Mechanism", *Nature*, 355:219–224, 1992.

Ferguson & Fangman, "A position effect on the time of replication origin activation in yeast", *Cell*, 68:333–339, 1992.

Ferguson et al., "A yeast origin of replication is activated late in S phase", *Cell*, 65:507–515, 1991.

Fetrow & Bryant, "New Programs for Protein Tertiary Structure Prediction," *BIOTECHNOLOGY*, 11:479–483, 1993.

Fleig et al., "Construction of LYS2 cartridges for use in genetic manipulations of *Saccharomyces cerevisiae*", *Gene*, 46:237–45, 1986.

Fleig et al., "Construction of LYS2 cartridges for use in genetic manipulations of *Saccharomyces cerevisiae*", *Gene*, 46:237–245, 1986.

Frank et al., "Architecture of the U5 small nuclear RNA," *Mol Cell Biol*, 14(3):2180–2190, 1994.

Fussell, "The Position of Interphase Chromosomes and Late Replicating DNA in Centromere and Telomere Regions of Allium cepa L.", *Chromosoma*, 50:201–210, 1975.

Gefter et al., *Somatic Cell Genet.* 3:231–236 (1977)

Geiduschek & Tocchini-Valentini, "Transcription by RNA polymerase III," *Annual Review of Biochemistry*, 57:873–914, 1988.

Goding, 1986, in Monoclonal Antibodies: Principles and Practice, 2d ed., Orlando, Fla., Academic Press, 1986, pp. 60–61, 65–66, 71–74.

Gottlieb & Esposito, "A new role for a yeast transcriptional silencer gene, SIR2, in regulation of recombination in ribosomal DNA", *Cell*, 56:771–6, 1989.

Gottschling, "Telomere-proximal DNA in *Saccharomyces cerevisiae* is refractory to methyltransferase activity in vivo", *Proc. Natl. Acad. Sci. USA*, 89:4062–4065, 1992.

Gottschling & Zakian, "Telomere proteins: specific recognition and protection of the natural termini of Oxytricha macronuclear DNA", *Cell*, 47:195–205, 1986.

Gottschling & Cech, "Chromatin structure of the molecular ends of oxytricha macronuclear DNA: phased nucleosomes and a telomeric complex", *Cell*, 38:501–10, 1984.

Gottschling et al., "Position effect at *S. cerevisiae* telomeres: reversible repression of Pol II transcription", *Cell*, 63:751–762, 1990.

Greider, "Telomere chromatin and gene expression", *Curr. Biol.*, 2:62–64, 1992.

Greider & Blackburn, *Nature*, 337:331, 1989.

Greider & Blackburn, "The telomere terminal transferase of Tetrahymena is a ribonucleoprotein enzyme with two kinds of primer specificity," *Cell*, 51(6):887–898, 1987.

Greider, "Mammalian telomer dynamics: healing, fragmentation shortening and stabilization," *Curr. Opinion in Gen. and Dev.*, 4(2):203–211, 1994.

Greider & Blackburn, "Identification of a specific telomer terminal transferase activity in Tetrahymena extracts," *Cell*, 43:405, 1985.

Grigliatti, "Position-effect variegation—An assay for non-histone chromosomal proteins and chromatin assembly and modifying factors", *Meth. Cell Biol.*, 35:587–627, 1991.

Guacci et al., "Chromosome condensation and sister chromatid pairing in budding yeast", *J. Cell Biol.* in press, 1994.

Gudenus et al., "Conditional mutants of RPC160, the gene encoding the largest subunit of RNA polymerase C in *Saccharomyces cerevisiae*," *Genetics*, 119(3):517–526, 1988.

Guthrie & Patterson, "Spliceosomal snRNAs," *Annual Review of Genetics*, 22:387–419, 1988.

Haber & George, "A mutation that permits the expression of normally silent copies of mating-type information in *Saccharomyces cerevisiae*", *Genetics*, 93:13–35, 1979.

Hardy et al., "A RAP1-interacting protein involved in transcriptional silencing and telomere length regulation," *Genes Dev.*, 6(5):801–814, 1992.

Harley et al., "The telomer hypothesis of cellular aging," *Exp. Gerontol.*, 27(4):375–382, 1992.

Harley et al., *Nature*, 345:458, 1990.

Harrington & Greider, "Telomerase Primer Specificity and Chromosome Healing," *Nature*, 353(6343):451–454, 1991.

Hartwell, "Sequential function of gene products relative to DNA synthesis in the yeast cell cycle", *J Mol Biol*, 104:803–17, 1976.

Hastie & Allshire, "Human telomeres: fusion and interstitial sites", *TIG*, 5:326–331, 1989.

Hastie et al., "Telomere reduction in human colorectal carcinoma and with aging," *Nature*, 346(6287):866–868, 1990.

Hazelrigg et al., "Transformation of white locus DNA in Drosophila: dosage compensation, zeste interaction, and position effects", *Cell*, 36:469–81, 1984.

Hegemann et al., "Mutational analysis of centromere DNA from chromosome VI of *Saccharomyces cerevisiae*", *Mol Cell Biol*, 8:2523–35, 1988.

Heitz, "Das Heterochromatin der Moose. I", *Jahrb. Wiss. Bot.*, 69:762–819, 1928.

Henderson & Larson, *Curr. Opinion in Gen. and Dev.*, 1:538, 1991.

Henikoff, "Position-Effect Variegation After 60 Years", *Trends Genet*, 6:422–426, 1990.

Henikoff & Eghtedarzadeh, "Conserved arrangement of nested genes at the Drosophila GART locus", *Genetics*, 117:711–725, 1987.

Herskowitz, "Functional inactivation of genes by dominant negative mutations," *Nature*, 329(6136):219–222, 1987.

Hess et al. (1968), *J. Adv. Enzyme Reg.*, 7:149.

Hill et al., "Saturation mutagenesis of the yeast his3 regulatory site: requirements for transcriptional induction and for binding by GCN4 activator protein," *Science*, 234 (4775):451–457, 1986.

Himmelfarb et al., "Isolation and characterization of temperature-sensitive RNA polymerase II mutants of *Saccharomyces cerevisiae*", *Mol. Cell. Biol.*, 7:2155–2164, 1987.

Hinnebusch, "A hierarchy of trans-acting factors modulates translation of an activator of amino acid biosynthetic genes in *Saccharomyces cerevisiae*", *Mol. Cell. Biol.*, 5:2349–2360, 1985.

Hinnebusch, "Mechanisms of gene regulation in the general control of amino acid biosynthesis in *Saccharomyces cerevisiae*", *Microbiol. Rev.*, 52:248–273, 1988.

Hitzeman et al. (1980), *J. Biol. Chem.*, 255:2073.

Hochstrasser, "Spatial organization of chromosomes in the salivary gland nuclei of *Drosophila melanogaster*", *J Cell Biol*, 102:112–23, 1986.

Holland et al. (1978), *Biochemistry*, 17:4900.

Holliday, "The Inheritance of Epigenetic Defects", 238:163–170, 1987.

Holmquist, "Role of replication time in the control of tissue-specific gene expression", *Am J Hum Genet*, 40:151–73, 1987.

Hope & Struhl, "GCN4 protein, synthesized in vitro, binds HIS3 regulatory sequences: implications for general control of amino acid biosynthetic genes in yeast", *Cell*, 43:177–188, 1985.

Hopper & Hall, "Mating type and sporulation in yeast. I. Mutations which alter mating-type control over sporulation", *Genetics*, 80:41–59, 1975.

Hopper & Hall, "Mutation of a heterothallic strain to homothallism", *Genetics*, 80:77–85, 1975.

Hopper et al., "The yeast RNA1 gene product necessary for RNA processing is located in the cytosol and apparently excluded from the nucleus," *Journal of Cell Biology*, 111(2):309–321, 1990.

Horowitz & Haber, "Identification of autonomously replicating circular subtelomeric Y' elements in *Saccharomyces cerevisiae*", *Mol Cell Biol*, 5:2369–80, 1985.

Huffaker et al., "Genetic analysis of the yeast cytoskeleton," *Annual Review of Genetics*, 21:259–284, 1987.

Innis et al., "PCR Protocols: a guide to methods and applications", eds. 482p., San Diego: Academic Press, Inc., 1990

Ito et al., "Transformation of intact yeast cells treated with alkali cations", *J. Bacteriol.*, 153:163–168, 1983.

Ivy et al., "Cloning and characterization of four SIR genes of *Saccharomyces cerevisiae*", *Mol. Cell. Biol.*, 6:688–702, 1986.

Ivy, "Map positions of yeast genes SIR1, SIR3 and SIR4", *Genetics*, 111:735–744, 1985.

Jacobs et al., "Function of microtubules in the *Saccharomyces cerevisiae* cell cycle", *J Cell Biol*, 107:1409–1426, 1988.

Jager & Philippsen, "Many yeast chromosomes lack the telomere-specific Y' sequence", *Mol Cell Biol*, 9:5754–7, 1989.

James et al., "Distribution patterns of HP1, a heterochromatin-associated nonhistone chromosomal protein of Drosophila", *Eur J Cell Biol*, 50:170–80, 1989.

Jameson and Wolf, "The Antigenic Index: A Novel Algorithm for Predicting Antigenic Determinants," *Comput. Appl. Biosci.*, 4(1):181–186, 1988.

Johnson et al., "Genetic evidence for an interaction between SIR3 and histone H4 in the repression of silent mating loci in *Saccharomyces cerevisiae*", *PNAS, USA*, 87:6286–6290, 1990.

Johnston, "A model fungal gene regulatory mechanism: the GAL genes of *Saccharomyces cerevisiae*", *Microbiol Rev*, 51:458–76, 1987.

Johnston & Dover, "Mutational analysis of the GAL4-encoded transcriptional activator protein of *Saccharomyces cerevisiae*", *Genetics*, 120:63–74, 1988.

Johnston & Davis, "Sequences that regulate the divergent GAL1–GAL10 promoter in *Saccharomyces cerevisiae*", *Mol. Cell. Biol.*, 4:1440–1448, 1984.

Jones, 1977 *Genetics*, 85:12.

Jones, "Three Proteolytic Systems in the Yeast *Saccharomyces-Cerevisiae*," *J Biol Chem*, 266(13):7963–7966, 1991.

Kammerer et al., "Yeast regulatory gene PPR1. I. Nucleotide sequences restriction map and codon usage", *J. Mol. Biol.*, 180:239–250, 1984.

Kayne, "Extremely conserved histone H4 N terminus is dispensable for growth but essential for repressing the silent mating loci in yeast", *Cell*, 55:27–39, 1988.

Kellum & Schedl, "A group of scs elements function as domain boundaries in an enhancer-blocking assay. *Mol. Cell. Biol.* 12:2424–2431, 1992.

Kijas et al., "Enrichment of microsatellites from the citrus genome using biotinylated oligonucleotide sequences bound to streptavidin-coated magnetic particles," *Biotechniques*, 16(4):656–660, 1994.

Kim, "Multiple control elements in the TRP1 promoter of *Saccharomyces cerevisiae*", *Mol Cell Biol*, 6:4251–8, 1986.

Kim et al., "Effects of histone H4 depletion on the cell cycle and transcription of *Saccharomyces cerevisiae*", *Embo J*, 7:2211–9, 1988.

Kimmerly & Rine, "Replication and segregation of plasmids containing cis-acting regulatory sites of silent mating-type genes in *Saccharomyces cerevisiae* are controlled by the SIR genes", *Mol. Cell. Biol.*, 7:4225–4237, 1987.

Kingsman et al., 1979; *Gene*, 7:141.

Klapholz & Esposito, "A New Mapping Method Employing a Meiotic Rec Mutant of Yeast", *Genetics*, 100:387–412, 1982.

Klar et al., "Regulation of transcription in expressed and unexpressed mating type cassettes of yeast", *Nature*, 289:239–244, 1981.

Klar et al., "Involvement of double-strand chromosomal breaks for mating-type switching in *Saccharomyces cerevisiae*", *Cold Spring Harbor Symp. Quant. Biol.*, 49:77–88, 1984.

Klar et al., "MAR1—A regulator of the HMa and HMa loci in *Saccharomyces cerevisiae*", *Genetics*, 93:37–50, 1979.

Klar et al., "A position-effect control for gene transposition: state of expression of yeast mating-type genes affect their ability to switch", *Cell*, 25:517–524, 1981.

Klingelhutz et al., *Mol. Cell. Biol.*, 14:961, 1994.

Kohler and Milstein, Nature 256:495–497 (1975)

Kohler and Milstein, Eur. J. Immunol. 6:511–519 (1976)

Kolodziej & Young, "Mutations in the three largest subunits of yeast RNA polymerase II that affect enzyme assembly," *Molecular & Cellular Biology*, 11(9):4669–4678, 1991.

Kostriken et al., "A site-specific endonuclease essential for mating-type switching in *Saccharomyces cerevisiae*", *Cell*, 35:165–174, 1983.

Kramer & Haber, "New telomeres in yeast are initiated with a highly selected subset of TG1-3 repeats," *Genes Dev.*, 7(12A):2345–2356, 1993.

Kurtz & Shore, "RAP1 protein activates and silences transcription of mating type genes in yeast", *Genes & Development*, 5:616–628, 1991.

Kyrion et al., "RAP1 and telomere structure regulate telomere position effects in *Saccharomyces cerevisiae*", *Genes Dev*, 7:1146–59, 1993.

Kyte, J. and Doolittle, R. F. A simple method for displaying the hydropathic character of a protein. *J. Mol. Biol.*, 157(1):105–132, 1982.

Lacroute, "Regulation of pyrimidine biosynthesis in *Saccharomyces cerevisiae*", *J Bacteriol*, 95:824–32, 1968.

Laurenson & Rine, "Silencers, silencing, and heritable transcriptional states", *Microbiol. Rev.*, 56:543–560, 1992.

Le Beau, "Editorial: Chromosomal fragile sites and cancer-specific breakpoints—A moderating viewpoint", *Cancer Genet Cytogenet*, 31:55–61, 1988.

Levis et al., "Effects of genomic position on the expression of transduced copies of the white gene of Drosophila", *Science*, 229:558–61, 1985.

Lewis, "The phenomenon of position effect", *Adv. Genet.*, 3:73–115, 1950.

Liljelund et al., "Yeast regulatory gene PPR1. II. Chromosomal localization, meiotic map, suppressibility, dominance/recessivity and dosage effect", *J Mol Biol*, 180:251–65, 1984.

Lima-de-Faria, "Processes of directing expression, mutation and rearrangements in Molecular evolution and organization of the chromosome", (Amsterdam, Elsevier Science Publishers B.V.), pp. 507–604, 1983b.

Lima-de-Faria, "Organization and function of telomeres in Molecular evolution and organization of the chromosome", (Amsterdam, Elsevier Science Publishers B.V.), pp. 701–721, 1983a.

Lindsey et al., "In vivo Loss of Telomeric Repeats with Age in Humans," *Mut. Res.*, 256(1):45–48, 1991.

Lingner et al., "Telomerase RNAs of different ciliates have a common secondary structure and a permuted template," *Genes Dev.*, 8:1984, 1994.

Link & Olson, *Genetics*, 127:681, 1991.

Liu & Gorovsky, "Mapping the 5' and 3' ends of Tetrahymena thermophila mRNAs using RNA ligase mediated amplification of cDNA ends (RLM-RACE)," *Nucleic Acids Research*, 21(21):4954–4960, 1993.

Loison et al., "Constitutive mutants for orotidine 5 phosphate decarboxylase and dihydroorotic acid dehydrogenase in *Saccharomyces cerevisiae*", *Curr. Genet.*, 2:39–44, 1980.

Longtine et al., "A yeast telomere binding activity binds to two related telomere sequence motifs and is indistinguishable from RAP1", *Curr Genet*, 16:225–39, 1989.

Losson et al., "Yeast promoters URA1 and URA3. Examples of positive control", *J Mol Biol*, 185:65–81, 1985.

Losson & Lacroute, "Plasmids carrying the yeast OMP decarboxylase structural and regulatory genes: transcription regulation in a foreign environment", *Cell*, 32:371–7, 1983.

Losson & Lacroute, "Cloning of a eukaryotic regulatory gene", *Mol Gen Genet*, 184:394–9, 1981.

Louis & Haber, "Mitotic recombination among subtelomeric Y' repeats in *Saccharomyces cerevisiae*", *Genetics*, 124:547–559, 1990.

Luhrmann, "snRNP Proteins," In: *Structure and Function of Major and Minor Small Nuclear Ribonucleoprotein Particles*, Birnstiel, Ed., Springer-Verlag: p. 71–99, 1988.

Lundblad & Blackburn, "An alternative pathway for yeast telomere maintenance rescues est1-senescence," *Cell*, 73(2):347–360, 1993.

Lundblad & Szostak, "A mutant with a defect in telomere elongation leads to senescence in yeast", *Cell*, 57:633–43, 1989.

Lustig & Petes, "Identification of yeast mutants with altered telomere structure," *Proc. Natl. Acad. Sci. U.S.A.*, 83(5):1398–1402, 1986.

Mahoney & Broach, "The HML mating-type cassette of *Saccharomyces cerevisiae* is regulated by two separate but functionally equivalent silencers", *Mol. Cell. Biol.*, 9:4621–4630, 1989.

Mahoney et al., "Mutations in the HML E silencer of *Saccharomyces cerevisiae* yield metastable inheritance of transcriptional repression", *Genes & Development*, 5:605–615, 1991.

Maniatis et al., "Molecular cloning: a laboratory manual", Cold Spring Harbor, New York, Cold Spring Harbor Laboratory, 1982.

Mantell & Greider, "Telomerase activity in germline and embryonic cells of Xenopus," *EMBO J.*, 13(13):3211–3217, 1994.

Marshall et al., "Functional domains of SIR4, a gene required for position effect regulation in *Saccharomyces cerevisiae*", *Mol. Cell. Biol.*, 7:4441–4452, 1987.

Mastrangelo et al., "Disruption of a silencer domain by a retrotransposon", *Genetics*, 131:519–529, 1992.

McCarroll & Fangman, "Time of replication of yeast centromeres and telomeres", *Cell*, 54:505–13, 1988.

Megee et al., "Genetic analysis of histone H4: essential role of lysines subject to reversible acetylation", *Science*, 247:841–845, 1990.

Messmer et al., "Analysis of the functional role of the Polycomb chromo domain in *Drosophila melanogaster*", *Genes & Dev.*, 6:1241–1254, 1992.

Miller & Nasmyth, "Role of DNA replication in the repression of silent mating type loci in yeast", *Nature*, 312:247–251, 1984.

Miraglia et al., "Limited functional equivalence of phylogenetic variation in small nuclear RNA: yeast U2 RNA with altered branchpoint complementarity inhibits splicing and produces a dominant lethal phenotype," *Proc Natl Acad Sci U S A*, 88(16):7061–7065, 1991.

Monk, "Variegation in epigenetic inheritance", *TIG*, 6:110–114, 1990.

Moore et al., "Splicing of Precursors to mRNAs by the Spliceosome," In: *The RNA World*, Gesteland & Atkins, Eds., Cold Spring Harbor Press, p. 303–358, 1993.

Morin, "The human telomere terminal transferase enzyme is a ribonucleoprotein that synthesizes TTAGGG repeats," 59(3):521–529, 1989.

Mortimer, "Genetic and physical maps of *Saccharomyces cerevisiae*, Edition 11", *Yeast*, 8:817–902, 1992.

Muhlrad & Parker, "Mutations affecting stability and deadenylation of the yeast MFA2 transcript," *Genes & Development*, 6(11):2100–2111, 1992.

Mullen et al., "Identification and characterization of genes and mutants for an N-terminal acetyltransferase from yeast", *EMBO J.*, 8:2067–2075, 1989.

Nasmyth et al., "Cell Cycle Regulation of SWI5 Is Required for Mother-Cell-Specific HO Transcription in Yeast", *Cell*, 49:549–558, 1987.

Nasmyth, "The regulation of yeast mating-type chromatin structure by SIR: an action at a distance affecting both transcription and transposition", *Cell*, 30:567–578, 1982.

Nasmyth et al., "A position effect in the control of transcription at yeast mating type loci", *Nature*, 289:244–250, 1981.

Nasmyth, "Regulating the HO endonuclease in yeast," *Curr. Opin. Genet. Dev.*, 3(2):286–294, 1993.

Ogden & Adams, "Electrophoresis in Agarose and Acrylamide Gels", *Methods Enzymol*, 152:61–87, 1987.

Olovnikov, *J. Theor. Biol.*, 41:181, 1973.

Olson et al., *Proc. Natl. Acad. Sci. U.S.A.*, 83:7826, 1986.

Olson, "Genome structure and organization in *Saccharomyces cerevisiae*. In The molecular and cellular biology of the yeast Saccharomyces", (eds. J. R. Broach, J. R. Pringle, and E. W. Jones), Vol. 1, pp. 1–39, Cold Spring Harbor Laboratory Press, New York, 1991.

Palladino et al., "SIR3 and SIR4 Proteins Are Required for the Positioning and Integrity of Yeast Telomeres", *Cell*, 75:543–555, 1993.

Park & Szostak, "Point mutations in the yeast histone H4 gene prevent silencing of the silent mating type locus HML", *Mol. Cell. Biol.*, 10:4932–4934, 1990.

Park & Szostak, "ARD1 and NAT1 proteins form a complex that has N-terminal acetyltransferase activity", *EMBO J.*, 11:2087–2093, 1992.

Park et al., "A strategy for the generation of conditional mutations by protein destabilization", *Proc. Natl. Acad. Sci. USA*, 89:1249–1252, 1992.

Parker, "Genetic methods for identification and characterization of RNA-RNA and RNA-protein interactions," *Methods in Enzymology*, 180:510–517, 1989.

Paro & Hogness, "The Polycomb protein shares a homologous domain with a heterochromatin-associated protein of Drosophila", *Proc. Natl. Acad. Sci. USA*, 88:263–267, 1991.

Parthun & Jaehning, "A Transcriptionally Active Form of GAL4 Is Phosphorylated and Associated with GAL80," *Mol Cell Biol*, 12(11):4981–4987, 1992.

Pays & Steinert, "Control of antigen gene expression in African trypanosomes", *Annu Rev Genet*, 22:107–26, 1988.

Pillus & Solomon, "Components of microtubular structures in *Saccharomyces cerevisiae*", *Proc Natl Acad Sci USA*, 83:2468–72, 1986.

Pillus & Rine, "Epigenetic inheritance of transcriptional states in *S. cerevisiae*", *Cell*, 59:637–47, 1989.

Piñon, "Folded chromosomes in non-cycling yeast cells. Evidence for a characteristic G0 form", *Chromosoma*, 67:263–274, 1978.

Pluta & Zakian, "Recombination occurs during telomere formation in yeast", *Nature*, 337:429–33, 1989.

Price, "Telomere structure in Euplotes crassus: characterization of DNA-protein interactions and isolation of a telomere-binding protein," *Mol. Cell Biol.*, 10(7):3421–3431, 1990.

Price, *Curr. Opinion in Cell Biol.*, 4:379, 1991.

Price & Cech, "Telomeric DNA-protein interactions of Oxytricha macronuclear DNA," *Genes Dev.*, 1(8):783–793, 1987.

Price & Cech, "Properties of the telomeric DNA-binding protein from *Oxytricha nova*", *Biochemistry*, 28:769–74, 1989.

Primig et al., "Anatomy of a transcription factor important for the start of the cell cycle in *Saccharomyces cerevisiae*," Nature, 358(6387):593–597, 1992.

Pringle & Hartwell, "The *Saccharomyces cerevisiae* cell cycle. In The Molecular Biology of the Yeast Saccharomyces", J. D. Strathern, E. W. Jones and J. R. Broach, eds. 97–142. Cold Spring Harbor, New York: Cold Spring Harbor Laboratory, 1981.

Prowse et al., "Identification of a nonprocessive telomerase activity from mouse cells," *Proc. Natl. Acad. Sci. U.S.A.*, 90:1493–1497, 1993.

Rawlins & Shaw, "Localization of ribosomal and telomeric DNA sequences in intact plant nuclei by in-situ hybridization and three-dimensional optical microscopy", *J Microsc*, 157:83–89, 1990.

Reddy & Busch, "Small Nuclear RNAs: RNA Sequences, Structure, and Modifications," In: Small Nuclear Ribonucleoprotein Particles, Birnstiel, Ed., Springer-Verlag, Berlin, p. 1–37, 1988.

Renauld et al., "Silent domains are assembled continuously from the telomere and are defined by promoter distance and strength, and by SIR3 dosage", *Genes and Development*, 7:1133–1145, 1993.

Rine & Herskowitz, "Four genes responsible for a position effect on expression from HML and HMR in *Saccharomyces cerevisiae*", *Genetics*, 116:9–22, 1987.

Rine et al., "A suppressor of mating-type locus mutations in *Saccharomyces cerevisiae*: evidence for and identification of cryptic mating-type loci", *Genetics*, 93:877–901, 1979.

Roman, "Studies of gene mutation in Saccharomyces", Cold Spring Harbor Symp., *Quant. Biol.*, 21:175–185, 1956.

Romero & Blackburn, "A Conserved Secondary Structure for Telomerase RNA," *Cell*, 67(2):343–353, 1991.

Roth et al., "A conserved family of nuclear phosphoproteins localized to sites of polymerase II transcription," *J Cell Biol*, 115(3):587–596, 1991.

Rose & Botstein, "Structure and function of the yeast URA3 gene. Differentially regulated expression of hybrid beta-galactosidase from overlapping coding sequences in yeast", *J Mol Biol*, 170:883–904, 1983.

Rose & Winston, "Identification of a Ty Insertion Within the Coding Sequence of the *S. cerevisiae* URA3 gene", *Mol Gen Genet*, 193:557–560, 1984.

Rose et al., "Structure and function of the yeast URA3 gene: expression in *Escherichia coli*", *Gene*, 29:113–24, 1984.

Rose et al., "Methods in yeast genetics: A laboratory course manual", Cold Spring Harbor Laboratory Press, New York, 1990.

Rotenberg & Woolford, Jr., "Tripartite upstream promoter element essential for expression of *Saccharomyces cerevisiae* ribosomal protein genes," *Molecular & Cellular Biology*, 6(2):674–687, 1986.

Rothstein, "One-Step Gene Disruption in Yeast", *Methods Enzymol*, 101:202–211, 1983.

Roy, "Nucleotide sequence of the URA1 gene of *Saccharomyces cerevisiae*", *Gene*, 118:149–50, 1992.

Roy et al., "cis- and trans-acting regulatory elements of the yeast URA3 promoter", *Mol. Cell. Biol.*, 10:5257–5270, 1990.

Runge & Zakian, "Introduction of extra telomeric DNA sequences into *Saccharomyces cerevisiae* results in telomere elongation", *Mol Cell Biol*, 9:1488–1497, 1989.

Runge & Zakian, "Properties of the Transcriptional Enhancer in *Saccharomyces cerevisiae* Telomeres", *Nucleic Acids Res.*, 18:1783–1787, 1990.

Sambrook et al., "Molecular cloning: a laboratory manual", eds. New York: Cold Spring Harbor Laboratory Press, 1989.

Sandell & Zakian, "Telomeric position effect in yeast", *Trends Cell Biol.*, 2:10–14, 1992.

Sandell & Zakian, "Loss of a yeast telomere: arrest, recovery, and chromosome loss," *Cell*, 75:729–739, 1993.

Scherer & Davis, *Proc. Natl. Acad. Sci. U.S.A.*, 76:4951, 1979.

Schiestl & Gietz, "High efficiency transformation of intact yeast cells using single stranded nucleic acids as a carrier", *Curr. Genet.*, 16:339–346, 1989.

Schmid et al., "Nucleosome Disruption at the Yeast PHO5 Promoter upon PHO5 Induction Occurs in the Absence of DNA Replication", *Cell*, 71:853–864, 1992.

Schnell & Rine, "A position effect on the expression of a tRNA gene mediated by the SIR genes in *Saccharomyces cerevisiae*", *Mol. Cell. Biol.*, 6:494–501, 1986.

Schulz & Zakian, "The saccharomyces PIF1 DNA helicase inhibits telomere elongation and de novo telomere formation," *Cell*, 76(1):145–155, 1994.

Seifert et al., "Shuttle mutagenesis: a method of transposon mutagenesis for *Saccharomyces cerevisiae*", *Proc. Natl. Acad. Sci. USA*, 83:735–739, 1986.

Shampay & Blackburn, "Generation of telomere-length heterogeneity in *Saccharomyces cerevisiae*", *Proc Natl Acad Sci USA*, 85:534–8, 1988.

Shampay et al., "DNA sequences of telomeres maintained in yeast", *Nature*, 310:154–7, 1984.

Shay et al., *Oncogene*, 8:1407, 1993.

Sherman et al., "Methods in Yeast Genetics", Cold Spring Harbor Laboratory, 1986.

Shippen-Lentz & Blackburn, "Telomere terminal transferase activity from Euplotes crassus adds large numbers of TTTTGGGG repeats onto telomeric primers," *Mol. Cell. Biol.*, 9(6):2761–2764, 1989.

Shippen et al., "DNA bound by the Oxytricha telomere protein is accessible to telomerase and other DNA polymerases," *Proc. Natl. Acad. Sci. U.S.A.*, 91(1):405–409, 1994.

Shoeman & Traub, "The in vitro DNA-binding properties of purified nuclear lamin proteins and vimentin", *J Biol Chem*, 265:9055–61, 1990.

Shore & Nasmyth, "Purification and cloning of a DNA binding protein from yeast that binds to both silencer and activator elements", *Cell*, 51:721–32, 1987.

Shore et al., "Characterization of two genes required for the position-effect control of yeast mating-type genes", *EMBO J.*, 3:2817–2823, 1984.

Shore et al., "Identification of silencer binding proteins from yeast: possible roles in SIR control and DNA replication", *EMBO J.*, 6:461–46, 1987.

Sikorski & Hieter, "A system of shuttle vectors and yeast host strains designed for efficient manipulation of DNA in *Saccharomyces cerevisiae*", *Genetics*, 122:19–27, 1989.

Sikorski & Boeke, "In vitro mutagenesis and plasmid shuffling: from cloned gene to mutant yeast," In: *Meth. in Enzymol.*, pp. 306–311, 1991.

Sikorski & Hieter, "A uniform set of multiple shuttle vectors and yeast host strains designed for efficient manipulation of DNA in *S. cerevisiae*", *Genetics*, 122:19–27, 1989.

Singh & Klar, "Active genes in budding yeast display enhanced in vivo accessibility to foreign DNA methylases: a novel in vivo probe for chromatin structure in yeast", *Genes & Dev.*, 6:186–196, 1992.

Slater, "Effect of Reversible Inhibition of Deoxyribonucleic Acid Synthesis on the Yeast Cell Cycle", *J Bacteriol*, 113:263–270, 1973.

Spofford, "Position-effect variegation in Drosophila. In *The genetics and biology of Drosophila* (eds. M. Ashburner and E. Novitski)", Vol.1C, pp. 955–1018, Academic Press, New York, 1976.

Spradling & Karpen, "Sixty years of mystery", *Genetics*, 126:779–84, 1990.

Sprague, "Assay of Yeast Mating Reaction", *Meth. Enzymol.*, 194:77–93, 1991.

Stinchcomb et al., 1979; *Nature*, 282:39.

Stone et al., "The SIR1 gene of *Saccharomyces cerevisiae* and its role as an extragenic suppressor of several mating-defective mutants", *Mol. Cell. Biol.*, 11:2253–2262, 1991.

Stotz & Linder, "The ADE2 gene from *Saccharomyces cerevisiae*: sequence and new vectors", *Gene*, 95:91–98, 1990.

Strathern et al., "Homothallic switching of yeast mating type cassettes is initiated by a double-stranded cut in the MAT locus", *Cell*, 31:183–192, 1982.

Strathern et al., "Isolation of a circular derivative of yeast chromosome III: implications for the mechanism of mating type interconversion", *Cell*, 18:309–19, 1979.

Struhl, "Nucleotide sequence and transcriptional mapping of the yeast pet56-his3-ded1 gene region", *Nucl. Acids Res.*, 13:8587–8601, 1985.

Struhl et al., "High-frequency transformation of yeast: autonomous replication of hybrid DNA molecules", *Proc. Natl. Acad. Sci. USA*, 76:1035–1039, 1979.

Surosky & Esposito, "Early meiotic transcripts are highly unstable in *Saccharomyces cerevisiae*", *Molecular and Cellular Biology*, 12:3948–3958, 1992.

Sussel & Shore, "Separation of transcriptional activation and silencing functions of the RAP1-encoded repressor/activator protein 1: Isolation of viable mutants affecting both silencing and telomere length", *Proc. Natl. Acad. Sci. USA*, 88:7749–7753, 1991.

Sutherland & Hecht, "Fragile Sites on Human Chromosomes. Oxford Monographs on Medical Genetics", New York, Oxford University Press, 1985.

Tartof et al., "A structural basis for variegating position effects", *Cell*, 37:869–878, 1984.

Traverse & Pardue, "Studies of He-T DNA sequences in the pericentric regions of Drosophila chromosomes", *Chromosoma*, 97:261–71, 1989.

Tschemper et al., 1980 *Gene*, 10:157.

ten Dam et al., *Nucleic Acids Res.*, 19:6951, 1991.

van Holde, "Chromatin. Springer Series in Molecular Biology, A. Rich, ed. (New York: Springer-Verlag), 497, 1989.

Vaziri et al., *Am. J. Hum. Genet.*, 52:661, 1993.

Verdier, "Regulatory DNA-binding proteins in yeast: an overview", *Yeast*, 6:271–97, 1990.

Wahl et al., "Northern and Southern Blots", *Methods Enzymol.*, 152:572–581, 1987.

Walmsley & Petes, "Genetic control of chromosome length in yeast", *Proc Natl Acad Sci USA*, 82:506–10, 1985.

Walmsley et al., "Unusual DNA sequences associated with the ends of yeast chromosomes", *Nature*, 310:157–60, 1984.

Walton et al., "Resistance to antimycin A in yeast by amplification of ADH4 on a linear, 42 kb palindromic plasmid", *Cell*, 46:857–63, 1986.

Watson, *Nature New Biol.*, 239:197, 1972.

Weinberger, C. et al. (1985) *Science*, 228:740–742.

Weintraub, "Histone-H1-dependent chromatin superstructures and the suppression of gene activity", *Cell*, 38:17–27, 1984.

Weintraub, "Assembly and Propagation of Repressed and Derepressed Chromosomal States", *Cell*, 42:705–711, 1985.

Wellinger & Zakian, "Lack of positional requirements for autonomously replicating sequence elements on artificial yeast chromosomes", *Proc Natl Acad Sci USA*, 86:973–7, 1989.

Wellinger et al., "Saccharomyces telomeres acquire single-strand TG1-3 tails late in S phase," *Cell*, 72(1):51–60, 1993.

Werner-Washburne et al., "Stationary phase in the yeast *Saccharomyces cerevisiae*", *Microbiol Rev*, 57:383–401, 1993.

White, "Chromosomes as supermolecular systems. Animal cytology and evolution", (Cambridge, Cambridge University Press), pp. 1–57, 1993.

Whiteway et al., "The yeast ARD1 gene product is required for repression of cryptic mating-type information at the HML locus", *Mol. Cell. Biol.*, 7;3713–3722, 1987.

Williamson & Paquin, "Homology of *Saccharomyces cerevisiae* ADH4 to an iron-activated alcohol dehydrogenase from *Zymomonas mobilis*", *Mol Gen Genet*. 209:374–81, 1987.

Williamson et al., "Monovalent cation-induced structure of telomeric DNA: the G-quartet model," *Cell*, 59(5):871–880, 1989.

Wilson et al., "Position Effects on Eukaryotic Gene Expression", *Annu. Rev. Cell Biol.*, 6:679–714, 1990.

Wittenberg et al., "G1-specific cyclins of *S. cerevisiae*: cell cycle periodicity, regulation by mating pheromone, and association with the p34CDC28 protein kinase", *Cell*, 62:225–37, 1990.

Wolf et al., "An Integrated Family of Amino Acid Sequence Analysis Programs," *Comput. Appl. Biosci.*, 4(1):187–191, 1988.

Wright et al., "Saccharomyces telomeres assume a non-nucleosomal chromatin structure", *Genes & Dev.*, 6:197–210, 1992.

Yoshikawa & Isono, "Chromosome III of *Saccharomyces cerevisiae*: An Ordered Clone Bank, a Detailed Restriction Map and Analysis of Transcripts Suggest the Presence of 160 Genes", *Yeast*, 6:383–401, 1990.

Young et al., "Telomere regions in Drosophila share complex DNA sequences with pericentric heterochromatin", *Cell*, 34:85–94, 1983.

Yu et al., "In vivo alteration of telomer sequences and senescence caused by mutated Tetrahymena telomerase RNAs," *Nature*, 344(6262):126–132, 1990.

Zahler & Prescott, *Nucleic Acids Res.*, 16:6953, 1988.

Zakian, "Structure and function of telomeres", *Annu. Rev. Genet.*, 23:579–604, 1989.

Zakian & Blanton, "Distribution of telomere-associated sequences on natural chromosomes in *Saccharomyces cerevisiae*", *Mol Cell Biol*, 8:2257–60, 1988.

Zaret & Sherman, "alpha-Aminoadipate as a primary nitrogen source for *Saccharomyces cerevisiae* mutants," *J Bacteriol*, 162(2):579–583, 1985.

Zuckerkandl, "Recherches sur les propriétés et l'activité biologique de la chromatine: A possible role of "inert" heterochromatin in cell differentiation—Action of and competition for "locking" molecules", *Biochimie*, 56:937–954, 1974.

What is claimed is:

1. A method of using a DNA segment that comprises an isolated gene associated with non-ciliate telomerase, wherein said DNA segment is characterized as encoding a polypeptide that includes a contiguous amino acid sequence of at least about 17 amino acids from SEQ ID NO:16, SEQ ID NO:18, SEQ ID NO:20, SEQ ID NO:22 or SEQ ID NO:24, or is characterized as specifically hybridizing to the nucleic acid segment of SEQ ID NO:29, SEQ ID NO:30, SEQ ID NO:19, SEQ ID NO:31 or SEQ ID NO:23, or the complement thereof, the method comprising the steps of:

(a) preparing a recombinant vector in which a non-ciliate telomerase-associated gene is positioned under the control of a promoter;
    (b) introducing said recombinant vector into a recombinant host cell;
    (c) culturing the recombinant host cell under conditions effective to allow expression of the telomerase-associated gene; and
    (d) collecting the expressed gene product.

2. A method for modifying the telomerase activity of a cell, comprising contacting a telomerase-containing cell with an amount of a composition effective to modify telomerase activity, said composition comprising:

(a) an isolated RNA segment of from 25 to about 1,500 nucleotides in length that comprises a non-ciliate telomerase RNA template, the RNA segment specifically hybridizing to the nucleic acid segment of SEQ ID NO:1 or the complement thereof under high stringency hybridization conditions; or
    (b) an isolated telomerase-associated protein or polypeptide that includes a contiguous amino acid sequence of at least about twelve amino acids from SEQ ID NO:16, SEQ ID NO:18, SEQ ID NO:20, SEQ ID NO:22 or SEQ ID NO:24, and assaying said cell for telomerase activity.

3. The method of claim 2, wherein said composition comprises:

(a) a nucleic acid segment that includes the DNA sequence of SEQ ID NO: 1; or (b) a nucleic acid segment that includes the contiguous DNA sequence from position 54 to position 1799 of SEQ ID NO:29, the contiguous DNA sequence from position 78 to position 1094 of SEQ ID NO:30, the contiguous DNA sequence from position 2 to position 2368 of SEQ ID NO: 19, the contiguous DNA sequence from position 55 to position 699 of SEQ ID NO:31, or the contiguous DNA sequence from position 3 to position 1955 of SEQ ID NO:23.

4. The method of claim 2, wherein said telomerase-containing cell is a human cell.

5. The method of claim 2, wherein said telomerase-containing cell is a sperm cell.

6. The method of claim 2, wherein said telomerase-containing cell is an egg cell.

7. The method of claim 2, wherein said telomerase-containing cell is a tumor cell.

8. The method of claim 2, wherein said telomerase-containing cell is a pathogenic cell.

9. The method of claim 2, wherein said telomerase-containing cell is located within an animal and a pharmaceutically acceptable formulation of said composition is administered to said animal.

10. A method for modifying the viability a cell with increased age, comprising contacting a telomerase-containing cell with an amount of a composition effective to modify telomerase activity, said composition comprising:

(a) an isolated RNA segment of from 25 to about 1,500 nucleotides in length that comprises a non-ciliate telomerase RNA template, the RNA segment specifically hybridizing to the nucleic acid segment of SEQ ID NO:1 or the complement thereof under high stringency hybridization conditions; or (b) an isolated telomerase-associated protein or polypeptide that includes a contiguous amino acid sequence of at least about twelve amino acids from SEQ ID NO:16, SEQ ID NO:18, SEQ ID NO:20, SEQ ID NO:22 or SEQ ID NO:24.

* * * * *

UNITED STATES PATENT AND TRADEMARK OFFICE
CERTIFICATE OF CORRECTION

PATENT NO. : 6,387,619 B1
DATED : May 14, 2002
INVENTOR(S) : Daniel E. Gottschling and Miriam S. Singer It is certified that error appears in the above-identified patent and that said Letters Patent is hereby corrected as shown below:

Column 158,
Line 3, after viability insert -- of -- therefor.

Signed and Sealed this

Eighth Day of October, 2002

Attest:

JAMES E. ROGAN
Attesting Officer    Director of the United States Patent and Trademark Office